(12) United States Patent
Short et al.

(10) Patent No.: US 11,851,499 B2
(45) Date of Patent: *Dec. 26, 2023

(54) CONDITIONALLY ACTIVE ANTI-EPCAM ANTIBODIES, ANTIBODY FRAGMENTS, THEIR IMMUNOCONJUGATES AND USES THEREOF

(71) Applicant: BioAtla, Inc., San Diego, CA (US)

(72) Inventors: Jay M. Short, Jackson, WY (US); Gerhard Frey, San Diego, CA (US); Hwai Wen Chang, San Marcos, CA (US)

(73) Assignee: BioAtla, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/616,113

(22) PCT Filed: Jun. 10, 2020

(86) PCT No.: PCT/US2020/037096
§ 371 (c)(1),
(2) Date: Dec. 2, 2021

(87) PCT Pub. No.: WO2020/252095
PCT Pub. Date: Dec. 17, 2020

(65) Prior Publication Data
US 2022/0315664 A1 Oct. 6, 2022

Related U.S. Application Data

(60) Provisional application No. 62/860,092, filed on Jun. 11, 2019.

(51) Int. Cl.
| | | |
|---|---|---|
| *C07K 16/30* | (2006.01) | |
| *A61K 47/68* | (2017.01) | |
| *A61K 39/00* | (2006.01) | |
| *C07K 16/28* | (2006.01) | |

(52) U.S. Cl.
CPC .......... *C07K 16/30* (2013.01); *A61K 47/6851* (2017.08); *C07K 16/2809* (2013.01); *A61K 2039/505* (2013.01); *C07K 2317/24* (2013.01); *C07K 2317/31* (2013.01); *C07K 2317/622* (2013.01); *C07K 2317/73* (2013.01); *C07K 2317/92* (2013.01)

(58) Field of Classification Search
CPC .......... A61K 47/6851; A61K 2039/505; A61K 39/001166; C07K 2317/73; C07K 2317/92; C07K 2317/94; C07K 2317/565
See application file for complete search history.

(56) References Cited

U.S. PATENT DOCUMENTS

| | | |
|---|---|---|
| 8,318,911 B2 | 11/2012 | Anastasi et al. |
| 8,709,755 B2 | 4/2014 | Short et al. |
| 9,777,073 B2 | 10/2017 | Zhou et al. |
| 2011/0165161 A1 | 7/2011 | Lin et al. |
| 2014/0112914 A1 | 4/2014 | Nezu et al. |
| 2014/0288275 A1 | 9/2014 | Moore et al. |
| 2015/0017230 A1 | 1/2015 | Wu et al. |
| 2016/0090426 A1 | 3/2016 | Zhou et al. |
| 2016/0237164 A1 | 8/2016 | Cizeau et al. |
| 2017/0002060 A1 | 1/2017 | Bolen et al. |
| 2017/0247447 A1 | 8/2017 | Dengl et al. |
| 2017/0247685 A1 | 8/2017 | Short |
| 2017/0260261 A1 | 9/2017 | Short |
| 2018/0125988 A1 | 5/2018 | Yang et al. |

FOREIGN PATENT DOCUMENTS

| | | |
|---|---|---|
| CN | 101701039 A | 5/2010 |
| CN | 104168916 A | 11/2014 |
| WO | 2008122551 A2 | 10/2008 |

OTHER PUBLICATIONS

Rabia et al Understanding and overcoming trade-offs between antibody affinity, specificity, stability and solubility (Biochemical Engineering Journal 137 (2018) 365-374) (Year: 2018).*
Examination Report for corresponding Australian application No. 2020292304; dated Apr. 1, 2022 (13 pages).
Armstrong, Andrew, et al. "EpCAM: A New Therapeutic Target for an Old Cancer Antigen." Cancer Biology & Therapy 2.4 (2003): 320-325.
Casaletto, Jessica B., et al. "MM-131, a bispecific anti-Met/EpCAM mAb, inhibits HGF-dependent and HGF-independent Met signaling through concurrent binding to EpCAM." Proceedings of the National Academy of Sciences 116.15 (2019): 7533-7542.
Liao, Mei-Ying, et al. "An anti-EpCAM antibody EpAb2-6 for the treatment of colon cancer." Oncotarget 6.28 (2015): 24947-24968.
Schmidt, M., et al. "Phase IB study of the EpCAM antibody adecatumumab combined with docetaxel in patients with EpCAM-positive relapsed or refractory advanced-stage breast cancer." Annals of Oncology 23.9 (2012): 2306-2313.
Notice of Reasons for Rejection for corresponding Japanese application No. 2021-573310; dated Jul. 5, 2022 (12 pages) Machine Translation.
Request for Submission of an Opinion for corresponding Korean application No. 10-2022-7000242; dated Jul. 20, 2022 (8 pages) Machine Translation.
Naundorf, Stefanie, et al. "In vitro and in vivo activity of MT201, a fully human monoclonal antibody for pancarcinoma treatment." International Journal of Cancer 100.1 (2002): 101-110.

(Continued)

*Primary Examiner* — Amy E Juedes
*Assistant Examiner* — Brian Hartnett
(74) *Attorney, Agent, or Firm* — Mendelsohn Dunleavy, P.C.

(57) ABSTRACT

Isolated polypeptides having a heavy chain variable region and/or light chain variable region that specifically binds to EpCAM protein as well as antibodies and antibody fragments containing the heavy chain variable region and/or the light chain variable region that bind to EpCAM protein Pharmaceutical compositions and kits comprising the polypeptide and antibodies and antibody fragments containing the polypeptide are also provided.

27 Claims, 60 Drawing Sheets

Specification includes a Sequence Listing.

(56) References Cited

OTHER PUBLICATIONS

International Search Report and Written Opinion for corresponding International application No. PCT/US2020/037096; dated Sep. 22, 2020 (15 pages).
Gillies, Robert J., et al. MRI of the Tumor Microenvironment. Journal of Magnetic Resonance Imaging 16.4 (2002): 430-450.
Ni, Jie, et al. "Role of the EpCAM (CD326) in prostate cancer metastasis and progression." Cancer and Metastasis Reviews 31.3 (2012): 779-791.
Notice of Reasons for Rejection for corresponding Japanese application No. 2021-573310; dated Dec. 13, 2022 (16 pAges).
Notice of Final Rejection for corresponding Korean application No. 10-2022-7000242; dated Dec. 27, 2022 (10 pages) Machine Translation.
First Office Action for corresponding Chinese application No. 202080042594.6; dated Aug. 4, 2023 (14 pages) Machine Translation.
Notice of Reasons for Refusal for corresponding Japanese application No. 2021-573310; dated May 9, 2023 (8 pages). Machine Translation.
Extended European Search Report for corresponding Eurpoean application No. 20823266.0; dated Mar. 20, 2023 (17 pages).
Office Action for corresponding Canadian application No. 3,143,039; dated Mar. 23, 2023 (4 pages).
Amann, Maria, et al. "Therapeutic window of MuS110, a single-chain antibody construct bispecific for murine EpCAM and murine CD3." Cancer Research 68.1 (2008): 143-151.
Bellone, Stefania, et al. "Solitomab, an EpCAM/CD3 bispecific antibody construct (BiTE), is highly active against primary uterine serous papillary carcinoma cell lines in vitro." American Journal of Obstetrics and Gynecology 214.1 (2015): 99-e1-99-e8.
Cioffi, Michele, et al. "EpCAM/CD3-Bispecific T-cell Engaging Antibody MT110 Eliminates Primary Human Pancreatic Cancer Stem Cells." Clinical Cancer Research 18.2 (2012): 465-474.
Deisting, Wibke, et al. "Impact of diverse immune evasion mechanisms of cancer cells on T cells engaged by EpCAM/CD3-bispecific antibody construct AMG 110." PLoS One 10.10 Article e0141669 (2015): 1-16.
Flieger, Dimitri, et al. "A bispecific single-chain antibody directed against EpCAM/CD3 in combination with the cytokines interferon α and interleukin-2 efficiently retargets T and CD3+ CD56+ natural-killer-like T lymphocytes to EpCAM-expressing tumor cells." Cancer Immunology, Immunotherapy 49.8 (2000): 441-448.
MacDonald, Joanna, et al. "EpCAM Immunotherapy versus Specific Targeted Delivery of Drugs." Cancers 10.1 (2018): 19-31.
Seimetz, Diane, et al. "Development and approval of the trifunctional antibody catumaxomab (anti-EpCAMx anti-CD3) as a targeted cancer immunotherapy." Cancer Treatment Reviews 36.6 (2010): 458-467.
Zhang, Pengfei, et al. "An EpCAM/CD3 bispecific antibody efficiently eliminates hepatocellular carcinoma cells with limited galectin-1 expression." Cancer Immunology, Immunotherapy 63.2 (2014): 121-132.
Examination Report for corresponding Taiwanese application No. 109119685; dated Oct. 17, 2023 (12 pages) Machine Translation.

* cited by examiner

```
                                            CDR H1
                         10         20         30        40
                    ....|....|....|....|....|....|....|....|...
BAP105-1-VH01    QVQLQQSGAELAKPGASVKVSCKASGYTFTSYWMHWVKQRPGQGLEWI
BAP105-1-VH02    QVQLQQSGAELAKPGASVKVSCKASGYTFTSYWMHWVKQRPGQGLEWI
BAP105-1-VH03    QVQLQQSGAELAKPGASVKVSCKASGYTFTSYWMHWVKQRPGQGLEWI
BAP105-4-VH01    EVQLVQSGAEVKKPGATVKISCKVSGYTFTSYWMHWVRQAPGQGLEWM
BAP105-4-VH02    EVQLVQSGAEVKKPGESLRISCKGSGYTFTSYWMHWIRQSPSRGLEWL
BAP105-4-VH04    EVQLVQSGAEVKKPGATVKISCKVSGYTFTSYWMHWIRQSPSRGLEWL
BAP105-4-VH05    EVQLVQSGAEVKKPGATVKISCKVSGYTFTSYWMHWIRQPPGKGLEWI

CDR H2                                        CDR H3
  50        60        70        80        90       100       110
.|....|....|....|....|....|....|....|....|....|.|....|..|....|...
GYIRPSTGYTEYNQKFKDKATLTADKSSSTAYMQLSSLTFEDSAVYYCGRGDNWVGFANWGQGTLVTVSA
GDIRPSTGYTEYNQKFKDKATLTADKSSSTAYMQLSSLTFEDSAVYYCGRGDNWVGFANWGQGTLVTVSA
GYIRPSTGYTEYNQKFKDKATLTADKSSSTAYMQLSSLTFEDSAVYYCGDGDNWVGFANWGQGTLVTVSA
GYIRPSTGYTEYNQKFKDRFTISRDNSKNTLYLQMNSLRAEDTAVYYCGRGDNWVGFANWGQGTLVTVSS
GYIRPSTGYTEYNQKFKDRVTISADKSISTAYLQWSSLKASDTAMYYCGRGDNWVGFANWGQGTLVTVSS
GYIRPSTGYTEYNQKFKDRFTISRDDSKNTAYLQMNSLKTEDTAVYYCGRGDNWVGFANWGQGTLVTVSS
GYIRPSTGYTEYNQKFKDRFTISRDNSKNTLYLQMNSLRAEDTAVYYCGRGDNWVGFANWGQGTLVTVSS
```

Fig. 2

CDR L1

```
                    10        20        30        40
             ....|....|....|....|....|....|....|....|..
BAP105-1-VK01  QIVLTQSPAIMSASLGEEIALTCSASSSISYMHWYQQKSGTSPKLLI
BAP105-1-VK02  QIVLTQSPAIMSASLGEEIALTCSASSSISYMHWYQQKSGTSPKLLI
BAP105-1-VK03  QIVLTQSPAIMSASLGEEIALTCSASSSISYMHWYQQKSGTSPKLLI
BAP105-1-VK04  QIVLTQSPAIMSASLGEEIALTCSASSSISYMHWYQQKSGTSPKLLI
BAP105-4-VK01  EIVLTQSPDFQSVTPKEKVTITCSASSSISYMHWYQQKPGKAPKLLI
BAP105-4-VK02  EIVMTQSPATLSVSPGERATLSCSASSSISYMHWYQQKPGKAPKLLI
BAP105-4-VK03  EIVMTQSPATLSVSPGERATLSCSASSSISYMHWYQQKPGKAPKLLI
BAP105-4-VK05  EIVMTQSPATLSVSPGERATLSCSASSSISYMHWYQQKPGKAPKLLI
BAP105-6-VK01  EIVLTQSPDFQSVTPKEKVTITCSASSSISYMHWYQQKPGKAPKLLI
BAP105-6-VK02  EIVLTQSPDFQSVTPKEKVTITCSASSSISYMHWYQQKPGKAPKLLI
```

CDR L2                              CDR L3

```
      50        60        70        80        90        100
  ..|....|....|....|....|....|....|....|....|....|....|....|
  YSTSNLASGVPSRFSGSGSGTFYSLTISSVEAEDAADYFCHQWSTYHTFGSGTKLEIK
  YSTSNLHSGVPSRFSGSGSGTFYSLTISSVEAEDAADYFCHQWSTYHTFGSGTKLEIK
  YSTSNLASGVPSRFSGSGSGTFYSLTISSVEAEDAADYFCEQWSTYHTFGSGTKLEIK
  YSTSNLASGVPSRFSGSGSGTFYSLTISSVEAEDAADYFCHQWSTYETFGSGTKLEIK
  YSTSNLASGVPDRFSGSGSGTDFTLKISRVEAEDVGVYYCHQWSTYETFGQGTKVEIK
  YSTSNLASGVPSRFSGSGSGTEFTLTISSLQPDDFATYYCHQWSTYETFGQGTKVEIK
  YSTSNLASGIPPRFSGSGYGTDFTLTINNIESEDAAYYFCHQWSTYETFGQGTKVEIK
  YSTSNLASGVPSRFSGSGSGTDFTLTISSLQPEDFATYYCHQWSTYETFGQGTKVEIK
  YSTSKLASGVPDRFSGSGSGTDFTLKISRVEAEDVGVYYCHQWSTYETFGQGTKVEIK
  YSTSSLASGVPDRFSGSGSGTDFTLKISRVEAEDVGVYYCHQWSTYETFGQGTKVEIK
```

FIG. 3

SEQUENCE LISTING

<160> NUMBER OF SEQ ID NOS: 64

<210> SEQ ID NO 1
<211> LENGTH: 10
<212> TYPE: PRT
<213> ORGANISM: Artificial sequence
<220> FEATURE:
<223> OTHER INFORMATION: Synthetic sequence

<400> SEQUENCE: 1

Gly Tyr Thr Phe Thr Ser Tyr Trp Met His
1               5                   10

<210> SEQ ID NO 2
<211> LENGTH: 17
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (1)..(1)
<223> OTHER INFORMATION: This position may be Y or D

<400> SEQUENCE: 2

Xaa Ile Arg Pro Ser Thr Gly Tyr Thr Glu Tyr Asn Gln Lys Phe Lys
1               5                   10                  15

Asp

<210> SEQ ID NO 3
<211> LENGTH: 9
<212> TYPE: PRT
<213> ORGANISM: Artificial sequence
<220> FEATURE:
<223> OTHER INFORMATION: Synthetic sequence

<400> SEQUENCE: 3

Gly Asp Asn Trp Val Gly Phe Ala Asn
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic sequence

<400> SEQUENCE: 4

Ser Ala Ser Ser Ser Ile Ser Tyr Met His
1               5                   10

<210> SEQ ID NO 5
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (6)..(6)
<223> OTHER INFORMATION: This position may be A or H

<400> SEQUENCE: 5

Ser Thr Ser Asn Leu Xaa Ser
1               5

<210> SEQ ID NO 6

```
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (1)..(1)
<223> OTHER INFORMATION: This position may be H or E
<220> FEATURE:
<221> NAME/KEY: VARIANT
<222> LOCATION: (7)..(7)
<223> OTHER INFORMATION: This position may be H or E

<400> SEQUENCE: 6

Xaa Gln Trp Ser Thr Tyr Xaa Thr
 1               5

<210> SEQ ID NO 7
<211> LENGTH: 118
<212> TYPE: PRT
<213> ORGANISM: Artificial sequence
<220> FEATURE:
<223> OTHER INFORMATION: Synthetic sequence

<400> SEQUENCE: 7

Gln Val Gln Leu Gln Gln Ser Gly Ala Glu Leu Ala Lys Pro Gly Ala
 1               5                  10                  15

Ser Val Lys Val Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Tyr Ile Arg Pro Ser Thr Gly Tyr Thr Glu Tyr Asn Gln Lys Phe
        50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Phe Glu Asp Ser Ala Val Tyr Tyr Cys
                85                  90                  95

Gly Arg Gly Asp Asn Trp Val Gly Phe Ala Asn Trp Gly Gln Gly Thr
            100                 105                 110

Leu Val Thr Val Ser Ala
        115

<210> SEQ ID NO 8
<211> LENGTH: 118
<212> TYPE: PRT
<213> ORGANISM: Artificial sequence
<220> FEATURE:
<223> OTHER INFORMATION: Synthetic sequence

<400> SEQUENCE: 8

Gln Val Gln Leu Gln Gln Ser Gly Ala Glu Leu Ala Lys Pro Gly Ala
 1               5                  10                  15

Ser Val Lys Val Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asp Ile Arg Pro Ser Thr Gly Tyr Thr Glu Tyr Asn Gln Lys Phe
        50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Phe Glu Asp Ser Ala Val Tyr Tyr Cys
```

85                  90                  95
Gly Arg Gly Asp Asn Trp Val Gly Phe Ala Asn Trp Gly Gln Gly Thr
                    100                 105                 110
Leu Val Thr Val Ser Ala
        115

<210> SEQ ID NO 9
<211> LENGTH: 118
<212> TYPE: PRT
<213> ORGANISM: Artificial sequence
<220> FEATURE:
<223> OTHER INFORMATION: Synthetic sequence

<400> SEQUENCE: 9

Gln Val Gln Leu Gln Gln Ser Gly Ala Glu Leu Ala Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Tyr Ile Arg Pro Ser Thr Gly Tyr Thr Glu Tyr Asn Gln Lys Phe
        50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Phe Glu Asp Ser Ala Val Tyr Tyr Cys
                85                  90                  95

Gly Asp Gly Asp Asn Trp Val Gly Phe Ala Asn Trp Gly Gln Gly Thr
                    100                 105                 110

Leu Val Thr Val Ser Ala
        115

<210> SEQ ID NO 10
<211> LENGTH: 118
<212> TYPE: PRT
<213> ORGANISM: Artificial sequence
<220> FEATURE:
<223> OTHER INFORMATION: Synthetic sequence

<400> SEQUENCE: 10

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Tyr Ile Arg Pro Ser Thr Gly Tyr Thr Glu Tyr Asn Gln Lys Phe
        50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Gly Asp Asn Trp Val Gly Phe Ala Asn Trp Gly Gln Gly Thr
                    100                 105                 110

Leu Val Thr Val Ser Ser
        115

<210> SEQ ID NO 11
<211> LENGTH: 118

```
<212> TYPE: PRT
<213> ORGANISM: Artificial sequence
<220> FEATURE:
<223> OTHER INFORMATION: Synthetic sequence

<400> SEQUENCE: 11

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
            20                  25                  30

Trp Met His Trp Ile Arg Gln Ser Pro Ser Arg Gly Leu Glu Trp Leu
        35                  40                  45

Gly Tyr Ile Arg Pro Ser Thr Gly Tyr Thr Glu Tyr Asn Gln Lys Phe
    50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Arg Gly Asp Asn Trp Val Gly Phe Ala Asn Trp Gly Gln Gly Thr
            100                 105                 110

Leu Val Thr Val Ser Ser
        115

<210> SEQ ID NO 12
<211> LENGTH: 118
<212> TYPE: PRT
<213> ORGANISM: Artificial sequence
<220> FEATURE:
<223> OTHER INFORMATION: Synthetic sequence

<400> SEQUENCE: 12

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met His Trp Ile Arg Gln Ser Pro Ser Arg Gly Leu Glu Trp Leu
        35                  40                  45

Gly Tyr Ile Arg Pro Ser Thr Gly Tyr Thr Glu Tyr Asn Gln Lys Phe
    50                  55                  60

Lys Asp Arg Phe Thr Ile Ser Arg Asp Ser Lys Asn Thr Ala Tyr
65                  70                  75                  80

Leu Gln Met Asn Ser Leu Lys Thr Glu Asp Thr Ala Val Tyr Tyr Cys
                85                  90                  95

Gly Arg Gly Asp Asn Trp Val Gly Phe Ala Asn Trp Gly Gln Gly Thr
            100                 105                 110

Leu Val Thr Val Ser Ser
        115

<210> SEQ ID NO 13
<211> LENGTH: 118
<212> TYPE: PRT
<213> ORGANISM: Artificial sequence
<220> FEATURE:
<223> OTHER INFORMATION: Synthetic sequence

<400> SEQUENCE: 13

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
```

```
                      20                  25                  30
Trp Met His Trp Ile Arg Gln Pro Pro Gly Lys Gly Leu Glu Trp Ile
        35                  40                  45

Gly Tyr Ile Arg Pro Ser Thr Gly Tyr Thr Glu Tyr Asn Gln Lys Phe
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Gly Asp Asn Trp Val Gly Phe Ala Asn Trp Gly Gln Gly Thr
            100                 105                 110

Leu Val Thr Val Ser Ser
        115

<210> SEQ ID NO 14
<211> LENGTH: 105
<212> TYPE: PRT
<213> ORGANISM: Artificial sequence
<220> FEATURE:
<223> OTHER INFORMATION: Synthetic sequence

<400> SEQUENCE: 14

Gln Ile Val Leu Thr Gln Ser Pro Ala Ile Met Ser Ala Ser Leu Gly
1               5                   10                  15

Glu Glu Ile Ala Leu Thr Cys Ser Ala Ser Ser Ser Ile Ser Tyr Met
                20                  25                  30

His Trp Tyr Gln Gln Lys Ser Gly Thr Ser Pro Lys Leu Leu Ile Tyr
            35                  40                  45

Ser Thr Ser Asn Leu Ala Ser Gly Val Pro Ser Arg Phe Ser Gly Ser
        50                  55                  60

Gly Ser Gly Thr Phe Tyr Ser Leu Thr Ile Ser Ser Val Glu Ala Glu
65                  70                  75                  80

Asp Ala Ala Asp Tyr Phe Cys His Gln Trp Ser Thr Tyr His Thr Phe
                85                  90                  95

Gly Ser Gly Thr Lys Leu Glu Ile Lys
            100                 105

<210> SEQ ID NO 15
<211> LENGTH: 105
<212> TYPE: PRT
<213> ORGANISM: Artificial sequence
<220> FEATURE:
<223> OTHER INFORMATION: Synthetic sequence

<400> SEQUENCE: 15

Gln Ile Val Leu Thr Gln Ser Pro Ala Ile Met Ser Ala Ser Leu Gly
1               5                   10                  15

Glu Glu Ile Ala Leu Thr Cys Ser Ala Ser Ser Ser Ile Ser Tyr Met
                20                  25                  30

His Trp Tyr Gln Gln Lys Ser Gly Thr Ser Pro Lys Leu Leu Ile Tyr
            35                  40                  45

Ser Thr Ser Asn Leu His Ser Gly Val Pro Ser Arg Phe Ser Gly Ser
        50                  55                  60

Gly Ser Gly Thr Phe Tyr Ser Leu Thr Ile Ser Ser Val Glu Ala Glu
65                  70                  75                  80

Asp Ala Ala Asp Tyr Phe Cys His Gln Trp Ser Thr Tyr His Thr Phe
                85                  90                  95
```

```
Gly Ser Gly Thr Lys Leu Glu Ile Lys
            100                 105

<210> SEQ ID NO 16
<211> LENGTH: 105
<212> TYPE: PRT
<213> ORGANISM: Artificial sequence
<220> FEATURE:
<223> OTHER INFORMATION: Synthetic sequence

<400> SEQUENCE: 16

Gln Ile Val Leu Thr Gln Ser Pro Ala Ile Met Ser Ala Ser Leu Gly
1               5                   10                  15

Glu Glu Ile Ala Leu Thr Cys Ser Ala Ser Ser Ser Ile Ser Tyr Met
            20                  25                  30

His Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Phe Cys Glu Gln Trp Ser Thr Tyr His Thr Phe
                85                  90                  95

Gly Ser Gly Thr Lys Leu Glu Ile Lys
            100                 105

<210> SEQ ID NO 17
<211> LENGTH: 105
<212> TYPE: PRT
<213> ORGANISM: Artificial sequence
<220> FEATURE:
<223> OTHER INFORMATION: Synthetic sequence

<400> SEQUENCE: 17

Gln Ile Val Leu Thr Gln Ser Pro Ala Ile Met Ser Ala Ser Leu Gly
1               5                   10                  15

Glu Glu Ile Ala Leu Thr Cys Ser Ala Ser Ser Ser Ile Ser Tyr Met
            20                  25                  30

His Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Phe Cys His Gln Trp Ser Thr Tyr Glu Thr Phe
                85                  90                  95

Gly Ser Gly Thr Lys Leu Glu Ile Lys
            100                 105

<210> SEQ ID NO 18
<211> LENGTH: 105
<212> TYPE: PRT
<213> ORGANISM: Artificial sequence
<220> FEATURE:
<223> OTHER INFORMATION: Synthetic sequence

<400> SEQUENCE: 18

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Tyr Met
```

```
                    20                  25                  30

His Trp Tyr Gln Gln Lys Pro Gly Lys Ala Pro Lys Leu Leu Ile Tyr
            35                  40                  45

Ser Thr Ser Asn Leu Ala Ser Gly Val Pro Asp Arg Phe Ser Gly Ser
        50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Thr Tyr Glu Thr Phe
                    85                  90                  95

Gly Gln Gly Thr Lys Val Glu Ile Lys
            100                 105

<210> SEQ ID NO 19
<211> LENGTH: 105
<212> TYPE: PRT
<213> ORGANISM: Artificial sequence
<220> FEATURE:
<223> OTHER INFORMATION: Synthetic sequence

<400> SEQUENCE: 19

Glu Ile Val Met Thr Gln Ser Pro Ala Thr Leu Ser Val Ser Pro Gly
1               5                   10                  15

Glu Arg Ala Thr Leu Ser Cys Ser Ala Ser Ser Ser Ile Ser Tyr Met
            20                  25                  30

His Trp Tyr Gln Gln Lys Pro Gly Lys Ala Pro Lys Leu Leu Ile Tyr
            35                  40                  45

Ser Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys His Gln Trp Ser Thr Tyr Glu Thr Phe
                    85                  90                  95

Gly Gln Gly Thr Lys Val Glu Ile Lys
            100                 105

<210> SEQ ID NO 20
<211> LENGTH: 105
<212> TYPE: PRT
<213> ORGANISM: Artificial sequence
<220> FEATURE:
<223> OTHER INFORMATION: Synthetic sequence

<400> SEQUENCE: 20

Glu Ile Val Met Thr Gln Ser Pro Ala Thr Leu Ser Val Ser Pro Gly
1               5                   10                  15

Glu Arg Ala Thr Leu Ser Cys Ser Ala Ser Ser Ser Ile Ser Tyr Met
            20                  25                  30

His Trp Tyr Gln Gln Lys Pro Gly Lys Ala Pro Lys Leu Leu Ile Tyr
            35                  40                  45

Ser Thr Ser Asn Leu Ala Ser Gly Ile Pro Pro Arg Phe Ser Gly Ser
        50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys His Gln Trp Ser Thr Tyr Glu Thr Phe
                    85                  90                  95

Gly Gln Gly Thr Lys Val Glu Ile Lys
            100                 105
```

```
<210> SEQ ID NO 21
<211> LENGTH: 105
<212> TYPE: PRT
<213> ORGANISM: Artificial sequence
<220> FEATURE:
<223> OTHER INFORMATION: Synthetic sequence

<400> SEQUENCE: 21

Glu Ile Val Met Thr Gln Ser Pro Ala Thr Leu Ser Val Ser Pro Gly
1               5                   10                  15

Glu Arg Ala Thr Leu Ser Cys Ser Ala Ser Ser Ser Ile Ser Tyr Met
                20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys His Gln Trp Ser Thr Tyr Glu Thr Phe
                85                  90                  95

Gly Gln Gly Thr Lys Val Glu Ile Lys
            100                 105

<210> SEQ ID NO 22
<211> LENGTH: 17
<212> TYPE: PRT
<213> ORGANISM: Artificial sequence
<220> FEATURE:
<223> OTHER INFORMATION: Synthetic sequence

<400> SEQUENCE: 22

Tyr Ile Arg Pro Ser Thr Gly Tyr Thr Glu Tyr Asn Gln Lys Phe Lys
1               5                   10                  15

Asp

<210> SEQ ID NO 23
<211> LENGTH: 17
<212> TYPE: PRT
<213> ORGANISM: Artificial sequence
<220> FEATURE:
<223> OTHER INFORMATION: Synthetic sequence

<400> SEQUENCE: 23

Asp Ile Arg Pro Ser Thr Gly Tyr Thr Glu Tyr Asn Gln Lys Phe Lys
1               5                   10                  15

Asp

<210> SEQ ID NO 24
<211> LENGTH: 7
<212> TYPE: PRT
<213> ORGANISM: Artificial sequence
<220> FEATURE:
<223> OTHER INFORMATION: Synthetic sequence

<400> SEQUENCE: 24

Ser Thr Ser Asn Leu Ala Ser
1               5

<210> SEQ ID NO 25
<211> LENGTH: 7
<212> TYPE: PRT
<213> ORGANISM: Artificial sequence
```

```
<220> FEATURE:
<223> OTHER INFORMATION: Synthetic sequence

<400> SEQUENCE: 25

Ser Thr Ser Asn Leu His Ser
1               5

<210> SEQ ID NO 26
<211> LENGTH: 8
<212> TYPE: PRT
<213> ORGANISM: Artificial sequence
<220> FEATURE:
<223> OTHER INFORMATION: Synthetic sequence

<400> SEQUENCE: 26

His Gln Trp Ser Thr Tyr His Thr
1               5

<210> SEQ ID NO 27
<211> LENGTH: 8
<212> TYPE: PRT
<213> ORGANISM: Artificial sequence
<220> FEATURE:
<223> OTHER INFORMATION: Synthetic sequence

<400> SEQUENCE: 27

His Gln Trp Ser Thr Tyr Glu Thr
1               5

<210> SEQ ID NO 28
<211> LENGTH: 8
<212> TYPE: PRT
<213> ORGANISM: Artificial sequence
<220> FEATURE:
<223> OTHER INFORMATION: Synthetic sequence

<400> SEQUENCE: 28

Glu Gln Trp Ser Thr Tyr His Thr
1               5

<210> SEQ ID NO 29
<211> LENGTH: 105
<212> TYPE: PRT
<213> ORGANISM: Artificial Sequence
<220> FEATURE:
<223> OTHER INFORMATION: Synthetic sequence

<400> SEQUENCE: 29

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Ser Thr Ser Lys Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Thr Tyr Glu Thr Phe
                85                  90                  95

Gly Gln Gly Thr Lys Val Glu Ile Lys
            100                 105
```

```
<210> SEQ ID NO 30
<211> LENGTH: 105
<212> TYPE: PRT
<213> ORGANISM: Artificial sequence
<220> FEATURE:
<223> OTHER INFORMATION: Synthetic sequence

<400> SEQUENCE: 30

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Ser Thr Ser Ser Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Thr Tyr Glu Thr Phe
                85                  90                  95

Gly Gln Gly Thr Lys Val Glu Ile Lys
            100                 105

<210> SEQ ID NO 31
<211> LENGTH: 105
<212> TYPE: PRT
<213> ORGANISM: Artificial sequence
<220> FEATURE:
<223> OTHER INFORMATION: Synthetic sequence

<400> SEQUENCE: 31

Gln Ile Val Leu Thr Gln Ser Pro Ala Ile Met Ser Ala Ser Leu Gly
1               5                   10                  15

Glu Glu Ile Ala Leu Thr Cys Ser Ala Ser Ser Ser Ile Ser Tyr Met
            20                  25                  30

His Trp Tyr Gln Gln Lys Ser Gly Thr Ser Pro Lys Leu Leu Ile Tyr
        35                  40                  45

Ser Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Phe Cys His Gln Trp Ser Thr Tyr His Thr Phe
                85                  90                  95

Gly Ser Gly Thr Lys Leu Glu Ile Lys
            100                 105

<210> SEQ ID NO 32
<211> LENGTH: 469
<212> TYPE: PRT
<213> ORGANISM: Artificial sequence
<220> FEATURE:
<223> OTHER INFORMATION: Synthetic sequence

<400> SEQUENCE: 32

Gln Ile Val Leu Thr Gln Ser Pro Ala Ile Met Ser Ala Ser Leu Gly
1               5                   10                  15

Glu Glu Ile Ala Leu Thr Cys Ser Ala Ser Ser Ser Ile Ser Tyr Met
            20                  25                  30

His Trp Tyr Gln Gln Lys Ser Gly Thr Ser Pro Lys Leu Leu Ile Tyr
        35                  40                  45
```

```
Ser Thr Ser Asn Leu Ala Ser Gly Val Pro Ser Arg Phe Ser Gly Ser
     50                  55                  60

Gly Ser Gly Thr Phe Tyr Ser Leu Thr Ile Ser Ser Val Glu Ala Glu
 65              70                  75                  80

Asp Ala Ala Asp Tyr Phe Cys His Gln Trp Ser Thr Tyr His Thr Phe
                 85                  90                  95

Gly Ser Gly Thr Lys Leu Glu Ile Lys Arg Thr Val Ala Ala Pro Ser
             100                 105                 110

Val Phe Ile Phe Pro Pro Ser Asp Glu Gln Leu Lys Ser Gly Thr Ala
         115                 120                 125

Ser Val Val Cys Leu Leu Asn Asn Phe Tyr Pro Arg Glu Ala Lys Val
     130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
             165                 170                 175

Leu Thr Leu Ser Lys Ala Asp Tyr Glu Lys His Lys Val Tyr Ala Cys
         180                 185                 190

Glu Val Thr His Gln Gly Leu Ser Ser Pro Val Thr Lys Ser Phe Asn
             195                 200                 205

Arg Gly Glu Cys Ser Arg Ser Gly Gly Gly Glu Val Gln Leu Val
     210                 215                 220

Glu Ser Gly Gly Gly Leu Val Gln Pro Gly Gly Ser Leu Arg Leu Ser
225                 230                 235                 240

Cys Ala Ala Ser Gly Phe Thr Phe Asn Thr Tyr Ala Met Asn Trp Val
                 245                 250                 255

Arg Gln Ala Pro Gly Lys Gly Leu Glu Trp Val Ala Arg Ile Arg Ser
             260                 265                 270

Lys Tyr Asn Asn Tyr Ala Thr Tyr Tyr Ala Asp Ser Val Lys Asp Arg
         275                 280                 285

Phe Thr Ile Ser Arg Asp Asp Ser Lys Asn Ser Leu Tyr Leu Gln Met
     290                 295                 300

Asn Ser Leu Lys Thr Glu Asp Thr Ala Val Tyr Tyr Cys Val Arg His
305                 310                 315                 320

Gly Asn Phe Gly Asn Ser Tyr Val Ser Trp Phe Ala Tyr Trp Gly Gln
             325                 330                 335

Gly Thr Leu Val Thr Val Ser Ser Gly Gly Ser Gly Gly Ser Gly Gly
         340                 345                 350

Ser Gly Gly Ser Gly Gly Gln Ala Val Val Thr Gln Glu Pro Ser Leu
     355                 360                 365

Thr Val Ser Pro Gly Gly Thr Val Thr Leu Thr Cys Arg Ser Ser Thr
     370                 375                 380

Gly Ala Val Thr Thr Ser Asn Tyr Ala Asn Trp Val Gln Gln Lys Pro
385                 390                 395                 400

Gly Gln Ala Pro Arg Gly Leu Ile Gly Gly Thr Asn Lys Arg Ala Pro
             405                 410                 415

Trp Thr Pro Ala Arg Phe Ser Gly Ser Leu Leu Gly Gly Lys Ala Ala
             420                 425                 430

Leu Thr Ile Thr Gly Ala Gln Ala Glu Asp Glu Ala Asp Tyr Tyr Cys
         435                 440                 445

Ala Leu Trp Tyr Ser Asn Leu Trp Val Phe Gly Gly Gly Thr Lys Leu
     450                 455                 460
```

Thr Val Leu Ser Arg
465

<210> SEQ ID NO 33
<211> LENGTH: 250
<212> TYPE: PRT
<213> ORGANISM: Artificial sequence
<220> FEATURE:
<223> OTHER INFORMATION: Synthetic sequence

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Ser
        115                 120                 125

Gly Gly Ser Gly Gly Ser Gly Gly Ser Gly Gly Gln Ala Val Val Thr
    130                 135                 140

Gln Glu Pro Ser Leu Thr Val Ser Pro Gly Gly Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Gln Lys Pro Gly Gln Ala Pro Arg Gly Leu Ile Gly Gly Thr
            180                 185                 190

Asn Lys Arg Ala Pro Trp Thr Pro Ala Arg Phe Ser Gly Ser Leu Leu
        195                 200                 205

Gly Gly Lys Ala Ala Leu Thr Ile Thr Gly Ala Gln Ala Glu Asp Glu
    210                 215                 220

Ala Asp Tyr Tyr Cys Ala Leu Trp Tyr Ser Asn Leu Trp Val Phe Gly
225                 230                 235                 240

Gly Gly Thr Lys Leu Thr Val Leu Ser Arg
                245                 250

<210> SEQ ID NO 34
<211> LENGTH: 118
<212> TYPE: PRT
<213> ORGANISM: Artificial sequence
<220> FEATURE:
<223> OTHER INFORMATION: Synthetic sequence

<400> SEQUENCE: 34

Gln Val Gln Leu Gln Gln Ser Gly Ala Glu Leu Ala Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Arg Pro Ser Thr Gly Tyr Thr Glu Tyr Asn Gln Lys Phe
            50                  55                  60

Lys Asp Lys Ala Thr Leu Thr Ala Asp Lys Ser Ser Thr Ala Tyr
 65                  70                  75                  80

Met Gln Leu Ser Ser Leu Thr Phe Glu Asp Ser Ala Val Tyr Tyr Cys
                 85                  90                  95

Gly Arg Gly Asp Asn Trp Val Gly Phe Ala Asn Trp Gly Gln Gly Thr
                100                 105                 110

Leu Val Thr Val Ser Ser
            115

<210> SEQ ID NO 35
<211> LENGTH: 105
<212> TYPE: PRT
<213> ORGANISM: Artificial sequence
<220> FEATURE:
<223> OTHER INFORMATION: Synthetic sequence

<400> SEQUENCE: 35

Gln Ile Val Leu Thr Gln Ser Pro Ala Ile Met Ser Ala Ser Leu Gly
 1               5                  10                  15

Glu Glu Ile Ala Leu Thr Cys Ser Ala Ser Ser Ser Ile Ser Tyr Met
                 20                  25                  30

His Trp Tyr Gln Gln Lys Ser Gly Thr Ser Pro Lys Leu Leu Ile Tyr
             35                  40                  45

Ser Thr Ser Asn Leu Ala Ser Gly Val Pro Ser Arg Phe Ser Gly Ser
         50                  55                  60

Gly Ser Gly Thr Phe Tyr Ser Leu Thr Ile Ser Ser Val Glu Ala Glu
 65                  70                  75                  80

Asp Ala Ala Asp Tyr Phe Cys His Gln Trp Ser Tyr His Thr Phe
                 85                  90                  95

Gly Ser Gly Thr Lys Leu Glu Ile Lys
                100                 105

<210> SEQ ID NO 36
<211> LENGTH: 469
<212> TYPE: PRT
<213> ORGANISM: Artificial sequence
<220> FEATURE:
<223> OTHER INFORMATION: Synthetic sequence

<400> SEQUENCE: 36

Gln Ile Val Leu Thr Gln Ser Pro Ala Ile Met Ser Ala Ser Leu Gly
 1               5                  10                  15

Glu Glu Ile Ala Leu Thr Cys Ser Ala Ser Ser Ser Ile Ser Tyr Met
                 20                  25                  30

His Trp Tyr Gln Gln Lys Ser Gly Thr Ser Pro Lys Leu Leu Ile Tyr
             35                  40                  45

Ser Thr Ser Asn Leu Ala Ser Gly Val Pro Ser Arg Phe Ser Gly Ser
         50                  55                  60

Gly Ser Gly Thr Phe Tyr Ser Leu Thr Ile Ser Ser Val Glu Ala Glu
 65                  70                  75                  80

Asp Ala Ala Asp Tyr Phe Cys His Gln Trp Ser Tyr His Thr Phe
                 85                  90                  95

Gly Ser Gly Thr Lys Leu Glu Ile Lys Arg Thr Val Ala Ala Pro Ser
                100                 105                 110

Val Phe Ile Phe Pro Pro Ser Asp Glu Gln Leu Lys Ser Gly Thr Ala

```
            115                 120                 125
Ser Val Val Cys Leu Leu Asn Asn Phe Tyr Pro Arg Glu Ala Lys Val
130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
                180                 185                 190

Glu Val Thr His Gln Gly Leu Ser Ser Pro Val Thr Lys Ser Phe Asn
                195                 200                 205

Arg Gly Glu Cys Ser Arg Ser Gly Gly Gly Glu Val Gln Leu Val
210                 215                 220

Glu Ser Gly Gly Gly Leu Val Gln Pro Gly Gly Ser Leu Arg Leu Ser
225                 230                 235                 240

Cys Ala Ala Ser Gly Phe Thr Phe Asn Thr Tyr Ala Met Asn Trp Val
                245                 250                 255

Arg Gln Ala Pro Gly Lys Gly Leu Glu Trp Val Ala Arg Ile Arg Ser
                260                 265                 270

Lys Tyr Asn Asn Tyr Ala Thr Tyr Tyr Ala Asp Ser Val Lys Asp Arg
                275                 280                 285

Phe Thr Ile Ser Arg Asp Asp Ser Lys Asn Ser Leu Tyr Leu Gln Met
290                 295                 300

Asn Ser Leu Lys Thr Glu Asp Thr Ala Val Tyr Tyr Cys Val Arg His
305                 310                 315                 320

Ser Asn Phe Gly Asn Ser Tyr Val Ser Trp Phe Ala Tyr Trp Gly Gln
                325                 330                 335

Gly Thr Leu Val Thr Val Ser Ser Gly Gly Ser Gly Gly Ser Gly Gly
                340                 345                 350

Ser Gly Gly Ser Gly Gly Gln Ala Val Val Thr Gln Glu Pro Ser Leu
                355                 360                 365

Thr Val Ser Pro Gly Gly Thr Val Thr Leu Thr Cys Arg Ser Ser Thr
370                 375                 380

Gly Ala Val Thr Thr Ser Asn Tyr Asp Asn Trp Val Gln Gln Lys Pro
385                 390                 395                 400

Gly Gln Ala Pro Arg Gly Leu Ile Gly Gly Thr Asn Lys Arg Ala Pro
                405                 410                 415

Trp Thr Pro Ala Arg Phe Ser Gly Ser Leu Leu Gly Gly Lys Ala Ala
                420                 425                 430

Leu Thr Ile Thr Gly Ala Gln Ala Glu Asp Glu Ala Asp Tyr Tyr Cys
                435                 440                 445

Ala Leu Trp Tyr Ser Asn Leu Trp Val Phe Gly Gly Gly Thr Lys Leu
                450                 455                 460

Thr Val Leu Ser Arg
465

<210> SEQ ID NO 37
<211> LENGTH: 250
<212> TYPE: PRT
<213> ORGANISM: Artificial sequence
<220> FEATURE:
<223> OTHER INFORMATION: Synthetic sequence

<400> SEQUENCE: 37

Glu Val Gln Leu Val Glu Ser Gly Gly Gly Leu Val Gln Pro Gly Gly
```

```
                1               5                  10                  15
            Ser Leu Arg Leu Ser Cys Ala Ala Ser Gly Phe Thr Phe Asn Thr Tyr
                            20                  25                  30

Ala Met Asn Trp Val Arg Gln Ala Pro Gly Lys Gly Leu Glu Trp Val
                            35                  40                  45

Ala Arg Ile Arg Ser Lys Tyr Asn Asn Tyr Ala Thr Tyr Tyr Ala Asp
                            50                  55                  60

Ser Val Lys Asp Arg Phe Thr Ile Ser Arg Asp Asp Ser Lys Asn Ser
             65                  70                  75                  80

Leu Tyr Leu Gln Met Asn Ser Leu Lys Thr Glu Asp Thr Ala Val Tyr
                            85                  90                  95

Tyr Cys Val Arg His Ser Asn Phe Gly Asn Ser Tyr Val Ser Trp Phe
                            100                 105                 110

Ala Tyr Trp Gly Gln Gly Thr Leu Val Thr Val Ser Ser Gly Gly Ser
                            115                 120                 125

Gly Gly Ser Gly Gly Ser Gly Gly Ser Gly Gly Gln Ala Val Val Thr
                            130                 135                 140

Gln Glu Pro Ser Leu Thr Val Ser Pro Gly Gly Thr Val Thr Leu Thr
            145                 150                 155                 160

Cys Arg Ser Ser Thr Gly Ala Val Thr Thr Ser Asn Tyr Asp Asn Trp
                            165                 170                 175

Val Gln Gln Lys Pro Gly Gln Ala Pro Arg Gly Leu Ile Gly Gly Thr
                            180                 185                 190

Asn Lys Arg Ala Pro Trp Thr Pro Ala Arg Phe Ser Gly Ser Leu Leu
                            195                 200                 205

Gly Gly Lys Ala Ala Leu Thr Ile Thr Gly Ala Gln Ala Glu Asp Glu
                            210                 215                 220

Ala Asp Tyr Tyr Cys Ala Leu Trp Tyr Ser Asn Leu Trp Val Phe Gly
            225                 230                 235                 240

Gly Gly Thr Lys Leu Thr Val Leu Ser Arg
                            245                 250

<210> SEQ ID NO 38
<211> LENGTH: 118
<212> TYPE: PRT
<213> ORGANISM: Artificial sequence
<220> FEATURE:
<223> OTHER INFORMATION: Synthetic sequence

<400> SEQUENCE: 38

Gln Val Gln Leu Gln Gln Ser Gly Ala Glu Leu Ala Lys Pro Gly Ala
             1               5                  10                  15

Ser Val Lys Val Ser Cys Lys Ala Ser Gly Tyr Thr Phe Thr Ser Tyr
                            20                  25                  30

Trp Met His Trp Val Lys Gln Arg Pro Gly Gln Gly Leu Glu Trp Ile
                            35                  40                  45

Gly Tyr Ile Arg Pro Ser Thr Gly Tyr Thr Glu Tyr Asn Gln Lys Phe
                            50                  55                  60

Lys Asp Lys Ala Thr Leu Thr Ala Asp Lys Ser Ser Thr Ala Tyr
             65                  70                  75                  80

Met Gln Leu Ser Ser Leu Thr Phe Glu Asp Ser Ala Val Tyr Tyr Cys
                            85                  90                  95

Gly Arg Gly Asp Asn Trp Val Gly Phe Ala Asn Trp Gly Gln Gly Thr
                            100                 105                 110

Leu Val Thr Val Ser Ser
```

-continued

```
        115

<210> SEQ ID NO 39
<211> LENGTH: 105
<212> TYPE: PRT
<213> ORGANISM: Artificial sequence
<220> FEATURE:
<223> OTHER INFORMATION: Synthetic sequence

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Thr Tyr His Thr Phe
                85                  90                  95

Gly Gln Gly Thr Lys Val Glu Ile Lys
            100                 105

<210> SEQ ID NO 40
<211> LENGTH: 469
<212> TYPE: PRT
<213> ORGANISM: Artificial sequence
<220> FEATURE:
<223> OTHER INFORMATION: Synthetic sequence

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Thr Tyr His Thr Phe
                85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190
```

Glu Val Thr His Gln Gly Leu Ser Ser Pro Val Thr Lys Ser Phe Asn
            195                 200                 205

Arg Gly Glu Cys Ser Arg Ser Gly Gly Glu Val Gln Leu Val
            210                 215                 220

Glu Ser Gly Gly Gly Leu Val Gln Pro Gly Gly Ser Leu Arg Leu Ser
225                 230                 235                 240

Cys Ala Ala Ser Gly Phe Thr Phe Asn Thr Tyr Ala Met Asn Trp Val
            245                 250                 255

Arg Gln Ala Pro Gly Lys Gly Leu Glu Trp Val Ala Arg Ile Arg Ser
            260                 265                 270

Lys Tyr Asn Asn Tyr Ala Thr Tyr Tyr Ala Asp Ser Val Lys Asp Arg
            275                 280                 285

Phe Thr Ile Ser Arg Asp Asp Ser Lys Asn Ser Leu Tyr Leu Gln Met
            290                 295                 300

Asn Ser Leu Lys Thr Glu Asp Thr Ala Val Tyr Tyr Cys Val Arg His
305                 310                 315                 320

Gly Asn Phe Gly Asn Ser Tyr Val Ser Trp Phe Ala Tyr Trp Gly Gln
            325                 330                 335

Gly Thr Leu Val Thr Val Ser Ser Gly Gly Ser Gly Gly Ser Gly Gly
            340                 345                 350

Ser Gly Gly Ser Gly Gly Gln Ala Val Val Thr Gln Glu Pro Ser Leu
            355                 360                 365

Thr Val Ser Pro Gly Gly Thr Val Thr Leu Thr Cys Arg Ser Ser Thr
            370                 375                 380

Gly Ala Val Thr Thr Ser Asn Tyr Ala Asn Trp Val Gln Gln Lys Pro
385                 390                 395                 400

Gly Gln Ala Pro Arg Gly Leu Ile Gly Gly Thr Asn Lys Arg Ala Pro
            405                 410                 415

Trp Thr Pro Ala Arg Phe Ser Gly Ser Leu Leu Gly Gly Lys Ala Ala
            420                 425                 430

Leu Thr Ile Thr Gly Ala Gln Ala Glu Asp Glu Ala Asp Tyr Tyr Cys
            435                 440                 445

Ala Leu Trp Tyr Ser Asn Leu Trp Val Phe Gly Gly Gly Thr Lys Leu
450                 455                 460

Thr Val Leu Ser Arg
465

<210> SEQ ID NO 41
<211> LENGTH: 250
<212> TYPE: PRT
<213> ORGANISM: Artificial sequence
<220> FEATURE:
<223> OTHER INFORMATION: Synthetic sequence

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Gly Gly Ser
        115                 120                 125

Gly Gly Ser Gly Gly Ser Gly Gly Ser Gly Gly Gln Ala Val Val Thr
    130                 135                 140

Gln Glu Pro Ser Leu Thr Val Ser Pro Gly Gly Thr Val Thr Leu Thr
145                 150                 155                 160

Cys Arg Ser Ser Thr Gly Ala Val Thr Thr Ser Asn Tyr Ala Asn Trp
                165                 170                 175

Val Gln Gln Lys Pro Gly Gln Ala Pro Arg Gly Leu Ile Gly Gly Thr
            180                 185                 190

Asn Lys Arg Ala Pro Trp Thr Pro Ala Arg Phe Ser Gly Ser Leu Leu
        195                 200                 205

Gly Gly Lys Ala Ala Leu Thr Ile Thr Gly Ala Gln Ala Glu Asp Glu
    210                 215                 220

Ala Asp Tyr Tyr Cys Ala Leu Trp Tyr Ser Asn Leu Trp Val Phe Gly
225                 230                 235                 240

Gly Gly Thr Lys Leu Thr Val Leu Ser Arg
                245                 250

<210> SEQ ID NO 42
<211> LENGTH: 118
<212> TYPE: PRT
<213> ORGANISM: Artificial sequence
<220> FEATURE:
<223> OTHER INFORMATION: Synthetic sequence

<400> SEQUENCE: 42

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Ser Tyr
            20                  25                  30

Trp Met His Trp Val Arg Gln Ala Arg Gly Gln Arg Leu Glu Trp Ile
        35                  40                  45

Gly Tyr Ile Arg Pro Ser Thr Gly Tyr Thr Glu Tyr Asn Gln Lys Phe
    50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Arg Gly Asp Asn Trp Val Gly Phe Ala Asn Trp Gly Gln Gly Thr
            100                 105                 110

Leu Val Thr Val Ser Ser
        115

<210> SEQ ID NO 43
<211> LENGTH: 105
<212> TYPE: PRT
<213> ORGANISM: Artificial sequence
<220> FEATURE:
<223> OTHER INFORMATION: Synthetic sequence

<400> SEQUENCE: 43

Glu Ile Val Leu Thr Gln Ser Pro Ala Thr Leu Ser Leu Ser Pro Gly
1               5                   10                  15

```
Glu Arg Ala Thr Leu Ser Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Thr Tyr His Thr Phe
                85                  90                  95

Gly Gln Gly Thr Lys Val Glu Ile Lys
            100                 105

<210> SEQ ID NO 44
<211> LENGTH: 469
<212> TYPE: PRT
<213> ORGANISM: Artificial sequence
<220> FEATURE:
<223> OTHER INFORMATION: Synthetic sequence

<400> SEQUENCE: 44

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Thr Tyr His Thr Phe
                85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys Ser Arg Ser Gly Gly Gly Glu Val Gln Leu Val
    210                 215                 220

Glu Ser Gly Gly Gly Leu Val Gln Pro Gly Gly Ser Leu Arg Leu Ser
225                 230                 235                 240

Cys Ala Ala Ser Gly Phe Thr Phe Asn Thr Tyr Ala Met Asn Trp Val
                245                 250                 255

Arg Gln Ala Pro Gly Lys Gly Leu Glu Trp Val Ala Arg Ile Arg Ser
            260                 265                 270
```

-continued

```
Lys Tyr Asn Asn Tyr Ala Thr Tyr Tyr Ala Asp Ser Val Lys Asp Arg
            275                 280                 285

Phe Thr Ile Ser Arg Asp Asp Ser Lys Asn Ser Leu Tyr Leu Gln Met
290                 295                 300

Asn Ser Leu Lys Thr Glu Asp Thr Ala Val Tyr Tyr Cys Val Arg His
305                 310                 315                 320

Thr Asn Phe Gly Asn Ser Lys Val Ser Trp Phe Ala Tyr Trp Gly Gln
                325                 330                 335

Gly Thr Leu Val Thr Val Ser Ser Gly Gly Ser Gly Gly
            340                 345                 350

Ser Gly Gly Ser Gly Gly Gln Ala Val Val Thr Gln Glu Pro Ser Leu
            355                 360                 365

Thr Val Ser Pro Gly Gly Thr Val Thr Leu Thr Cys Arg Ser Ser Ala
            370                 375                 380

Gly Ala Val Thr Thr Ser Asn Tyr Asp Asn Trp Val Gln Gln Lys Pro
385                 390                 395                 400

Gly Gln Ala Pro Arg Gly Leu Ile Gly Gly Thr Asn Lys Arg Ala Pro
                405                 410                 415

Trp Thr Pro Ala Arg Phe Ser Gly Ser Leu Leu Gly Gly Lys Ala Ala
                420                 425                 430

Leu Thr Ile Thr Gly Ala Gln Ala Glu Asp Glu Ala Asp Tyr Tyr Cys
                435                 440                 445

Ala Leu Trp Tyr Ser Asn Leu Trp Val Phe Gly Gly Gly Thr Lys Leu
            450                 455                 460

Thr Val Leu Ser Arg
465

<210> SEQ ID NO 45
<211> LENGTH: 250
<212> TYPE: PRT
<213> ORGANISM: Artificial sequence
<220> FEATURE:
<223> OTHER INFORMATION: Synthetic sequence

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Thr Asn Phe Gly Asn Ser Lys Val Ser Trp Phe
            100                 105                 110

Ala Tyr Trp Gly Gln Gly Thr Leu Val Thr Val Ser Ser Gly Gly Ser
        115                 120                 125

Gly Gly Ser Gly Gly Ser Gly Gly Ser Gly Gly Gln Ala Val Val Thr
    130                 135                 140

Gln Glu Pro Ser Leu Thr Val Ser Pro Gly Gly Thr Val Thr Leu Thr
145                 150                 155                 160
```

```
Cys Arg Ser Ser Ala Gly Ala Val Thr Thr Ser Asn Tyr Asp Asn Trp
                165                 170                 175
Val Gln Gln Lys Pro Gly Gln Ala Pro Arg Gly Leu Ile Gly Gly Thr
            180                 185                 190
Asn Lys Arg Ala Pro Trp Thr Pro Ala Arg Phe Ser Gly Ser Leu Leu
        195                 200                 205
Gly Gly Lys Ala Ala Leu Thr Ile Thr Gly Ala Gln Ala Glu Asp Glu
    210                 215                 220
Ala Asp Tyr Tyr Cys Ala Leu Trp Tyr Ser Asn Leu Trp Val Phe Gly
225                 230                 235                 240
Gly Gly Thr Lys Leu Thr Val Leu Ser Arg
                245                 250

<210> SEQ ID NO 46
<211> LENGTH: 118
<212> TYPE: PRT
<213> ORGANISM: Artificial sequence
<220> FEATURE:
<223> OTHER INFORMATION: Synthetic sequence

<400> SEQUENCE: 46

Glu Val Gln Leu Val Gln Ser Gly Ala Glu Val Lys Lys Pro Gly Ala
1               5                   10                  15
Thr Val Lys Ile Ser Cys Lys Val Ser Gly Tyr Thr Phe Thr Ser Tyr
            20                  25                  30
Trp Met His Trp Val Arg Gln Ala Arg Gly Gln Arg Leu Glu Trp Ile
        35                  40                  45
Gly Tyr Ile Arg Pro Ser Thr Gly Tyr Thr Glu Tyr Asn Gln Lys Phe
    50                  55                  60
Lys Asp Arg Val Thr Ile Ser Ala Asp Lys Ser Ile Ser Thr Ala Tyr
65                  70                  75                  80
Leu Gln Trp Ser Ser Leu Lys Ala Ser Asp Thr Ala Met Tyr Tyr Cys
                85                  90                  95
Gly Arg Gly Asp Asn Trp Val Gly Phe Ala Asn Trp Gly Gln Gly Thr
            100                 105                 110
Leu Val Thr Val Ser Ser
        115

<210> SEQ ID NO 47
<211> LENGTH: 105
<212> TYPE: PRT
<213> ORGANISM: Artificial sequence
<220> FEATURE:
<223> OTHER INFORMATION: Synthetic sequence

<400> SEQUENCE: 47

Glu Ile Val Leu Thr Gln Ser Pro Asp Phe Gln Ser Val Thr Pro Lys
1               5                   10                  15
Glu Lys Val Thr Ile Thr Cys Ser Ala Ser Ser Ser Ile Ser Tyr Met
            20                  25                  30
His Trp Tyr Gln Gln Lys Pro Gly Lys Ala Pro Lys Leu Leu Ile Tyr
        35                  40                  45
Ser Thr Ser Asn Leu Ala Ser Gly Val Pro Asp Arg Phe Ser Gly Ser
    50                  55                  60
Gly Ser Gly Thr Asp Phe Thr Leu Lys Ile Ser Arg Val Glu Ala Glu
65                  70                  75                  80
Asp Val Gly Val Tyr Tyr Cys His Gln Trp Ser Thr Tyr Glu Thr Phe
```

85                  90                  95

Gly Gln Gly Thr Lys Val Glu Ile Lys
            100                 105

<210> SEQ ID NO 48
<211> LENGTH: 469
<212> TYPE: PRT
<213> ORGANISM: Artificial Sequence
<220> FEATURE:
<223> OTHER INFORMATION: Synthetic sequence

<400> SEQUENCE: 48

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Ser Tyr Met
            20                  25                  30

His Trp Tyr Gln Gln Lys Pro Gly Lys Ala Pro Lys Leu Leu Ile Tyr
        35                  40                  45

Ser Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys His Gln Trp Ser Thr Tyr Thr Phe
                85                  90                  95

Gly Gln Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys Ser Arg Ser Gly Gly Gly Glu Val Gln Leu Val
    210                 215                 220

Glu Ser Gly Gly Gly Leu Val Gln Pro Gly Gly Ser Leu Arg Leu Ser
225                 230                 235                 240

Cys Ala Ala Ser Gly Phe Thr Phe Asn Thr Tyr Ala Met Asn Trp Val
                245                 250                 255

Arg Gln Ala Pro Gly Lys Gly Leu Glu Trp Val Ala Arg Ile Arg Ser
            260                 265                 270

Lys Tyr Asn Asn Tyr Ala Thr Tyr Tyr Ala Asp Ser Val Lys Asp Arg
        275                 280                 285

Phe Thr Ile Ser Arg Asp Asp Ser Lys Asn Ser Leu Tyr Leu Gln Met
    290                 295                 300

Asn Ser Leu Lys Thr Glu Asp Thr Ala Val Tyr Tyr Cys Val Arg His
305                 310                 315                 320

Ser Asn Phe Gly Asn Ser Lys Val Ser Trp Phe Ala Tyr Trp Gly Gln
                325                 330                 335

Gly Thr Leu Val Thr Val Ser Ser Gly Gly Ser Gly Gly Ser Gly Gly

```
               340                 345                 350
Ser Gly Gly Ser Gly Gly Gln Ala Val Val Thr Gln Glu Pro Ser Leu
            355                 360                 365

Thr Val Ser Pro Gly Gly Thr Val Thr Leu Thr Cys Arg Ser Ser Ala
        370                 375                 380

Gly Ala Val Thr Thr Ser Asn Tyr Asp Asn Trp Val Gln Gln Lys Pro
385                 390                 395                 400

Gly Gln Ala Pro Arg Gly Leu Ile Gly Gly Thr Asn Lys Arg Ala Pro
                405                 410                 415

Trp Thr Pro Ala Arg Phe Ser Gly Ser Leu Leu Gly Lys Ala Ala
            420                 425                 430

Leu Thr Ile Thr Gly Ala Gln Ala Glu Asp Glu Ala Asp Tyr Tyr Cys
            435                 440                 445

Ala Leu Trp Tyr Ser Asn Leu Trp Val Phe Gly Gly Thr Lys Leu
            450                 455                 460

Thr Val Leu Ser Arg
465

<210> SEQ ID NO 49
<211> LENGTH: 250
<212> TYPE: PRT
<213> ORGANISM: Artificial sequence
<220> FEATURE:
<223> OTHER INFORMATION: Synthetic sequence

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Ser Asn Phe Gly Asn Ser Lys Val Ser Trp Phe
            100                 105                 110

Ala Tyr Trp Gly Gln Gly Thr Leu Val Thr Val Ser Ser Gly Gly Ser
            115                 120                 125

Gly Gly Ser Gly Gly Ser Gly Gly Ser Gly Gly Gln Ala Val Val Thr
        130                 135                 140

Gln Glu Pro Ser Leu Thr Val Ser Pro Gly Gly Thr Val Thr Leu Thr
145                 150                 155                 160

Cys Arg Ser Ser Ala Gly Ala Val Thr Thr Ser Asn Tyr Asp Asn Trp
                165                 170                 175

Val Gln Gln Lys Pro Gly Gln Ala Pro Arg Gly Leu Ile Gly Gly Thr
            180                 185                 190

Asn Lys Arg Ala Pro Trp Thr Pro Ala Arg Phe Ser Gly Ser Leu Leu
        195                 200                 205

Gly Gly Lys Ala Ala Leu Thr Ile Thr Gly Ala Gln Ala Glu Asp Glu
    210                 215                 220

Ala Asp Tyr Tyr Cys Ala Leu Trp Tyr Ser Asn Leu Trp Val Phe Gly
```

```
                225                 230                 235                 240

Gly Gly Thr Lys Leu Thr Val Leu Ser Arg
                245                 250

<210> SEQ ID NO 50
<211> LENGTH: 118
<212> TYPE: PRT
<213> ORGANISM: Artificial sequence
<220> FEATURE:
<223> OTHER INFORMATION: Synthetic sequence

<400> SEQUENCE: 50

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Ser Tyr
                20                  25                  30

Trp Met His Trp Ile Arg Gln Ser Pro Ser Arg Gly Leu Glu Trp Leu
            35                  40                  45

Gly Tyr Ile Arg Pro Ser Thr Gly Tyr Thr Glu Tyr Asn Gln Lys Phe
    50                  55                  60

Lys Asp Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Gly Arg Gly Asp Asn Trp Val Gly Phe Ala Asn Trp Gly Gln Gly Thr
                100                 105                 110

Leu Val Thr Val Ser Ser
            115

<210> SEQ ID NO 51
<211> LENGTH: 242
<212> TYPE: PRT
<213> ORGANISM: Artificial Sequence
<220> FEATURE:
<223> OTHER INFORMATION: synthetic sequence

<400> SEQUENCE: 51

Gln Glu Glu Cys Val Cys Glu Asn Tyr Lys Leu Ala Val Asn Cys Phe
1               5                   10                  15

Val Asn Asn Asn Arg Gln Cys Gln Cys Thr Ser Val Gly Ala Gln Asn
                20                  25                  30

Thr Val Ile Cys Ser Lys Leu Ala Ala Lys Cys Leu Val Met Lys Ala
            35                  40                  45

Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
                85                  90                  95

Asn Thr Ala Gly Val Arg Arg Thr Asp Lys Asp Thr Glu Ile Thr Cys
                100                 105                 110

Ser Glu Arg Val Arg Thr Tyr Trp Ile Ile Glu Leu Lys His Lys
            115                 120                 125

Ala Arg Glu Lys Pro Tyr Asp Ser Lys Ser Leu Arg Thr Ala Leu Gln
    130                 135                 140

Lys Glu Ile Thr Thr Arg Tyr Gln Leu Asp Pro Lys Phe Ile Thr Ser
145                 150                 155                 160
```

```
Ile Leu Tyr Glu Asn Asn Val Ile Thr Ile Asp Leu Val Gln Asn Ser
            165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
            195                 200                 205

Asp Leu Thr Val Asn Gly Glu Gln Leu Asp Leu Asp Pro Gly Gln Thr
            210                 215                 220

Leu Ile Tyr Tyr Val Asp Glu Lys Ala Pro Glu Phe Ser Met Gln Gly
225                 230                 235                 240

Leu Lys

<210> SEQ ID NO 52
<211> LENGTH: 242
<212> TYPE: PRT
<213> ORGANISM: Artificial Sequence
<220> FEATURE:
<223> OTHER INFORMATION: synthetic sequence

<400> SEQUENCE: 52

Gln Glu Glu Cys Val Cys Glu Asn Tyr Lys Leu Ala Val Asn Cys Phe
1               5                   10                  15

Leu Asn Asp Asn Gly Gln Cys Gln Cys Thr Ser Ile Gly Ala Gln Asn
            20                  25                  30

Thr Val Leu Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Thr Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Glu Leu Lys His Lys
            115                 120                 125

Ala Arg Glu Lys Pro Tyr Asp Val Gln Ser Leu Arg Thr Ala Leu Glu
        130                 135                 140

Glu Ala Ile Lys Thr Arg Tyr Gln Leu Asp Pro Lys Phe Ile Thr Asn
145                 150                 155                 160

Ile Leu Tyr Glu Asp Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Arg Val Asn Gly Glu Gln Leu Asp Leu Asp Pro Gly Gln Thr
        210                 215                 220

Leu Ile Tyr Tyr Val Asp Glu Lys Ala Pro Glu Phe Ser Met Gln Gly
225                 230                 235                 240

Leu Lys

<210> SEQ ID NO 53
<211> LENGTH: 252
<212> TYPE: PRT
<213> ORGANISM: Artificial Sequence
```

<220> FEATURE:
<223> OTHER INFORMATION: synthetic sequence

<400> SEQUENCE: 53

```
Gln Arg Asp Cys Val Cys Asp Asn Tyr Lys Leu Ala Thr Ser Cys Ser
1               5                   10                  15

Leu Asn Glu Tyr Gly Glu Cys Gln Cys Thr Ser Tyr Gly Thr Gln Asn
            20                  25                  30

Thr Val Ile Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Glu Leu Lys His Lys
        115                 120                 125

Ala Arg Glu Lys Pro Tyr Asp Ser Lys Ser Leu Arg Thr Ala Leu Gln
130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Thr Val Asn Gly Glu Gln Leu Asp Leu Asp Pro Gly Gln Thr
210                 215                 220

Leu Ile Tyr Tyr Val Asp Glu Lys Ala Pro Glu Phe Ser Met Gln Gly
225                 230                 235                 240

Leu Lys Ser Arg His His His His His His
                245                 250
```

<210> SEQ ID NO 54
<211> LENGTH: 252
<212> TYPE: PRT
<213> ORGANISM: Artificial Sequence
<220> FEATURE:
<223> OTHER INFORMATION: synthetic sequence

<400> SEQUENCE: 54

```
Gln Glu Glu Cys Val Cys Glu Asn Tyr Lys Leu Ala Val Asn Cys Phe
1               5                   10                  15

Val Asn Asn Asn Arg Gln Cys Gln Cys Thr Ser Val Gly Ala Gln Asn
            20                  25                  30

Thr Val Ile Cys Ser Lys Leu Ala Ser Lys Cys Leu Ala Met Lys Ala
        35                  40                  45

Glu Met Thr His Ser Lys Ser Gly Arg Arg Ile Lys Pro Glu Gly Ala
50                  55                  60

Ile Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
```

```
Asn Thr Ala Gly Val Arg Arg Thr Asp Lys Asp Thr Glu Ile Thr Cys
                100                 105                 110

Ser Glu Arg Val Arg Thr Tyr Trp Ile Ile Ile Glu Leu Lys His Lys
            115                 120                 125

Ala Arg Glu Lys Pro Tyr Asp Ser Lys Ser Leu Arg Thr Ala Leu Gln
        130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Lys Lys Met
        195                 200                 205

Asp Leu Thr Val Asn Gly Glu Gln Leu Asp Leu Asp Pro Gly Gln Thr
210                 215                 220

Leu Ile Tyr Tyr Val Asp Glu Lys Ala Pro Glu Phe Ser Met Gln Gly
225                 230                 235                 240

Leu Lys Ser Arg His His His His His His
                245                 250

<210> SEQ ID NO 55
<211> LENGTH: 252
<212> TYPE: PRT
<213> ORGANISM: Artificial Sequence
<220> FEATURE:
<223> OTHER INFORMATION: synthetic sequence

<400> SEQUENCE: 55

Gln Glu Glu Cys Val Cys Glu Asn Tyr Lys Leu Ala Val Asn Cys Phe
1               5                   10                  15

Val Asn Asn Asn Arg Gln Cys Gln Cys Thr Ser Val Gly Ala Gln Asn
            20                  25                  30

Thr Val Ile Cys Ser Lys Leu Ala Ala Lys Cys Leu Val Met Lys Ala
        35                  40                  45

Glu Met Asn Gly Ser Lys Leu Gly Arg Arg Ala Lys Pro Glu Gly Ala
50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
                85                  90                  95

Asn Thr Ala Gly Val Arg Arg Thr Asp Lys Asp Thr Glu Ile Thr Cys
                100                 105                 110

Ser Glu Arg Val Arg Thr Tyr Trp Ile Ile Ile Glu Leu Lys His Lys
            115                 120                 125

Glu Arg Glu Ser Pro Tyr Asp His Gln Ser Leu Gln Thr Ala Leu Gln
        130                 135                 140

Glu Ala Phe Thr Ser Arg Tyr Lys Leu Asn Gln Lys Phe Ile Lys Asn
145                 150                 155                 160

Ile Met Tyr Glu Asn Asn Val Ile Thr Ile Asp Leu Met Gln Asn Ser
                165                 170                 175

Ser Gln Lys Thr Gln Asp Asp Val Asp Ile Ala Asp Val Ala Tyr Tyr
            180                 185                 190

Phe Glu Lys Asp Val Lys Gly Glu Ser Leu Phe His Ser Lys Lys Met
```

```
                195                 200                 205
Asp Leu Thr Val Asn Gly Glu Gln Leu Asp Leu Asp Pro Gly Gln Thr
    210                 215                 220

Leu Ile Tyr Tyr Val Asp Glu Lys Ala Pro Glu Phe Ser Met Gln Gly
225                 230                 235                 240

Leu Lys Ser Arg His His His His His His His
                245                 250

<210> SEQ ID NO 56
<211> LENGTH: 252
<212> TYPE: PRT
<213> ORGANISM: Artificial Sequence
<220> FEATURE:
<223> OTHER INFORMATION: synthetic sequence

<400> SEQUENCE: 56

Gln Glu Glu Cys Val Cys Glu Asn Tyr Lys Leu Ala Val Asn Cys Phe
1               5                   10                  15

Val Asn Asn Asn Arg Gln Cys Gln Cys Thr Ser Val Gly Ala Gln Asn
                20                  25                  30

Thr Val Ile Cys Ser Lys Leu Ala Ala Lys Cys Leu Val Met Lys Ala
            35                  40                  45

Glu Met Asn Gly Ser Lys Leu Gly Arg Arg Ala Lys Pro Glu Gly Ala
    50                  55                  60

Leu Gln Asn Asn Asp Gly Leu Tyr Asp Pro Asp Cys Asp Glu Ser Gly
65                  70                  75                  80

Leu Phe Lys Ala Lys Gln Cys Asn Gly Thr Ser Met Cys Trp Cys Val
                85                  90                  95

Asn Thr Ala Gly Val Arg Arg Thr Asp Lys Asp Thr Glu Ile Thr Cys
                100                 105                 110

Ser Glu Arg Val Arg Thr Tyr Trp Ile Ile Glu Leu Lys His Lys
            115                 120                 125

Ala Arg Glu Lys Pro Tyr Asp Ser Lys Ser Leu Arg Thr Ala Leu Gln
    130                 135                 140

Lys Glu Ile Thr Thr Arg Tyr Gln Leu Asp Pro Lys Phe Ile Thr Ser
145                 150                 155                 160

Ile Leu Tyr Glu Asn Asn Val Ile Thr Ile Asp Leu Val Gln Asn Ser
                165                 170                 175

Ser Gln Lys Thr Gln Asn Asp Val Asp Ile Ala Asp Val Ala Tyr Tyr
            180                 185                 190

Phe Glu Lys Asp Val Lys Gly Glu Ser Leu Phe His Ser Ser Lys Ser
    195                 200                 205

Met Asp Leu Arg Val Asn Gly Glu Pro Leu Asp Leu Asp Pro Gly Gln
    210                 215                 220

Thr Leu Ile Tyr Tyr Val Asp Glu Lys Ala Pro Glu Phe Ser Met Gln
225                 230                 235                 240

Gly Leu Ser Arg His His His His His His His
                245                 250

<210> SEQ ID NO 57
<211> LENGTH: 242
<212> TYPE: PRT
<213> ORGANISM: Artificial Sequence
<220> FEATURE:
<223> OTHER INFORMATION: synthetic sequence

<400> SEQUENCE: 57
```

Gln Arg Asp Cys Val Cys Asp Asn Tyr Lys Leu Ala Thr Ser Cys Ser
1               5                   10                  15

Leu Asn Glu Tyr Gly Glu Cys Gln Cys Thr Ser Tyr Gly Thr Gln Asn
            20                  25                  30

Thr Val Ile Cys Ser Lys Leu Ala Ser Lys Cys Leu Ala Met Lys Ala
        35                  40                  45

Glu Met Thr His Ser Lys Ser Gly Arg Arg Ile Lys Pro Glu Gly Ala
    50                  55                  60

Ile Gln Asn Asn Asp Gly Leu Tyr Asp Pro Asp Cys Asp Glu Gln Gly
65                  70                  75                  80

Leu Phe Lys Ala Lys Gln Cys Asn Gly Thr Ala Thr Cys Trp Cys Val
                85                  90                  95

Asn Thr Ala Gly Val Arg Arg Thr Asp Lys Asp Thr Glu Ile Thr Cys
            100                 105                 110

Ser Glu Arg Val Arg Thr Tyr Trp Ile Ile Glu Leu Lys His Lys
            115                 120                 125

Glu Arg Glu Ser Pro Tyr Asp His Gln Ser Leu Gln Thr Ala Leu Gln
            130                 135                 140

Glu Ala Phe Thr Ser Arg Tyr Lys Leu Asn Gln Lys Phe Ile Lys Asn
145                 150                 155                 160

Ile Met Tyr Glu Asn Asn Val Ile Thr Ile Asp Leu Met Gln Asn Ser
                165                 170                 175

Ser Gln Lys Thr Gln Asp Val Asp Ile Ala Asp Val Ala Tyr Tyr
            180                 185                 190

Phe Glu Lys Asp Val Lys Gly Glu Ser Leu Phe His Ser Ser Lys Ser
            195                 200                 205

Met Asp Leu Arg Val Asn Gly Glu Pro Leu Asp Leu Asp Pro Gly Gln
    210                 215                 220

Thr Leu Ile Tyr Tyr Val Asp Glu Lys Ala Pro Glu Phe Ser Met Gln
225                 230                 235                 240

Gly Leu

<210> SEQ ID NO 58
<211> LENGTH: 40
<212> TYPE: PRT
<213> ORGANISM: Artificial Sequence
<220> FEATURE:
<223> OTHER INFORMATION: synthetic sequence

<400> SEQUENCE: 58

Gln Arg Asp Cys Val Cys Glu Asn Tyr Lys Leu Ala Val Asn Cys Phe
1               5                   10                  15

Val Asn Asn Arg Gln Cys Gln Cys Thr Ser Val Gly Ala Gln Asn
            20                  25                  30

Thr Val Ile Cys Ser Lys Leu Ala
        35                  40

<210> SEQ ID NO 59
<211> LENGTH: 40
<212> TYPE: PRT
<213> ORGANISM: Artificial Sequence
<220> FEATURE:
<223> OTHER INFORMATION: synthetic sequence

<400> SEQUENCE: 59

Gln Glu Glu Cys Val Cys Glu Asn Tyr Lys Leu Ala Thr Ser Cys Phe
1               5                   10                  15

Val Asn Asn Asn Arg Gln Cys Gln Cys Thr Ser Val Gly Ala Gln Asn
            20                  25                  30

Thr Val Ile Cys Ser Lys Leu Ala
        35                  40

<210> SEQ ID NO 60
<211> LENGTH: 40
<212> TYPE: PRT
<213> ORGANISM: Artificial Sequence
<220> FEATURE:
<223> OTHER INFORMATION: synthetic sequence

<400> SEQUENCE: 60

Gln Glu Glu Cys Val Cys Glu Asn Tyr Lys Leu Ala Val Asn Cys Phe
1               5                   10                  15

Val Asn Asn Asn Arg Gln Cys Gln Cys Thr Ser Tyr Gly Ala Gln Asn
            20                  25                  30

Thr Val Ile Cys Ser Lys Leu Ala
        35                  40

<210> SEQ ID NO 61
<211> LENGTH: 40
<212> TYPE: PRT
<213> ORGANISM: Artificial Sequence
<220> FEATURE:
<223> OTHER INFORMATION: synthetic sequence

<400> SEQUENCE: 61

Gln Arg Asp Cys Val Cys Glu Asn Tyr Lys Leu Ala Thr Ser Cys Phe
1               5                   10                  15

Val Asn Asn Asn Arg Gln Cys Gln Cys Thr Ser Val Gly Ala Gln Asn
            20                  25                  30

Thr Val Ile Cys Ser Lys Leu Ala
        35                  40

<210> SEQ ID NO 62
<211> LENGTH: 40
<212> TYPE: PRT
<213> ORGANISM: Artificial Sequence
<220> FEATURE:
<223> OTHER INFORMATION: synthetic sequence

<400> SEQUENCE: 62

Gln Glu Glu Cys Val Cys Glu Asn Tyr Lys Leu Ala Thr Ser Cys Phe
1               5                   10                  15

Val Asn Asn Asn Arg Gln Cys Gln Cys Thr Ser Tyr Gly Ala Gln Asn
            20                  25                  30

Thr Val Ile Cys Ser Lys Leu Ala
        35                  40

<210> SEQ ID NO 63
<211> LENGTH: 40
<212> TYPE: PRT
<213> ORGANISM: Artificial Sequence
<220> FEATURE:
<223> OTHER INFORMATION: synthetic sequence

<400> SEQUENCE: 63

Gln Arg Asp Cys Val Cys Glu Asn Tyr Lys Leu Ala Val Asn Cys Phe
1               5                   10                  15

Val Asn Asn Asn Arg Gln Cys Gln Cys Thr Ser Tyr Gly Ala Gln Asn
            20                  25                  30

```
Thr Val Ile Cys Ser Lys Leu Ala
        35                  40

<210> SEQ ID NO 64
<211> LENGTH: 40
<212> TYPE: PRT
<213> ORGANISM: Artificial Sequence
<220> FEATURE:
<223> OTHER INFORMATION: synthetic sequence

<400> SEQUENCE: 64

Gln Arg Asp Cys Val Cys Glu Asn Tyr Lys Leu Ala Thr Ser Cys Phe
1               5                   10                  15

Val Asn Asn Arg Gln Cys Gln Cys Thr Ser Tyr Gly Ala Gln Asn
            20                  25                  30

Thr Val Ile Cys Ser Lys Leu Ala
        35                  40
```

CONDITIONALLY ACTIVE ANTI-EPCAM ANTIBODIES, ANTIBODY FRAGMENTS, THEIR IMMUNOCONJUGATES AND USES THEREOF

CROSS-REFERENCE TO RELATED APPLICATIONS

This application is a national stage application filed under 35 U.S.C. 371 of International Patent Application No. PCT/US2020/037096 filed Jun. 10, 2020, which claims the benefit of U.S. provisional application No. 62/860,092, filed on Jun. 11, 2019, the disclosures of each of which are hereby incorporated by reference in their entirety.

INCORPORATION OF MATERIAL OF ASCII TEXT SEQUENCE LISTING BY REFERENCE

The sequence listing submitted herewith as a Text file named "BIAT-1029USSubstituteSequenceListing" created on Dec. 1, 2022, which is 81,000 bytes in size, is hereby incorporated by reference herein in its entirety.

FIELD OF THE DISCLOSURE

This disclosure relates anti-EpCAM antibodies, antibody fragments and immunoconjugates of such antibodies and antibody fragments and uses of the antibodies, antibody fragments and immunoconjugates in diagnostic and therapeutic methods.

BACKGROUND OF THE DISCLOSURE

Epithelial cell adhesion/activating molecule (EpCAM, also known as CD326, HEA125, MK-1, EGP-2, EGP34, GA733-2, KSA, TROP-1, KS1/4 and ESA) is one of the first and most important immunotherapeutic targets in cancer therapy, due to its high-level and frequent expression on most carcinomas of different origin (Herlyn et al., *Proc Natl Acad Sci USA*, 76:1438-1442, 1979; Went et al., *Hum Pathol*, 35:122-128, 2004). This molecule is a relatively small type I transmembrane glycoprotein of 314 amino acids (aa) in length that is highly conserved during evolution. It is reported to mediate calcium-independent homotypic cell-cell adhesions (Litvinov et al., *J Cell Biology*, 125:437-446, 1994). The molecule consists of a short intracellular domain of 26 aa in which two binding sites for α-actinin are present for interaction with the actin cytoskeleton (Balzar et al., *Mol Cell Biol.*, 18(8): 4833-4843, 1998), a 23-aa transmembrane domain, a 242-aa extracellular domain (ECD), and a 23-aa signal peptide which is cleaved from its mature form. The extracellular domain of EpCAM has three N-linked glycosylation sites. Differential glycosylation status between normal and malignant tissues has been reported in certain types of cancer (Pauli et al., *Cancer Lett*, 193:25-32, 2003).

The extracellular domain contains 3 domains. The first two are believed to resemble epidermal growth factor (EGF)-like repeats in which twelve cysteine residues exist among them (Balzar et al., *Mol Cell Biol*, 21:2570-2580, 2001). However, some studies suggest that the second EGF-like repeat of EpCAM is in fact a thyroglobulin (TY) domain (Linnenbach et al., *Proc Natl Acad Sci* USA, 86:27-31, 1989; Chong and Speicher, *J Biol Chem*, 276:5804-5813, 2001). The third domain is a unique cysteine-poor region (CPR) unrelated to any known molecules (Baeuerle and Gires, *Br J Cancer*, 96:417-423, 2007). EpCAM plays an important role in the prevention of cell-cell adhesion, cell signalling, migration, proliferation and differentiation (FIG. 1).

EpCAM expression in humans is epithelia-specific. The majority of human epithelial cells express EpCAM, except squamous epithelium and some specific epithelial cell types, such as epidermal keratinocytes, hepatocytes, gastric parietal cells, and myoepithelial cells (Balzar et al., *J Mol Med*, 77: 699-712, 1999; Momburg et al., *Cancer Res*, 47:2883-2891, 1987). In tumors of epithelial origin, generally a higher expression level is observed (Balzar et al., *J Mol Med*, 77: 699-712, 1999; Winter et al., *Am J Pathol*, 163: 2139-2148, 2003; Went et al., *Hum Pathol*, 35:122-128, 2004; Went et al., *Br J Cancer*, 94:128-135, 2006). For example, it has been found that the EpCAM protein is expressed on a great variety of human adenocarcinomas and squamous cell carcinomas (Went et al., *Hum Pathol*, 35:122-128, 2004). Recent studies using immunohistochemistry (IHC) staining together with microarrays technology has discovered EpCAM expression in a fairly large number of samples from patients with breast, ovarian, renal, esophageal, colon, gastric, prostate and lung cancer (Spizzo et al., *Breast Cancer Res Treat*, 86:207-213, 2004; Spizzo et al., *Gynecol Oncol*, 103:483-488, 2006; Stoecklein et al., *BMC Cancer*, 6:165, 2006; Kimura et al., *Int J Oncol*, 30:171-179, 2007; Went et al., *Am J Surg Pathol*, 29:83-88, 2005; Went et al., *Br J Cancer*, 94:128-135, 2006). The data underscore the potential utility of EpCAM as an immunotherapeutic target for treatment of human cancers.

Since epithelial cells are known to be the most important cell type in the development of human malignancies, and more than 90% of all malignant tumors are of epithelial origin (Birchmeiera et al., *Acta Anatomica*, 156 (3):217-226, 1996), EpCAM is now considered to be one of the most frequently and intensely expressed tumor-associated antigens. The molecule has many times been independently discovered as an immunogenic tumor-associated antigen for development of monoclonal antibodies (Gottlinger et al., *Int J Cancer*, 38:47-53, 1986; Edwards et al., *Cancer Res*, 46:1306-1317, 1986; Spurr et al., *Int J Cancer*, 38:631-636, 1986; Momburg et al., *Cancer Res*, 47:2883-2891, 1987; Schon et al., *J Investig Dermatol*, 102: 987-991, 1994; Bumol et al., *Hybridoma*, 7:407-415, 1988; Quak et al., *Hybridoma*, 9:377-387, 1990).

Indeed, the first monoclonal antibody ever applied for human cancer therapy was in fact a murine IgG2a antibody called mAb 17-1A (later named edrecolomab and Panorexs) which targets EpCAM (Sears et al., *Lancet*, 1(8275):762-765, 1982; Sears et al., *J Biol Response Mod*, 3(2):138-150, 1984). Since then, edrecolomab and other EpCAM-specific murine, chimeric and humanized monoclonal antibodies were also tested pre-clinically and clinically either in the form of native (naked) antibody, hybrid bispecific (trifunctional) antibody or as conjugates with toxins, radioisotopes, or the cytokines (IL-2 or GM-CSF) for cancer treatment (Velders et al., *Cancer Res*, 54(7):1753-1759, 1994; Raum et al., *Cancer Immunol Immunother*, 50(3):141-150, 2001; Elias et al., *Am J Respir Crit Care Med*, 150:1114-1122, 1994; Di Paolo et al., *Clin Cancer Res*, 9:2837-2848, 2003; Andratschke et al., *Anticancer Res*, 27(1A):431-436, 2007; Xiang et al., *Cancer Res*, 57(21):4948-4955, 1997; Schanzer et al., *J Immunother*, 29(5):477-488, 2006; Wimberger et al., *Int J Cancer*, 105(2):241-248, 2003; Amann et al., *Cancer Res*, 68(1):143-151, 2008). To date numerous different immunotherapeutic approaches targeting EpCAM are still currently in clinical trials (Baeuerle and Gires, *Br J Cancer*, 96:417-423, 2007). Data from clinical trials have suggested that naked anti-EpCAM antibodies such as edrecolomab (17-1A; Panorexs) and adecatumumab (MT201) have only limited anti-tumor effect (Punt et al., *Lancet,* 360: 671-677, 2002), likely through the activation of the complement system (CDC) and the antibody-dependent cytotoxicity (ADCC) effect (Schwartzberg, *Crit Rev Oncol Hematol,* 40(1):17-24, 2001; Naundorf et al., *Int J Cancer,* 100(1): 101-110, 2002; Prang et al., *Br J Cancer,* 92(2):342-349, 2005; Oberneder et al., *Eur J Cancer,* 42(15):2530-2538, 2006). Antibodies conjugated with very potent effector mechanisms such as IL-2, PE toxin, or anti-CD3 seem to have a better anti-tumor effect. However, some adverse effects limit the systemic use of such anti-EpCAM antibodies (Baeuerle and Gires, *Br J Cancer,* 96:417-423, 2007).

ING-1 is a high affinity human engineered monoclonal antibody that targets EpCAM positive cells. It has been used in a phase I clinical trial in patients with advanced adenocarcinomas, refractory to standard therapy and the data from this study suggested that antibodies with high affinity to EpCAM, while being more cytotoxic to tumor cells, can also induce rapid pancreatic toxic injury thus, limiting their therapeutic window for systemic administration (De Bono et al., *Clin Cancer Res,* 10(22):7555-65, 2004). The possible systemic toxic effects associated with the therapeutic use of high affinity anti-EpCAM antibodies, might be reduced by pre-targeting strategies which include a chasing step to eliminate, at a given time, the circulating antibody. Alternatively, the use of high affinity anti-EpCAM antibodies might be restricted to loco-regional treatments.

The side effects of known anti-EpCAM antibodies are associated with the presence of EpCAM on normal epithelial cells, albeit with a lower density compared to tumor cells (Kim et al., *Clin Cancer Res,* 10:5464-5471, 2004; Osta et al., *Cancer Res,* 64:5818-5824, 2004). Thus, increasing the affinity or specificity of the anti-EpCAM antibodies does not lead to a reduction of the anti-EpCAM antibodies in the normal tissues that express EpCAM, which produces the side effects.

The present invention aims at providing anti-EpCAM antibodies or antibody fragments with reduced or minimal side effects suitable for therapeutic and diagnostic use, especially for diagnosis and treatment of cancers. Some of these anti-EpCAM antibodies or antibody fragments may have a higher binding affinity to EpCAM in a tumor in comparison with EpCAM present in normal tissues. These anti-EpCAM antibodies or antibody fragments typically have at least comparable efficacy to known anti-EpCAM antibodies. In addition, the present anti-EpCAM antibodies or antibody fragments may exhibit reduced side effects in comparison with monoclonal anti-EpCAM antibodies known in the art for having a relatively low binding affinity to EpCAM in normal tissues. These advantages may provide a more selective targeting of the EpCAM for a tumor and may permit use of higher dosages of these anti-EpCAM antibodies or antibody fragments as a result of the selectivity of the antibodies for EpCAM present in a tumor, whereby more effective therapeutic treatments can be realized without a corresponding increase in undesirable side effects.

SUMMARY OF THE DISCLOSURE

In one aspect, the present invention provides an isolated polypeptide that specifically binds to EpCAM. The polypeptide comprises a heavy chain variable region including three complementarity determining regions (CDRs) having sequences H1, H2, and H3, wherein:

the H1 sequence is GYTFTSYWMH (SEQ ID NO: 1);
the H2 sequence is $X_1$IRPSTGYTEYNQKFKD (SEQ ID NO: 2); and
the H3 sequence is GDNWVGFAN (SEQ ID NO: 3);
wherein $X_1$ is Y or D.

In the previous embodiment, the H2 sequence may be YIRPSTGYTEYNQKFKD (SEQ ID NO: 22) or the H2 sequence may be DIRPSTGYTEYNQKFKD (SEQ ID NO: 23).

In another aspect, the present invention includes a product formed by a combination of any of the above-described isolated polypeptides with an isolated polypeptide comprising a light chain variable region including three CDRs having sequences L1, L2, and L3, wherein:

the L1 sequence is SASSSISYMH (SEQ ID NO: 4);
the L2 sequence is STSNL$X_2$S (SEQ ID NO: 5); and
the L3 sequence is $X_3$QWSTY$X_4$T (SEQ ID NO: 6),
wherein $X_2$ is A or H; $X_3$ is H or E; and $X_4$ is H or E.

In another aspect, the present invention provides isolated polypeptides comprising a heavy chain variable region and a light chain variable region that specifically bind to EpCAM, especially human EpCAM protein, wherein the heavy chain variable region includes three complementarity determining regions having sequences H1, H2, and H3, wherein:

the H1 sequence is GYTFTSYWMH (SEQ ID NO: 1);
the H2 sequence is $X_1$IRPSTGYTEYNQKFKD (SEQ ID NO: 2); and
the H3 sequence is GDNWVGFAN (SEQ ID NO: 3);
wherein $X_1$ is Y or D; and the light chain variable region includes three complementarity determining regions having sequences L1, L2, and L3, wherein:
the L1 sequence is SASSSISYMH (SEQ ID NO: 4);
the L2 sequence is STSNL$X_2$S (SEQ ID NO: 5); and
the L3 sequence is $X_3$QWSTY$X_4$T (SEQ ID NO: 6);
wherein $X_2$ is A or H; $X_3$ is H or
E; and $X_4$ is H or E; and with the proviso that $X_1$, $X_2$, $X_3$ and $X_4$ cannot be Y, A, H,
and H at the same time.

In the previous embodiment, the H2 sequence may be YIRPSTGYTEYNQKFKD (SEQ ID NO: 22) or the H2 sequence may be DIRPSTGYTEYNQKFKD (SEQ ID NO: 23).

In each of the previous embodiments, the L2 sequence may be STSNLAS (SEQ ID NO: 24) or the L2 sequence may be STSNLHS (SEQ ID NO: 25).

In each of the previous embodiments, the L3 sequence may be HQWSTYHT (SEQ ID NO: 26), the L3 sequence may be HQWSTYET (SEQ ID NO: 27), or the L3 sequence may be EQWSTYHT (SEQ ID NO: 28).

In each of the previous embodiments, the heavy chain variable region may have a sequence selected from SEQ ID NOS: 7-13.

In each of the foregoing embodiments, the light chain variable region may have a sequence selected from SEQ ID NOS: 14-21.

In another embodiment, isolated polypeptides of the present invention comprise a heavy chain variable region and a light chain variable region having any one pair of sequences selected from: SEQ ID NOS: 8 and 14, SEQ ID NOS: 9 and 14, SEQ ID NOS: 7 and 15, SEQ ID NOS: 7 and 16, SEQ ID NOS: 7 and 17, SEQ ID NOS: 11 and 20, SEQ ID NOS: 12 and 21, SEQ ID NOS: 11 and 18, SEQ ID NOS: 13 and 18, SEQ ID NOS: 10 and 19.

In another embodiment, the isolated polypeptides of the present invention comprise a heavy chain variable region and a light chain variable region each region independently having at least 80%, 85%, 90%, 95%, 98% or 99% identity to a pair of amino acid sequences selected from: SEQ ID NOS: 8 and 14, SEQ ID NOS: 9 and 14, SEQ ID NOS: 7 and 15, SEQ ID NOS: 7 and 16, SEQ ID NOS: 7 and 17, SEQ ID NOS: 11 and 20, SEQ ID NOS: 12 and 21, SEQ ID NOS: 11 and 18, SEQ ID NOS: 13 and 18, and SEQ ID NOS: 10 and 19, respectively; and said isolated polypeptides specifically bind to human EpCAM protein.

In another aspect, the present invention provides an antibody or antibody fragment comprising a heavy chain variable region and a light chain variable region, wherein the heavy chain variable region includes three complementarity determining regions having sequences H1, H2, and H3, wherein:
 the H1 sequence is GYTFTSYWMH (SEQ ID NO: 1);
 the H2 sequence is $X_1$IRPSTGYTEYNQKFKD (SEQ ID NO: 2); and
 the H3 sequence is GDNWVGFAN (SEQ ID NO: 3);
wherein $X_1$ is Y or D; and the light chain variable region includes three complementarity determining regions, having sequences L1, L2, and L3, wherein:
 the L1 sequence is SASSSISYMH (SEQ ID NO: 4);
 the L2 sequence is STSNL$X_2$S (SEQ ID NO: 5); and
 the L3 sequence is $X_3$QWSTY$X_4$T (SEQ ID NO: 6);
 wherein $X_2$ is A or H; $X_3$ is H or E; and $X_4$ is H or E; with the proviso that $X_1$, $X_2$, $X_3$ and $X_4$ cannot be Y, A, H, and H, respectively, at the same time.

In the previous embodiment, the H2 sequence may be YIRPSTGYTEYNQKFKD (SEQ ID NO: 22) or the H2 sequence may be DIRPSTGYTEYNQKFKD (SEQ ID NO: 23).

In each of the previous embodiments, the L2 sequence may be STSNLAS (SEQ ID NO: 24) or the L2 sequence may be STSNLHS (SEQ ID NO: 25).

In each of the previous embodiments, the L3 sequence may be HQWSTYHT (SEQ ID NO: 26), the L3 sequence may be HQWSTYET (SEQ ID NO: 27), or the L3 sequence may be EQWSTYHT (SEQ ID NO: 28).

In each of the previous embodiments, the heavy chain variable region may have an amino acid sequence selected from SEQ ID NOS: 7-13.

In each of the previous embodiments, the light chain variable region may have an amino acid sequence selected from SEQ ID NOS: 14-21.

In each of the previous embodiments, the heavy chain variable region and the light chain variable region may have any one pair of sequences selected from: SEQ ID NOS: 8 and 14, SEQ ID NOS: 9 and 14, SEQ ID NOS: 7 and 15, SEQ ID NOS: 7 and 16, SEQ ID NOS: 7 and 17, SEQ ID NOS: 11 and 20, SEQ ID NOS: 12 and 21, SEQ ID NOS: 11 and 18, SEQ ID NOS: 13 and 18, SEQ ID NOS: 10 and 19.

In another embodiment, the antibody or antibody fragment of the present invention comprises a heavy chain variable region and a light chain variable region each region independently having at least 80%, 85%, 90%, 95%, 98% or 99% identity to a pair of amino acid sequences selected from: SEQ ID NOS: 8 and 14, SEQ ID NOS: 9 and 14, SEQ ID NOS: 7 and 15, SEQ ID NOS: 7 and 16, SEQ ID NOS: 7 and 17, SEQ ID NOS: 11 and 20, SEQ ID NOS: 12 and 21, SEQ ID NOS: 11 and 18, SEQ ID NOS: 13 and 18, and SEQ ID NOS: 10 and 19, respectively; and said antibody or antibody fragment specifically binds to human EpCAM protein.

In each of the previous embodiments, the antibody or antibody fragment may have a higher binding affinity to EpCAM protein at a value of a condition in a tumor microenvironment in comparison with a different value of the same condition that occurs in a non-tumor microenvironment. In one embodiment, the condition is pH.

In each of the previous embodiments, the antibody or antibody fragment may have a higher antigen binding activity to EpCAM protein at a value of a condition in a tumor microenvironment in comparison with a different value of the same condition that occurs in a non-tumor microenvironment. In one embodiment, the condition is pH.

In each of the previous embodiments, the conditionally active antibody or antibody fragment may have at least 70% of the antigen binding activity at pH 6.0 as compared to the same antigen binding activity of the parent antibody or antibody fragment at pH 6.0 and the conditionally active antibody or antibody fragment may have less than 50%, or less than 40%, or less than 30%, or less than 20% or less than 10% of the antigen binding activity at pH 7.4 as compared to the same antigen binding activity of the parent antibody or antibody fragment at pH 7.4. The antigen binding activity may be binding to EpCAM protein or binding to CD3.

In each of the previous embodiments, the antigen binding activity may be measured by an ELISA assay.

In yet another aspect, the present invention provides an immunoconjugate that includes any of the antibody or antibody fragments of the invention described above. In the immunoconjugate, the antibody or antibody fragment may be conjugated to an agent selected from a chemotherapeutic agent, a radioactive atom, a cytostatic agent and a cytotoxic agent.

In yet another aspect, the present invention provides a pharmaceutical composition that includes any of the polypeptides, the antibody or antibody fragments, or the immunoconjugates of the invention described above, together with a pharmaceutically acceptable carrier.

A single dose of the pharmaceutical composition of may include an amount of the polypeptide, the antibody or antibody fragment, or the immunoconjugate of about 135 mg, 235 mg, 335 mg, 435 mg, 535 mg, 635 mg, 735 mg, 835 mg, 935 mg, 1035 mg, 1135 mg, 1235 mg, or 1387 mg.

A single dose of the pharmaceutical composition of may include an amount of the polypeptide, the antibody or antibody fragment, or the immunoconjugate in a range of 135-235 mg, 235-335 mg, 335-435 mg, 435-535 mg, 535-635 mg, 635-735 mg, 735-835 mg, 835-935 mg, 935-1035 mg, 1035-1135 mg, 1135-1235 mg, or 1235-1387 mg.

Each of the foregoing pharmaceutical compositions may further include an immune checkpoint inhibitor molecule. The immune checkpoint inhibitor molecule may be an antibody or antibody fragment against an immune checkpoint. The immune checkpoint may be selected from LAG3, TIM3, TIGIT, VISTA, BTLA, OX40, CD40, 4-1BB, CTLA4, PD-1, PD-L1, GITR, B7-H3, B7-H4, KIR, A2aR, CD27, CD70, DR3, and ICOS or the immune checkpoint may be CTLA4, PD-1 or PD-L1.

Each of the foregoing pharmaceutical compositions may further include an antibody or antibody fragment against an antigen selected from PD1, PD-L1, CTLA4, AXL, ROR2, CD3, HER2, B7-H3, ROR1, SFRP4 and a WNT protein. The WNT protein may be selected from WNT1, WNT2, WNT2B, WNT3, WNT4, WNT5A, WNT5B, WNT6, WNT7A, WNT7B, WNT8A, WNT8B, WNT9A, WNT9B, WNT10A, WNT10B, WNT11 and WNT16.

In yet another aspect, the present invention provides a kit for diagnosis or treatment including any of the polypeptides, the antibody or antibody fragments, or the immunoconjugates of the present invention described above.

BRIEF DESCRIPTION OF THE DRAWINGS

FIG. 2 shows a sequence alignment of exemplary heavy chain variable regions of anti-EpCAM antibodies of the present invention.

FIG. 3 shows a sequence alignment of exemplary light chain variable regions of anti-EpCAM antibodies of the present invention.

DEFINITIONS

Figure 1:
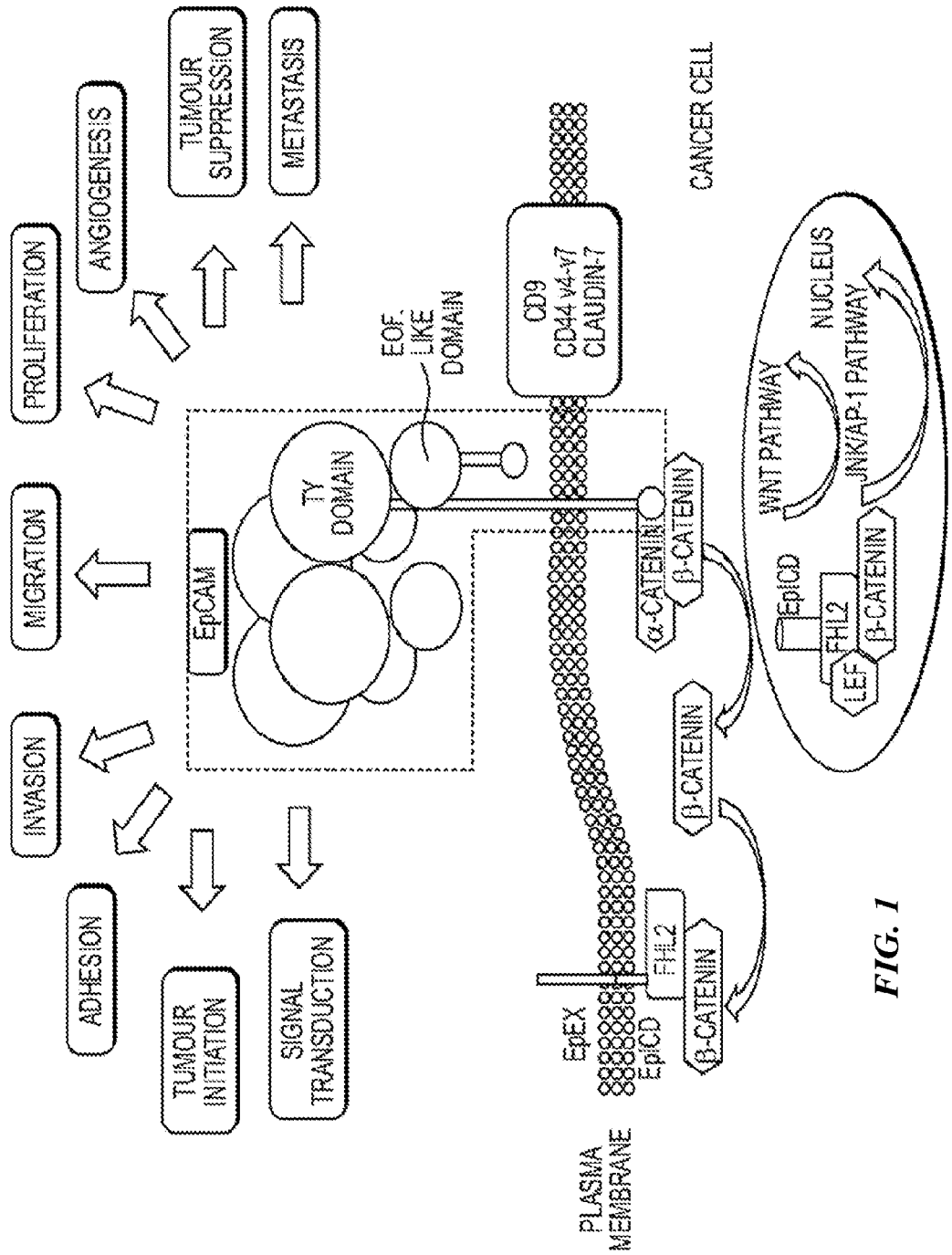
FIG. 1 shows a schematic representation of the functions of EpCAM in cancer metastasis and progression.

In order to facilitate understanding of the examples provided herein, certain frequently occurring terms are defined herein.

In connection with a measured quantity, the term "about" as used herein refers to the normal variation in that measured quantity that would be expected by a skilled person making the measurement and exercising a level of care commensurate with the objective of the measurement and the precision of the measuring equipment used. Unless otherwise indicated, "about" refers to a variation of +/−10% of the value provided.

The term "affinity" as used herein refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "affinity matured" antibody as used herein refers to an antibody with one or more alterations in one or more heavy chain or light chain variable regions, compared to a parent antibody which does not possess such alterations, such alterations resulting in an improvement in the affinity of the antibody for antigen.

The term "amino acid" as used herein refers to any organic compound that contains an amino group (—NH2) and a carboxyl group (—COOH); preferably either as free groups or alternatively after condensation as part of peptide bonds. The "twenty naturally encoded polypeptide-forming alpha-amino acids" are understood in the art and refer to: alanine (ala or A), arginine (arg or R), asparagine (asn or N), aspartic acid (asp or D), cysteine (cys or C), glutamic acid (glu or E), glutamine (gin or Q), glycine (gly or G), histidine (his or H), isoleucine (ile or I), leucine (leu or L), lysine (lys or K), methionine (met or M), phenylalanine (phe or F), proline (pro or P), serine (ser or S), threonine (thr or T), tryptophan (tip or W), tyrosine (tyr or Y), and valine (val or V).

The term "antibody" as used herein refers to intact immunoglobulin molecules, as well as fragments of immunoglobulin molecules, such as Fab, Fab', (Fab')2, Fv, and SCA fragments, that are capable of binding to an epitope of an antigen. These antibody fragments, which retain some ability to selectively bind to an antigen (e.g., a polypeptide antigen) of the antibody from which they are derived, can be made using well known methods in the art (see, e.g., Harlow and Lane, supra), and are described further, as follows. Antibodies can be used to isolate preparative quantities of the antigen by immunoaffinity chromatography. Various other uses of such antibodies are to diagnose and/or stage disease (e.g., neoplasia) and for therapeutic application to treat disease, such as for example: neoplasia, autoimmune disease, AIDS, cardiovascular disease, infections, and the like. Chimeric, human-like, humanized or fully human antibodies are particularly useful for administration to human patients. Antibodies and antibody fragments of the invention can be obtained by evolving or mutation of a parent antibody or antibody fragment that has the same type of activity, e.g. binding activity or affinity to EpCAM protein.

An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

An (Fab')2 fragment of an antibody can be obtained by treating a whole antibody molecule with the enzyme pepsin, without subsequent reduction. A (Fab')2 fragment is a dimer of two Fab' fragments, held together by two disulfide bonds.

An Fv fragment is defined as a genetically engineered fragment containing the variable region of a light chain and the variable region of a heavy chain expressed as two chains.

The term "antibody fragment" as used herein refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$;

diabodies; linear antibodies; single-chain antibody molecules (e.g. scFv); and multispecific antibodies formed from antibody fragments.

The terms "anti-EpCAM antibody," "EpCAM antibody" and "an antibody that binds to EpCAM" as used herein refer to an antibody that is capable of binding EpCAM with sufficient affinity such that the antibody is useful as a diagnostic and/or therapeutic agent in targeting EpCAM. In one embodiment, the extent of binding of an anti-EpCAM antibody to an unrelated, non-EpCAM protein is less than about 10% of the binding of the antibody to EpCAM as measured, e.g., by a radioimmunoassay (RIA). In certain embodiments, an antibody that binds to EpCAM has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$M). In certain embodiments, an anti-EpCAM antibody binds to an epitope of EpCAM that is conserved among EpCAM from different species, for example, the extracellular domain of EpCAM.

The term "binding" as used herein refers to interaction of the variable region or an Fv of an antibody with an antigen with the interaction depending upon the presence of a particular structure (e.g., an antigenic determinant or epitope) on the antigen. For example, an antibody variable region or Fv recognizes and binds to a specific protein structure rather than to proteins generally. As used herein, the term "specifically binding" or "binding specifically" means that an antibody variable region or Fv binds to or associates with more frequently, more rapidly, with greater duration and/or with greater affinity with a particular antigen than with other proteins. For example, an antibody variable region or Fv specifically binds to its antigen with greater affinity, avidity, more readily, and/or with greater duration than it binds to other antigens. For another example, an antibody variable region or Fv binds to a cell surface protein (antigen) with materially greater affinity than it does to related proteins or other cell surface proteins or to antigens commonly recognized by polyreactive natural antibodies (i.e., by naturally occurring antibodies known to bind a variety of antigens naturally found in humans). However, "specifically binding" does not necessarily require exclusive binding or non-detectable binding of another antigen, this is meant by the term "selective binding". In one example, "specific binding" of an antibody variable region or Fv (or other binding region) binds to an antigen, means that the an antibody variable region or Fv binds to the antigen with an equilibrium constant (KD) of 100 nM or less, such as 50 nM or less, for example 20 nM or less, such as, 15 nM or less, or 10 nM or less, or 5 nM or less, 2 nM or less, or 1 nM or less.

The terms "cancer" and "cancerous" as used herein refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The terms "cell proliferative disorder" and "proliferative disorder" as used herein refer to disorders that are associated with some degree of abnormal cell proliferation. In one embodiment, the cell proliferative disorder is cancer.

The term "chemotherapeutic agent" as used herein refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem. Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid;

aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMF®); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics," which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASINCI), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "chimeric" antibody as used herein refers to an antibody in which a portion of the heavy and/or light chain is derived from a particular source or species, while the remainder of the heavy and/or light chain is derived from a different source or species.

The term "conditionally active antibody" as used herein refers to an anti-EpCAM antibody which is more active under a condition in the tumor microenvironment compared to under a condition in the non-tumor microenvironment. The conditions in the tumor microenvironment include lower pH, higher concentrations of lactate and pyruvate, hypoxia, lower concentration of glucose, and slightly higher temperature in comparison with non-tumor microenvironment. For example, a conditionally active antibody is virtually inactive at normal body temperature, but is active at a higher temperature in a tumor microenvironment. In yet another aspect, the conditionally active antibody is less active in normal oxygenated blood, but more active under a less oxygenated environment exists in tumor. In yet another aspect, the conditionally active antibody is less active in normal physiological pH 7.2-7.8, but more active under an acidic pH 5.8-7.0, or 6.0-6.8 that exists in a tumor microenvironment. There are other conditions in the tumor microenvironment know to a person skilled in the field may also be used as the condition in the present invention under which the anti-EpCAM antibodies to have different binding affinity to EpCAM.

The term "cytostatic agent" as used herein refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. Cytotoxic agents include, but are not limited to radioactive isotopes (e.g., $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "diabodies" as used herein refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites.

The term "detectably label" as used herein refers to any substance whose detection or measurement, either directly or indirectly, by physical or chemical means, is indicative of the presence of an antigen in a sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

The term "diagnostics" as used herein refers to determination of a subject's susceptibility to a disease or disorder, determination as to whether a subject is presently affected by a disease or disorder, prognosis of a subject affected by a disease or disorder (e. g., identification of pre-metastatic or metastatic cancerous states, stages of cancer, or responsiveness of cancer to therapy), and therametrics (e. g., monitoring a subject's condition to provide information as to the effect or efficacy of therapy). In some embodiments, the diagnostic method of this invention is particularly useful in detecting early stage cancers.

The term "diagnostic agent" as used herein refers to a molecule which can be directly or indirectly detected and is used for diagnostic purposes. The diagnostic agent may be administered to a subject or a sample. The diagnostic agent can be provided per se or may be conjugated to a vehicle such as a conditionally active antibody.

The term "effector functions" as used herein refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "effective amount" of an agent as used herein, e.g., a pharmaceutical formulation, refers to an amount effective, at dosages and for periods of time necessary, to achieve the desired therapeutic or prophylactic result.

The term "Fc region" as used herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "framework" or "FR" as used herein refers to variable domain residues other than complementarity determining regions (CDRs or H1-3 in the heavy chain and L1-3 in the light chain) residues. The FR of a variable domain generally consists of four FR domains: FR1, FR2, FR3, and FR4. Accordingly, the CDR and FR sequences generally appear in the following sequence in $V_H$ (or $V_L$): FR1-H1 (L1)-FR2-H2(L2)-FR3-H3(L3)-FR4.

The term "full length antibody," "intact antibody," or "whole antibody" refers to an antibody which comprises an antigen-binding variable region ($V_H$ or $V_L$) as well as a light chain constant domain (CL) and heavy chain constant domains, CH1, CH2 and CH3. The constant domains may be native sequence constant domains (e.g. human native sequence constant domains) or amino acid sequence variants thereof. Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The term "function-conservative variants" as used herein refers a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like) Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

The terms "host cell," "host cell line," and "host cell culture" as used herein are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "human antibody" as used herein is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "humanized" antibody as used herein refers to a chimeric antibody comprising amino acid residues from non-human CDRs and amino acid residues from human FRs. In certain embodiments, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "immunoconjugate" as used herein is an antibody conjugated to one or more heterologous molecule(s), including but not limited to a cytotoxic agent.

The term "individual" or "subject" as used herein refers to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human The term "inhibiting cell growth or proliferation" as used herein means decreasing a cell's growth or proliferation by at least 10%, 20%, 30%, 40%, 50%, 60%, 70%, 80%, 90%, 95%, or 100%, and includes inducing cell death.

The term "isolated" antibody as used herein is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase High Performance Liquid Chromatography (HPLC)). For review of methods for assessment of antibody purity, see, e.g., Flatman et al., *J. Chromatogr.* B, vol. 848, pp. 79-87, 2007.

The term "isolated nucleic acid encoding an anti-EpCAM antibody" as used herein refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "metastasis" as used herein refers to all EpCAM-involving processes that support cancer cells to disperse from a primary tumor, penetrate into lymphatic and/or blood vessels, circulate through the bloodstream, and grow in a distant focus (metastasis) in normal tissues elsewhere in the body. In particular, it refers to cellular events of tumor cells such as proliferation, migration, anchorage independence, evasion of apoptosis, or secretion of angiogenic factors, that underlie metastasis and are stimulated or mediated by EpCAM.

The term "microenvironment" as used herein means any portion or region of a tissue or body that has constant or temporal, physical or chemical differences from other regions of the tissue or regions of the body. For tumors, the term "tumor microenvironment" as used herein refers to the environment in which a tumor exists, which is the non-cellular area within the tumor and the area directly outside the tumorous tissue but does not pertain to the intracellular compartment of the cancer cell itself. The tumor and the tumor microenvironment are closely related and interact constantly. A tumor can change its microenvironment, and the microenvironment can affect how a tumor grows and spreads. Typically, the tumor microenvironment has a low pH in the range of 5.0 to 7.0, or in the range of 5.0 to 6.8, or in the range of 5.8 to 6.8, or in the range of 6.2-6.8. On the other hand, a normal physiological pH is in the range of 7.2-7.8. The tumor microenvironment is also known to have lower concentration of glucose and other nutrients, but higher concentration of lactic acid, in comparison with blood plasma. Furthermore, the tumor microenvironment can have a temperature that is 0.3 to 1° C. higher than the normal physiological temperature. The tumor microenvironment has been discussed in Gillies et al., "MRI of the Tumor Microenvironment," *Journal of Magnetic Resonance Imaging*, vol. 16, pp. 430-450, 2002, hereby incorporated by reference herein its entirety. The term "non-tumor microenvironment" refers to a microenvironment at a site other than a tumor.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "naked antibody" as used herein refers to an antibody that is not conjugated to a heterologous moiety (e.g., a cytotoxic moiety) or radiolabel. The naked antibody may be present in a pharmaceutical formulation.

The term "package insert" as used herein is used to refer to instructions customarily included in commercial packages of therapeutic products, that contain information about the indications, usage, dosage, administration, combination therapy, contraindications and/or warnings concerning the use of such therapeutic products.

The term "percent (%) amino acid sequence identity" with respect to a reference polypeptide sequence as used herein is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" as used herein refers to a preparation which is in such form as to permit the biological activity of an active ingredient contained therein to be effective, and which contains no additional components which are unacceptably toxic to a subject to which the formulation would be administered.

The term "pharmaceutically acceptable carrier" as used herein refers to an ingredient in a pharmaceutical formulation, other than an active ingredient, which is nontoxic to a subject., A pharmaceutically acceptable carrier includes, but is not limited to, a buffer, excipient, stabilizer, or preservative.

The terms "purified" and "isolated" used herein refer to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

The term "recombinant antibody" as used herein refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia. coli* cells or *Bacillus subtilis* cells, etc.

The term "single chain Fv" ("scFv") as used herein is a covalently linked $V_H$::$V_L$ heterodimer which is usually expressed from a gene fusion including $V_H$ and $V_L$ encoding genes linked by a peptide-encoding linker. "dsFv" is a $V_H$::$V_L$ heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "therapeutically effective amount" of the antibody of the invention is meant a sufficient amount of the antibody to treat said cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

The term "treatment," "treat," or "treating" as used herein refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "tumor" as used herein refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "variable region" or "variable domain" as used herein refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three complementarity determining regions (CDRs). (See, e.g., Kindt et al. Kuby Immunology, 6th ed., W. H. Freeman and Co., page 91 (2007).) A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., *J. Immunol.*, vol. 150, pp. 880-887, 1993; Clarkson et al., *Nature*, vol. 352, pp. 624-628, 1991.

The term "vector" as used herein refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

DETAILED DESCRIPTION

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in, other systems and methods. Before explaining the disclosed embodiments of the present invention in detail, it is to be understood that the invention is not limited in its application to the details of any particular embodiment shown. Additionally, the terminology used herein is for the purpose of description and not for limitation. Furthermore, although certain methods are described with reference to steps that are presented herein in a certain order, in many instances, these steps can be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more", and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent, or parameter disclosed herein is to be interpreted as being disclosed for use alone or in combination with one or more of each and every other component, compound, substituent, or parameter disclosed herein.

It is also to be understood that each amount/value or range of amounts/values for each component, compound, substituent, or parameter disclosed herein is to be interpreted as also being disclosed in combination with each amount/value or range of amounts/values disclosed for any other component(s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

A. Anti-EpCAM Polypeptides and Antibodies

In one aspect, the present invention provides an isolated polypeptide comprising a heavy chain variable region that specifically binds to EpCAM, especially human EpCAM protein. The heavy chain variable region includes three complementarity determining regions having sequences H1, H2, and H3, wherein:

the H1 sequence is GYTFTSYWMH (SEQ ID NO: 1);
the H2 sequence is $X_1$IRPSTGYTEYNQKFKD (SEQ ID NO: 2); and
the H3 sequence is GDNWVGFAN (SEQ ID NO: 3);
wherein $X_1$ is Y or D.

The H2 sequence may be selected from YIRPSTGYTEYNQKFKD (SEQ ID NO: 22), and DIRPSTGYTEYNQKFKD (SEQ ID NO: 23).

The alignments of exemplary heavy chain variable regions of the present invention are shown in FIG. 2, where the complementarity determining regions H1, H2, and H3 are enclosed in boxes.

In another aspect, the present invention provides an isolated polypeptide comprising a light chain variable region that specifically binds to human EpCAM. The light chain variable region includes three complementarity determining regions having sequences L1, L2, and L3, wherein:
the L1 sequence is SASSSISYMH (SEQ ID NO: 4);
the L2 sequence is STSNL$X_2$S (SEQ ID NO: 5); and
the L3 sequence is $X_3$QWSTY$X_4$T (SEQ ID NO: 6),
wherein $X_2$ is A or H; $X_3$ is H or E; and $X_4$ is H or E.

The L2 sequence may be selected from STSNLAS (SEQ ID NO: 24), and STSNLHS (SEQ ID NO: 25). The L3 sequence may be selected from HQWSTYHT (SEQ ID NO: 26), HQWSTYET (SEQ ID NO: 27), and EQWSTYHT (SEQ ID NO: 28).

The alignments of exemplary light chain variable regions of the present invention are shown in FIG. 3, where the complementarity determining regions L1, L2, and L3 are enclosed in boxes.

The heavy chain variable regions and the light chain variable regions of the present invention were each obtained from a parent antibody using a method disclosed in U.S. Pat. No. 8,709,755. This method of generating the heavy chain variable regions and the light chain variable regions, as well as the method of generating antibodies and antibody fragments disclosed in U.S. Pat. No. 8,709,755, are hereby incorporated by reference herein.

In another aspect, the present invention includes the heavy chain variable regions shown in FIG. 2 and the light chain variable regions shown in FIG. 3. The amino acid sequences of the 7 heavy chain variable regions of FIG. 2 are set forth in SEQ ID NOS: 7-13. The amino acid sequences of the 8 light chain variable regions of FIG. 3 are set forth in SEQ ID NOS:14-21.

In a more specific aspect, the present invention provides an antibody or antibody fragment comprising a heavy chain variable region and a light chain variable region, wherein the heavy chain variable region includes three complementarity determining regions having sequences H1, H2, and H3, wherein:
the H1 sequence is GYTFTSYWMH (SEQ ID NO: 1);
the H2 sequence is $X_1$IRPSTGYTEYNQKFKD (SEQ ID NO: 2); and
the H3 sequence is GDNWVGFAN (SEQ ID NO: 3);
wherein $X_1$ is Y or D; and the light chain variable region includes three complementarity determining regions, having sequences L1, L2, and L3, wherein:
the L1 sequence is SASSSISYMH (SEQ ID NO: 4);
the L2 sequence is STSNL$X_2$S (SEQ ID NO: 5); and
the L3 sequence is $X_3$QWSTY$X_4$T (SEQ ID NO: 6),
wherein $X_2$ is A or H; $X_3$ is H or E; and $X_4$ is H or E. and with the proviso that $X_1$, $X_2$, $X_3$ and $X_4$ cannot be Y, A, H, and H at the same time.

In one embodiment, the antibody or antibody fragment comprises a heavy chain variable region and a light chain variable region having any one pair of sequences selected from: SEQ ID NOS: 8 and 14, SEQ ID NOS: 9 and 14, SEQ ID NOS: 7 and 15, SEQ ID NOS: 7 and 16, SEQ ID NOS: 7 and 17, SEQ ID NOS: 11 and 20, SEQ ID NOS: 12 and 21, SEQ ID NOS: 11 and 18, SEQ ID NOS: 13 and 18, and SEQ ID NOS: 10 and 19.

In another embodiment, the antibody or antibody fragment of the present invention comprises a heavy chain variable region and a light chain variable region each region independently having at least 80%, 85%, 90%, 95%, 98% or 99% identity to a pair of amino acid sequences selected from: SEQ ID NOS: 8 and 14, SEQ ID NOS: 9 and 14, SEQ ID NOS: 7 and 15, SEQ ID NOS: 7 and 16, SEQ ID NOS: 7 and 17, SEQ ID NOS: 11 and 20, SEQ ID NOS: 12 and 21, SEQ ID NOS: 11 and 18, SEQ ID NOS: 13 and 18, and SEQ ID NOS: 10 and 19, respectively, and said antibody or antibody fragment specifically binds to human EpCAM.

Antibodies and antibody fragments including these heavy chain variable regions and light chain variable regions can specifically bind to EpCAM, especially human EpCAM. Antibodies or antibody fragments comprising a combination of one of these heavy chain variable regions and one of these light chain variable regions have been found to have higher binding affinity to EpCAM at a pH in the tumor microenvironment (e.g. pH 6.0-6.8) than at a pH in a non-tumor microenvironment (e.g. pH 7.0-7.6). As a result, the anti-EpCAM antibodies or antibody fragments have a higher binding affinity to EpCAM in a tumor microenvironment in comparison with their binding affinity to EpCAM in a typical normal tissue microenvironment.

Anti-EpCAM antibodies or antibody fragments of the present invention are thus expected to exhibit reduced side-effects, relative to non-conditionally active anti-EpCAM antibodies, due to their reduced binding affinity to EpCAM in the normal tissue microenvironment. Anti-EpCAM antibodies or antibody fragments of the present invention are also expected to have a comparable efficacy to monoclonal anti-EpCAM antibodies known in the art. This combination of features permits use of a higher dosage of these anti-EpCAM antibodies or antibody fragments due to the reduced side effects, which may provide a more effective therapy option.

In each of the previous embodiments, the antibody or antibody fragment may have a higher antigen binding activity to EpCAM protein at a value of a condition in a tumor microenvironment in comparison with a different value of the same condition that occurs in a non-tumor microenvironment. In one embodiment, the condition is pH.

The anti-EpCAM antibody or antibody fragment may have at least 70% of the antigen binding activity at pH 6.0 as compared to the same antigen binding activity of a parent antibody or antibody fragment from which it is derived, also at pH 6.0 and the antibody or antibody fragment may have less than 50%, or less than 40%, or less than 30%, or less than 20% or less than 10% of the antigen binding activity at pH 7.4 as compared to the same antigen binding activity of a parent antibody or antibody fragment from which it is derived at pH 7.4. The antigen binding activity may be, for example, binding to EpCAM protein or binding to CD3.

In each of the previous embodiments, the antigen binding activity may be measured by an ELISA assay.

The present invention includes the heavy chain variable regions and light chain variable regions presented in FIGS. 2-3 and polypeptides having the amino acid sequences of SEQ ID NOS: 7-21. The present invention also includes variants of the heavy chain variable regions and light chain variable regions presented in FIGS. 2-3 and the polypeptides having the amino acid sequences of SEQ ID NOS: 7-21, that can specifically bind to EpCAM, especially human EpCAM. In some embodiments, these variants have different H1, H2, H3, L1, L2 or L3 sequences. In other embodiments, the amino acid sequence of the heavy and light chain variable regions outside of the complementarity determining regions may be mutated in accordance with the principles of substitution, insertion and deletion, as discussed in this application to provide these variants. In still further embodiments, the constant regions may be modified to provide these variants.

In deriving these variants, one is guided by the process as described herein. The variants of the heavy chain and light chain variable regions may be prepared by introducing appropriate modifications into the nucleotide sequence encoding the heavy and light chain variable regions, or by peptide synthesis. Such modifications include, for example, deletions from, and/or insertions into and/or substitutions of residues within the amino acid sequences of the heavy and light chain variable regions. Any combination of deletion, insertion, and substitution can be made to arrive at the antibodies or antibody fragments of the present invention, provided that they possess the desired characteristics, e.g., antigen-binding to human EpCAM and/or conditional activity.

Substitution, Insertion, and Deletion Variants

In certain embodiments, antibody or antibody fragment variants having one or more amino acid substitutions are provided. Sites of interest for substitutional mutagenesis include the CDRs and framework regions (FRs). Conservative substitutions are shown in Table 1 under the heading of "conservative substitutions." More substantial changes are provided in Table 1 under the heading of "exemplary substitutions," and as further described below in reference to amino acid side chain classes Amino acid substitutions may be introduced into an antibody or antibody fragment of interest and the products screened for a desired activity, e.g., retained/improved antigen binding, or decreased immunogenicity.

TABLE 1

Amino acid substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucinel Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more complementarity determining region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g. binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, Methods Mol. Biol., vol. 207, pp. 179-196, 2008), and/or SDRs (a-CDRs), with the resulting variant $V_H$ or $V_L$ being tested for binding affinity. Affinity maturation by constructing and reselecting from secondary libraries has been described, e.g., in Hoogenboom et al. in Methods in Molecular Biology, vol. 178, pp. 1-37, 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody or antibody fragment to bind antigen. For example, conservative alterations (e.g., conservative substitutions as provided herein) that do not substantially reduce binding affinity may be made in CDRs. Such alterations may be outside of CDR "hotspots" or SDRs. In certain embodiments of the variant $V_H$ and $V_L$ sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells, Science, vol. 244, pp. 1081-1085, 1989. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or antibody fragment with antigen is affected. Further substitutions may be introduced at the amino acid locations demonstrating functional sensitivity to the initial substitutions. Alternatively, or additionally, a crystal structure of an antigen-antibody complex to identify contact points between the antibody or antibody fragment and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody include the fusion to the N- or C-terminus of the antibody to an enzyme (e.g. for ADEPT) or a polypeptide which increases the serum half-life of the antibody.

Amino acid sequence modification(s) of the antibodies described herein are contemplated. For example, it may be desirable to improve the binding affinity and/or other biological properties of the antibody. It is known that when a humanized antibody is produced by simply grafting only CDRs in $V_H$ and $V_L$ of an antibody derived from a non-human animal in FRs of the $V_H$ and $V_L$ of a human antibody, the antigen binding activity is reduced in comparison with that of the original antibody derived from a non-human animal. It is considered that several amino acid residues of the $V_H$ and $V_L$ of the non-human antibody, not only in CDRs but also in FRs, are directly or indirectly associated with the antigen binding activity. Hence, substitution of these amino acid residues with different amino acid residues derived from FRs of the $V_H$ and $V_L$ of the human antibody would reduce of the binding activity. In order to resolve the problem, in antibodies grafted with human CDR, attempts have to be made to identify, among amino acid sequences of the FR of the $V_H$ and $V_L$ of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the sequences of the antibodies or antibody fragments of the invention, or corresponding DNA sequences which encode said antibodies or antibody fragments, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Glycosylation Variants

In certain embodiments, the anti-EpCAM antibodies or antibody fragments provided herein are altered to increase or decrease the extent to which the antibodies or antibody fragments are glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH*, vol. 15, pp. 26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.*, vol. 336, pp. 1239-1249, 2004; Yamane-Ohnuki et al. *Biotech. Bioeng.*, vol. 87, pp. 614-622, 2004. Examples of cell lines capable of producing defucosylated antibodies include Lec13 CHO cells deficient in protein fucosylation (Ripka et al. *Arch. Biochem. Biophys.*, vol. 249, pp. 533-545, 1986; US Pat Appl No US 2003/0157108 A; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.*, vol. 87, pp. 614-622, 2004; Kanda, Y. et al., *Biotechnol. Bioeng.*, vol. 94, pp. 680-688, 2006; and WO2003/085107).

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

Fc Region Variants

In certain embodiments, one or more amino acid modifications may be introduced into the Fc region of the anti-EpCAM antibodies or antibody fragments provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.*, vol. 9, pp. 457-492, 1991. Non-limiting examples of in vitro assays to assess ADCC activity of a molecule of interest is described in U.S. Pat. No. 5,500,362 (see also, e.g. Hellstrom et al. *Proc. Nat'l Acad. Sci. USA*, vol. 83, pp. 7059-7063, 1986) and Hellstrom, I et al., *Proc. Nat'l Acad. Sci. USA*, vol. 82, pp. 1499-1502, 1985; U.S. Pat. No. 5,821,337 (see also Bruggemann et al., *J. Exp. Med.*, vol. 166, pp. 1351-1361, 1987). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA*, vol. 95, pp. 652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods*, vol. 202, pp. 163-171, 1996; Cragg, M. S. et al., *Blood*, vol. 101, pp. 1045-1052, 2003; and Cragg, M. S, and M. J. Glennie, *Blood*, vol. 103, pp. 2738-2743, 2004). FcRn binding and in vivo clearance/half life determinations can also be performed using methods known in the art (see, e.g., Petkova, S. B. et al., *Intl. Immunol.*, vol. 18, pp. 1759-1769, 2006).

The variants of the antibodies or antibody fragments with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.*, vol. 9, pp. 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.*, vol. 164, pp. 4178-4184, 2000.

Antibodies with increased half lives and improved binding to the neonatal Fc receptor (FcRn), which is responsible for the transfer of maternal IgGs to the fetus (Guyer et al., *J. Immunol.*, vol. 117, pp. 587-593, 1976 and Kim et al., *J. Immunol.*, vol. 24, p. 249, 1994), are described in US2005/0014934. Those antibodies comprise an Fc region with one or more substitutions therein which improve binding of the Fc region to FcRn. Such Fc variants include/e those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature*, vol. 322, pp. 738-740, 1988; U.S. Pat. Nos. 5,648,260; 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of the anti-EpCAM antibodies or antibody fragments are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, the anti-EpCAM antibodies or antibody fragments provided herein may be further modified to contain additional nonproteinaceous moieties that are known in the art and readily available. The moieties suitable for derivatization of the antibody or antibody fragment include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody or antibody fragment may vary, and if more than one polymer are attached, they can be the same or different molecules. In general, the number and/or type of polymers used for derivatization can be determined based on considerations including, but not limited to, the particular properties or functions of the antibody or antibody fragment to be improved, whether the derivative will be used in a therapy under defined conditions, etc.

In another embodiment, conjugates of the antibodies or antibody fragments and nonproteinaceous moiety that may be selectively heated by exposure to radiation are provided. In one embodiment, the nonproteinaceous moiety is a carbon nanotube (Kam et al., *Proc. Natl. Acad. Sci. USA*, vol. 102, pp. 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

The anti-EpCAM antibodies or antibody fragments of the invention, or their variants, have a higher binding affinity to EpCAM under a condition in a tumor microenvironment than under a condition in a non-tumor microenvironment. In one embodiment, the condition in tumor microenvironment and the condition in a non-tumor microenvironment are both pH. The anti-EpCAM antibodies or antibody fragments of the invention thus can selectively bind to EpCAM at a pH about 5.0-6.8 but will have a lower binding affinity to EpCAM at a pH about 7.2-7.8 encountered in a normal non-tumor microenvironment. As shown Examples 3 and 6, the anti-EpCAM antibodies or antibody fragments have higher binding affinity to EpCAM at pH 6.0 that at pH 7.4.

In certain embodiments, the anti-EpCAM antibodies or antibody fragments of the present invention have a dissociation constant (Kd) with EpCAM under a condition in tumor microenvironment of about ≤1 µM, ≤100 nM, ≤10 nM, ≤1 nM, ≤0.1 nM, ≤0.01 nM, or ≤0.001 nM (e.g. $10^{-8}$M or less, or from $10^{-8}$M to $10^{-13}$M, or from $10^{-9}$M to $10^{-13}$M). In one embodiment, the ratio of the Kd of the antibody or antibody fragment with EpCAM at the condition in tumor microenvironment to the Kd at the same condition in non-tumor microenvironment is at least about 1.5:1, at least about 2:1, at least about 3:1, at least about 4:1, at least about 5:1, at least about 6:1, at least about 7:1, at least about 8:1, at least about 9:1, at least about 10:1, at least about 20:1, at least about 30:1, at least about 50:1, at least about 70:1, or at least about 100:1.

In one embodiment, Kd is measured by a radiolabeled antigen binding assay (RIA) performed with the Fab version of an antibody of interest and its antigen using the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CMS chips at about 10 response units (RU). Briefly, carboxymethylated dextran biosensor chips (CMS, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, twofold serial dilutions of Fab (0.78 nM to 500 nM) are injected in PBS with 0.05% polysorbate 20 (TWEEN-20™) surfactant (PBST) at 25° C. at a flow rate of approximately 25 μl/min Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

The anti-EpCAM antibodies of the invention may be a chimeric, humanized or human antibody. In one embodiment, an anti-EpCAM antibody fragment is employed, e.g., a Fv, Fab, Fab', Fab'-SH, scFv, a diabody, a triabody, a tetrabody or an F(ab')₂ fragment and multispecific antibodies formed from antibody fragments. In another embodiment, the antibody is a full length antibody, e.g., an intact IgG antibody or other antibody class or isotype as defined herein. For a review of certain antibody fragments, see Hudson et al. *Nat. Med.*, vol. 9, pp. 129-134, 2003. For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')₂ fragments comprising salvage receptor binding epitope residues and having increased in vivo half-life, see U.S. Pat. No. 5,869,046.

The diabodies of the invention may be bivalent or bispecific. See, for example, EP 404,097; WO 1993/01161; Hudson et al., *Nat. Med.* 9:129-134 (2003); and Hollinger et al., *Proc. Natl. Acad. Sci. USA*, vol. 90, pp. 6444-6448, 1993 for examples of diabodies. Examples of triabodies and tetrabodies are also described in Hudson et al., *Nat. Med.*, vol. 9, pp. 129-134, 2003.

In some embodiments, the invention comprises singledomain antibody fragments comprising all or a portion of the heavy chain variable domain or all or a portion of the light chain variable domain of an antibody. In certain embodiments, a single-domain antibody is a human singledomain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

In some embodiments, the anti-EpCAM antibodies of the invention may be chimeric antibodies. Certain chimeric antibodies are described, e.g., in U.S. Pat. No. 4,816,567; and Morrison et al., *Proc. Natl. Acad. Sci. USA*, vol. 81, pp. 6851-6855, 1984). In one example, the chimeric antibody comprises a non-human variable region (e.g., a variable region derived from a mouse, rat, hamster, rabbit, or nonhuman primate, such as a monkey) and a human constant region. In a further example, the chimeric antibody is a "class switched" antibody in which the class or subclass of the antibody has been changed relative to the class or subclass of the parent antibody. Chimeric antibodies include antigen-binding fragments thereof.

In certain embodiments, the chimeric antibody of the invention is a humanized antibody. Typically, such a nonhuman antibody is humanized to reduce immunogenicity to humans, while retaining the specificity and affinity of the parental non-human antibody. Generally, a humanized antibody comprises one or more variable domains in which CDRs (or portions thereof) are derived from a non-human antibody, and FRs (or portions thereof) are derived from human antibody sequences. A humanized antibody may optionally also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, *Front. Biosci.*, vol. 13, pp. 1619-1633, 2008, and are further described, e.g., in Riechmann et al., *Nature*, vol. 332, pp. 323-329, 1988; Queen et al., *Proc. Nat'l Acad. Sci. USA*, vol. 86, pp. 10029-10033, 1989; U.S. Pat. Nos. 5,821,337, 7,527,791, 6,982,321, and 7,087,409; Kashmiri et al., *Methods*, vol. 36, pp. 25-34, 2005 (describing SDR (a-CDR) grafting); Padlan, *Mol. Immunol.*, vol. 28, pp. 489-498, 1991 (describing "resurfacing"); Dall'Acqua et al., *Methods*, vol. 36, pp. 43-60, 2005 (describing "FR shuffling"); and Osbourn et al., *Methods*, vol. 36, pp. 61-68, 2005 and Klimka et al., *Br. J. Cancer*, vol. 83, pp. 252-260, 2000 (describing the "guided selection" approach to FR shuffling).

Human framework regions that may be used for humanization include but are not limited to: framework regions selected using the "best-fit" method (see, e.g., Sims et al. *J. Immunol.*, vol. 151, p. 2296, 1993); framework regions derived from the consensus sequence of human antibodies of a particular subgroup of light or heavy chain variable regions (see, e.g., Carter et al. *Proc. Natl. Acad. Sci. USA*, vol. 89, p. 4285, 1992; and Presta et al. *J. Immunol.*, vol. 151, p. 2623, 1993); human mature (somatically mutated) framework regions or human germline framework regions (see, e.g., Almagro and Fransson, *Front. Biosci.*, vol. 13, pp. 1619-1633, 2008); and framework regions derived from screening FR libraries (see, e.g., Baca et al., *J. Biol. Chem.*, vol. 272, pp. 10678-10684, 1997 and Rosok et al., *J. Biol. Chem.*, vol. 271, pp. 22611-22618, 1996).

In some embodiments, the anti-EpCAM antibodies of the invention are multispecific, e.g. bispecific antibodies. Multispecific antibodies are monoclonal antibodies that have binding specificities for at least two different sites. In certain embodiments, one of the binding specificities is for EpCAM and the other is for another antigen such as CD3. One specific example of this is a bispecific antibody with binding specificities for EpCAM and CD3+. A bispecific conditionally active antibody may be mono conditionally active or dual conditionally active. Thus, in the case of the mono conditionally active bispecific antibody, one of the binding sites is conditionally active and the other is not, e.g. a wild type (WT) EpCAM paired with a conditionally active (CAB) CD3+ or a CAB EpCAM paired with a WT CD3+. In the case of a dual conditionally active antibody, both binding sites are conditionally active as in CAB EpCAM x CAB CD3+.

The bispecific antibodies of the present invention may include antibodies as set forth in the following table:

| Antibody or Antibody Fragment | VK region | Light Chain | VH region | Anti-CD3-scFv |
|---|---|---|---|---|
| BA-150-06-BF3 Mono CAB | SEQ ID NO: 35 | SEQ ID NO: 36 | SEQ ID NO: 37 | SEQ ID NO: 38 |
| BA-150-15-01-03-BF46 Dual CAB | SEQ ID NO: 43 | SEQ ID NO: 44 | SEQ ID NO: 45 | SEQ ID NO: 46 |
| BA-150-16-01-02 BF45 Mono CAB | SEQ ID NO: 47 | SEQ ID NO: 48 | SEQ ID NO: 49 | SEQ ID NO: 50 |

The bispecific antibody or antibody fragment may be specified by the VK region or by the entire light chain. Thus, the bispecific antibody may also be a bispecific antibody or antibody fragment which includes a heavy chain variable region and a light chain variable region each region independently having at least 80%, 85%, 90%, 95%, 98%, 99% or 100% identity to a combination of a VK region selected from the group consisting of: SEQ ID NOS: 35, 43 and 47 and a VH region selected from the group consisting of SEQ ID NOS: 37, 45 and 49. The same bispecific antibody or antibody fragment may instead include a light chain having at least 80%, 85%, 90%, 95%, 98%, 99% or 100% identity to a light chain selected from the group consisting of: SEQ ID NOS: 36, 44 and 48. The same bispecific antibody or antibody fragment may include an anti-CD3-scFv having at least 80%, 85%, 90%, 95%, 98%, 99% or 100% identity to an anti-CD3-scFv selected from the group consisting of: SEQ ID NOS: 38, 46 and 50.

Multispecific antibodies can be mono, dual, tri-, etc. conditionally active. Thus, any one or more of the binding regions of the multispecific antibody may be conditionally active.

In certain embodiments, bispecific antibodies may bind to two different epitopes of EpCAM. Bispecific antibodies may also be used to localize cytotoxic agents to cells which express EpCAM. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, Nature, vol. 305, pp. 537-540, 1983), WO 93/08829, and Traunecker et al., EMBO J. vol. 10, pp. 3655-3659, 1991), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, vol. 229, pp. 81-83, 1985); using leucine zippers to produce bi-specific antibodies (see, e.g., Kostelny et al., J. Immunol., vol. 148, pp. 1547-1553, 1992); using "diabody" technology for making bispecific antibody fragments (see, e.g., Hollinger et al., Proc. Natl. Acad. Sci. USA, vol. 90, pp. 6444-6448, 1993); and using single-chain Fv (scFv) dimers (see, e.g. Gruber et al., J. Immunol., vol. 152, pp. 5368-5374, 1994); and preparing trispecific antibodies as described, e.g., in Tutt et al. J. Immunol., vol. 147, pp. 60-69, 1991.

Engineered antibodies with three or more functional antigen binding sites, including "Octopus antibodies," are also included herein (see, e.g. US 2006/0025576A1).

The anti-EpCAM antibodies or antibody fragments of the invention may be produced using recombinant methods and compositions, which are described in detail in US 2016/0017040.

The physical/chemical properties and/or biological activities of the anti-EpCAM antibodies or antibody fragments of the invention may be tested and measured by various assays known in the art. Some of these assays are described in U.S. Pat. No. 8,853,369.

B. Immunoconjugates

In another aspect, the invention also provides immunoconjugates comprising an anti-EpCAM antibody or antibody fragment conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), and radioactive isotopes.

In one embodiment, the immunoconjugate is an antibody-drug conjugate (ADC) in which an antibody or antibody fragment is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res., vol. 53, pp. 3336-3342, 1993; and Lode et al., Cancer Res., vol. 58, pp. 2925-2928, 1998); an anthracycline such as daunomycin or doxorubicin (see Kratz et al., Current Med. Chem., vol. 13, pp. 477-523, 2006; Jeffrey et al., Bioorganic & Med. Chem. Letters, vol. 16, pp. 358-362, 2006; Torgov et al., Bioconj. Chem., vol. 16, pp. 717-721, 2005; Nagy et al., Proc. Natl. Acad. Sci. USA, vol. 97, pp. 829-834, 2000; Dubowchik et al., Bioorg. & Med. Chem. Letters, vol. 12, vol. 1529-1532, 2002; King et al., J. Med. Chem., vol. 45, pp. 4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody or antibody fragment as described herein conjugated to an enzymatically active toxin or fragment thereof, including but not limited to diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), Momordica charantiainhibitor, curcin, crotin, Sapaonaria officinalis inhibitor, gelonin, mitogellin, restrictocin, phenomycin, enomycin, and the tricothecenes.

In another embodiment, an immunoconjugate comprises an antibody or antibody fragment as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese and iron.

In some embodiments, the immunoconjugate comprises a radioactive agent, which may be selected from an alpha emitter, a beta emitter and a gamma emitter. Examples of alpha emitters are $^{211}$At, $^{210}$Bi, $^{212}$Bi, $^{211}$Bi, $^{223}$Ra, $^{224}$K, $^{225}$Ac and $^{227}$Th. Examples of beta-emitters are $^{67}$Cu. $^{90}$Y, $^{131}$I, $^{153}$Sm, $^{166}$Ho and $^{186}$Re. Examples of gamma emitters are $^{60}$Co, $^{137}$Ce, $^{55}$Fe, $^{54}$Mg, $^{203}$Hg, and $^{133}$Ba.

Conjugates of an antibody/antibody fragment and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science*, vol. 238, pp. 1098-, 1987. Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.*, vol. 52, pp. 127-131, 1992; U.S. Pat. No. 5,208,020) may be used.

The immunoconjugates herein expressly contemplate, but are not limited to conjugates prepared with cross-linker reagents including, but not limited to, BMPS, EMCS, GMBS, HBVS, LC-SMCC, MBS, MPBH, SBAP, SIA, SLAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

An exemplary embodiment of an ADC includes an antibody or antibody fragment (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I as Ab-(L-D)$_p$, where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC's of Formula I include, but are not limited to, antibodies that have 1, 2, 3, or 4 engineered cysteine amino acids (Lyon et al., *Methods in Enzym.*, vol. 502, pp. 123-138, 2012). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

Linkers are used to conjugate a moiety to the antibody to form an immunoconjugate such as an ADC. Suitable linkers are described in WO 2017/180842.

Some drug moieties that may be conjugated to the antibodies are described in WO 2017/180842.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu. In some embodiments, when an immunoconjugate is used for detection, it may comprise a radioactive atom for scintigraphic studies, for example Tc$^{99}$ or I$^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as Tc$^{99}$, I$^{123}$, Re$^{186}$, Re$^{188}$ and In$^{111}$ can be attached via a cysteine residue in the antibody. In some embodiments, yttrium-90 can be attached via a lysine residue of the antibody. In some embodiments, the IODOGEN method (Fraker et al., *Biochem. Biophys. Res. Commun.*, vol. 80, pp. 49-57, 1978) can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysis, subtilisin, carboxypeptidases and cathepsins (such as cathepsins B and L), which are useful for converting peptide-containing prodrugs into free drugs; D-alanyl-carboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature*, vol. 312, pp. 604-608, 1984.

Drug loading in the conjugates is represented by p, the average number of drug moieties per antibody. Drug loading may range from 1 to 20 drug moieties per antibody. The conjugates of the present invention may have a range of drug moieties, from 1 to 20. The average number of drug moieties per antibody use in the preparation of the conjugates from conjugation reactions may be characterized by conventional means such as mass spectroscopy, ELISA assay, and HPLC.

For some antibody-drug conjugates (ADC), the drug loading may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety. Indeed, most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

C. Methods and Compositions for Diagnostics and Detection

In certain embodiments, any of the anti-EpCAM antibodies or antibody fragments provided herein may be used for detecting the presence of EpCAM in a biological sample, either quantitatively or qualitatively. In certain embodiments, a biological sample comprises a cell or tissue, such as breast, pancreas, esophagus, lung and/or brain cells or tissue.

A further aspect of the invention relates to an anti-EpCAM antibody or antibody fragment of the invention for diagnosing and/or monitoring a cancer or another disease in which EpCAM expression levels are increased or decreased from a normal physiological level at least one location in the body.

In a preferred embodiment, antibodies or antibody fragments of the invention may be labelled with a detectable molecule or substance, such as a fluorescent molecule, a radioactive molecule or any other label known in the art as above described. For example, an antibody or antibody fragment of the invention may be labelled with a radioactive molecule. For example, suitable radioactive molecules include but are not limited to radioactive atoms used for scintigraphic studies such as $^{123}$I, $^{124}$I, $^{111}$In, $^{186}$Re, and $^{188}$Re. Antibodies or antibody fragments of the invention may also be labelled with a spin label for nuclear magnetic resonance (NMR) imaging, such as iodine-123, iodine-131, indium-III, fluorine-19, carbon-13, nitrogen-15, oxygen-17, gadolinium, manganese or iron. Following administration of the antibody, the distribution of the radiolabeled antibody within the patient is detected. Any suitable known method can be used. Some non-limiting examples include, computed tomography (CT), position emission tomography (PET), magnetic resonance imaging (MRI), fluorescence, chemiluminescence and sonography.

Antibodies or antibody fragments of the invention may be useful for diagnosing and staging of cancer and diseases associated with EpCAM overexpression. Cancers associated with EpCAM overexpression may include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer or other EpCAM expressing or overexpressing hyperproliferative diseases.

Antibodies or antibody fragments of the invention may be useful for diagnosing diseases other than cancers for which EpCAM expression is increased or decreased. Both the (soluble or cellular EpCAM forms can be used for such diagnoses. Typically, such diagnostic methods involve use of a biological sample obtained from the patient. The biological sample encompasses a variety of sample types obtained from a subject that can be used in a diagnostic or monitoring assay. Biological samples include but are not limited to blood and other liquid samples of biological origin, solid tissue samples such as a biopsy specimen or a tissue culture or cells derived therefrom, and the progeny thereof. For example, biological samples include cells obtained from a tissue sample collected from an individual suspected of having a cancer associated with EpCAM overexpression, and in preferred embodiments from glioma, gastric, lung, pancreatic, breast, prostate, renal, hepatic and endometrial. Biological samples encompass clinical samples, cells in culture, cell supernatants, cell lysates, serum, plasma, biological fluid, and tissue samples.

In a particular embodiment, the invention is a method of diagnosing a cancer associated with EpCAM overexpression in a subject by detecting EpCAM on cells from the subject using the antibody of the invention. In particular, said method may include steps of:

1) contacting a biological sample of a subject with an antibody or antibody fragment according to the invention under conditions suitable for the antibody or antibody fragment to form complexes with cells in the biological sample that express EpCAM; and (b) detecting and/or quantifying said complexes, whereby detection of said complexes is indicative of a cancer associated with EpCAM overexpression.

In order to monitor the progress of a cancer, the method according to the invention may be repeated at different times, in order to determine if antibody binding to the samples increases or decreases, wherefrom it can be determined if the cancer has progressed, regressed or stabilized.

In a particular embodiment, the invention is a method of diagnosing a disease associated with the expression or overexpression of EpCAM. Examples of such diseases may include cancers, human immune disorders, thrombotic diseases (thrombosis and atherothrombosis), and cardiovascular diseases In one embodiment, an anti-EpCAM antibody or antibody fragment for use in a method of diagnosis or detection is provided. In a further aspect, a method of detecting the presence of EpCAM4 in a biological sample is provided. In a further aspect, a method of quantifying the amount of EpCAM in a biological sample is provided. In certain embodiments, the method comprises contacting the biological sample with an anti-EpCAM antibody or antibody fragment as described herein under conditions permissive for binding of the anti-EpCAM antibody or antibody fragment to EpCAM, and detecting whether a complex is formed between the anti-EpCAM antibody or antibody fragment and EpCAM. Such a method may be carried out in vitro or in vivo. In one embodiment, an anti-EpCAM4 antibody or antibody fragment is used to select subjects eligible for therapy. In some embodiments, the therapy will include administration of an anti-EpCAM antibody or antibody fragment to the subject.

In certain embodiments, labeled anti-EpCAM antibodies or antibody fragments are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

D. Pharmaceutical Formulations

The anti-EpCAM antibodies or antibody fragments have cell killing activity. This cell killing activity extends to multiple different types of cell lines. Further, these antibodies or antibody fragments, once conjugated to a cytotoxic agent, can reduce tumor size and may exhibit reduced toxicity. Thus, the anti-EpCAM antibodies, fragments or immunoconjugates thereof may be useful for treating proliferative diseases associated with EpCAM expression. The antibodies, fragments or immunoconjugates may be used alone or in combination with any suitable agent or other conventional treatments.

The anti-EpCAM antibody or antibody fragment may be used to treat diseases associated with EpCAM expression, overexpression or activation. There are no particular limitations on the types of cancer or tissue that can be treated other than the requirement for EpCAM expression. Examples include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer. More preferable cancers are glioma, gastric, lung, pancreatic, breast, prostate, renal, hepatic and endometrial cancer.

Anti-EpCAM antibodies or antibody fragments are potential activators of the innate immune response and thus may be used in the treatment of human immune disorders, such as sepsis. The anti-EpCAM antibody or antibody fragment of the invention may also be used as adjuvants for immunization such as for vaccines and as anti-infection agents against, for example, bacteria, viruses and parasites.

Anti-EpCAM antibody or antibody fragment may be used to protect against, prevent or treat thrombotic diseases such as venous and arterial thrombosis and atherothrombosis. Anti-EpCAM antibody or antibody fragment may also be used to protect against, prevent or treat cardiovascular diseases as well as to prevent or inhibit the entry of viruses such as Lassa and Ebola viruses and to treat viral infections.

In each of the embodiments of the treatment methods described herein, the anti-EpCAM antibody, antibody fragment or anti-EpCAM antibody or antibody fragment immunoconjugate may be delivered in a manner consistent with conventional methodologies associated with management of the disease or disorder for which treatment is sought. In accordance with the disclosure herein, an effective amount of the antibody, antibody fragment or immunoconjugate is administered to a subject in need of such treatment for a time and under conditions sufficient to prevent or treat the disease or disorder. Thus, an aspect of the invention relates to a method for treating a disease associated with the expression of EpCAM comprising administering to a subject in need thereof with a therapeutically effective amount of an antibody, antibody fragment or immunoconjugate of the invention.

For administration, the anti-EpCAM antibody, antibody fragment or immunoconjugate may be formulated as a pharmaceutical composition. The pharmaceutical composition including anti-EpCAM antibody, antibody fragment or immunoconjugate can be formulated according to known methods for preparing pharmaceutical compositions. In such methods, the therapeutic molecule is typically combined with a mixture, solution or composition containing a pharmaceutically acceptable carrier.

A pharmaceutically acceptable carrier is a material that can be tolerated by a recipient patient. Sterile phosphate-buffered saline is one example of a pharmaceutically acceptable carrier. Other suitable pharmaceutically acceptable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc. These considerations can be taken into account by a skilled person to formulate suitable pharmaceutical compositions. The pharmaceutical compositions of the invention can be formulated for topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition of, for example, sterilized water or physiological saline, permit the constitution of injectable solutions.

In some embodiments, tonicity agents, sometimes known as "stabilizers" are present to adjust or maintain the tonicity of a liquid in a composition. When used with large, charged biomolecules such as proteins and antibodies, they are often termed "stabilizers" because they can interact with the charged groups of the amino acid side chains, thereby lessening the potential for inter- and intra-molecular interactions. Tonicity agents can be present in any amount of from 0.1% to 25% by weight, preferably 1 to 5% of the pharmaceutical composition. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients may include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") may be employed to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants may be present in a concentration range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride The doses used for the administration can be adapted as a function of various parameters, and in particular as a function of the mode of administration used, of the relevant pathology, or alternatively of the desired duration of treatment. To prepare pharmaceutical compositions, an effective amount of the antibody or antibody fragment may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in a water suitably mixed with a surfactant. Dispersions can also be prepared in glycerol, liquid polyethylene glycols, and mixtures thereof and in oils. Under ordinary conditions of storage and use, these preparations contain a preservative to prevent the growth of microorganisms.

The anti-EpCAM antibody or antibody fragment can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with one or more of the other ingredients enumerated above, as may be required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of dimethyl sulfoxide (DMSO) as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies or antibody fragments may be formulated within a therapeutic mixture to deliver about 0.0001 to 10.0 milligrams, or about 0.001 to 5 milligrams, or about 0.001 to 1 milligrams, or about 0.001 to 0.1 milligrams, or about 0.1 to 1.0 or even about 10 milligrams per dose. Multiple doses can also be administered at selected time intervals.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies or antibody fragments into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to degrade in vivo. Biodegradable polyalkyl-cyanoacrylate nanoparticles that meet these requirements are contemplated for use in the present invention, and such particles may be easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 ∈, containing an aqueous solution in the core. The physical characteristics of liposomes depend on pH, ionic strength and the presence of divalent cations Pharmaceutical formulations containing an anti-EpCAM antibody or antibody fragment as described herein are prepared by mixing such antibody or antibody fragment having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredient as necessary for the particular indication being treated. Preferably, ingredients with complementary activities that do not adversely affect each other may be combined into a single formulation. For example, it may be desirable to provide an EGFR antagonist (such as erlotinib), an anti-angiogenic agent (such as a VEGF antagonist which may be an anti-VEGF antibody) or a chemotherapeutic agent (such as a taxoid or a platinum agent) in addition to the anti-CTLA4 antibody, antibody fragment or immunoconjugate of the present invention. Such active ingredients are suitably present in combination in amounts that are effective for the purpose intended.

In one embodiment, the anti-EpCAM antibody, antibody fragment or immunoconjugate of the present invention is combined in a formulation with another antibody or antibody fragment against an antigen selected from CTLA4, PD1, PD-L1, AXL, ROR2, CD3, HER2, B7-H3, ROR1, SFRP4 and a WNT protein including WNT1, WNT2, WNT2B, WNT3, WNT4, WNTSA, WNTSB, WNT6, WNT7A, WNT7B, WNT8A, WNT8B, WNT9A, WNT9B, WNT10A, WNT10B, WNT11, WNT16. The combination may be in the form of two separate molecules: the anti-EpCAM antibody, antibody fragment or immunoconjugate of the present invention, and another antibody or antibody fragment. Alternatively, the combination may also be the form of a single molecule with binding affinity to both EpCAM and the other antigen, thus forming a multispecific (e.g. bispecific) antibody.

Active ingredients may be encapsulated in microcapsules prepared, for example, by coacervation techniques or by interfacial polymerization. For example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions may be employed. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or antibody fragment, which matrices may be in the form of shaped articles, e.g. films, or microcapsules.

The formulations to be used for in vivo administration are generally sterile. Sterility may be readily accomplished, e.g., by filtration through sterile filtration membranes.

E. Therapeutic Methods and Compositions

Any of the anti-EpCAM antibodies or antibody fragments provided herein may be used in therapeutic methods. In one aspect, an anti-EpCAM antibody or antibody fragment for use as a medicament is provided. In further aspects, an anti-EpCAM antibody or antibody fragment for use in treating cancer (e.g., breast cancer, non-small cell lung cancer, pancreatic cancer, brain cancer, cancer of pancreas, brain, kidney, ovary, stomach, leukemia, uterine endometrium, colon, prostate, thyroid, liver, osteosarcoma, and/or melanoma) is provided. In certain embodiments, an anti-EpCAM antibody or antibody fragment for use in a method of treatment is provided. In certain embodiments, the invention provides an anti-EpCAM antibody or antibody fragment for use in a method of treating an individual having cancer comprising administering to the individual an effective amount of the anti-EpCAM antibody or antibody fragment. In certain embodiments, the invention provides an anti-EpCAM antibody or antibody fragment for use in a method of treating an individual having an immune disorder (e.g., an autoimmune disorder), a cardiovascular disorder (e.g., atherosclerosis, hypertension, thrombosis), an infectious disease (e.g., Ebola virus, Marburg virus) or diabetes, comprising administering to the individual an effective amount of the anti-EpCAM antibody or antibody fragment. In one such embodiment, the method further comprises administering to the individual an effective amount of at least one additional therapeutic agent, e.g., as described below. In further embodiments, the invention provides an anti-EpCAM antibody or antibody fragment for use in inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function.

In certain embodiments, the invention provides an anti-EpCAM antibody or antibody fragment for use in a method of inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual comprising administering to the individual an effective of the anti-EpCAM antibody or antibody fragment to inhibit angiogenesis, inhibit cell proliferation, inhibit immune function, inhibit inflammatory cytokine secretion (e.g., from tumor-associated macrophages), inhibit tumor vasculature development (e.g., intratumoral vasculature or tumor-associated vasculature), and/or inhibit tumor stromal function. An "individual" according to any of the above embodiments is preferably a human.

In a further aspect, the invention provides for the use of an anti-EpCAM antibody or antibody fragment in the manufacture or preparation of a medicament. In one embodiment, the medicament is for treatment of cancer (in some embodiments, breast cancer, non-small cell lung cancer, pancreatic cancer, brain cancer, cancer of the pancreas, brain, kidney, ovary, stomach, leukemia, uterine endometrium, colon, prostate, thyroid, liver, osteosarcoma, and/or melanoma). In a further embodiment, the medicament is for use in a method of treating cancer comprising administering to an individual having cancer an effective amount of the medicament. In a further embodiment, the medicament is for use in a method of treating an immune disorder (e.g., an autoimmune disorder), a cardiovascular disorder (e.g., atherosclerosis, hypertension, thrombosis), an infectious disease (e.g., Ebola virus, Marburg virus) or diabetes, comprising administering to the individual an effective amount of the anti-EpCAM antibody or antibody fragment. In one such embodiment, the method further comprises administering to the individual an effective amount of at least one additional therapeutic agent, e.g., as described below. In a further embodiment, the medicament is for inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function. In a further embodiment, the medicament is for use in a method of inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual comprising administering to the individual an amount effective of the medicament to inhibit angiogenesis, inhibit cell proliferation, promote immune function, induce inflammatory cytokine section (e.g., from tumor-associated macrophages), inhibit tumor vasculature development (e.g., intratumoral vasculature or tumor-associated vasculature), and/or inhibit tumor stromal function. An "individual" according to any of the above embodiments may be a human.

In a further aspect, the invention provides a method for treating a cancer. In one embodiment, the method comprises administering to an individual having such cancer an effective amount of an anti-EpCAM antibody or antibody fragment. In one such embodiment, the method further comprises administering to the individual an effective amount of at least one additional therapeutic agent, as described below. An "individual" according to any of the above embodiments may be a human In a further aspect, the invention provides a method for treating an immune disorder (e.g., an autoimmune disorder), a cardiovascular disorder (e.g., atherosclerosis, hypertension, thrombosis), an infectious disease (e.g., Ebola virus, Marburg virus) or diabetes. In one such embodiment, the method further comprises administering to the individual an effective amount of at least one additional therapeutic agent, as described below. An "individual" according to any of the above embodiments may be a human.

In a further aspect, the invention provides a method for inhibiting angiogenesis, inhibiting cell proliferation, inhibiting immune function, inhibiting inflammatory cytokine secretion (e.g., from tumor-associated macrophages), inhibiting tumor vasculature (e.g., intratumoral vasculature or tumor-associated vasculature), and/or inhibiting tumor stromal function in an individual. In one embodiment, the method comprises administering to the individual an effective amount of an anti-EpCAM antibody or antibody fragment to inhibit angiogenesis, inhibit cell proliferation, promote immune function, induce inflammatory cytokine section (e.g., from tumor-associated macrophages), inhibit tumor vasculature development (e.g., intratumoral vasculature or tumor-associated vasculature), and/or inhibit tumor stromal function. In one embodiment, an "individual" is a human.

In a further aspect, the invention provides pharmaceutical formulations comprising any of the anti-EpCAM antibodies or antibody fragments provided herein, e.g., for use in any of the above therapeutic methods. In one embodiment, a pharmaceutical formulation comprises any of the anti-EpCAM antibodies or antibody fragments provided herein and a pharmaceutically acceptable carrier. In another embodiment, a pharmaceutical formulation comprises any of the anti-EpCAM antibodies or antibody fragments provided herein and at least one additional therapeutic agent, e.g., as described below.

In each and every treatment described above, the antibodies or antibody fragments of the invention can be used alone, as immunoconjugates or in combination with other agents in a therapy. For instance, an antibody of the invention may be co-administered with at least one additional therapeutic agent. In certain embodiments, an additional therapeutic agent is an anti-angiogenic agent. In certain embodiments, an additional therapeutic agent is a VEGF antagonist (in some embodiments, an anti-VEGF antibody, for example bevacizumab). In certain embodiments, an additional therapeutic agent is an EGFR antagonist (in some embodiment, erlotinib). In certain embodiments, an additional therapeutic agent is a chemotherapeutic agent and/or a cytostatic agent. In certain embodiments, an additional therapeutic agent is a taxoid (e.g., paclitaxel) and/or a platinum agent (e.g., carbo platinum). In certain embodiments the additional therapeutic agent is an agent that enhances the patient's immunity or immune system.

Such combination therapies noted above encompass combined administration (where two or more therapeutic agents are included in the same or separate formulations), and separate administration, in which case, administration of the antibody or antibody fragment can occur prior to, simultaneously, and/or following, administration of the additional therapeutic agent and/or adjuvant. Antibodies or antibody fragments can also be used in combination with radiation therapy.

The anti-EpCAM antibodies or antibody fragments may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or antibody fragment need not be, but is optionally formulated with one or more agents currently used to prevent or treat the disorder in question. The effective amount of such other agents depends on the amount of antibody or antibody fragment present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or antibody fragment (when used alone or in combination with one or more other additional therapeutic agents) will depend on the type of disease to be treated, the type of antibody or antibody fragment, the severity and course of the disease, whether the antibody or antibody fragment is administered for preventive or therapeutic purposes, previous therapy, the patient's clinical history and response to the antibody or antibody fragment, and the discretion of the attending physician. The antibody or antibody fragment is suitably administered to the patient at one time or over a series of treatments. Depending on the type and severity of the disease, about 1 µg of antibody or antibody fragment/kg bodyweight of the patient to 40 mg of antibody or antibody fragment/kg bodyweight of the patient can be an initial candidate dosage for administration to the patient, whether, for example, by one or more separate administrations, or by continuous infusion. One typical daily dosage might range from about 1 µg of antibody or antibody fragment/kg bodyweight of the patient to 100 mg of antibody or antibody fragment/kg bodyweight of the patient or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody or antibody fragment). An initial higher loading dose, followed by one or more lower doses may be administered. However, other dosage regimens may be useful. The progress of this therapy is easily monitored by conventional techniques and assays.

Specific dosages of the anti-EpCAM antibody or antibody fragment of the present invention that may be administered for the prevention or treatment of a disease in a subject may be about 0.3, 0.6, 1.2, 18, 2.4, 3.0, 3.6, 4.2, 4.8, 5.4, 6.0, 6.6, 7.2, 7.8, 8.4, 9.0, 9.6 or 10.2 mg of antibody or antibody fragment/kg bodyweight of the patient. In certain embodiments, the dosage may be in a range of 0.3-2.4, 2.4-4.2, 4.2-6.0, 6.0-7.8, 7.8-10.2, 10.2-12, 12-14, 14-16, 16-18 or 18-20 mg of antibody or antibody fragment/kg bodyweight of the patient. The dosage of the antibody or antibody fragment will remain the same if administered in the form of a bispecific antibody, in combination with another immune checkpoint inhibitor or another antibody or antibody fragment or as an immunoconjugate. Further, a polypeptide having anti-EpCAM activity will be administered in the same amounts as the antibody or antibody fragment.

A single dose of pharmaceutical formulation of the present invention may contain an amount of the anti-EpCAM antibody or antibody fragment of the present invention of from about 45 µg of antibody or antibody fragment from about 13,600 mg, or from about 45 µg of antibody or antibody fragment from about 5440 mg. In some embodiments, a single dose of pharmaceutical formulation of the present invention may contain an amount of the anti-EpCAM antibody or antibody fragment of the present invention of from to 135 mg to 1,387 mg, or an amount such as 135, 235, 335, 435, 535, 635, 735, 835, 935, 1035, 1135, 1235, 1387 mg. In certain embodiments, the amount of the anti-EpCAM antibody or antibody fragment of the present invention in a single dose of the pharmaceutical formulation is in the range of 135-235, 235-335, 335-435, 435-535, 535-635, 635-735, 735-835, 835-935, 935-1035, 1035-1135, 1135-1235, 1235-1387 mg. The amount of the antibody or antibody fragment in the single dose of the pharmaceutical formulation will remain the same if administered in the form of a bispecific antibody, in combination with another immune checkpoint inhibitor or as an immunoconjugate, or in combination with another antibody or antibody fragment against another antigen as disclosed herein. Further, a polypeptide having anti-EpCAM activity will be included in the single dose of the pharmaceutical formulation in the same amounts as the antibody or antibody fragment.

In one example, the anti-EpCAM antibody or antibody fragment may be conjugated to an immune checkpoint inhibitor molecule or may form part of a bispecific antibody with an immune checkpoint inhibitor.

The combination can be the anti-EpCAM antibody or antibody fragment disclosed in this application and the immune checkpoint inhibitor molecule administered as separate molecules or as a bispecific antibody. Such a bispecific antibody has a binding activity to EpCAM and a second binding activity to the immune checkpoint.

The immune checkpoint may be selected from CTLA4, LAG3, TIM3, TIGIT, VISTA, BTLA, OX40, CD40, 4-1BB, PD-1, PD-L1, and GITR (Zahavi and Weiner, *International Journal of Molecular Sciences*, vol. 20, 158, 2019). Additional immune checkppoints include B7-H3, B7-H4, KIR, A2aR, CD27, CD70, DR3, and ICOS (Manni et al., Immune checkpoint blockade and its combination therapy with small-molecule inhibitors for cancer treatment, Bbacan, https://doi.org/10.1016/j.bbcan.2018.12.002, 2018).

The immune checkpoint is preferably CTLA4, PD-1 or PD-L1.

It is understood that any of the above formulations or therapeutic methods may be carried out using an antibody fragment or an immunoconjugate of the invention in place of or in addition to an anti-EpCAM antibody.

Enhancing the host's immune function to combat tumors is the subject of increasing interest. Conventional methods include (i) APC enhancement, such as (a) injection into the tumor of DNA encoding foreign MHC alloantigens, or (b) transfecting biopsied tumor cells with genes that increase the probability of immune antigen recognition (e.g., immune stimulatory cytokines, GM-CSF, co-stimulatory molecules B7.1, B7.2) of the tumor, (iii) adoptive cellular immunotherapy, or treatment with activated tumor-specific T-cells. Adoptive cellular immunotherapy includes isolating tumor-infiltrating host T-lymphocytes, expanding the population in vitro, such as through stimulation by IL-2 or tumor or both. Additionally, isolated T-cells that are dysfunctional may be also be activated by in vitro application of the anti-PD-L1 antibodies of the invention. T-cells that are so-activated may then be readministered to the host. One or more of these methods may be used in combination with administration of the antibody, antibody fragment or immunoconjugate of the present invention.

Traditional therapies for cancer include the following: (i) radiation therapy (e.g., radiotherapy, X-ray therapy, irradiation) or the use of ionizing radiation to kill cancer cells and shrink tumors. Radiation therapy can be administered either externally via external beam radiotherapy (EBRT) or internally via brachytherapy; (ii) chemotherapy, or the application of cytotoxic drug which generally affect rapidly dividing cells; (iii) targeted therapies, or agents which specifically affect the deregulated proteins of cancer cells (e.g., tyrosine kinase inhibitors imatinib, gefitinib; monoclonal antibodies, photodynamic therapy); (iv) immunotherapy, or enhancement of the host's immune response (e.g., vaccine); (v) hormonal therapy, or blockade of hormone (e.g., when tumor is hormone sensitive), (vi) angiogenesis inhibitor, or blockade of blood vessel formation and growth, and (vii) palliative care, or treatment directed to improving the quality of care to reduce pain, nausea, vomiting, diarrhea and hemorrhage. Pain medication such as morphine and oxycodone, anti-emetics such as ondansetron and aprepitant, can permit more aggressive treatment regimens.

In the treatment of cancer, any of the previously described conventional treatments for the treatment of cancer immunity may be conducted, prior, subsequent or simultaneous with the administration of the anti-EpCAM antibodies or antibody fragments. Additionally, the anti-EpCAM antibodies or antibody fragments may be administered prior, subsequent or simultaneous with conventional cancer treatments, such as the administration of tumor-binding antibodies (e.g., monoclonal antibodies, toxin-conjugated monoclonal antibodies) and/or the administration of chemotherapeutic agents.

F. Articles of Manufacture and Kits

In another aspect of the invention, an article of manufacture containing an anti-EpCAM antibody or antibody fragment and other materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody or antibody fragment of the invention. The label or package insert indicates that the composition is used for treating the condition of choice. Moreover, the article of manufacture may comprise (a) a first container with a composition contained therein, wherein the composition comprises an antibody or antibody fragment; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-EpCAM antibody or antibody fragment.

Finally, the invention also provides kits comprising at least one antibody or antibody fragment of the invention. Kits containing polypeptide, antibodies or antibody fragments, or antibody drug conjugate of the invention find use in detecting EpCAM expression (increase or decrease), or in therapeutic or diagnostic assays. Kits of the invention can contain an antibody coupled to a solid support, e.g., a tissue culture plate or beads (e.g., sepharose beads). Kits can be provided which contain antibodies for detection and quantification of EpCAM in vitro, e.g. in an ELISA or a Western blot. Such antibody useful for detection may be provided with a label such as a fluorescent or radiolabel.

The kits further contain instructions on the use thereof. In some embodiments, the instructions comprise instructions required by the U.S. Food and Drug Administration for in vitro diagnostic kits. In some embodiments, the kits further comprise instructions for diagnosing the presence or absence of cerebrospinal fluid in a sample based on the presence or absence of EpCAM in said sample. In some embodiments, the kits comprise one or more antibodies or antibody fragments. In other embodiments, the kits further comprise one or more enzymes, enzyme inhibitors or enzyme activators. In still other embodiments, the kits further comprise one or more chromatographic compounds. In yet other embodiments, the kits further comprise one or more compounds used to prepare the sample for spectroscopic assay. In further embodiments, the kits further comprise comparative reference material to interpret the presence or absence of EpCAM according to intensity, color spectrum, or other physical attributes of an indicator.

The following examples are illustrative, but not limiting, of the anti-EPCAM antibodies of the present disclosure.

Other suitable modifications and adaptations of the variety of conditions and parameters normally encountered in the field, and which are obvious to those skilled in the art, are within the scope of the disclosure.

EXAMPLES

Example 1

Hybridoma Clones from Mice Immunized with EpCAM

Mice were immunized with recombinant human EpCAM extracellular domain (ECD). Hybridoma clones generated using the B cells of the immunized mice were screened with both human EpCAM ECD and stable CHO cells expressing human EpCAM. Hybridoma clones were selected based on their ability to bind to human EpCAM ECD, to cyno EpCAM and the CHO cells expressing human EpCAM, but not mouse or rat EpCAM. The selected hybridoma clones are shown in Table 2.

TABLE 2

Selected hybridoma clones expressing anti-EpCAM antibodies

| hybridoma clone | Affinity ELISA | | | |
|---|---|---|---|---|
| | Human | Cyno | Rat | Mouse |
| 12C10F12 | 2.1376 | 1.8965 | 0.0459 | 0.0458 |
| 14H10G11 | 0.5211 | 1.0191 | 0.0505 | 0.0521 |
| 15A8F1 | 1.8209 | 1.7352 | 0.0491 | 0.0529 |
| 16A11E2 | 0.563 | 0.7719 | 0.0442 | 0.0458 |
| 19C2B9 | 0.5816 | 1.1019 | 0.0462 | 0.0455 |
| 20A5C2 | 0.1979 | 0.9125 | 0.0438 | 0.0454 |

Example 2

Conditionally Active Biological (CAB) Anti-EpCAM Antibodies

Figure 4:
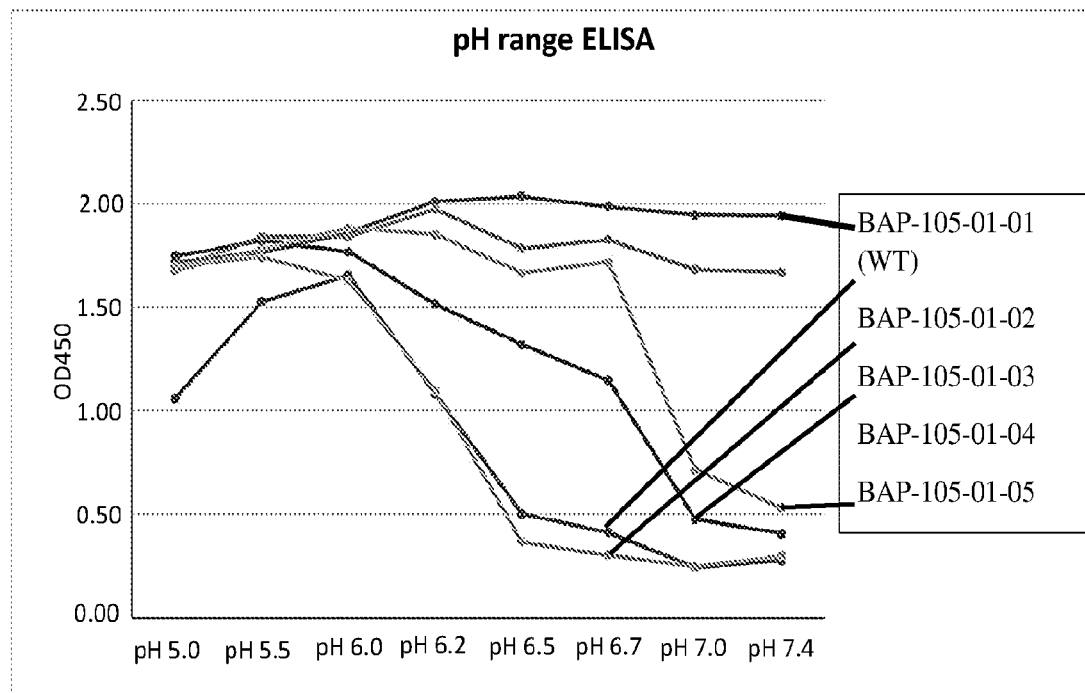
FIG. 4 shows the binding activity of exemplary anti-EpCAM antibodies of the present invention to human EpCAM at different values of pH, as measured by enzyme linked immunosorbent assay (ELISA).
Figure 5A:
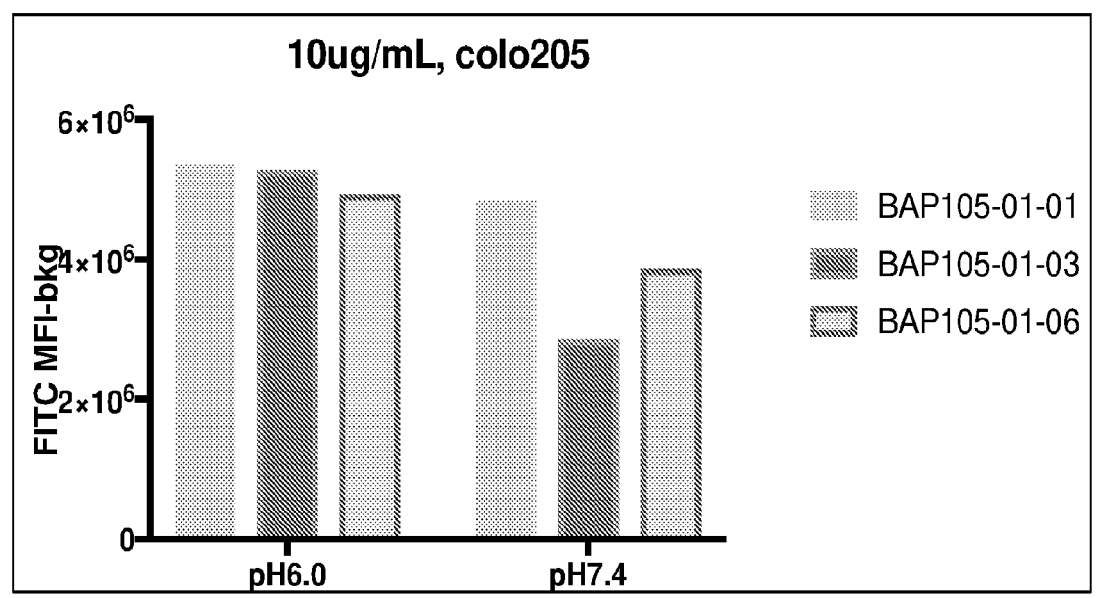
FIGS. 5A-5D show binding activities of anti-EpCAM antibodies of the present invention to Colo205 cells that express human EpCAM at different values of pH for two different amounts of the antibodies as measured by fluorescence activated cell sorting (FACS).
Figure 5B:
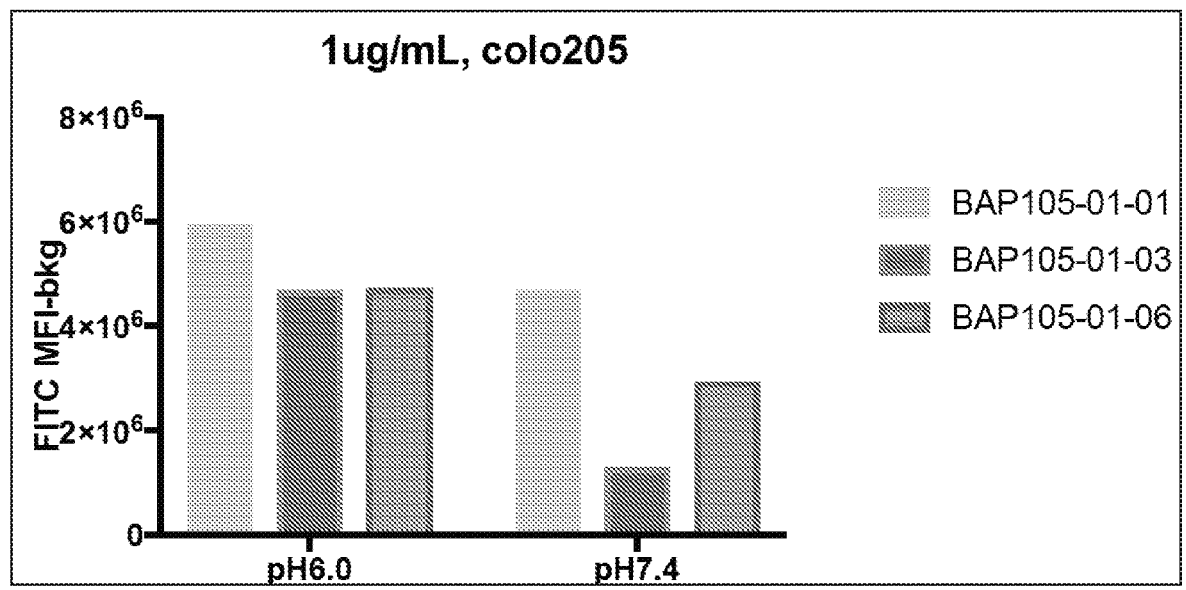
Figure 5C:
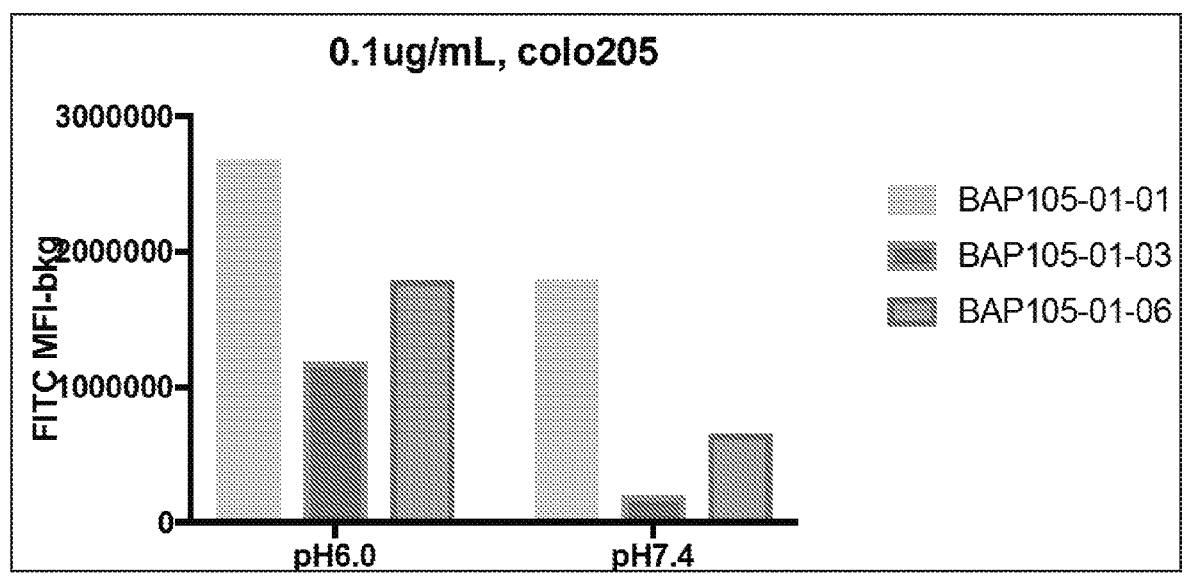
Figure 5D:
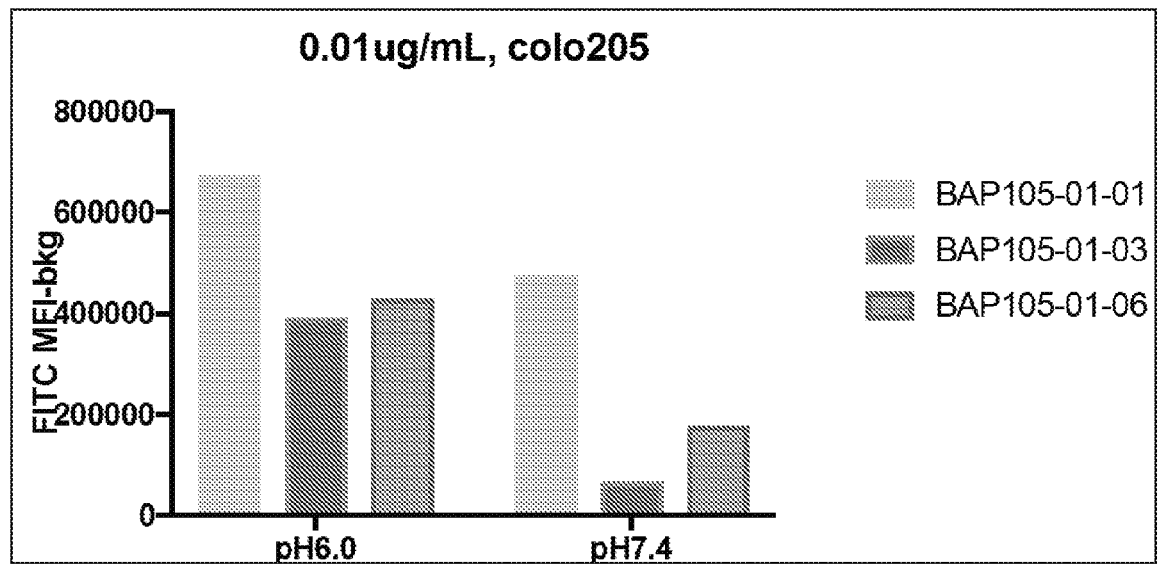
Figure 6A:
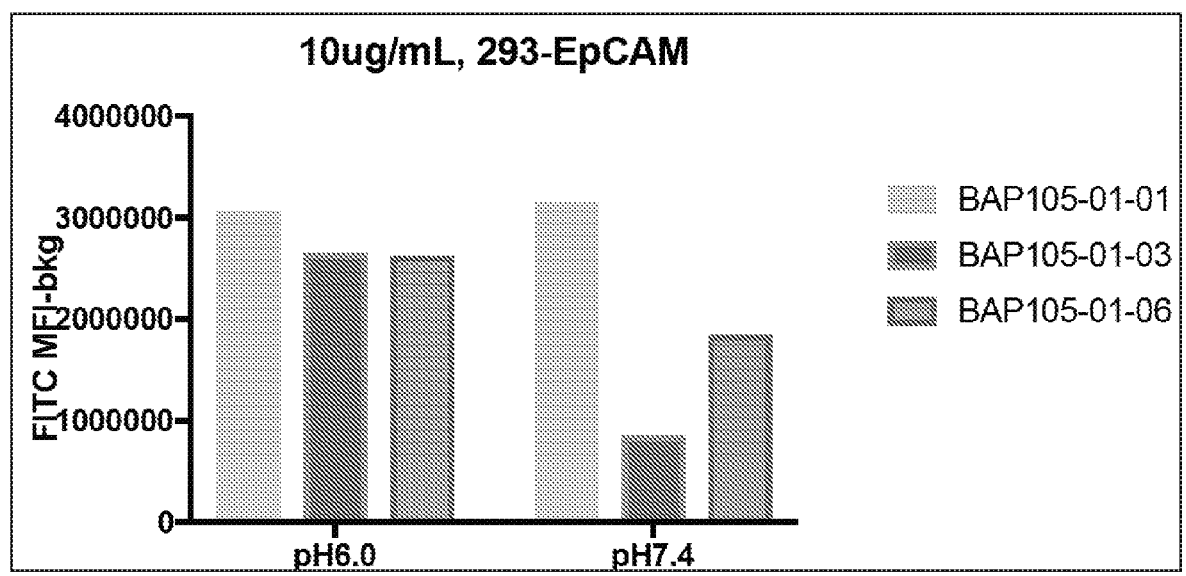
FIGS. 6A-6D show the binding activity of the anti-EpCAM antibodies of the present invention to 293 cells that express human EpCAM at different values of pH for two different amounts of the antibodies as measured by FACS.
Figure 6B:
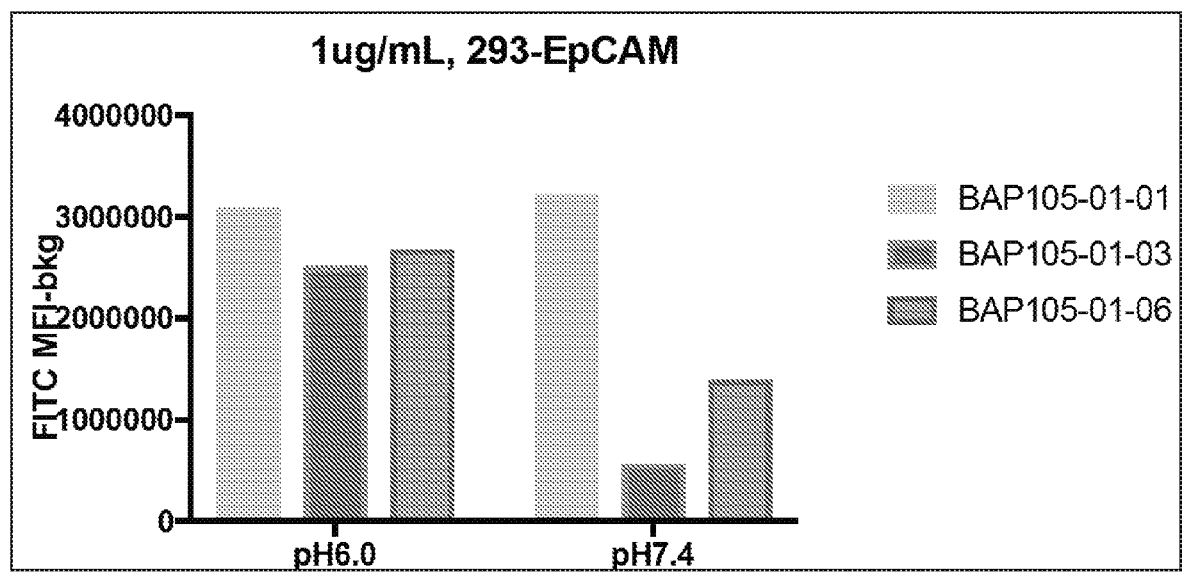
Figure 6C:
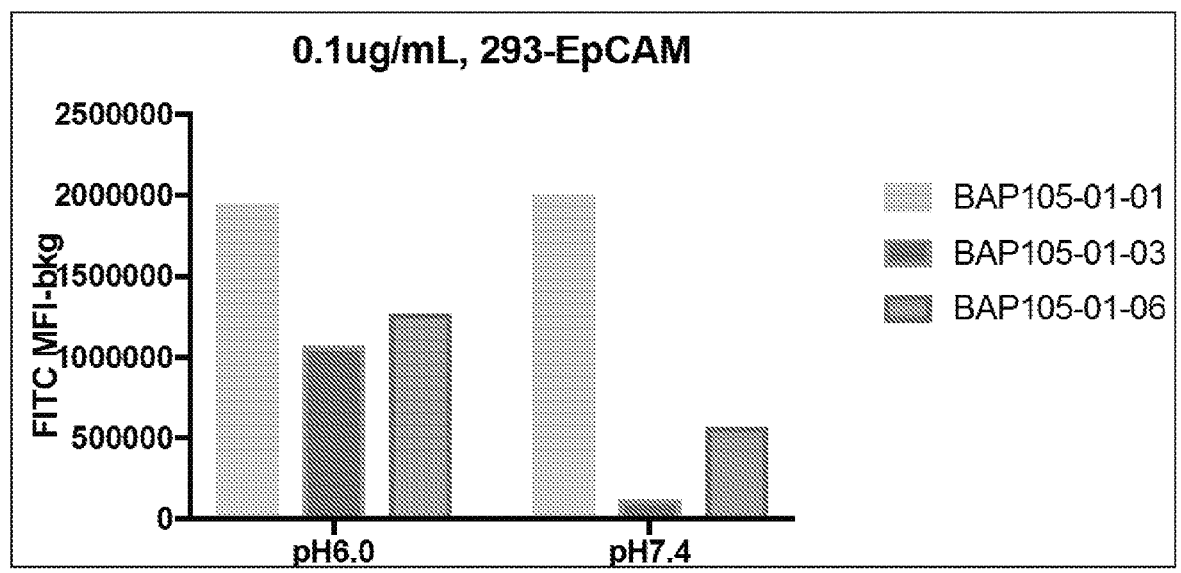
Figure 6D:
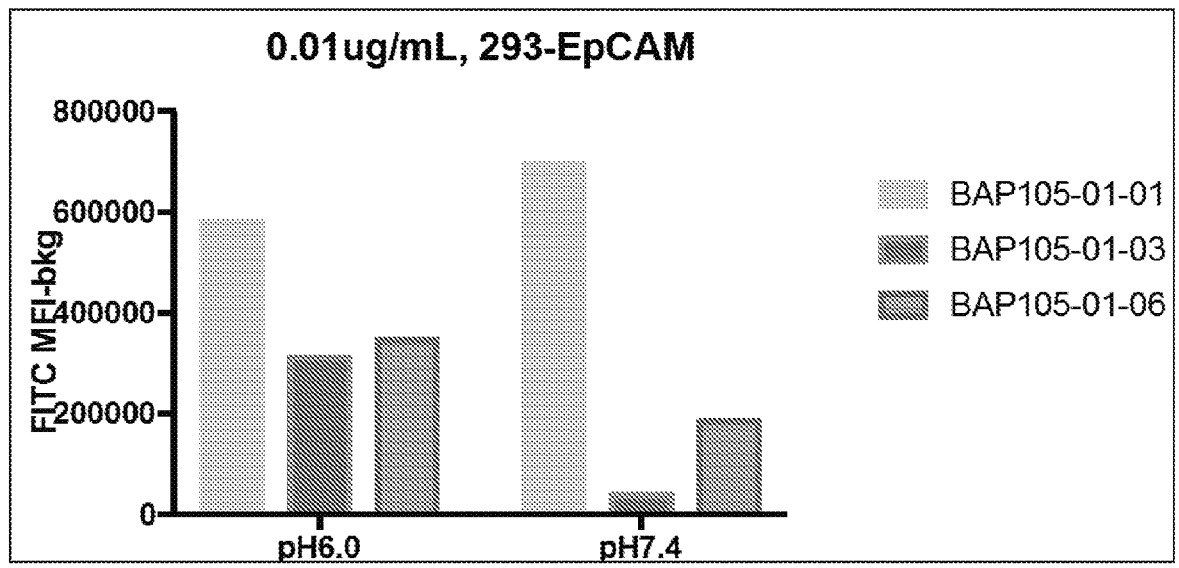

The anti-EpCAM antibody expressed by the hybridoma clone 12C10F12 was used as the template antibody for generating conditionally active anti-EpCAM antibodies. DNA encoding the template antibody was mutated using comprehensive positional evolution (CPE™) to produce mutant antibodies. The mutant antibodies were screened for conditionally active anti-EpCAM antibodies that have an increased binding activity to human EpCAM at a lower pH of a tumor microenvironment in comparison with the binding activity to EpCAM at a normal physiological pH present in a non-tumor microenvironment, as shown in FIG. 4 and Table 3. The antibody clone BAP-105-01-01 is the template antibody (WT) as shown in FIG. 4.

TABLE 3

Conditionally active anti-EpCAM antibodies

| Antibody Clones | Light chain variable region | Heavy chain variable region |
|---|---|---|
| BAP-105-01-01 | BAP105-1-VK01 (SEQ ID NO: 14) | BAP105-1-VH01 (SEQ ID NO: 7) |
| BAP-105-01-02 | BAP105-1-VK01 (SEQ ID NO: 14) | BAP105-1-VH02 (SEQ ID NO: 8) |
| BAP-105-01-03 | BAP105-1-VK01 (SEQ ID NO: 14) | BAP105-1-VH03 (SEQ ID NO: 9) |
| BAP-105-01-04 | BAP105-1-VK02 (SEQ ID NO: 15) | BAP105-1-VH01 (SEQ ID NO: 7) |
| BAP-105-01-05 | BAP105-1-VK03 (SEQ ID NO: 16) | BAP105-1-VH01 (SEQ ID NO: 7) |
| BAP-105-01-06 | BAP105-1-VK04 (SEQ ID NO: 17) | BAP105-1-VH01 (SEQ ID NO: 7) |

These conditionally active anti-EpCAM antibodies were further characterized.

Example 3

Binding Activity of the Conditionally Active Anti-EpCAM Antibodies

The selected conditionally active anti-EpCAM antibodies, exemplified by BAP-105-01-03 and BAP-105-01-06, were analyzed for binding to EpCAM using BAP-105-01-01 as a control. The binding activity of these anti-EpCAM antibodies to EpCAM expressing Colo205 cells were measured by fluorescence activated cell sorting (FACS) at two different pH values of 6.0 and 7.4. Different dosages of the antibodies of 10 µg/mL, 1 µg/mL, 0.1 µg/mL and 0.01 µg/mL were used. The conditionally active anti-EpCAM antibodies consistently showed a higher binding activity to the EpCAM expressing Colo205 cells at pH 6.0 than at pH 7.4. See FIGS. 5A-5D.

A similar FACS analysis was also carried out using 293 cells expressing human EpCAM. The conditionally active anti-EpCAM antibodies also showed a consistently higher binding activity to the EpCAM expressing 293 cells at pH 6.0 than at pH 7.4. See FIGS. 6A-6D.

Example 4

Cell Killing of the Conditionally Active Anti-EpCAM Antibody Conjugates

Figure 7A:
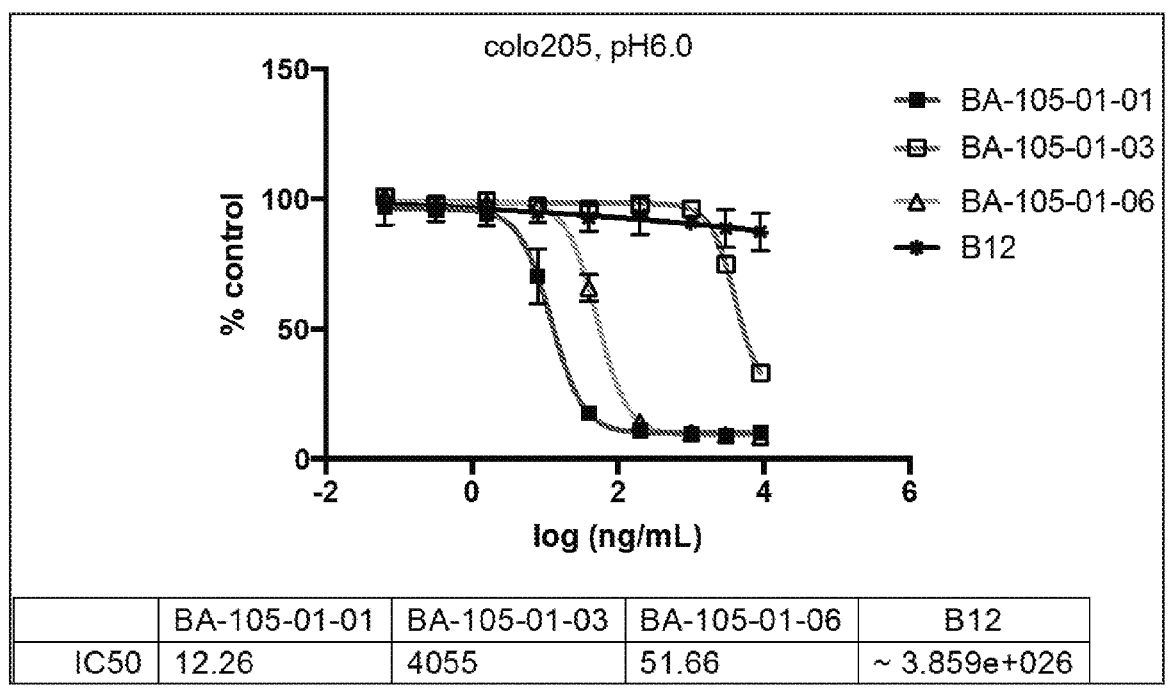
FIGS. 7A-7C show the cell killing activity of MMAE conjugated anti-EpCAM antibodies of the present invention for killing EpCAM expressing Colo205 cells.
Figure 7B:
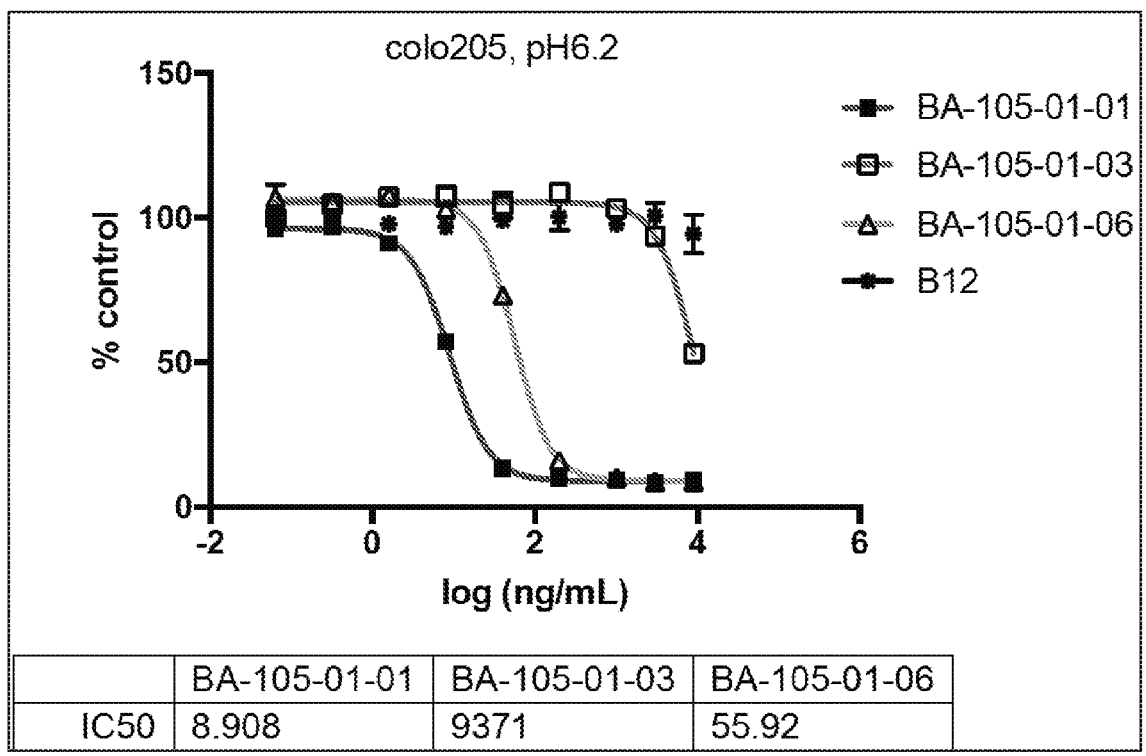
Figure 7C:
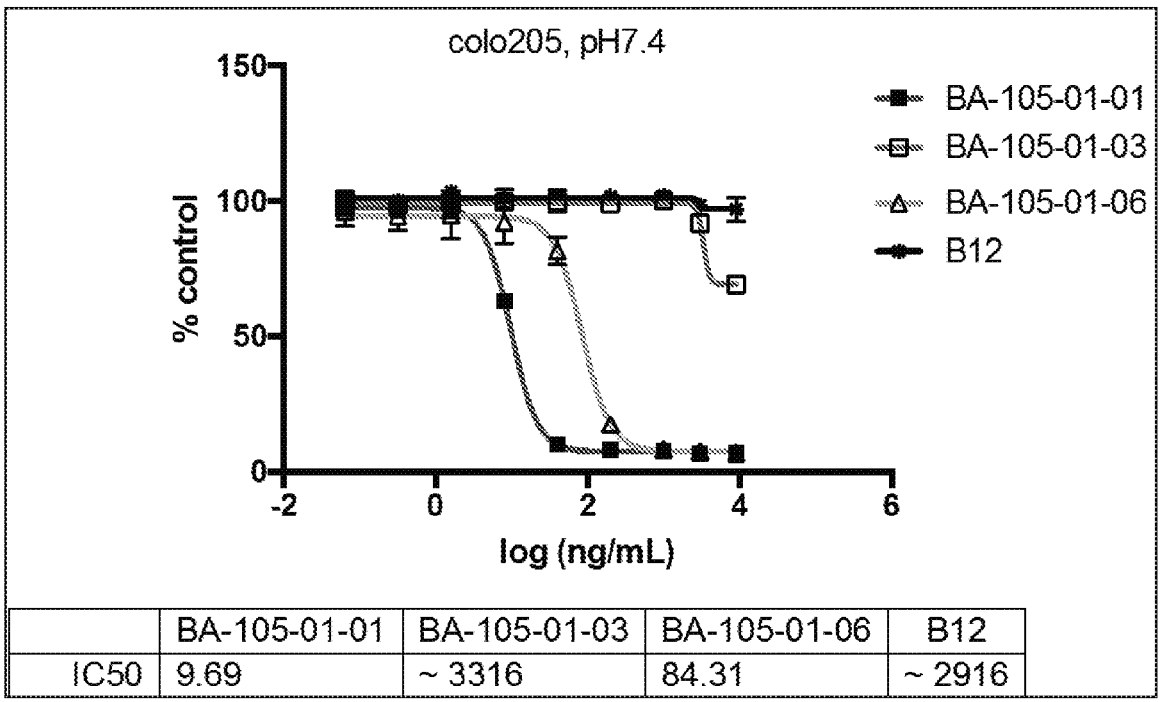

The selected conditionally active anti-EpCAM antibodies BAP-105-01-03 and BAP-105-01-06 were conjugated to monomethyl auristatin E (MMAE), a potent antimitotic agent, to create antibody drug conjugates (ADCs). Antibody BAP-105-01-01 was used as a non-conditionally active antibody control and B12 was used as a negative control. In vitro cell killing of EpCAM expressing Colo205 cells was measured at three pH values of 6.0, 6.2 and 7.4. IC50 for the in vitro killing of the Colo205 cells by the conditionally active anti-EpCAM antibodies was also determined. See FIGS. 7A-7C.

Figure 8A:
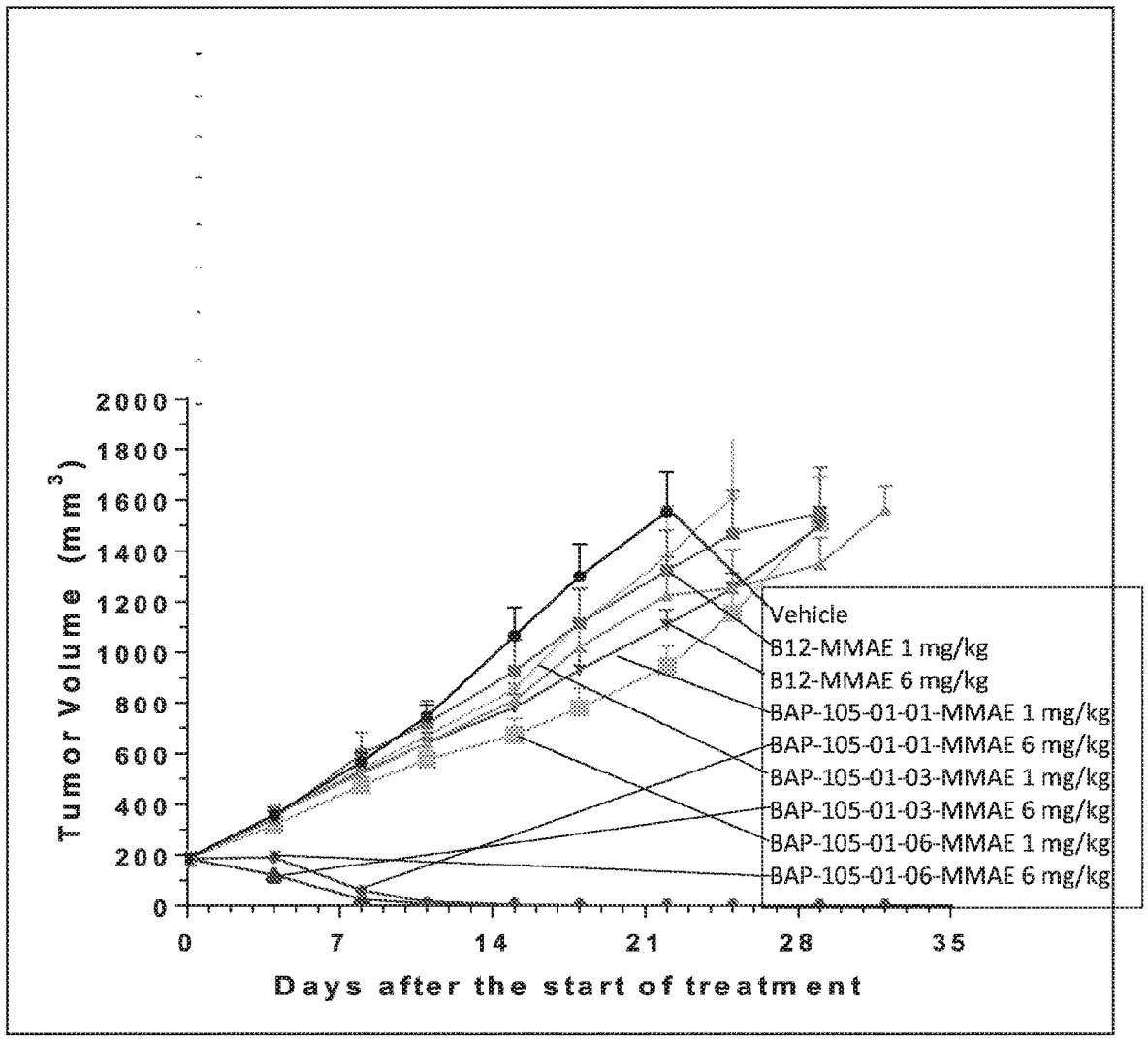
FIG. 8A-8B show results of treatment of tumor xenografts in mice with conjugated anti-EpCAM antibodies of the present invention.
Figure 8B:
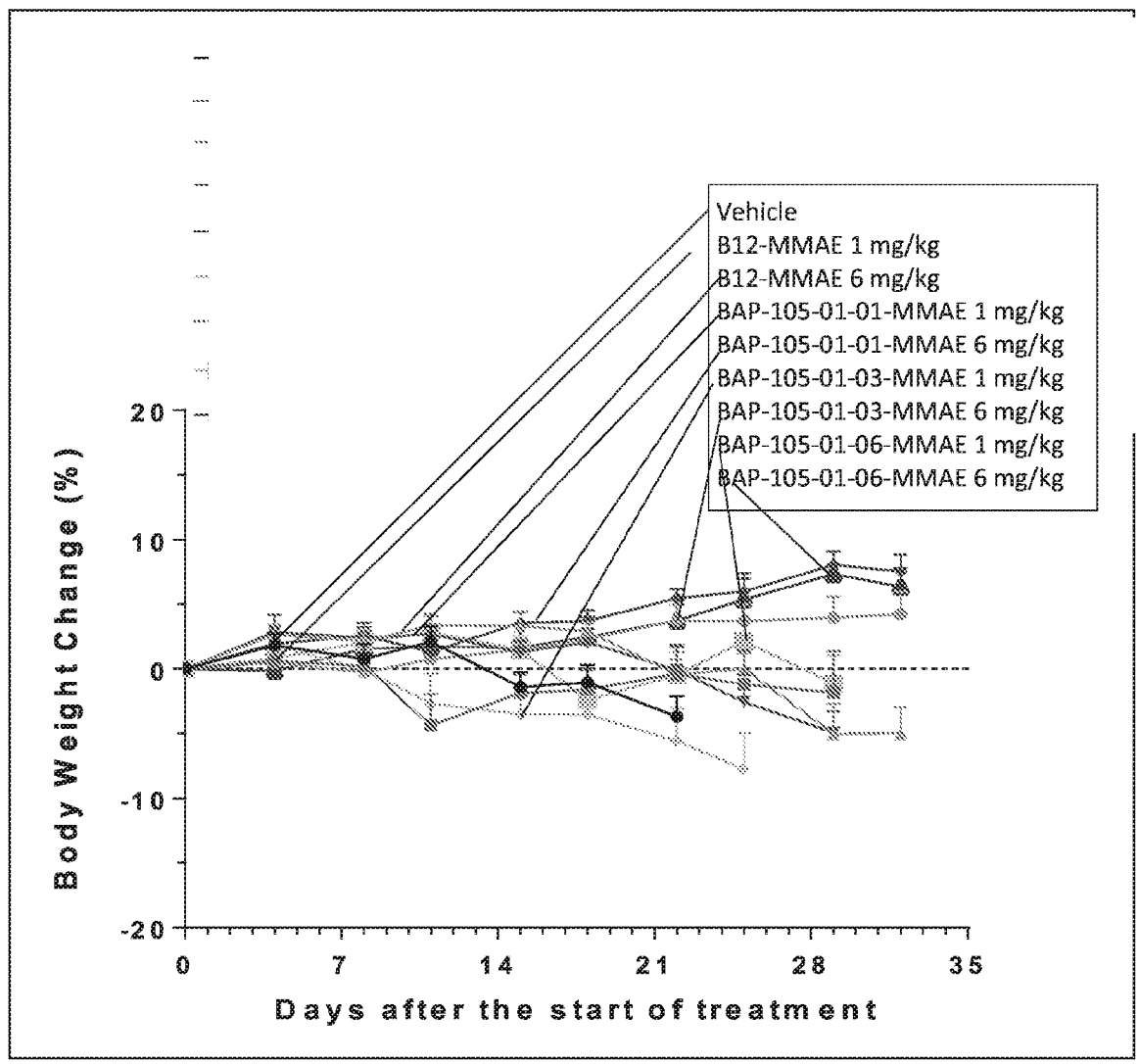
Figure 9A:
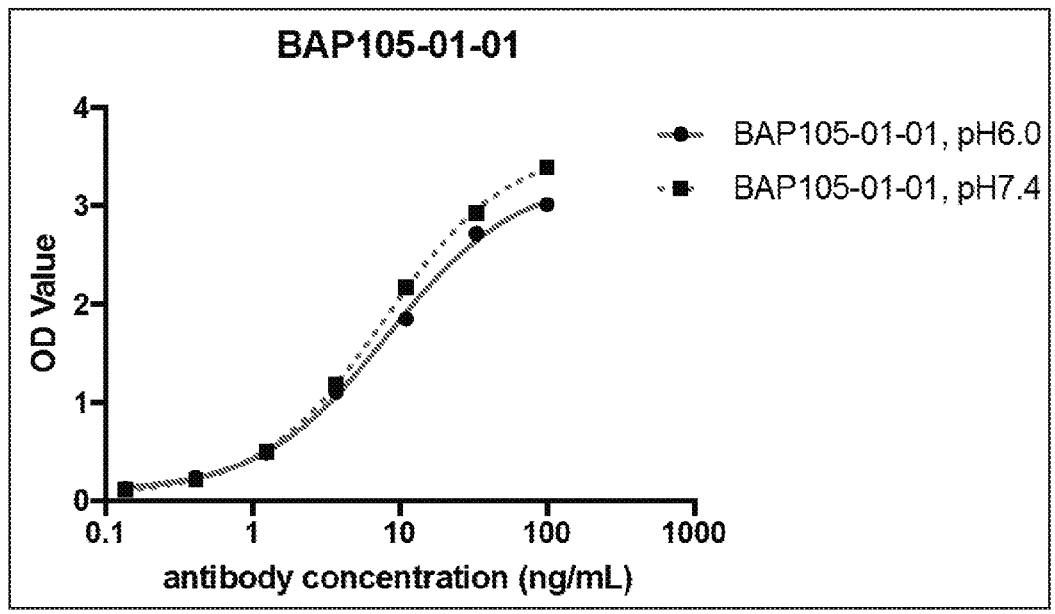
FIGS. 9A-9E show binding activities of humanized conditionally active anti-EpCAM antibodies of the present invention to human EpCAM as measured by ELISA.
Figure 9B:
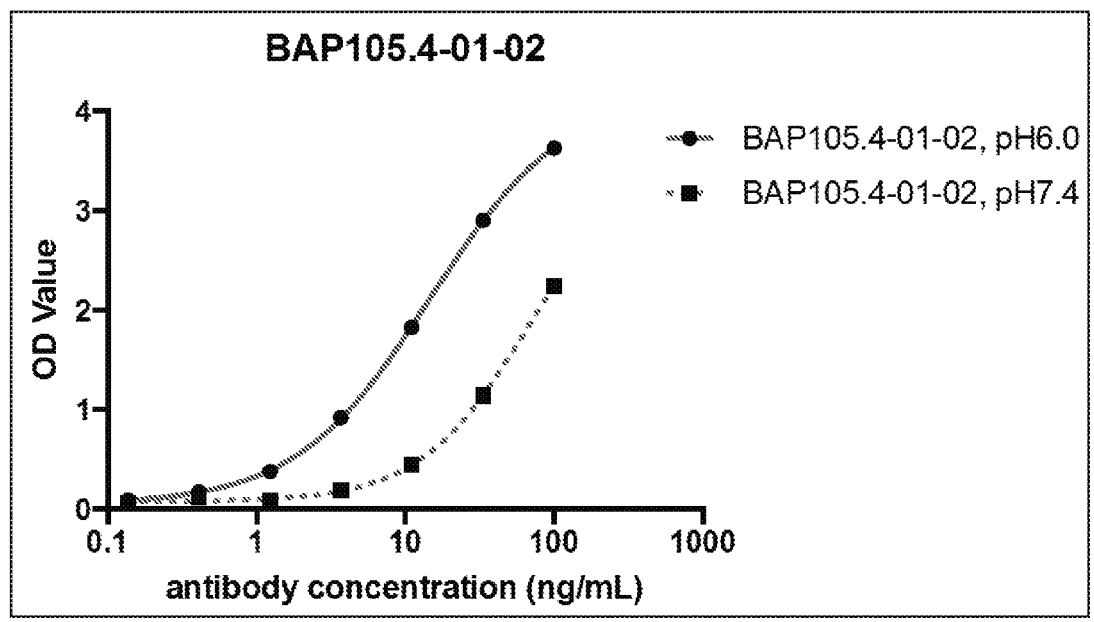
Figure 9C:
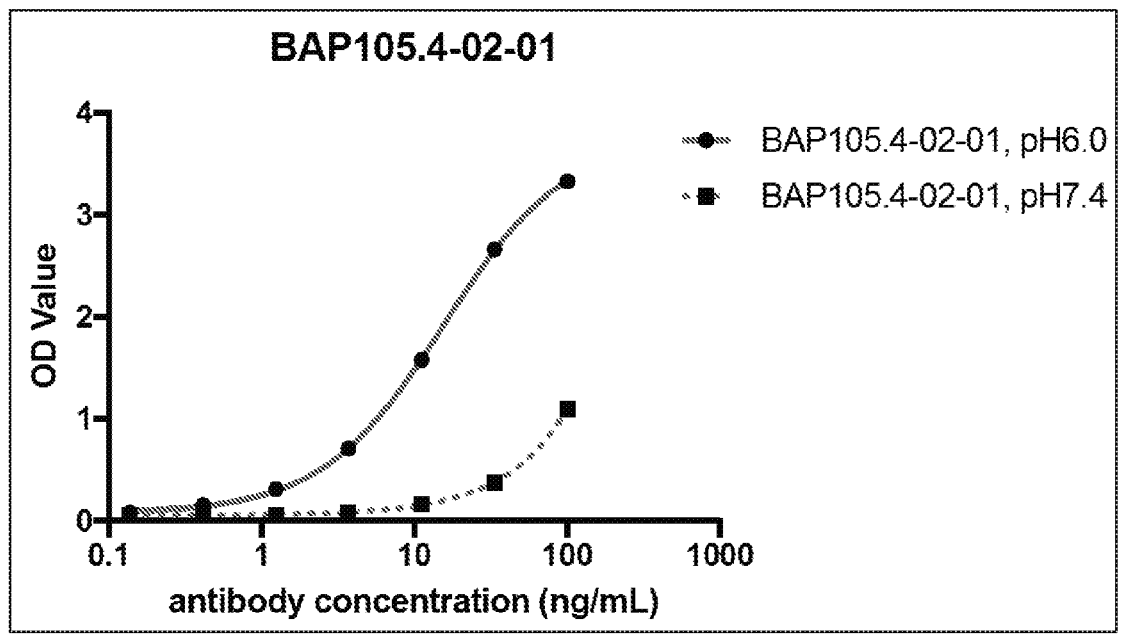
Figure 9D:
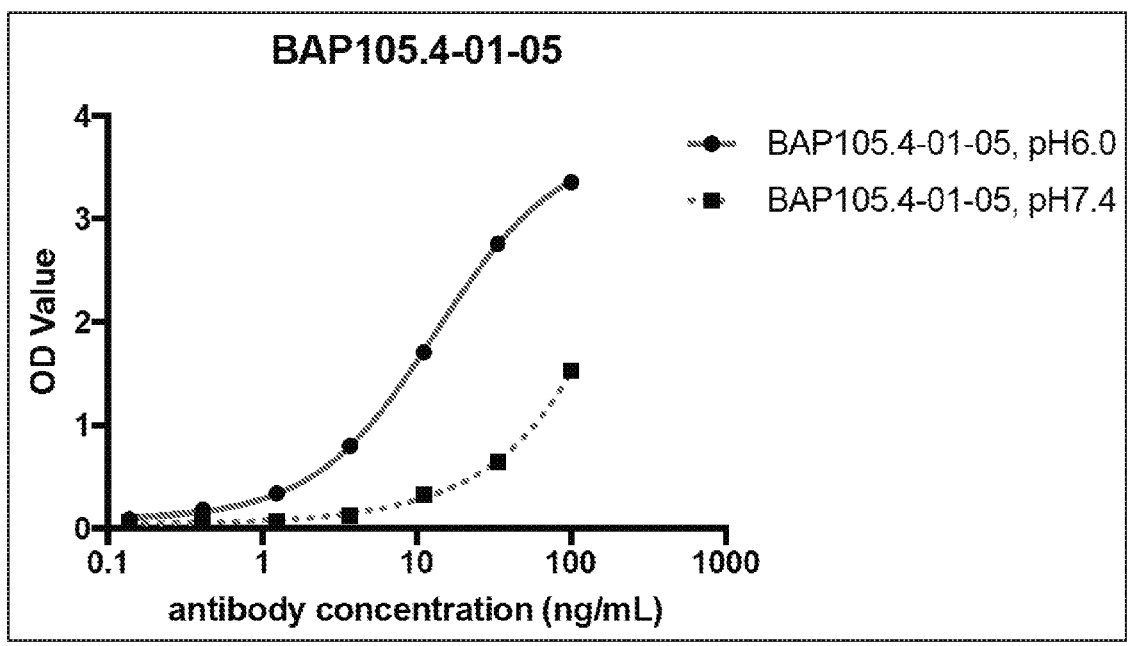
Figure 9E:
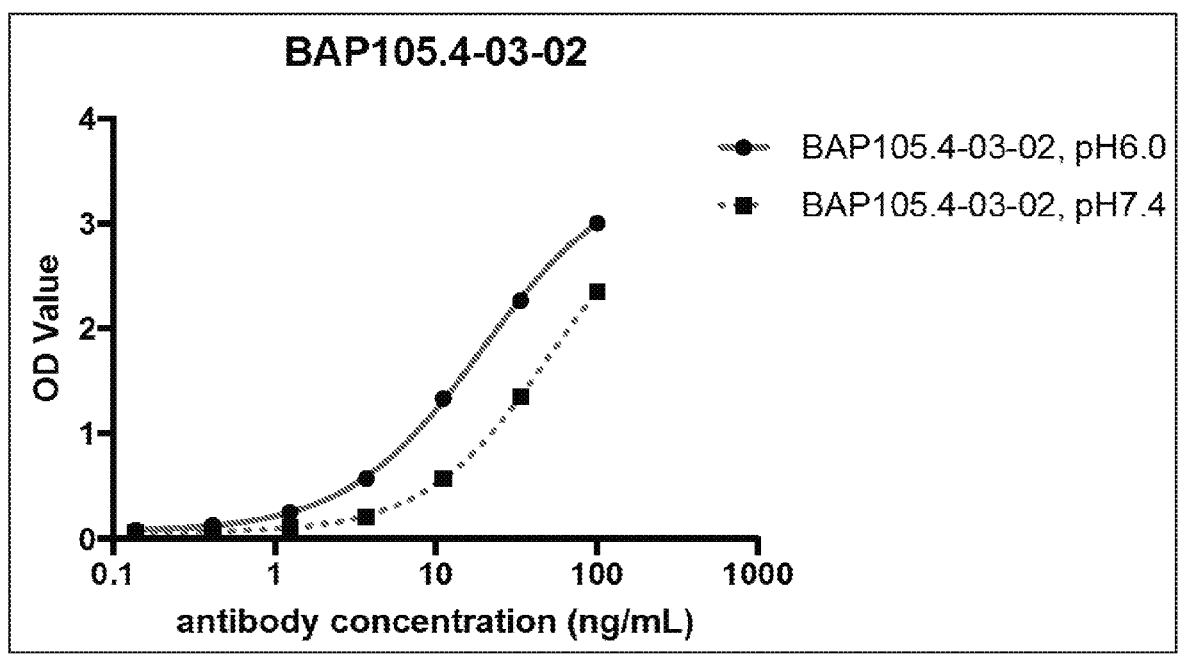

In vivo cell killing by the conditionally active anti-EpCAM antibody ADC was also measured using Colo205 xenograft mouse models. The xenograft mouse models were treated with an intermittent schedule Q4Dx4 (four times every fourth day) by IV injection. Two dosages were used, 1 mg/kg and 6 mg/kg. Eight (8) mice were used for each treatment group. The conditionally active anti-EpCAM antibody ADC significantly reduced the volume of the tumors but did not significantly reduce the weight of the animals at the dose of 6 mg/kg, in comparison with the controls. See FIGS. 8A-8B. This indicated that the conditionally active anti-EpCAM antibody ADC was effective in treating the tumor while exhibiting reduced side effects.

Example 5

Humanization of the Conditionally Active Anti-EpCAM Antibody

One of the conditionally active anti-EpCAM antibodies, BAP-1-5-01-06, was humanized to produce additional humanized conditionally active anti-EpCAM antibodies. See Table 4.

TABLE 4

Humanized conditionally active anti-EpCAM antibodies against EpCAM

| Antibody Clones | Light chain variable region | Heavy chain variable region |
| --- | --- | --- |
| BAP-105.4-03-02 | BAP105-4-VK03 (SEQ ID NO: 20) | BAP105-4-VH02 (SEQ ID NO: 11) |
| BAP-105.4-05-04 | BAP105-4-VK05 (SEQ ID NO: 21) | BAP105-4-VH04 (SEQ ID NO: 12) |
| BAP-105.4-01-02 | BAP105-4-VK01 (SEQ ID NO: 18) | BAP105-4-VH02 (SEQ ID NO: 11) |
| BAP-105.4-01-05 | BAP105-4-VK01 (SEQ ID NO: 18) | BAP105-4-VH05 (SEQ ID NO: 13) |
| BAP-105.4-02-01 | BAP105-4-VK02 (SEQ ID NO: 19) | BAP105-4-VH01 (SEQ ID NO: 10) |

Example 6

Binding Activity of the Humanized Conditionally Active Anti-EpCAM Antibodies to Human EpCAM The binding activities of the humanized conditionally active anti-EpCAM antibodies to human EpCAM were measured by ELISA, using the template antibody BAP 105-01-01 as a control. See FIGS. 9A-9E. The EC50 values of the humanized conditionally active anti-EpCAM antibodies for binding to human EpCAM at pH 6.0 and pH 7.4 are summarized in Table 5.

TABLE 5

EC50 of humanized conditionally active anti-EpCAM antibodies against human EpCAM

| | EC50 (ng/mL), human EpCAM | |
| --- | --- | --- |
| Clone | pH 6.0 | pH 7.4 |
| BAP105-01-01 | 8.33 | 7.806 |
| BAP105.4-01-02 | 14.72 | 66.01 |
| BAP105.4-01-05 | 13.36 | 50044 |
| BAP105.4-02-01 | 15.44 | 114000 |
| BAP105.4-03-02 | 19.1 | 48.72 |

Figure 10:
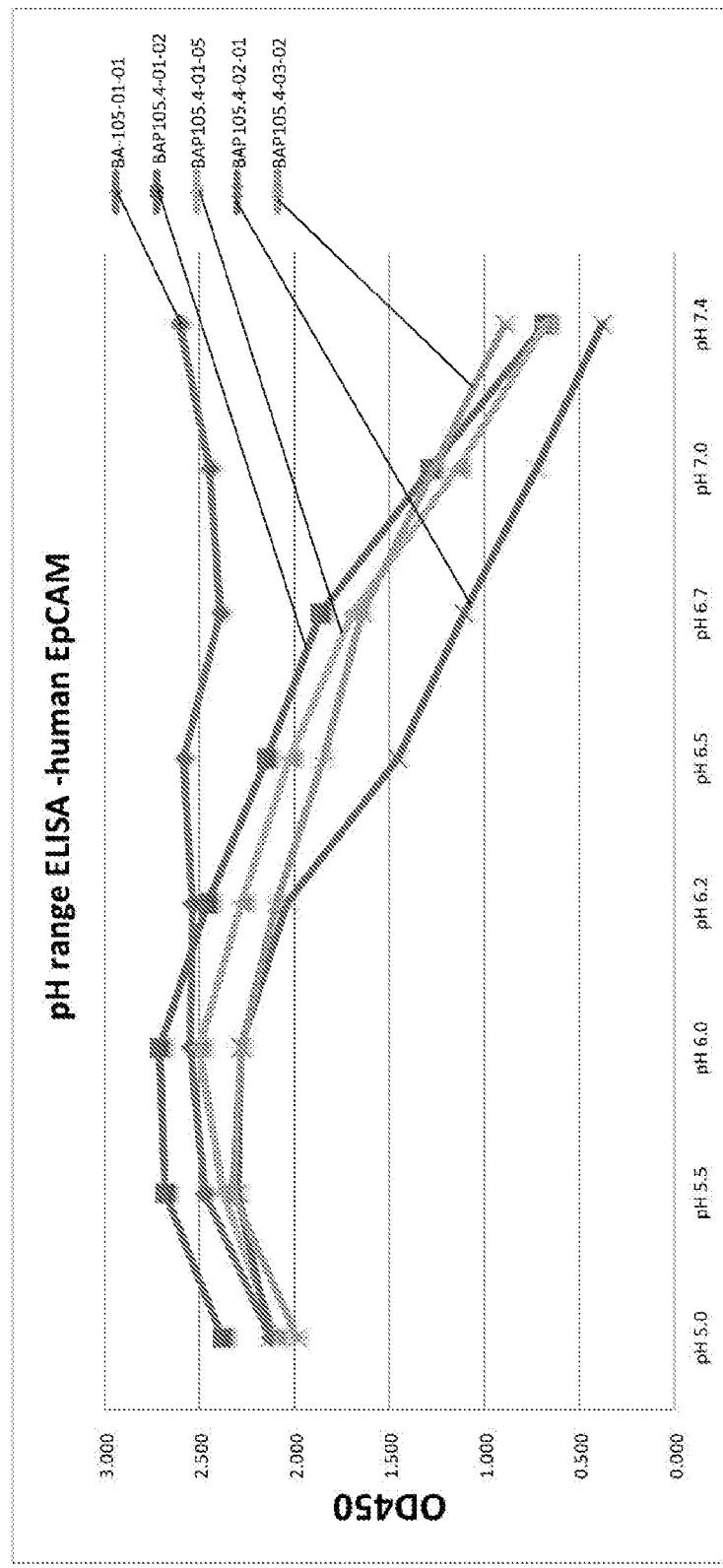
FIG. 10 shows binding activities of humanized conditionally active anti-EpCAM antibodies to human EpCAM under pH titration, as measured by ELISA.
Figure 11A:
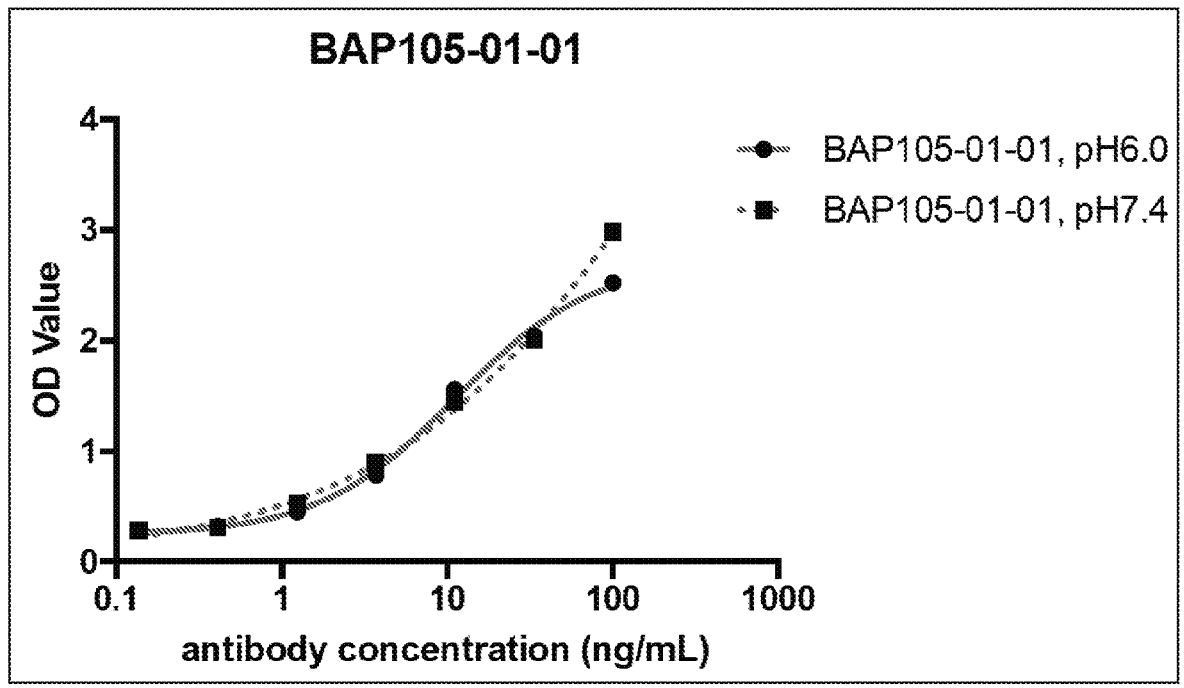
FIGS. 11A-11E show binding activities of humanized conditionally active anti-EpCAM antibodies to cyno EpCAM, as measured by ELISA.
Figure 11B:
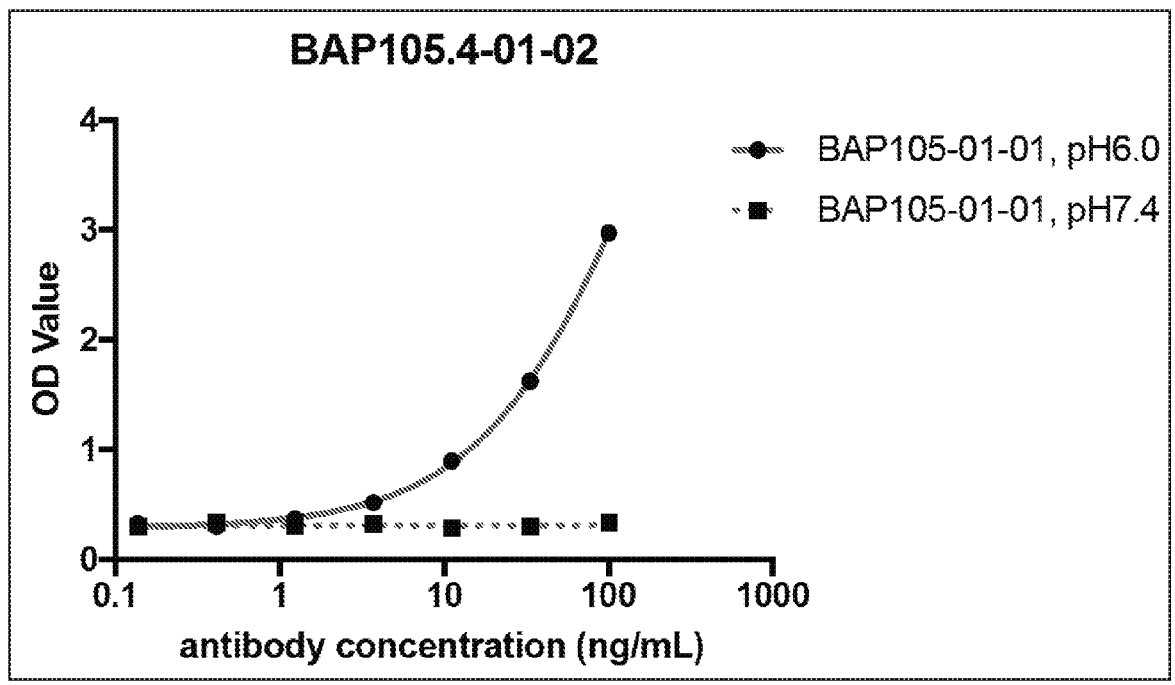
Figure 11C:
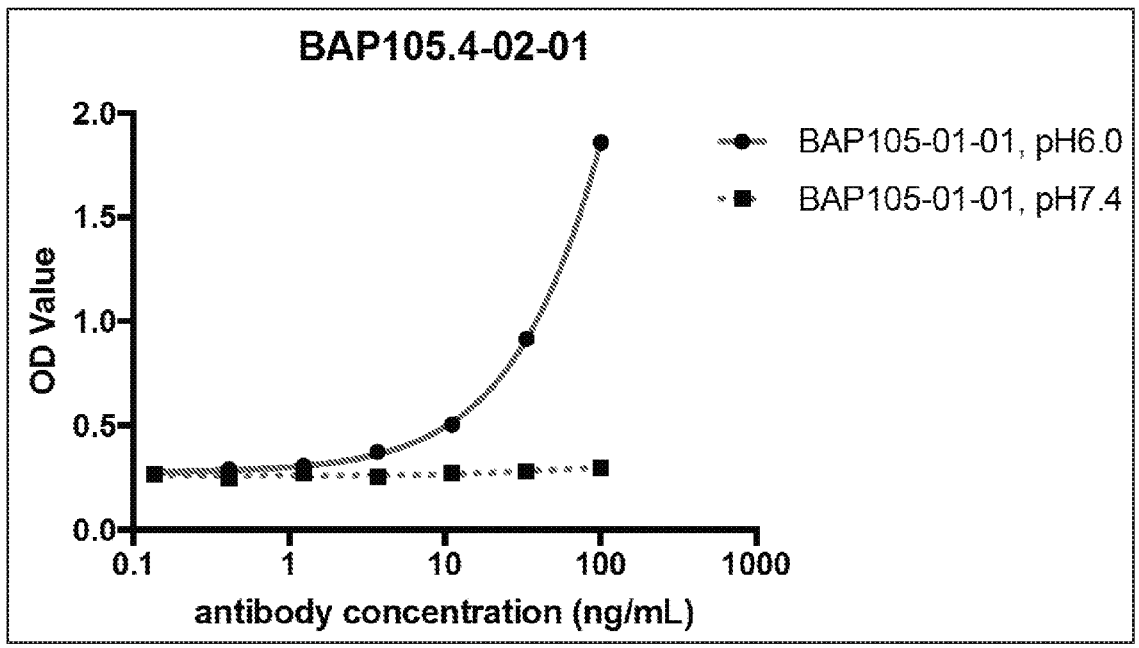
Figure 11D:
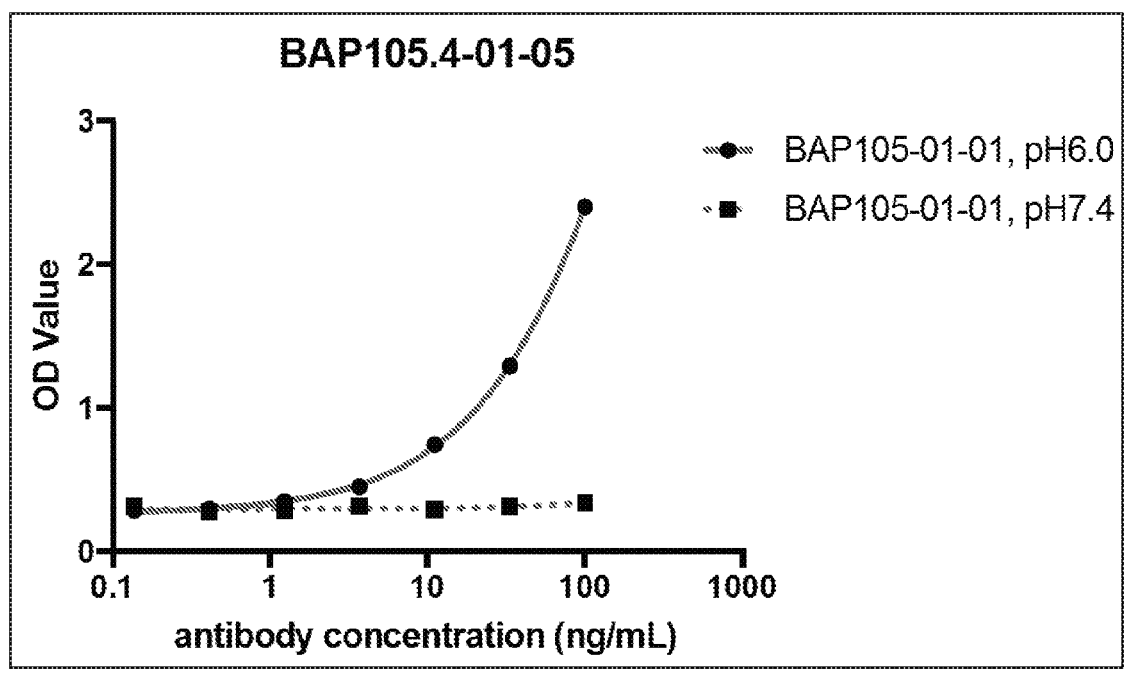
Figure 11E:
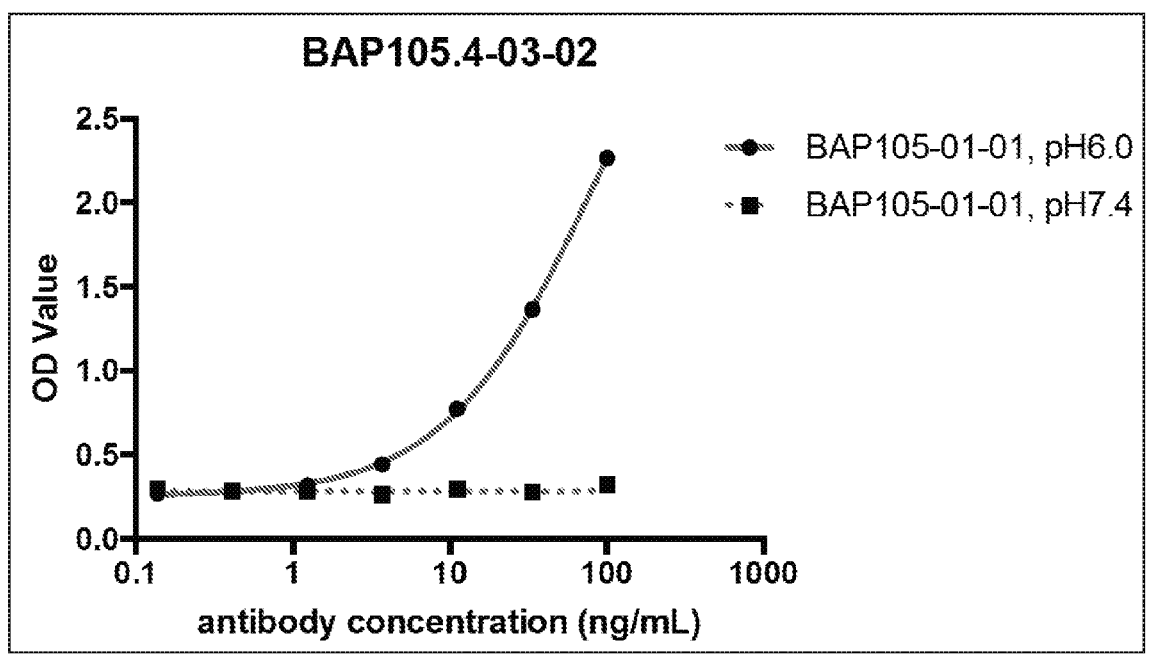

The binding activities of the humanized conditionally active anti-EpCAM antibodies to human EpCAM with pH titration were also measured by ELISA. See FIG. 10. The pH inflection points of the humanized conditionally active anti-EpCAM antibodies to human EpCAM are summarized in Table 6.

TABLE 6 pH Inflection point of humanized conditionally active anti-EpCAM antibodies against human EpCAM

| | BAP-105-01-01 | BAP105.4-01-02 | BAP105.4-01-05 | BAP105.4-02-01 | BAP105.4-03-02 |
| --- | --- | --- | --- | --- | --- |
| pH inflection point | N/A | 6.87 | 6.83 | 6.60 | 6.82 |

Example 7

Binding Activity of the Humanized Conditionally Active Anti-EpCAM Antibodies to Cyno EpCAM The binding activities of the humanized conditionally active anti-EpCAM antibodies to cyno EpCAM were similarly measured. See FIGS. 11A-11E. The EC50 for binding to the cyno EpCAM at pH 6.0 and pH 7.4 for the humanized conditionally active anti-EpCAM antibodies are summarized in Table 7.

TABLE 7

EC50 of humanized conditionally active anti-EpCAM antibodies against cyno EpCAM

| | EC50 (ng/mL), cyno EpCAM | |
| --- | --- | --- |
| Clone | pH 6.0 | pH 7.4 |
| BAP105-01-01 | 11.19 | 299.9 |
| BAP105.4-01-02 | 193.8 | 208 |
| BAP105.4-01-05 | 489.7 | 7167 |
| BAP105.4-02-01 | 673.8 | 35.88 |
| BAP105.4-03-02 | 84 | 104.9 |

Figure 12:
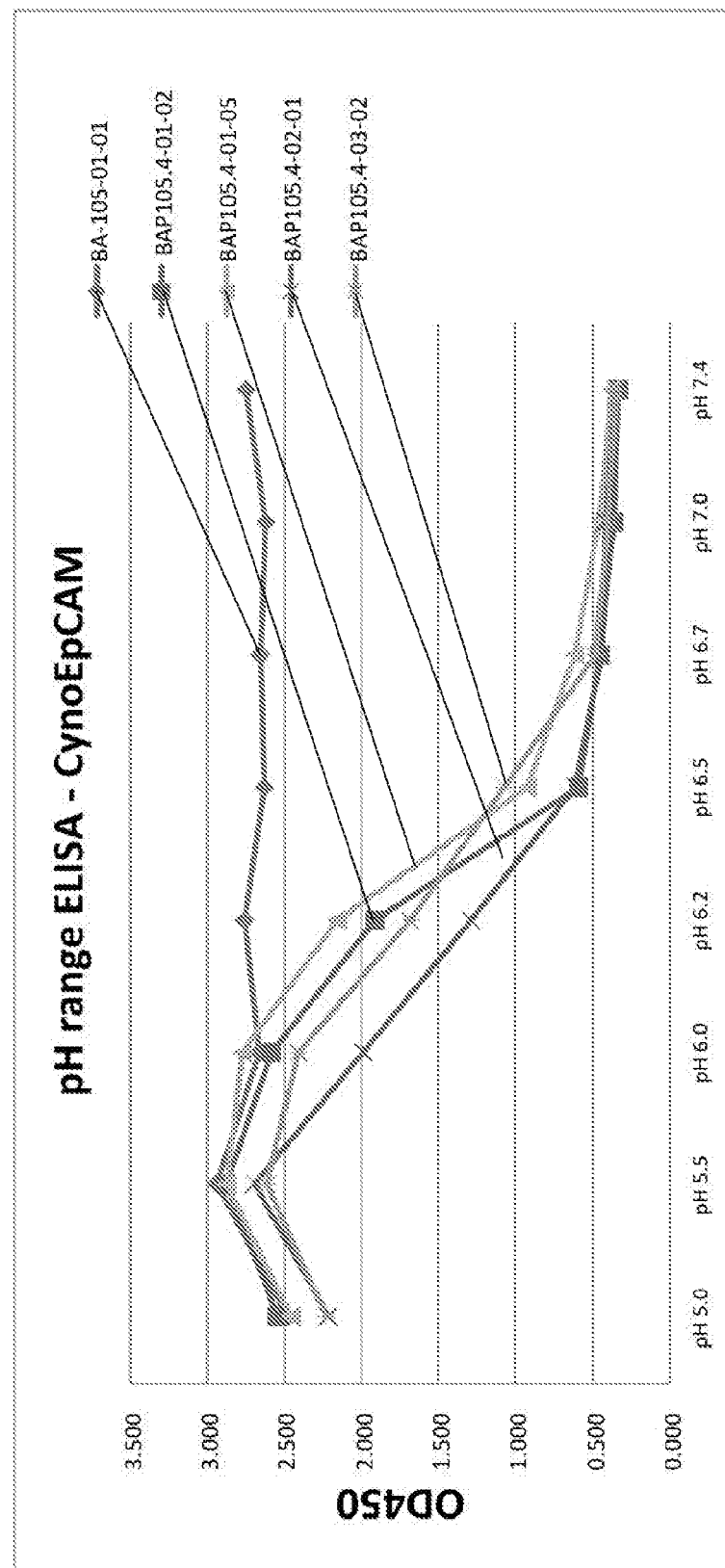
FIG. 12 shows binding activities of humanized conditionally active anti-EpCAM antibodies to cyno EpCAM under pH titration, as measured by ELISA.

The binding activities of the humanized conditionally active anti-EpCAM antibodies to cyno EpCAM with pH titration was similarly measured by ELISA. See FIG. 12. The pH inflection points of the humanized conditionally active anti-EpCAM antibodies to cyno EpCAM are summarized in Table 8.

TABLE 8

Inflection point of humanized conditionally active anti-EpCAM antibodies against cyno EpCAM

|  | BAP-105-01-01 | BAP105.4-01-02 | BAP105.4-01-05 | BAP105.4-02-01 | BAP105.4-03-02 |
|---|---|---|---|---|---|
| pH inflection point | N/A | 6.27 | 6.35 | 6.17 | 6.35 |

Example 8

Thermostability of the Humanized Conditionally Active Anti-EpCAM Antibodies

Figure 13A:
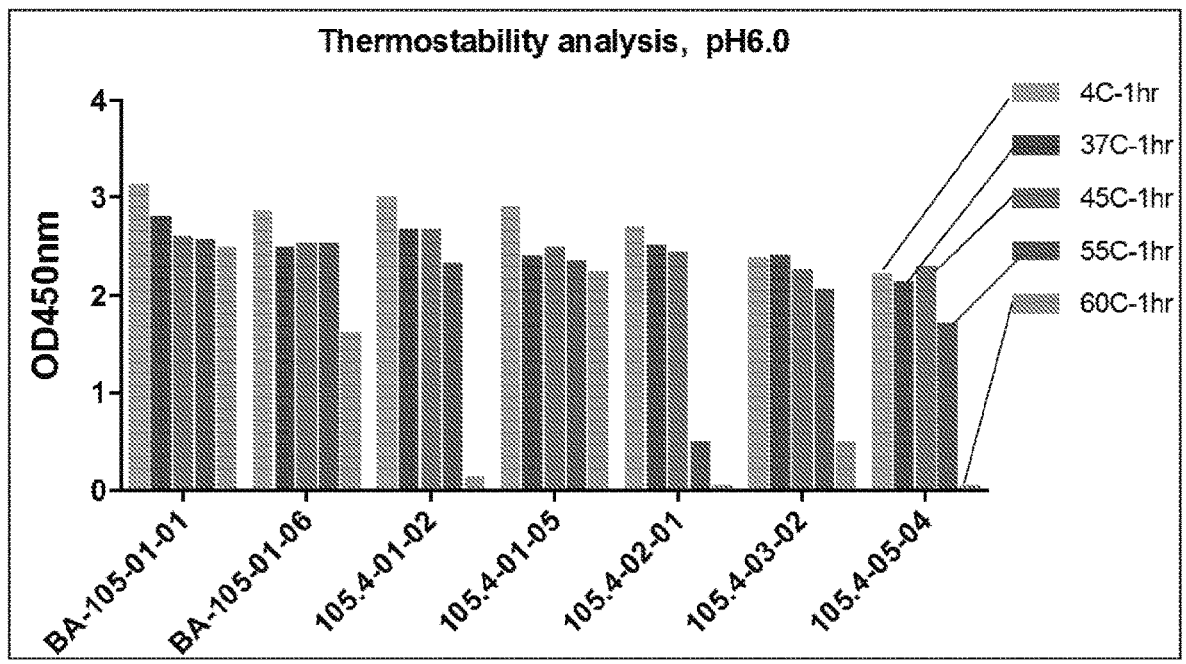
FIGS. 13A-13B show binding activities of humanized conditionally active anti-EpCAM antibodies to human EpCAM at pH 6.0 (FIG. 13A) and pH 7.4 (FIG. 13B) after heat treatment at different temperatures, as measured by ELISA.
Figure 13B:
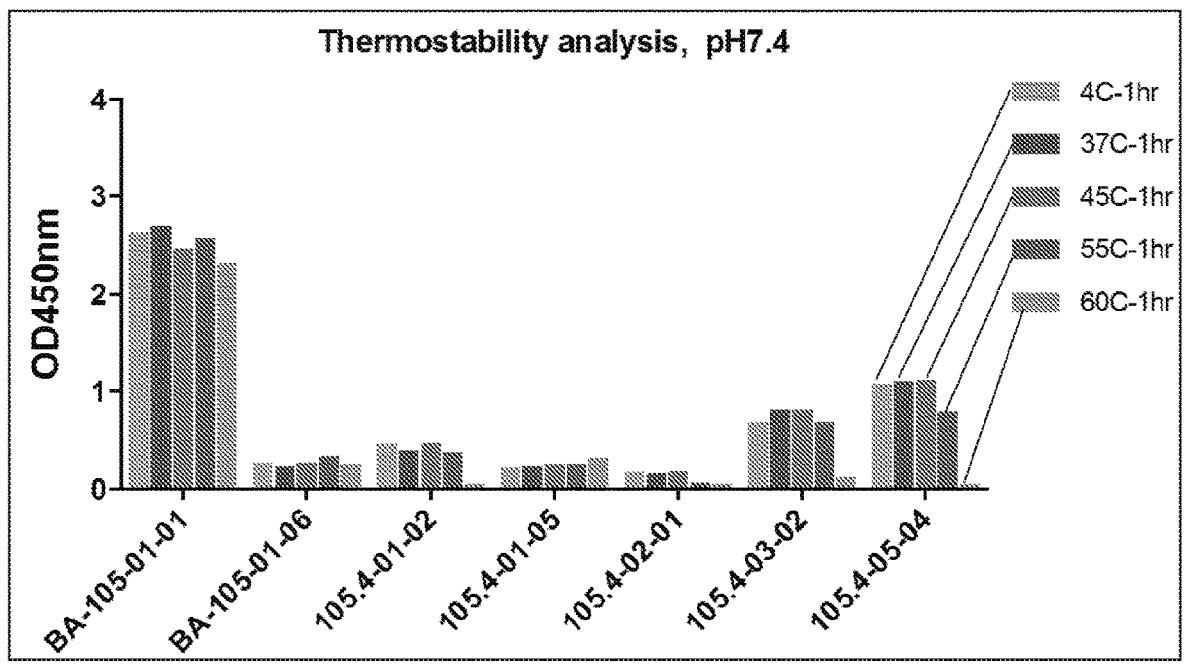

The thermostability of the humanized conditionally active anti-EpCAM antibodies was evaluated by measuring their binding activities after heat treatment. The binding activities of the humanized conditionally active anti-EpCAM antibodies to human EpCAM after heat treatment for one (1) hour at different temperatures at pH 6.0 and pH 7.4 were measured by ELISA. See FIGS. 13A-13B. Heat treatment up to temperatures of 45° C. did not markedly affect the binding affinities showing good heat stability at these temperatures.

Example 9

Figure 14A:
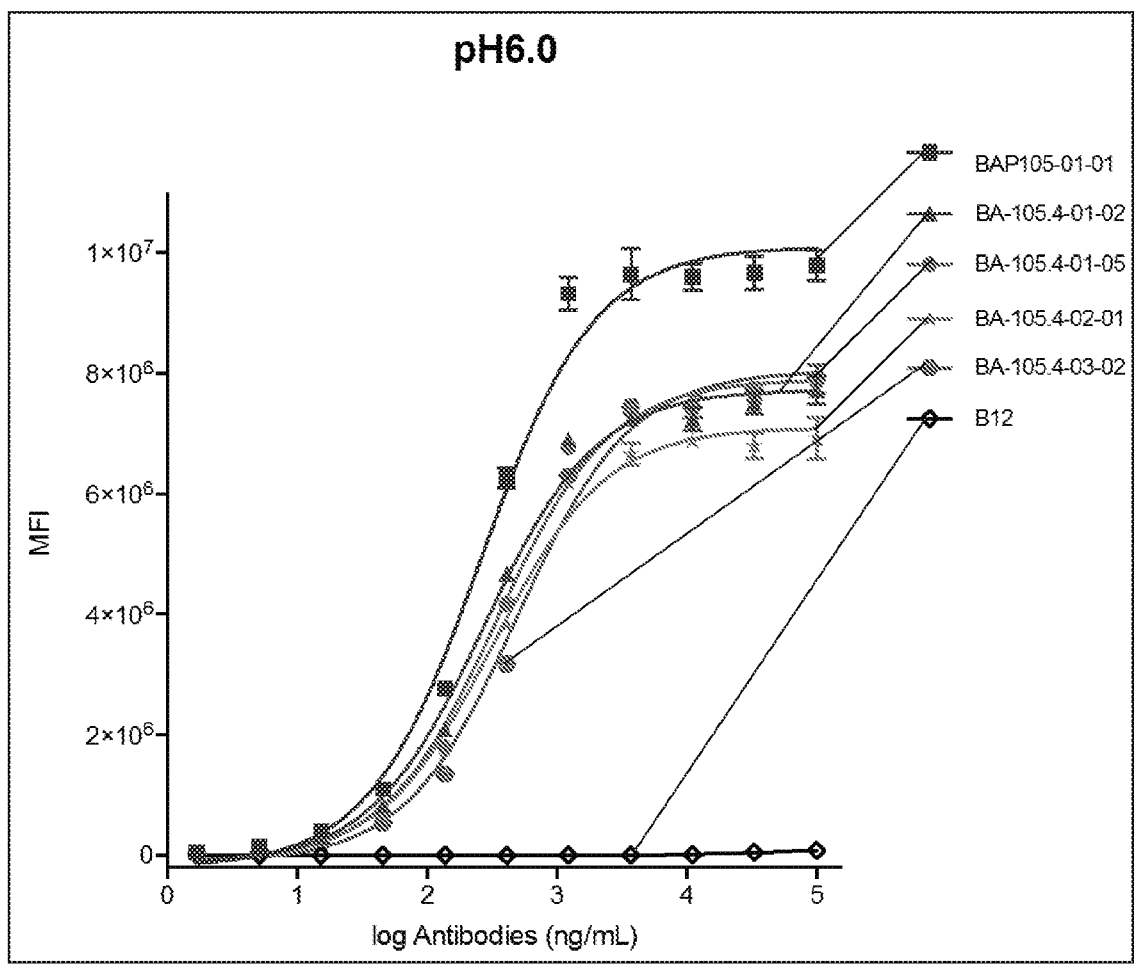
FIGS. 14A-14B show binding activities of humanized conditionally active anti-EpCAM antibodies to Colo205 cells expressing human EpCAM, as measured by FACS.
Figure 14B:
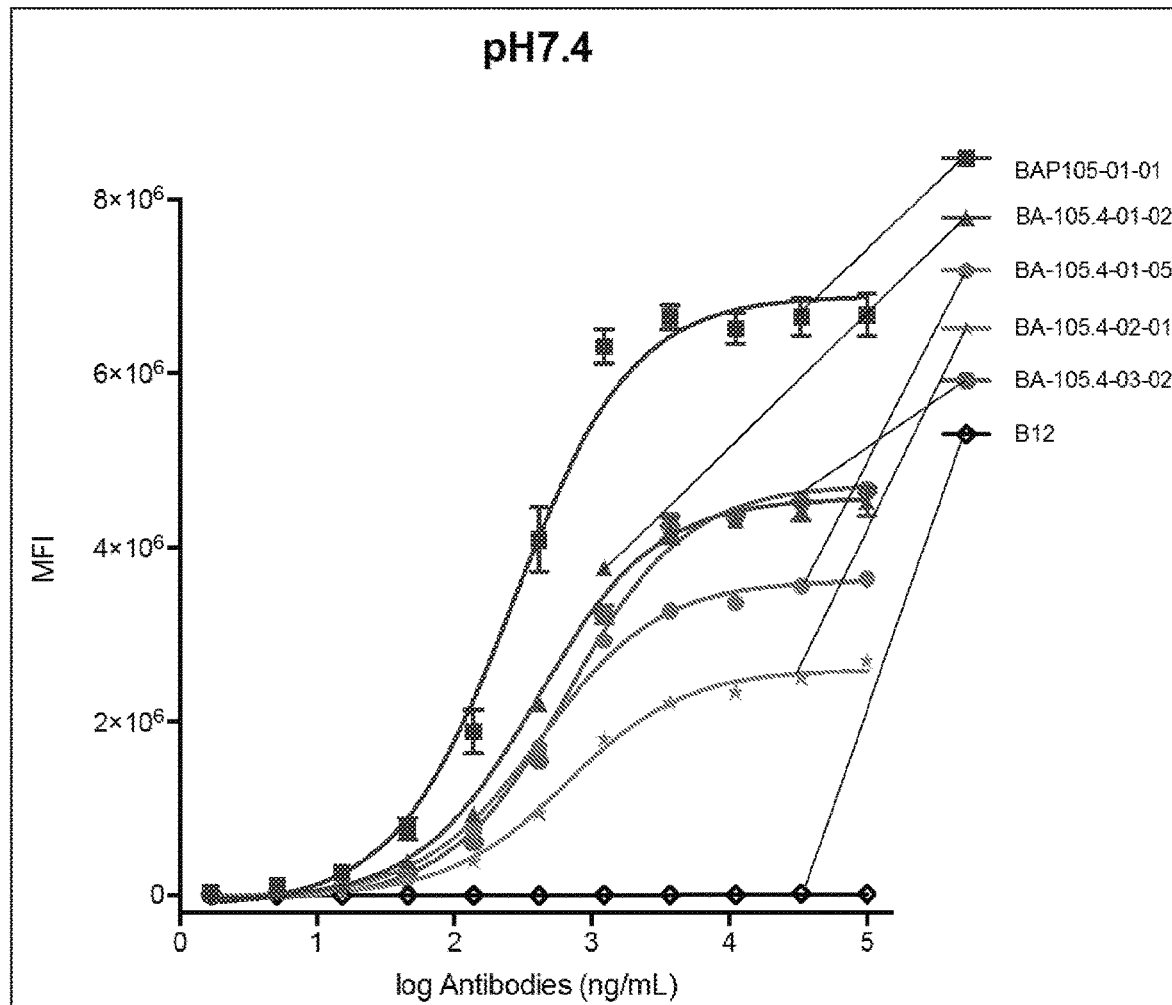

Binding Activity of the Humanized Conditionally Active Anti-EpCAM Antibodies Measured by FACS Binding activities of the humanized conditionally active anti-EpCAM antibodies to Colo205 cells expressing human EpCAM were measured by FACS at pH 6.0 and pH 7.4. The humanized conditionally active anti-EpCAM antibodies consistently showed higher binding activities to the Colo205 cells expressing human EpCAM at pH 6.0 than at pH 7.4. See FIGS. 14A-14B. The EC50 values for binding to the Colo205 cells expressing human EpCAM by the humanized conditionally active anti-EpCAM antibodies are summarized in Table 9.

TABLE 9

EC50 to Colo205 cells expressing human EpCAM of humanized conditionally active anti-EpCAM antibodies

| E50 (ng/mL) | BA-105-01-01 | 105.4-01-02 | 105.4-01-05 | 105.4-02-01 | 105.4-03-02 |
|---|---|---|---|---|---|
| pH 6.0 | 263.4 | 272.8 | 341.6 | 321.2 | 496.8 |
| pH 7.4 | 267.8 | 397.1 | 418 | 652.4 | 669.6 |

Figure 15A:
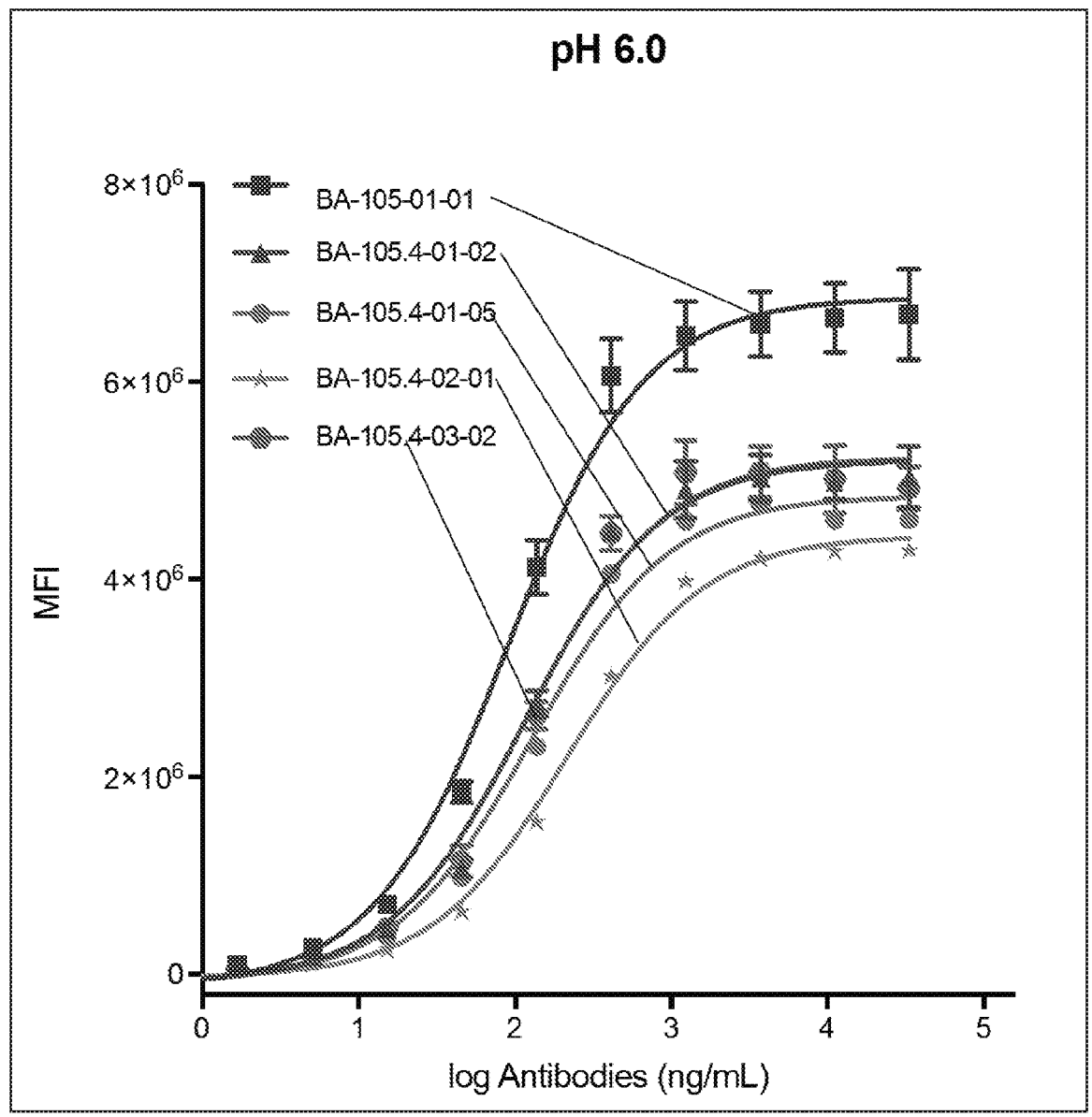
FIGS. 15A-15B show binding activities of humanized conditionally active anti-EpCAM antibodies to 293 cells expressing human EpCAM, as measured by FACS.
Figure 15B:
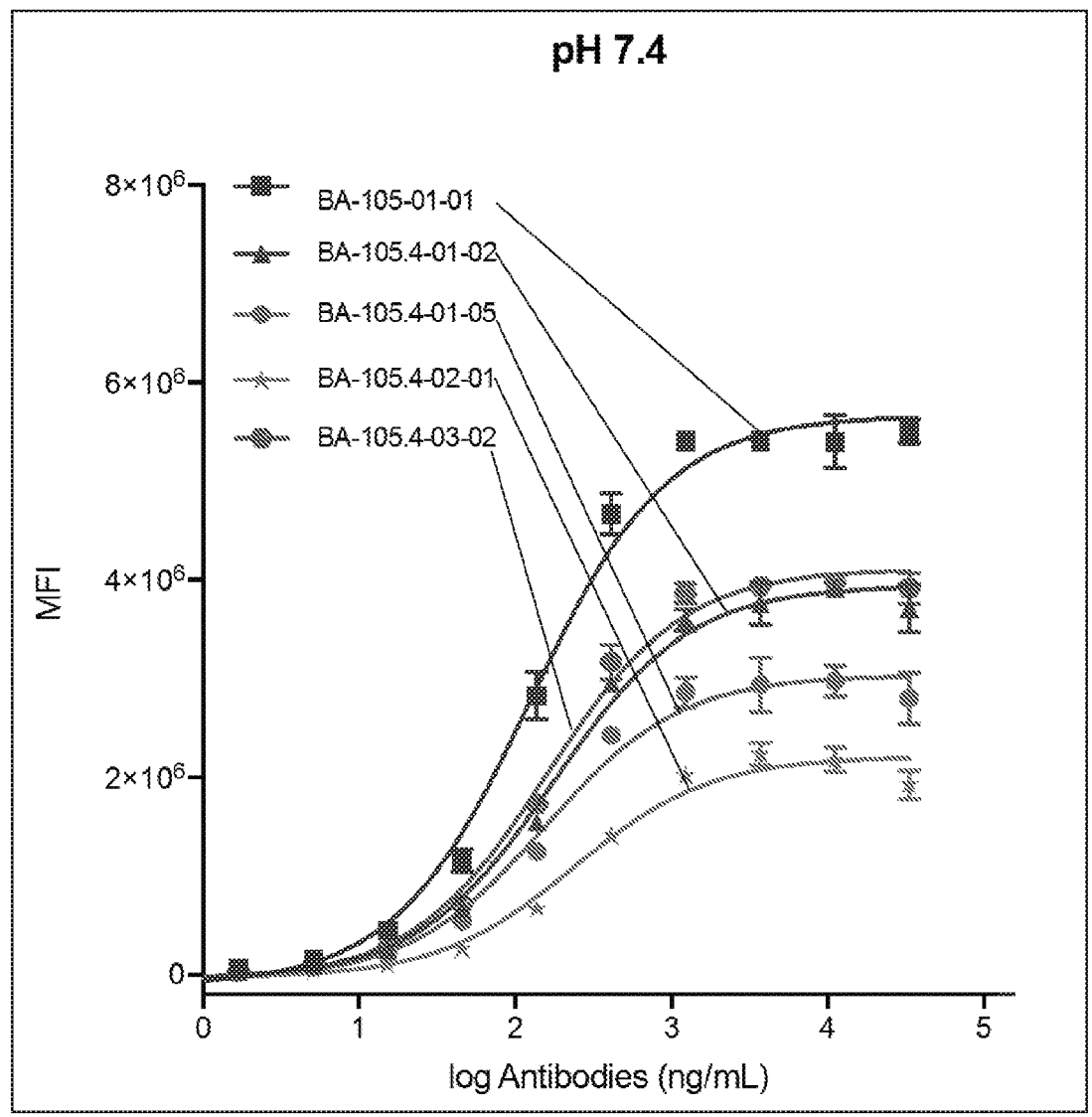

A similar FACS analysis was also carried out using 293 cells expressing human EpCAM. The humanized conditionally active anti-EpCAM antibodies also consistently showed higher binding activity to the 293 cells expressing human EpCAM at pH 6.0 than at pH 7.4. See FIGS. 15A-15B. The EC50 values for binding to the 293 cells expressing human EpCAM by the humanized conditionally active anti-EpCAM antibodies are summarized in Table 10.

TABLE 10

EC50 to 293 cells expressing human EpCAM of humanized conditionally active anti-EpCAM antibodies

| EC50 (ng/mL) | BA-105-01-01 | 105.4-01-02 | 105.4-01-05 | 105.4-02-01 | 105.4-03-02 |
|---|---|---|---|---|---|
| pH 6.0 | 91.95 | 115.5 | 128.6 | 215.4 | 117.7 |
| pH 7.4 | 124.8 | 174.5 | 153.7 | 237.7 | 158.5 |

Figure 16A:
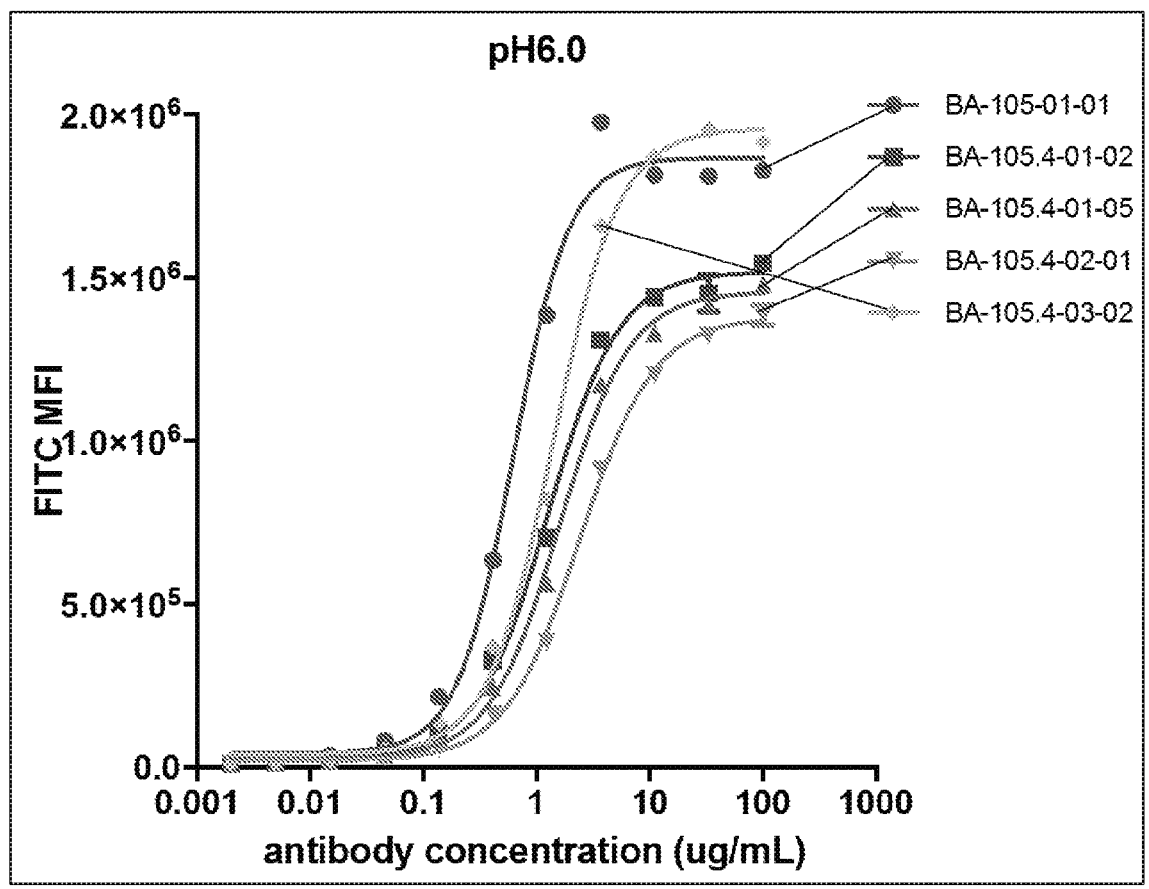
FIGS. 16A-16B show binding activities of humanized conditionally active anti-EpCAM antibodies to 293 cells expressing cyno EpCAM, as measured by FACS.
Figure 16B:
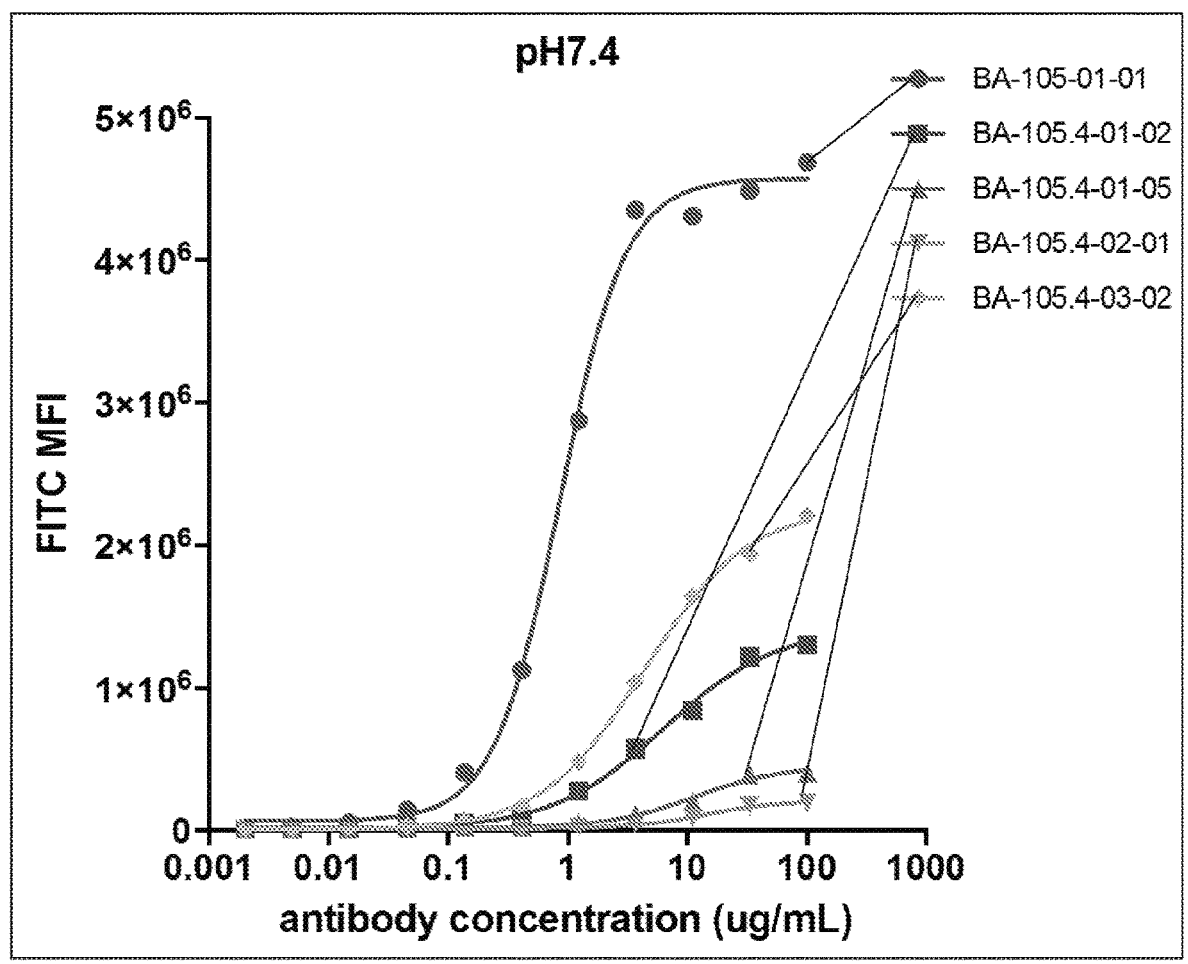

A similar FACS analysis was also carried out using 293 cells expressing cyno EpCAM. The humanized conditionally active anti-EpCAM antibodies also consistently showed higher binding activity to the 293 cells expressing cyno EpCAM at pH 6.0 than at pH 7.4. See FIGS. 16A-16B. The EC50 values for binding to the 293 cells expressing cyno EpCAM by the humanized conditionally active anti-EpCAM antibodies are summarized in Table 11.

TABLE 11

EC50 to 293 cells expressing cyno EpCAM of humanized conditionally active anti-EpCAM antibodies

| EC50 (ug/mL) | BA-105-01-01 | 105.4-01-02 | 105.4-01-05 | 105.4-02-01 | 105.4-03-02 |
|---|---|---|---|---|---|
| pH6.0 | 0.6248 | 1.263 | 1.6 | 2.417 | 1.417 |
| pH7.4 | 0.8625 | 6.36 | 11.58 | 14.09 | 4.465 |

Example 10

Figure 17A:
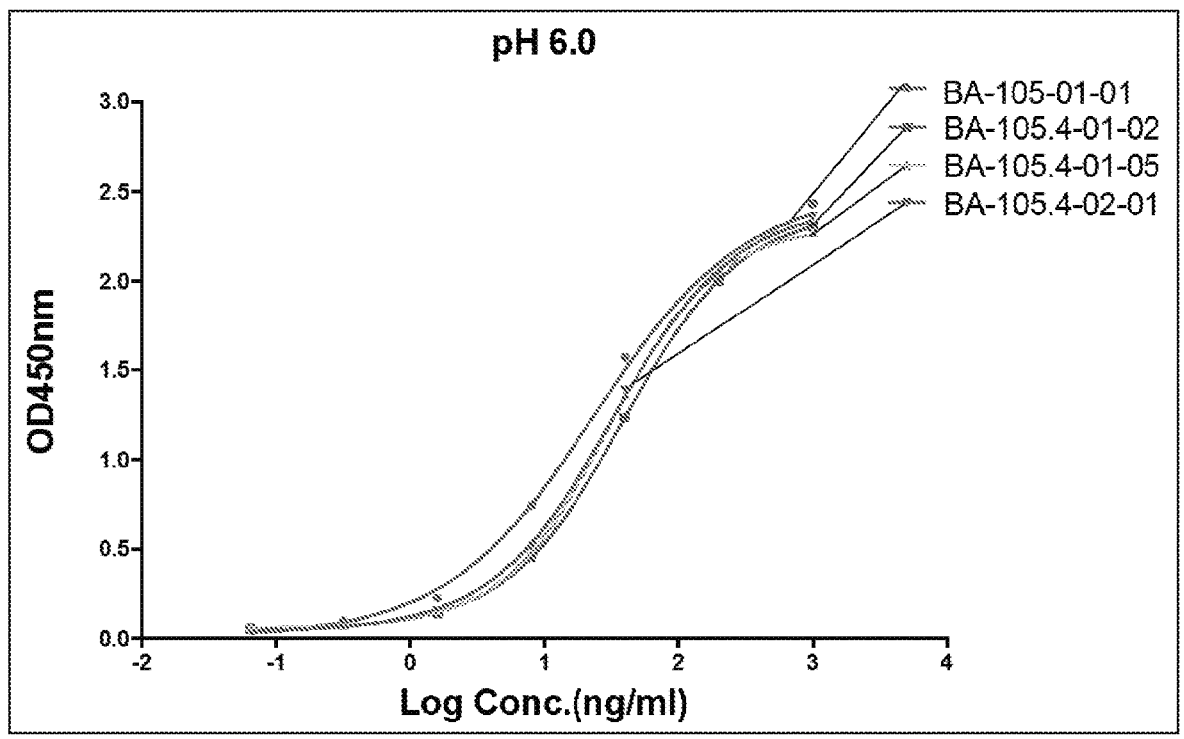
FIGS. 17A-17B show binding activities of conjugated humanized conditionally active anti-EpCAM antibodies of the present invention to human EpCAM, as measured by ELISA.
Figure 17B:
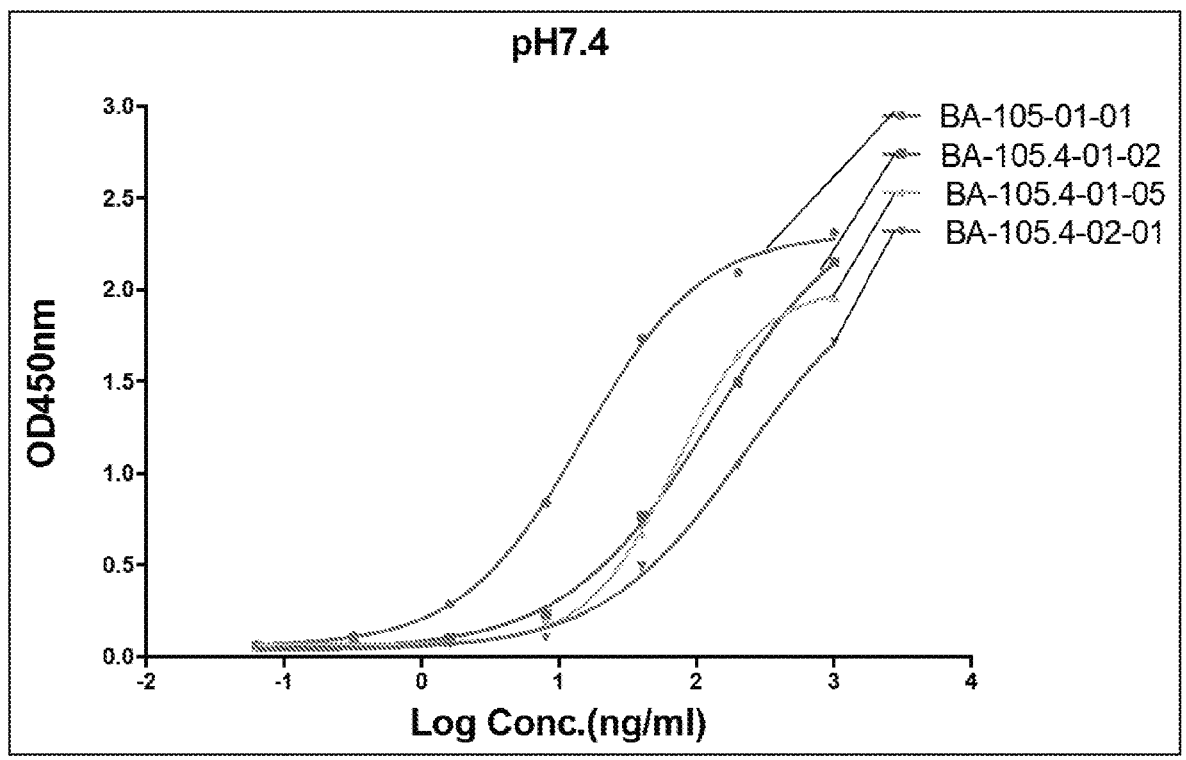

Binding Activity of the Humanized Conditionally Active Anti-EpCAM Antibody ADCs The humanized conditionally active anti-EpCAM antibodies were conjugated to MMAE to create antibody drug conjugates. Binding activities of the conjugated humanized conditionally active anti-EpCAM antibodies to human EpCAM were measured by ELISA at pH 6.0 and pH 7.4 at different antibody concentrations. The conjugated humanized conditionally active anti-EpCAM antibodies consistently showed higher binding activities to human EpCAM at pH 6.0 than at pH 7.4. See FIGS. 17A-17B. The EC50 values for binding to the human EpCAM by the conjugated humanized conditionally active anti-EpCAM antibodies are summarized in Table 12.

TABLE 12

EC50 of conjugated humanized conditionally active anti-EpCAM antibodies to human EpCAM

| EC50 (ng/mL) | pH6.0 | pH7.4 |
|---|---|---|
| BA-105-01-01 | 23.96 | 14.74 |
| BA-105.4-01-02 | 39.16 | 126.5 |
| BA-105.4-01-05 | 30.55 | 70.27 |
| BA-105.4-02-01 | 32.41 | 220.2 |

Figure 18A:
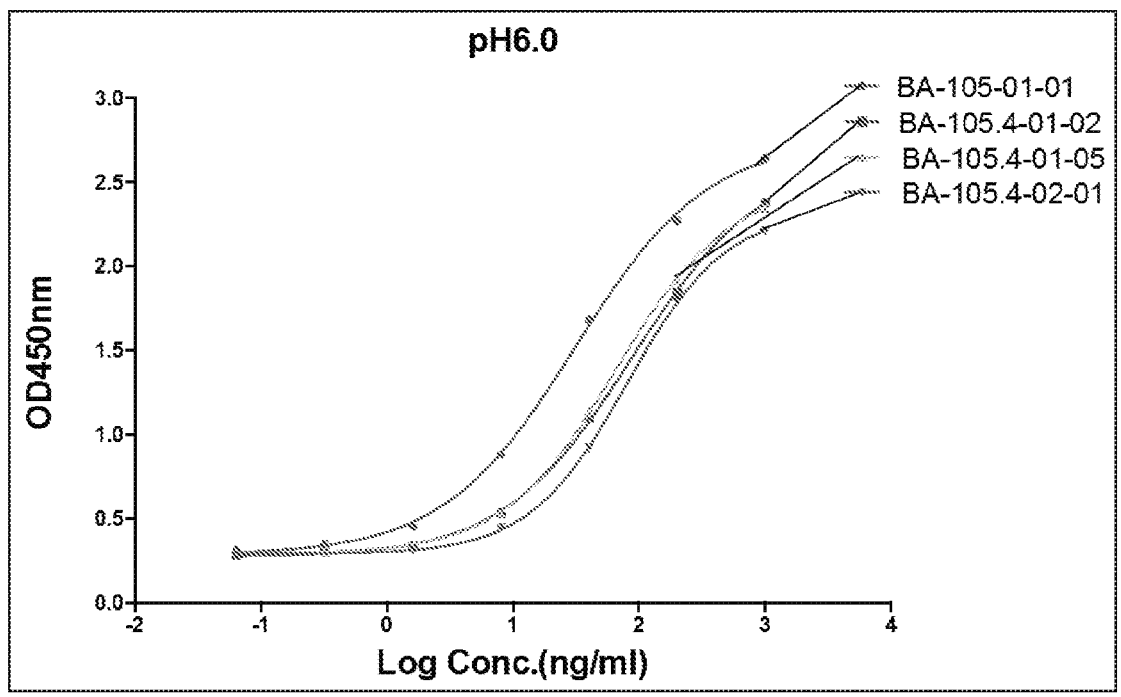
FIGS. 18A-18B show binding activities of conjugated humanized conditionally active anti-EpCAM antibodies of the present invention to cyno EpCAM, as measured by ELISA.
Figure 18B:
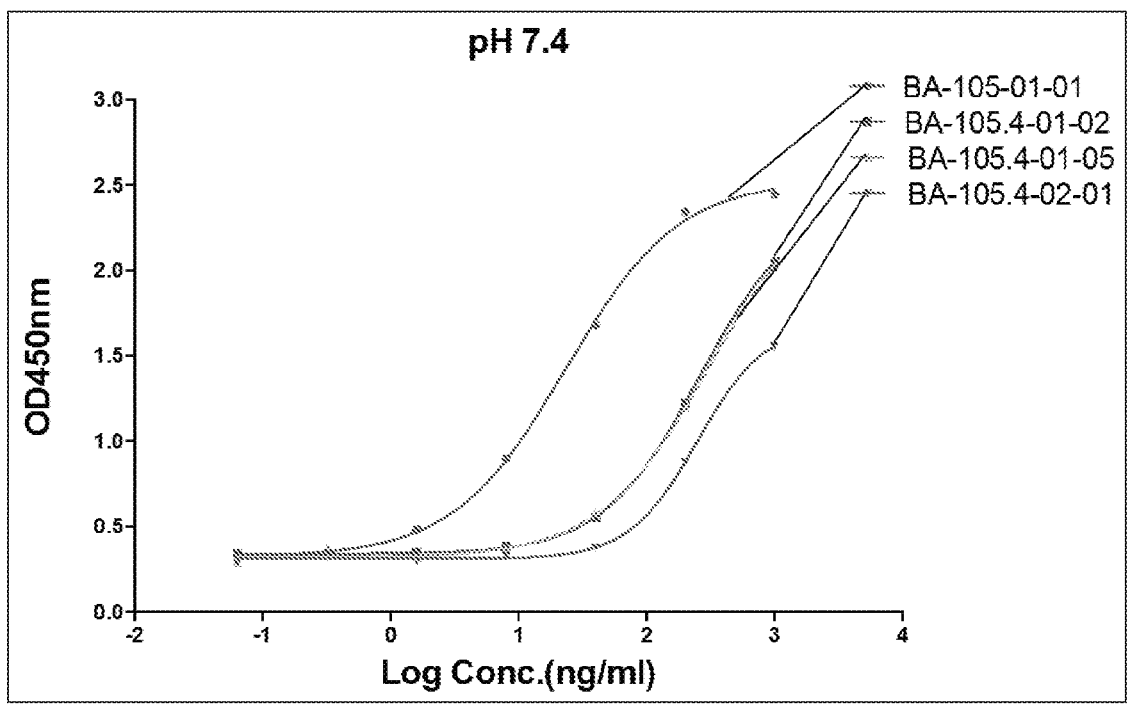

A similar ELISA analysis was also carried out using cyno EpCAM to measure the binding affinities of the conjugated humanized conditionally active anti-EpCAM antibodies. The conjugated humanized conditionally active anti-EpCAM antibodies also consistently showed a higher binding activity to cyno EpCAM at pH 6.0 than at pH 7.4. See FIGS. 18A-18B. The EC50 values for binding to the cyno EpCAM by the conjugated humanized conditionally active anti-EpCAM antibodies are summarized in Table 13.

TABLE 13

EC50 of conjugated humanized conditionally active anti-EpCAM antibodies to cyno EpCAM

| EC50 (ng/mL) | pH6.0 | pH7.4 |
|---|---|---|
| BA-105-01-01 | 31.1 | 23.45 |
| BA-105.4-01-02 | 87.74 | 256.6 |
| BA-105.4-01-05 | 65.87 | 300.2 |
| BA-105.4-02-01 | 80.9 | 248.7 |

Example 11

Figure 19A:
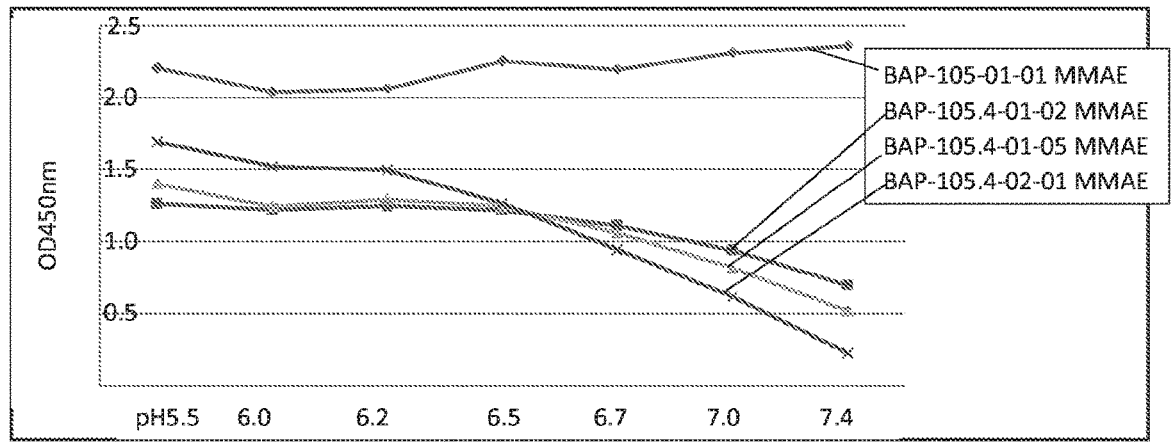
FIG. 19A shows binding activities of conjugated humanized conditionally active anti-EpCAM antibody to human EpCAM, as measured by ELISA with pH titration.

Binding Activity of the Humanized Conditionally Active Anti-EpCAM Antibody ADCs with pH Titration Binding activities of conjugated humanized conditionally active anti-EpCAM antibodies to human EpCAM were measured by ELISA with pH titration. The conjugated humanized conditionally active anti-EpCAM antibodies showed a decreasing binding activity to human EpCAM as pH increases from pH 5.5. See FIG. 19A. The ratios of binding activities to human EpCAM of the conjugated humanized conditionally active anti-EpCAM antibodies at pH 6.0 and pH 7.4, as well as their pH inflection points are summarized in Table 14.

TABLE 14

Binding characteristic of conjugated humanized conditionally active anti-EpCAM antibodies to human EpCAM

| Human EpCAM | ratio (pH 6.0/7.4) | pH inflection points |
|---|---|---|
| BA-105-01-01 7376-vcMMAE | 0.86 | 6.71 |
| BA-105.4-01-02 8316-vcMMAE | 1.75 | NA |
| BA-105.4-01-05 8317-vcMMAE | 2.39 | 6.98 |
| BA-105.4-02-01 8318-vcMMAE | 6.74 | 6.83 |

Figure 19B:
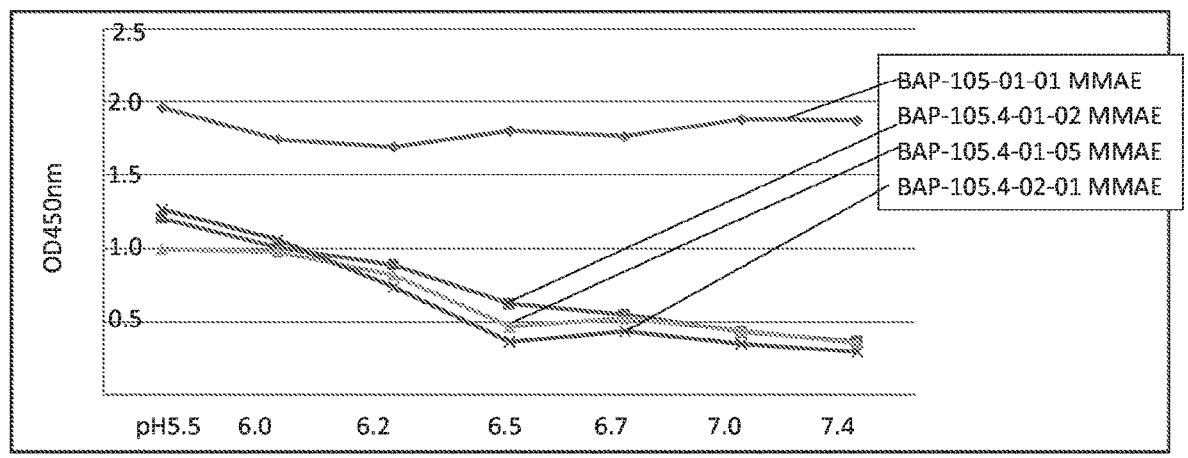
FIG. 19B shows binding activities of conjugated humanized conditionally active anti-EpCAM antibody to cyno EpCAM as measured by ELISA with pH titration.

Binding activities of the conjugated humanized conditionally active anti-EpCAM antibodies to cyno EpCAM were also measured by ELISA with pH titration. The conjugated humanized conditionally active anti-EpCAM antibodies showed a similar decreasing binding activity to cyno EpCAM as pH increases from pH 5.5. See FIG. 19B. The ratios of binding activities at pH 6.0 and pH 7.4 to the cyno EpCAM by the conjugated humanized conditionally active anti-EpCAM antibodies, as well as their pH inflection points are summarized in Table 15.

TABLE 15

Binding characteristic of conjugated humanized conditionally active anti-EpCAM antibodies to cyno EpCAM

| Cyno-EpCAM | ratio (pH 6.0/7.4) | pH inflection points |
|---|---|---|
| BA-105-01-01 7376-vcMMAE | 0.93 | 5.07 |
| BA-105.4-01-02 8316-vcMMAE | 2.75 | 6.30 |
| BA-105.4-01-05 8317-vcMMAE | 2.76 | 6.28 |
| BA-105.4-02-01 8318-vcMMAE | 3.61 | 6.16 |

Example 12

Figure 20A:
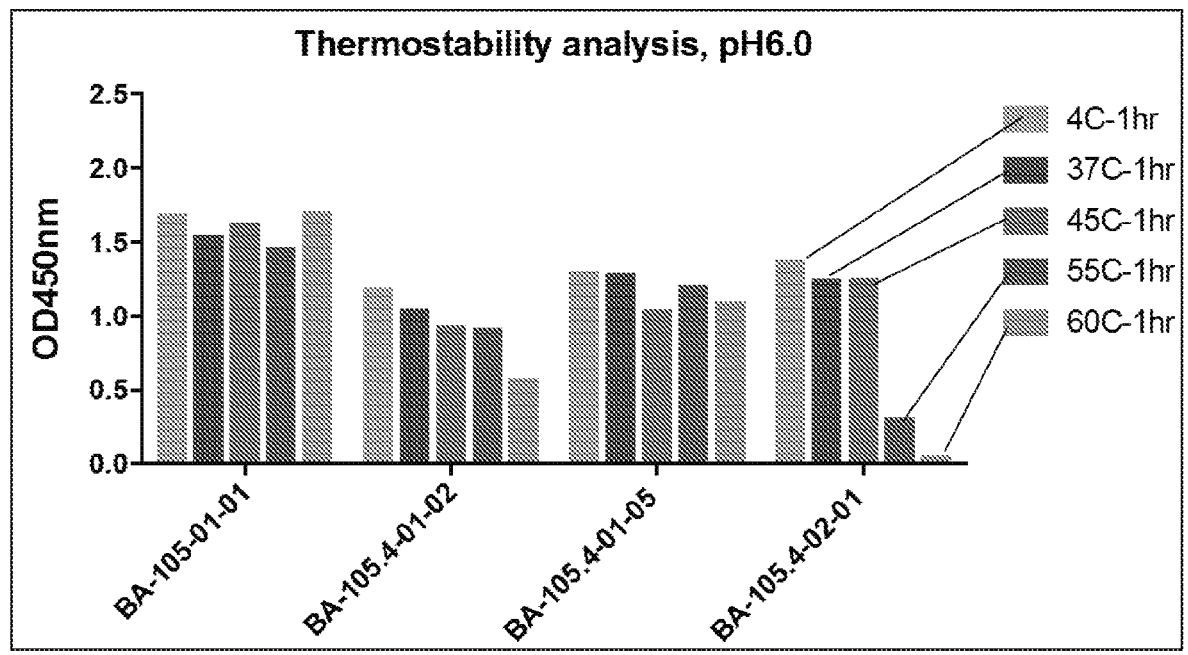
FIGS. 20A-20B show binding activities of conjugated humanized conditionally active anti-EpCAM antibodies to human EpCAM at pH 6.0 (FIG. 20A) and pH 7.4 (FIG. 20B) after heat treatment at different temperatures, as measured by ELISA.
Figure 20B:
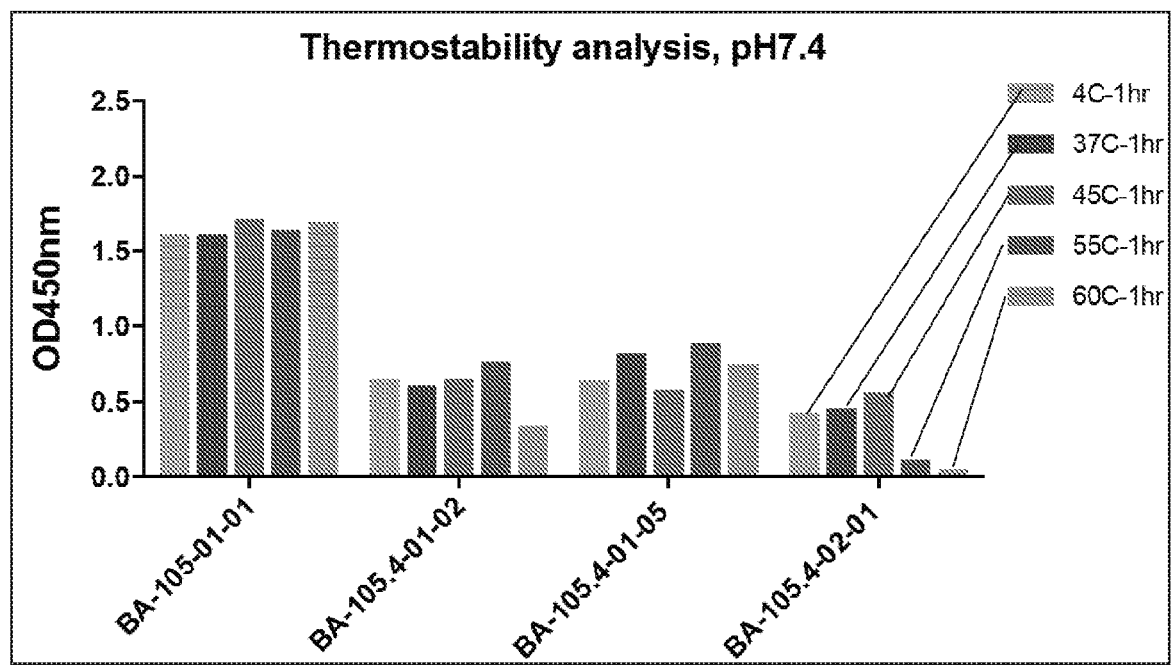

Thermostability of the Humanized Conditionally Active Anti-EpCAM Antibody ADC The thermostability of the conjugated humanized conditionally active anti-EpCAM antibodies (with MMAE) was evaluated by measuring their binding activities after heat treatment. The binding activities of the conjugated humanized conditionally active anti-EpCAM antibodies to human EpCAM after heat treatment for one (1) hour at different temperatures, were determined at pH 6.0 and pH 7.4 by ELISA. See FIGS. 20A-20B. Heat treatment up to temperatures of 45° C. did not markedly affect the binding affinities showing good heat stability at these temperatures.

Example 13

Figure 21A:
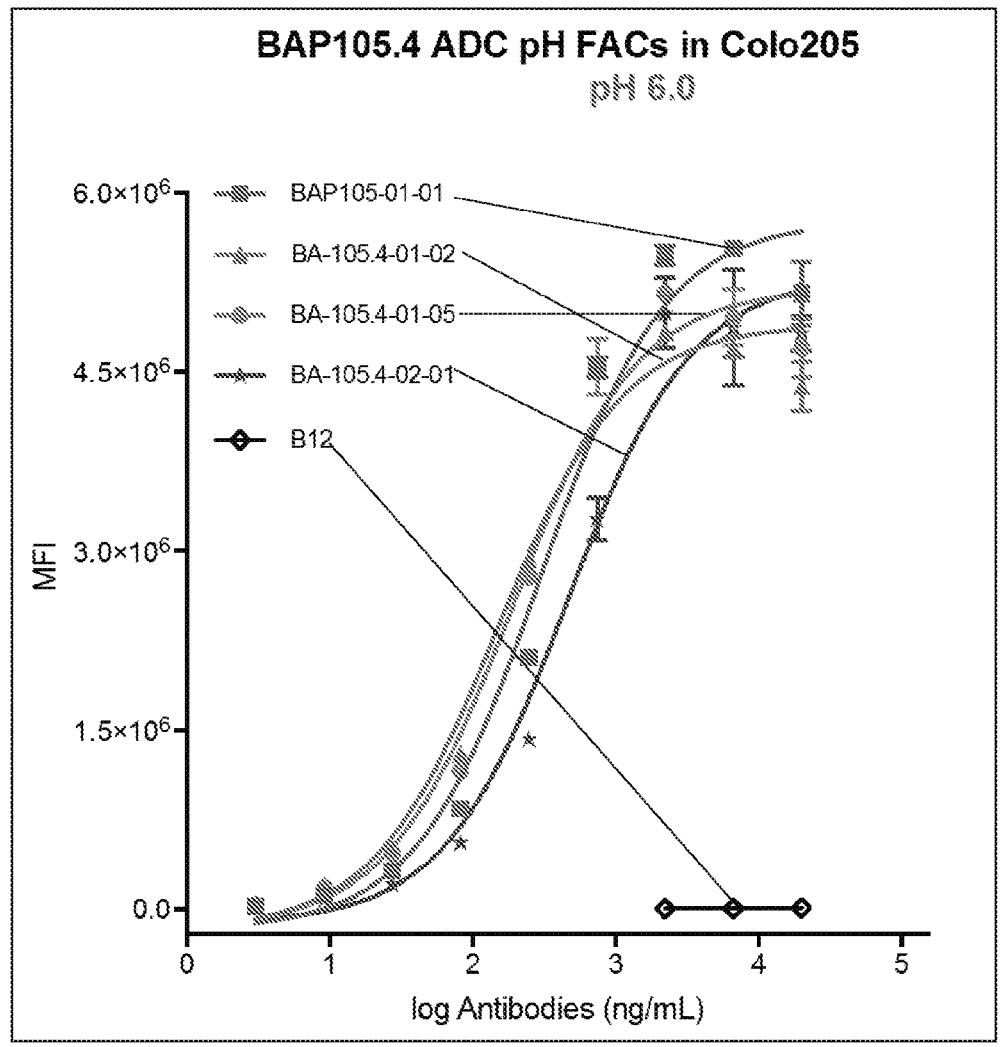
FIGS. 21A-21B show binding activities of conjugated humanized conditionally active anti-EpCAM antibodies to Colo205 cells expressing human EpCAM at pH 6.0 (FIG. 21A) and pH 7.4 (FIG. 21B). as measured by FACS.
Figure 21B:
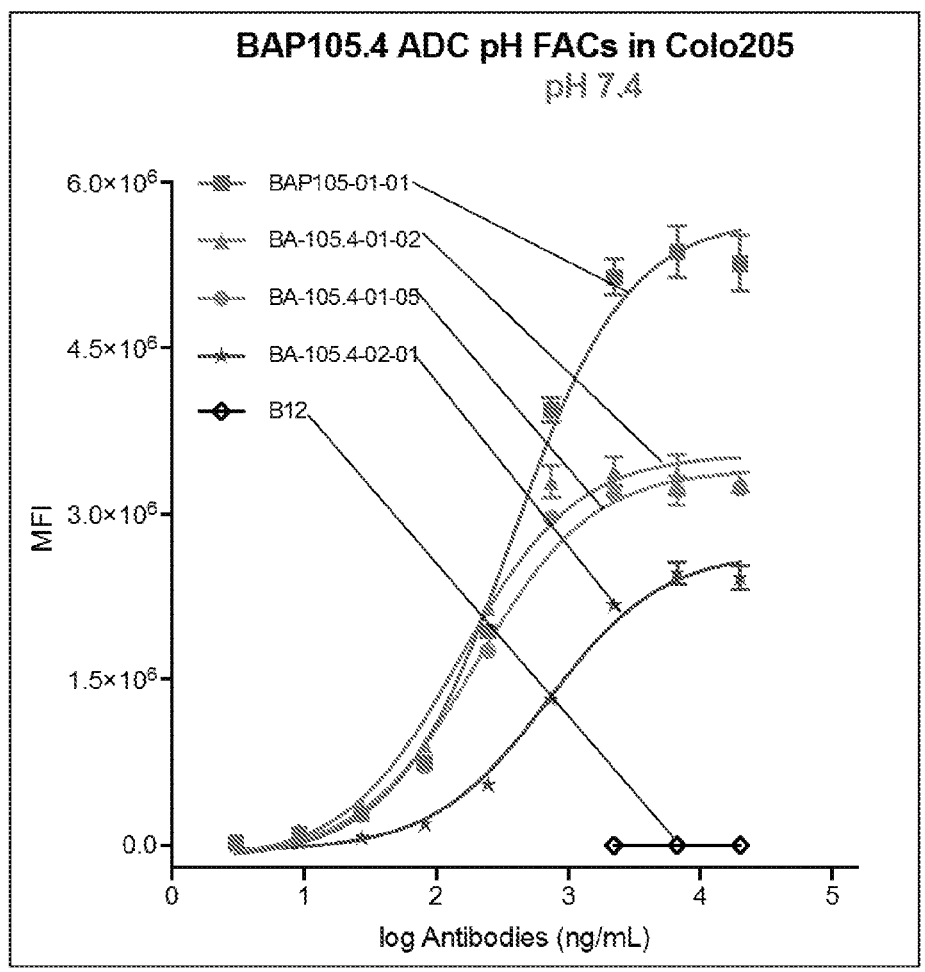

Binding Activity of the Humanized Conditionally Active Anti-EpCAM Antibody ADCs by FACS Binding activities of the conjugated humanized conditionally active anti-EpCAM antibodies (with MMAE) to Colo205 cells expressing human EpCAM was measured by FACS at two different pH: 6.0 and 7.4. The conjugated humanized conditionally active anti-EpCAM antibodies consistently showed higher binding activities to Colo205 cells expressing human EpCAM at pH 6.0 than at pH 7.4. See FIGS. 21A-21B. The EC50 values for binding to the Colo205 cells expressing human EpCAM by the conjugated humanized conditionally active anti-EpCAM antibodies are summarized in Table 16.

TABLE 16

EC50 to Colo205 cells expressing human EpCAM of the
conjugated humanized conditionally active anti-EpCAM antibodies

| EC50 (ng/mL) | BAP105-01-01 | BA-105.4-01-02 | BA-105.4-01-05 | BA-105.4-02-01 |
|---|---|---|---|---|
| pH 6.0 | 300.7 | 150.4 | 187.9 | 463.9 |
| pH 7.4 | 375 | 152.7 | 202.6 | 693.2 |

Figure 22A:
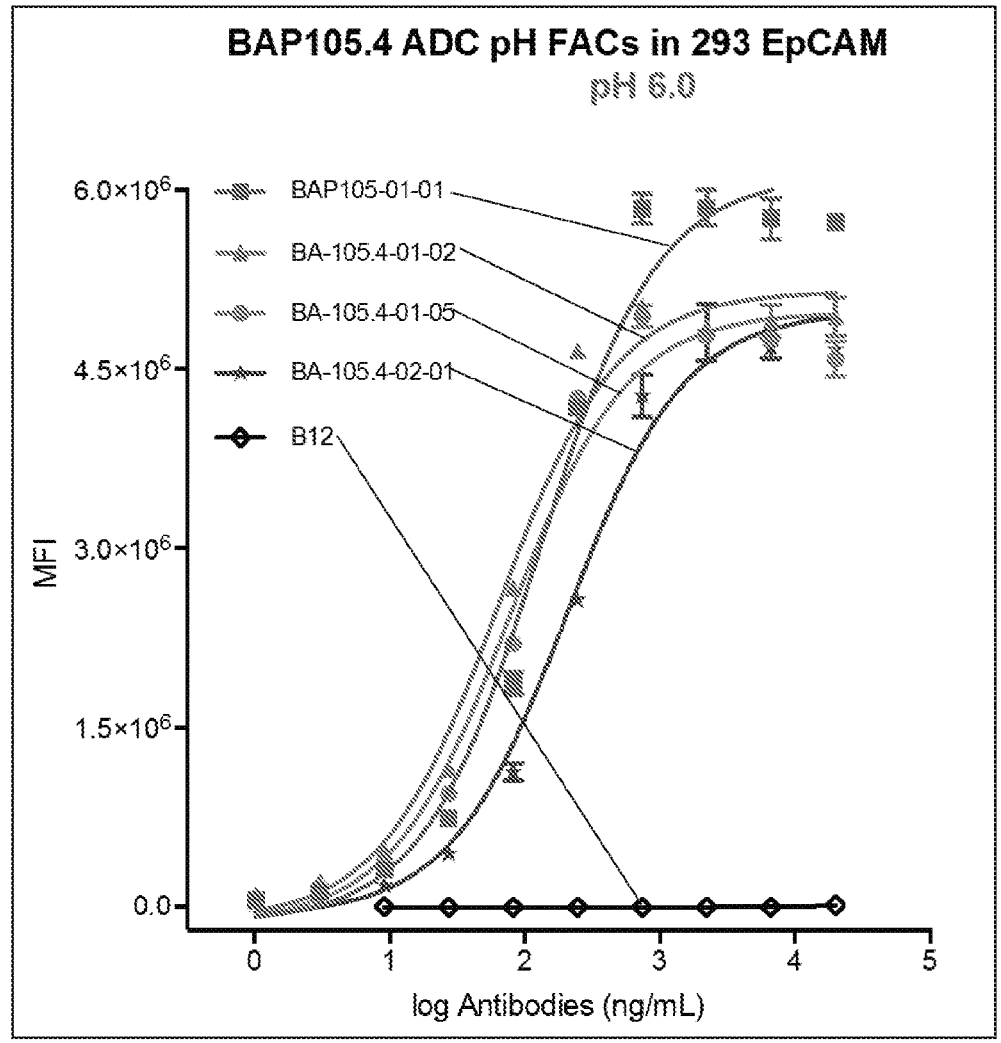
FIGS. 22A-22B show binding activities of conjugated humanized conditionally active anti-EpCAM antibodies to 293 cells expressing human EpCAM at pH 6.0 (FIG. 22A) and pH 7.4 (FIG. 22B), as measured by FACS.
Figure 22B:
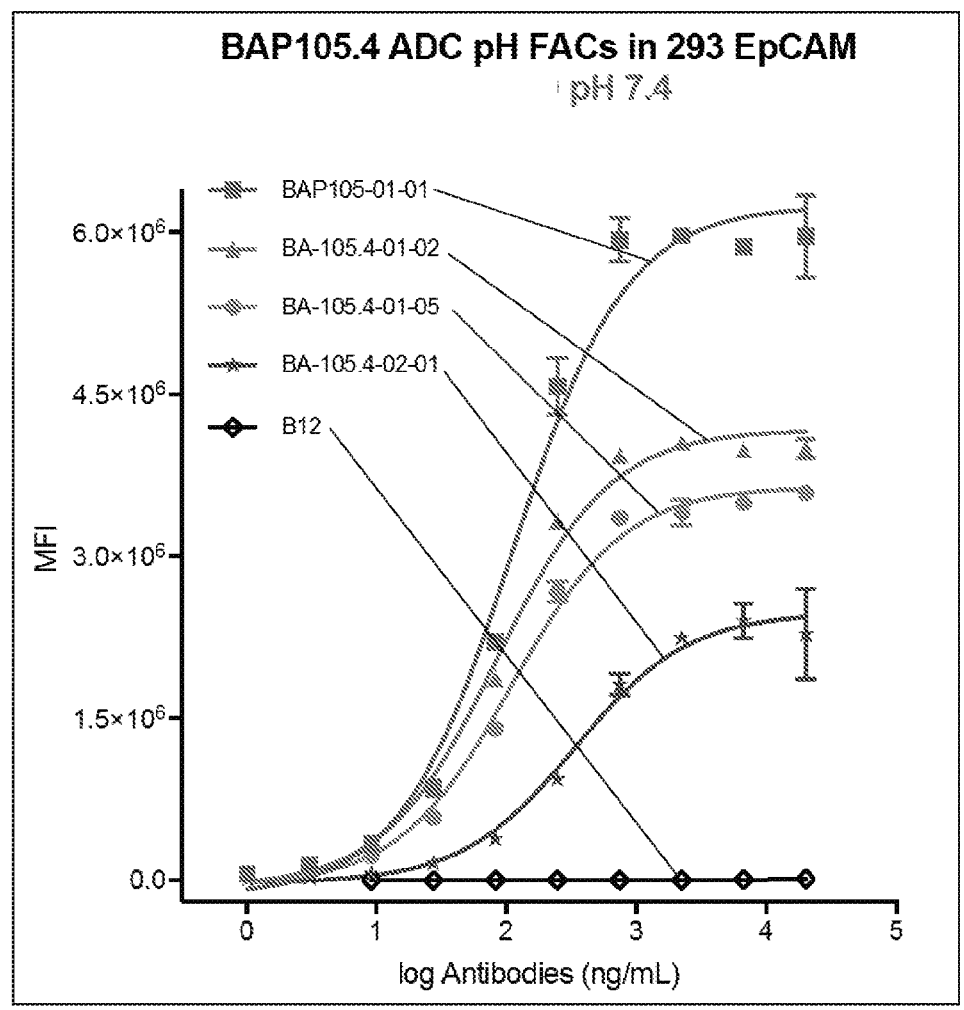

A similar FACS analysis was also carried out using 293 cells expressing human EpCAM. The conjugated humanized conditionally active anti-EpCAM antibodies also consistently showed higher binding activities to the 293 cells expressing human EpCAM at pH 6.0 than at pH 7.4. See FIGS. 22A-22B. The EC50 values for binding to the 293 cells expressing human EpCAM by the conjugated humanized conditionally active anti-EpCAM antibodies are summarized in Table 17.

TABLE 17

EC50 to 293 cells expressing human EpCAM of conjugated
humanized conditionally active anti-EpCAM antibodies

| EC50 (ng/mL) | BAP105-01-01 | BA-105.4-01-02 | BA-105.4-01-05 | BA-105.4-02-01 |
|---|---|---|---|---|
| pH 6.0 | 129.3 | 63.7 | 77.18 | 206.5 |
| pH 7.4 | 111.8 | 84.95 | 108.8 | 335 |

Figure 23A:
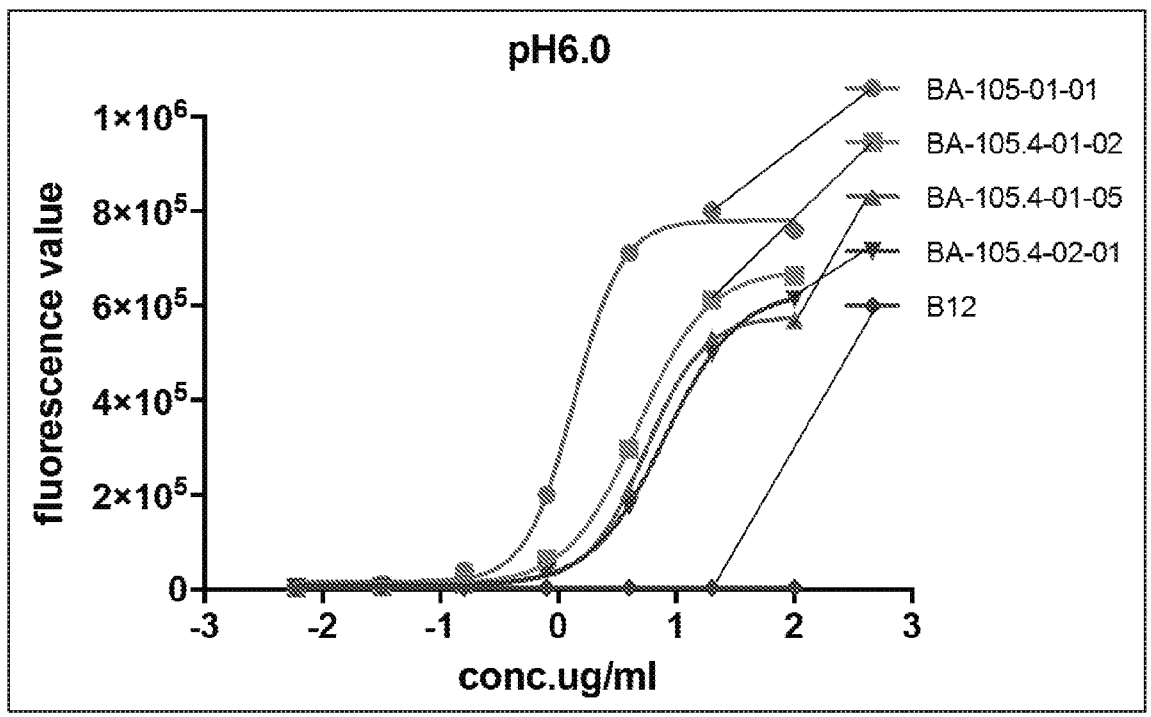
FIGS. 23A-23B show binding activities of conjugated humanized conditionally active anti-EpCAM antibodies to 293 cells expressing cyno EpCAM at pH 6.0 (FIG. 23A) and pH 7.4 (FIG. 23B), as measured by FACS.
Figure 23B:
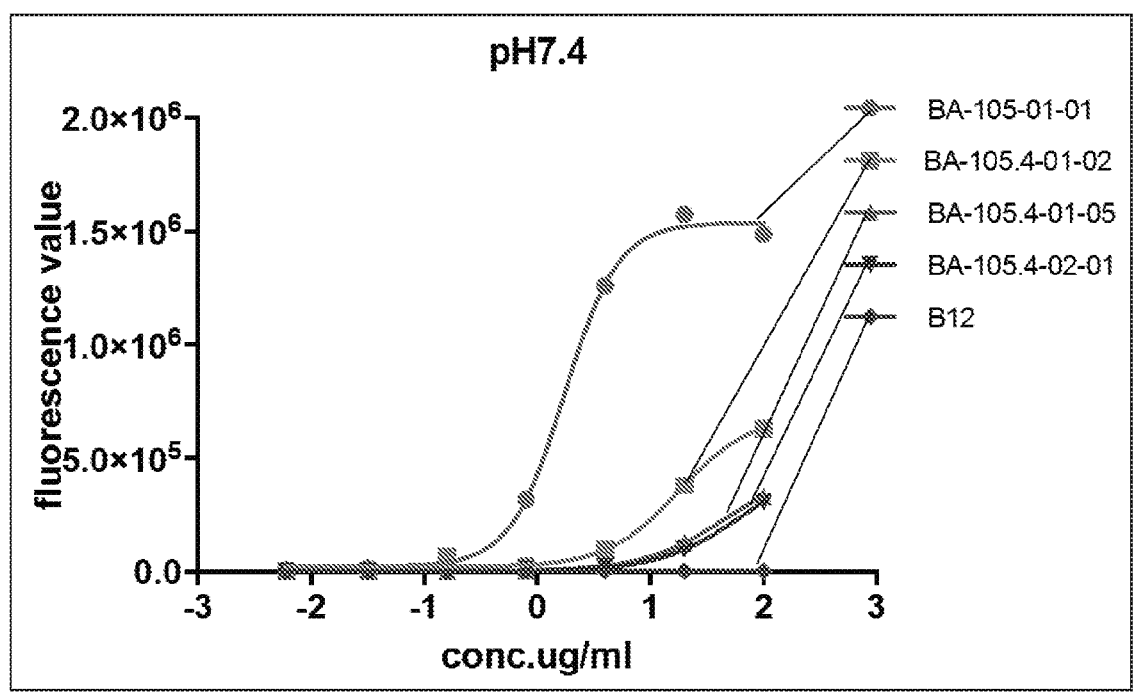

A similar FACS analysis was also carried out using 293 cells expressing cyno EpCAM. The conjugated human conditionally active anti-EpCAM antibodies (with MMAE) also consistently showed higher binding activities to the 293 cells expressing cyno EpCAM at pH 6.0 than at pH 7.4. See FIGS. 23A-23B. The EC50 values for binding to the 293 cells expressing cyno EpCAM by the conjugated humanized conditionally active anti-EpCAM antibodies are summarized in Table 18.

TABLE 18

EC50 to 293 cells expressing cyno EpCAM of conjugated humanized
conditionally active anti-EpCAM antibodies

| EC50 (ug/mL) | BA-105-01-01 | 105.4-01-02 | 105.4-01-05 | 105.4-02-01 |
|---|---|---|---|---|
| pH6.0 | 1.361 | 4.722 | 5.541 | 7.964 |
| pH7.4 | 1.741 | 17.68 | 43.36 | 61.07 |

Example 14

Cell Killing of the Humanized Conditionally Active Anti-EpCAM Antibody ADC

Figure 24A:
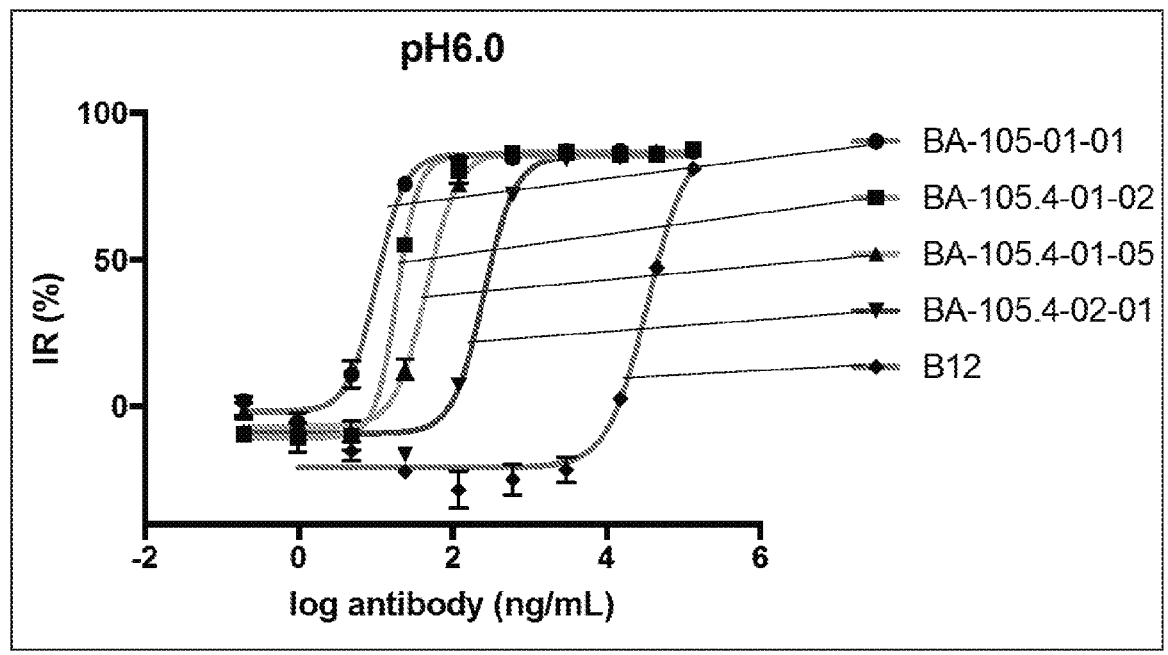
FIGS. 24A-24C show the cell killing activity of the conjugated humanized conditionally active anti-EpCAM antibodies against Colo205 cells expressing human EpCAM at pH 6.0 (FIG. 24A), pH 6.5 (FIG. 24B) and pH 7.4 (FIG. 24C).
Figure 24B:
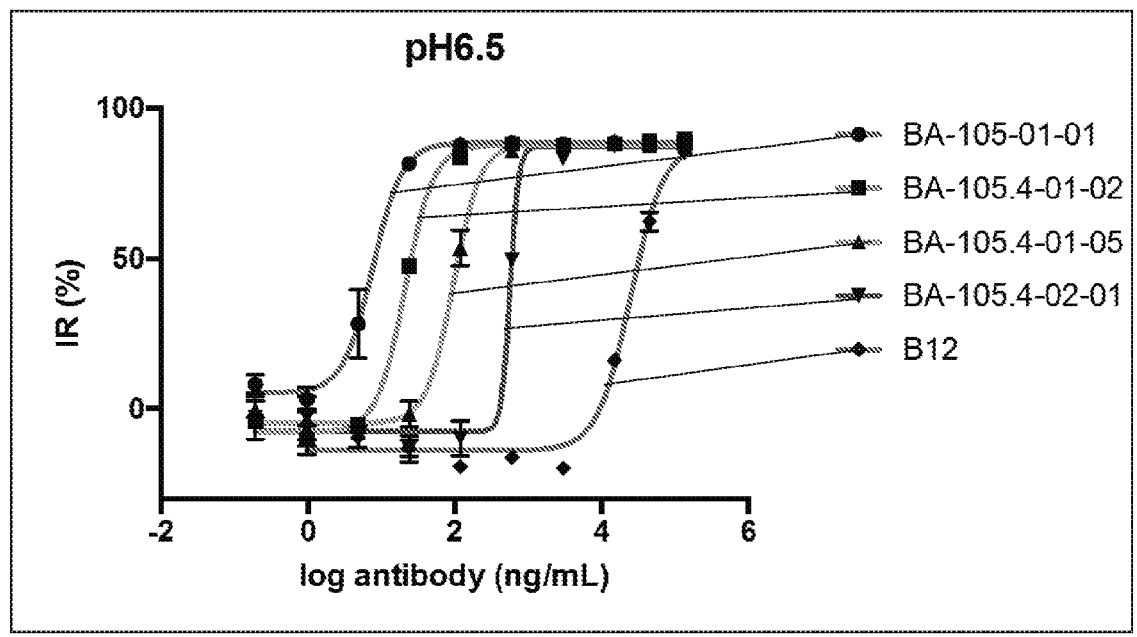
Figure 24C:
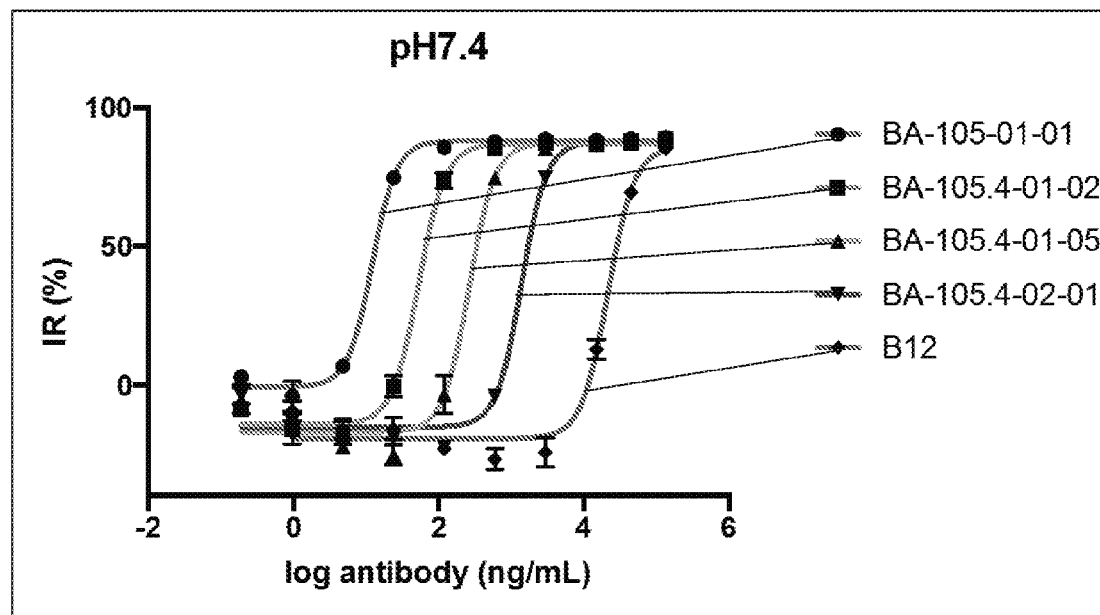

The conjugated humanized conditionally active anti-EpCAM antibodies (with MMAE) were analyzed for cell killing. Antibody BAP-105-01-01 was used as a non-conditionally active antibody control and B12 was used as a negative control. In vitro cell killing was analyzed using human EpCAM expressing Colo205 cells at three pH values of 6.0, 6.5 and 7.4. The in vitro killing of the Colo205 cells expressing human EpCAM by the conjugated humanized conditionally active anti-EpCAM antibodies is shown in FIGS. 24A-24C. The IC50 values for the cell killing of Colo205 cells expressing human EpCAM are shown in Table 19.

TABLE 19

IC50 for the cell killing of Colo205 cells by the humanized
conditionally active anti-EpCAM antibody conjugates

| | BA-105-01-01 | BA-105.4-01-02 | BA-105.4-01-05 | BA-105.4-02-01 | B12 |
|---|---|---|---|---|---|
| pH6.0 | 10.24 | 18.83 | 45.66 | 255.5 | 34409 |
| pH6.5 | 7.624 | 21.06 | 96.45 | ~567.9 | 24797 |
| pH7.4 | 12.21 | 53.46 | 264.6 | 1399 | 21567 |

Figure 25A:
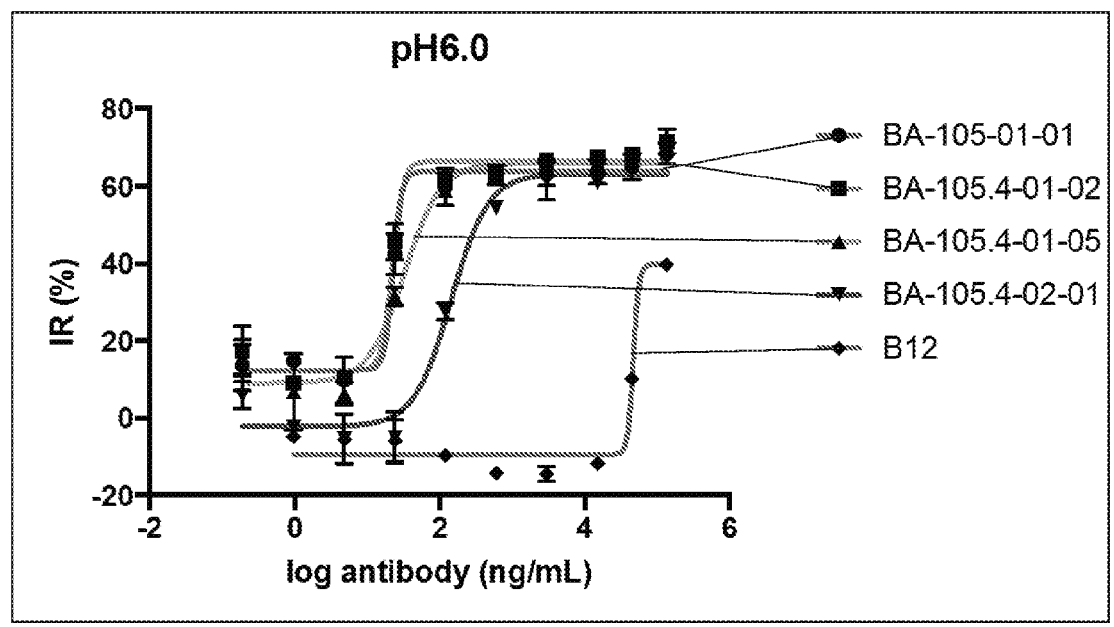
FIGS. 25A-25C show the cell killing activity of the conjugated humanized conditionally active anti-EpCAM antibodies against 293 cells expressing human EpCAM at pH 6.0 (FIG. 25A), pH 6.5 (FIG. 25B) and pH 7.4 (FIG. 25C).
Figure 25B:
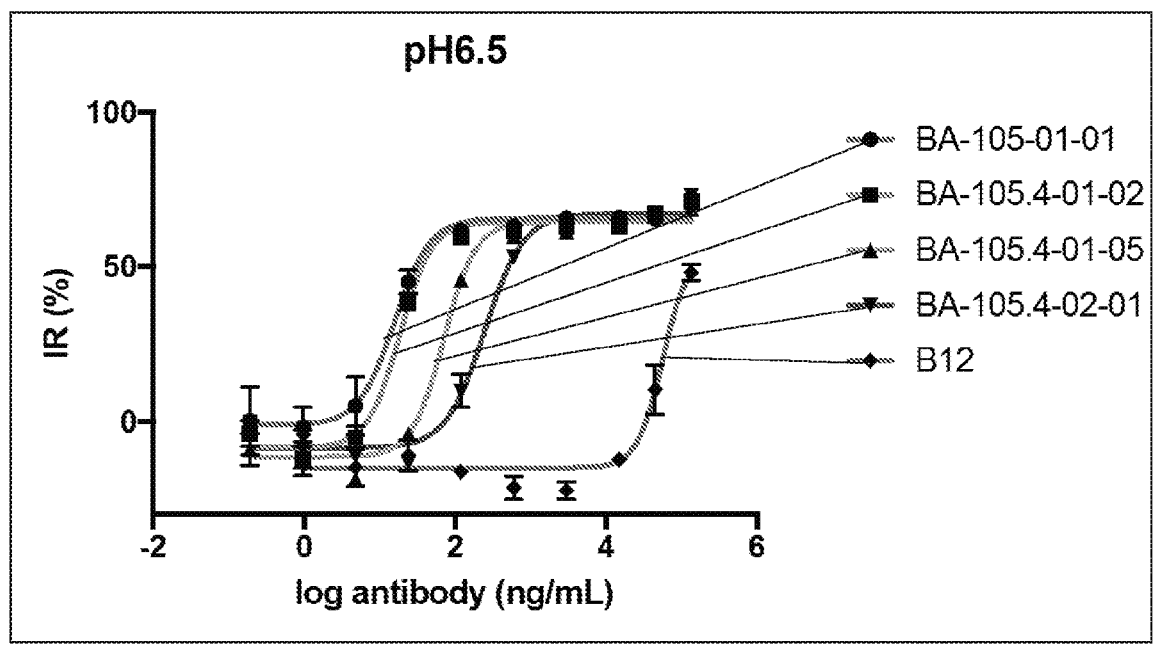
Figure 25C:
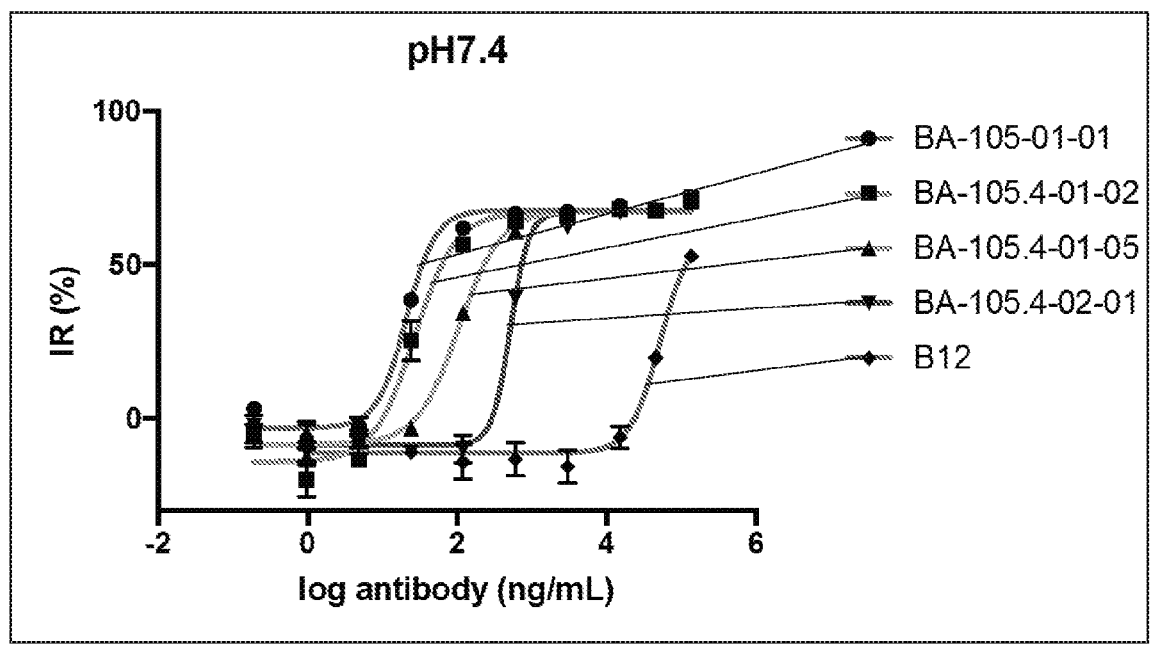

In vitro cell killing of 293 cells expressing human EpCAM was similarly analyzed using human EpCAM expressing 293 cells at three pH values of 6.0, 6.5 and 7.4. The in vitro killing of the 293 cells expressing human EPCAM by the conjugated humanized conditionally active anti-EpCAM antibodies is shown in FIGS. 25A-25C. The IC50 values for the cell killing of 293 cells expressing human EPCAM by the conjugated humanized conditionally active anti-EpCAM antibodies are shown in Table 20.

TABLE 20

IC50 for the cell killing of 293 cells by the humanized
conditionally active anti-EpCAM antibody conjugates

| | BA-105-01-01 | BA-105.4-01-02 | BA-105.4-01-05 | BA-105.4-02-01 | B12 |
|---|---|---|---|---|---|
| pH6.0 | ~22.92 | ~22.14 | 32.58 | 143.7 | ~46655 |
| pH6.5 | 15.78 | 18.47 | 70.79 | 247.3 | 56126 |
| pH7.4 | 20.72 | 26.73 | 105.7 | 516.1 | 51285 |

Figure 26A:
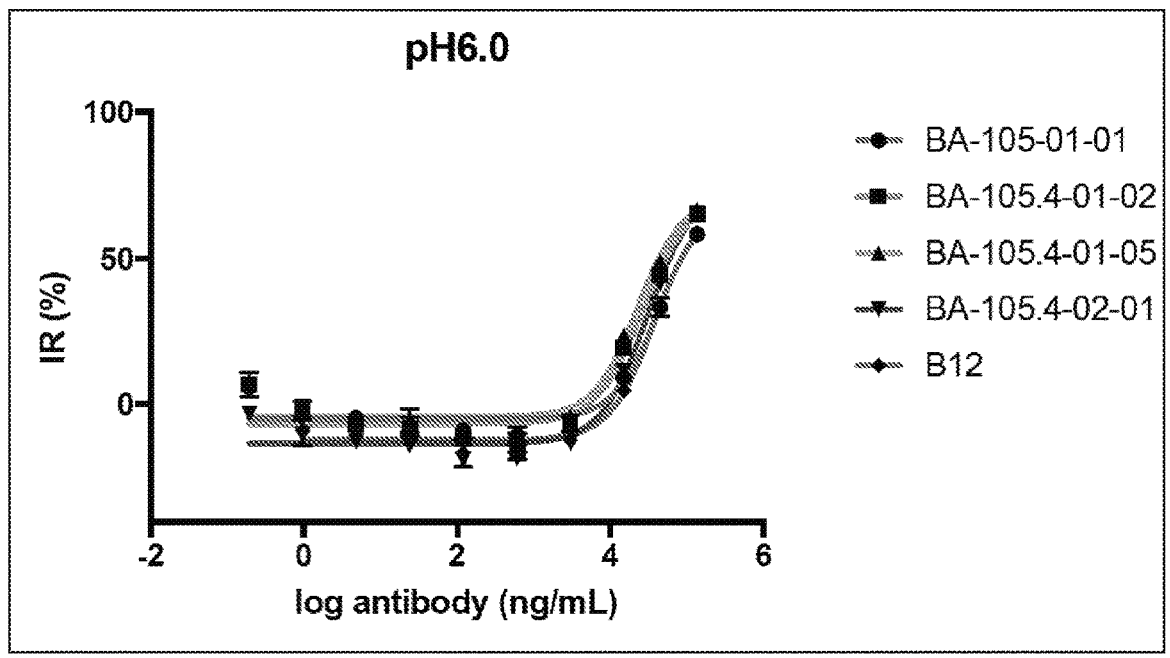
FIGS. 26A-26C show the cell killing activity of the conjugated humanized conditionally active anti-EpCAM antibodies against 293F cells that were free of human EpCAM at pH 6.0 (FIG. 26A), pH 6.5 (FIG. 26B) and pH 7.4 (FIG. 26C).
Figure 26B:
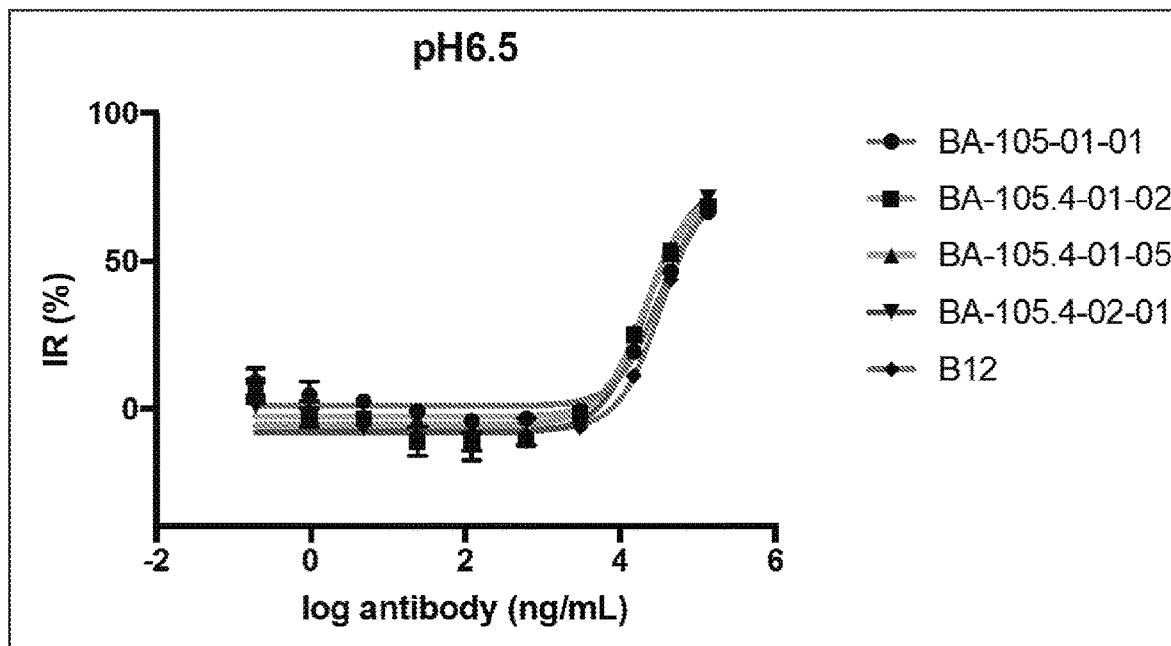
Figure 26C:
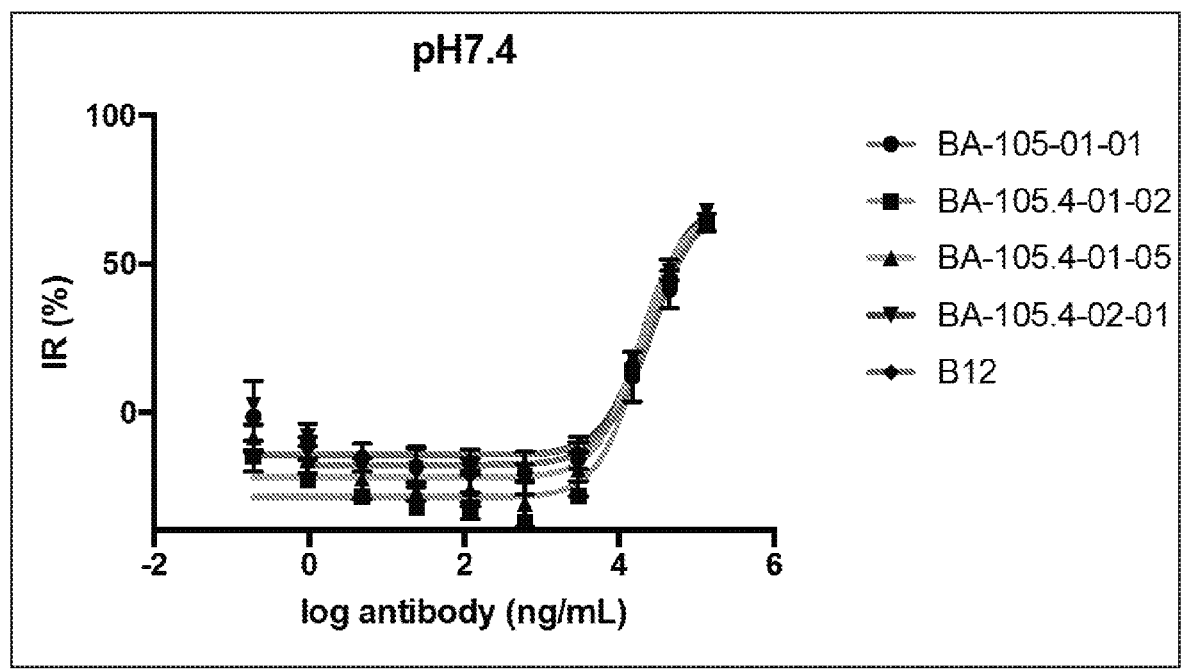

In vitro cell killing of 293F cells free of human EpCAM was similarly analyzed using EpCAM free 293F cells at three pH values of 6.0, 6.2 and 7.4. The in vitro killing of the 293F cells by the conjugated humanized conditionally active anti-EpCAM antibodies is shown in FIGS. 26A-26C. The cell killing of the conjugated humanized conditionally active anti-EpCAM antibodies was not significantly different from the controls. The IC50 values for the cell killing of 293F cells by the conjugated humanized conditionally active anti-EpCAM antibodies are shown in Table 21.

TABLE 21

IC50 for the cell killing of 293F cells by the humanized
conditionally active anti-EpCAM antibody conjugates

| | BA-105-01-01 | BA-105.4-01-02 | BA-105.4-01-05 | BA-105.4-02-01 | B12 |
|---|---|---|---|---|---|
| pH6.0 | 41775 | 26422 | 22381 | 30263 | 37512 |
| pH6.5 | 30566 | 21116 | 21000 | 21545 | 32412 |
| pH7.4 | 27499 | 18458 | 17729 | 22446 | 23925 |

Example 15

Figure 27A:
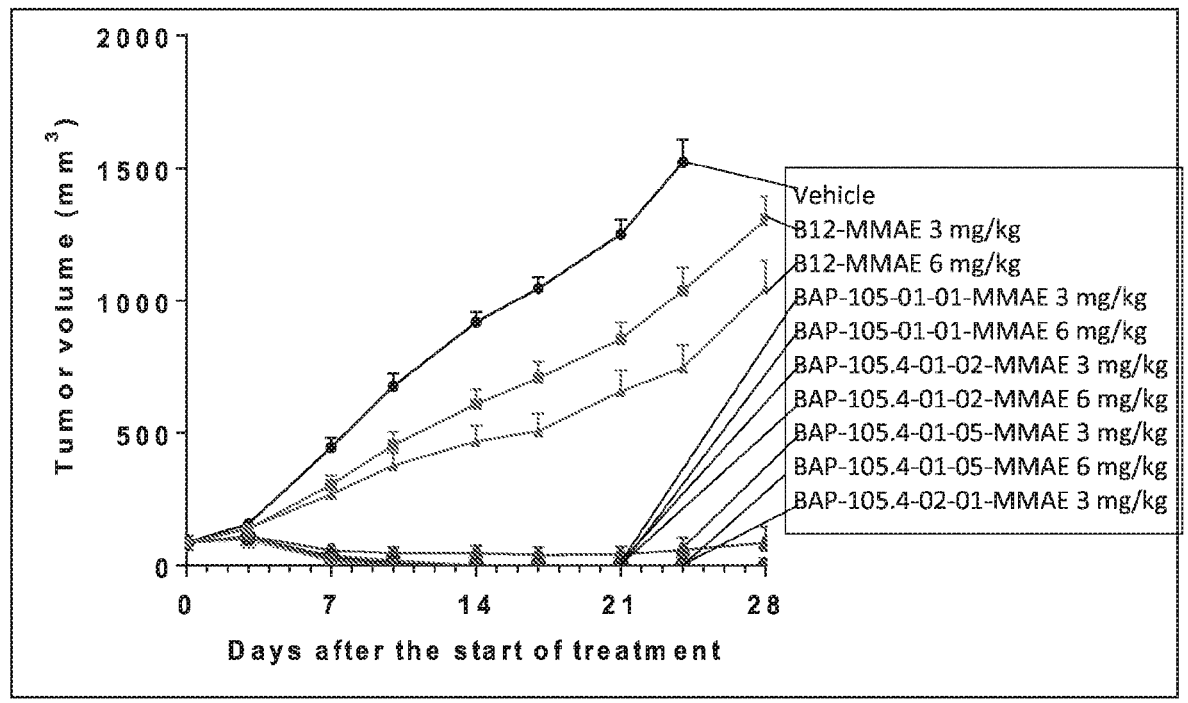
FIGS. 27A-27C show results of the treatment of tumor xenograft mice using conjugated humanized conditionally active anti-EpCAM antibodies.
Figure 27B:
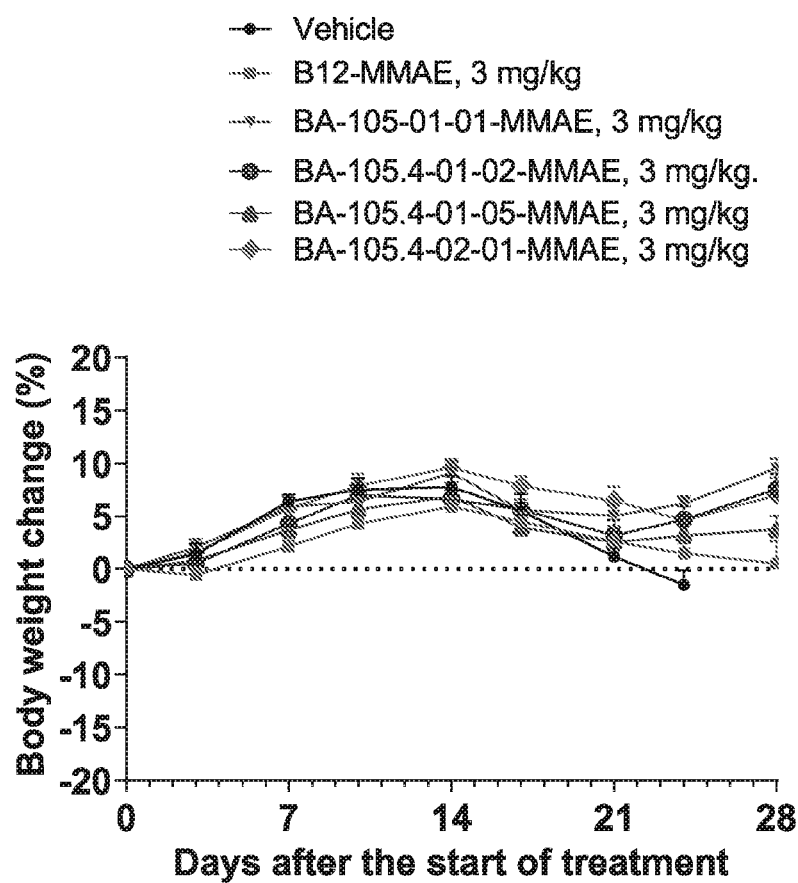
Figure 27C:
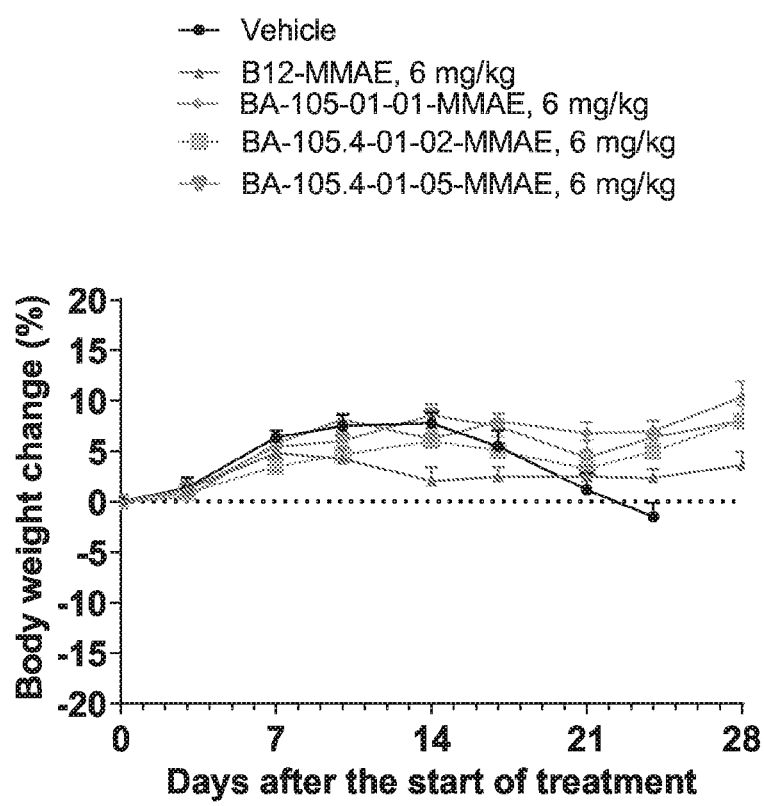

Treatment of a Tumor by the Humanized Conditionally Active Anti-EpCAM Antibody ADC In vivo treatment of a tumor by the conjugated humanized conditionally active anti-EpCAM antibodies (with MMAE) was measured in Colo205 xenograft mouse models. Antibody BAP-105-01-01 was used as a non-conditionally active antibody control and B12 was used as a negative control. The xenograft models were treated with an intermittent schedule Q4Dx4 (four times every fourth day) by IV injection. Two dosages of 3 mg/kg and 6 mg/kg were used. Eight (8) mice were used for each treatment group. The conjugated conditionally active anti-EpCAM antibodies (BAP-105.4-01-02, BAP-105.4-01-05, and BAP-105.4-02-01) significantly reduced the volume of the tumors but did not significantly reduce the weight of the animals at the doses of 3 and 6 mg/kg, in comparison with the controls, indicating both more effective treatment and reduced side effects for the conjugated humanized conditionally active anti-EpCAM antibodies. See FIGS. 27A-27C.

Example 16

Figure 28A:
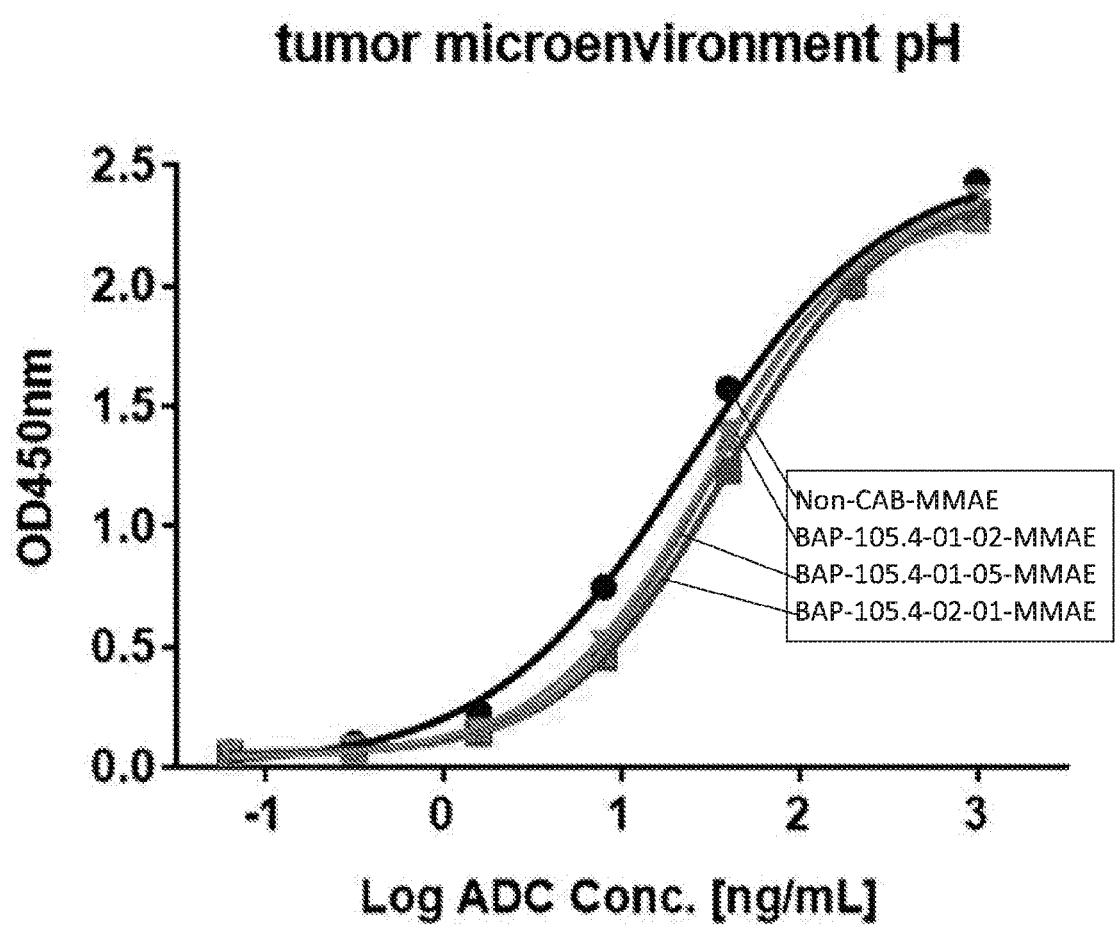
FIGS. 28A-28B show binding activities of conjugated humanized conditionally active anti-EpCAM antibodies at a pH in a tumor microenvironment (FIG. 28A) and a normal physiological pH (FIG. 28B).
Figure 28B:
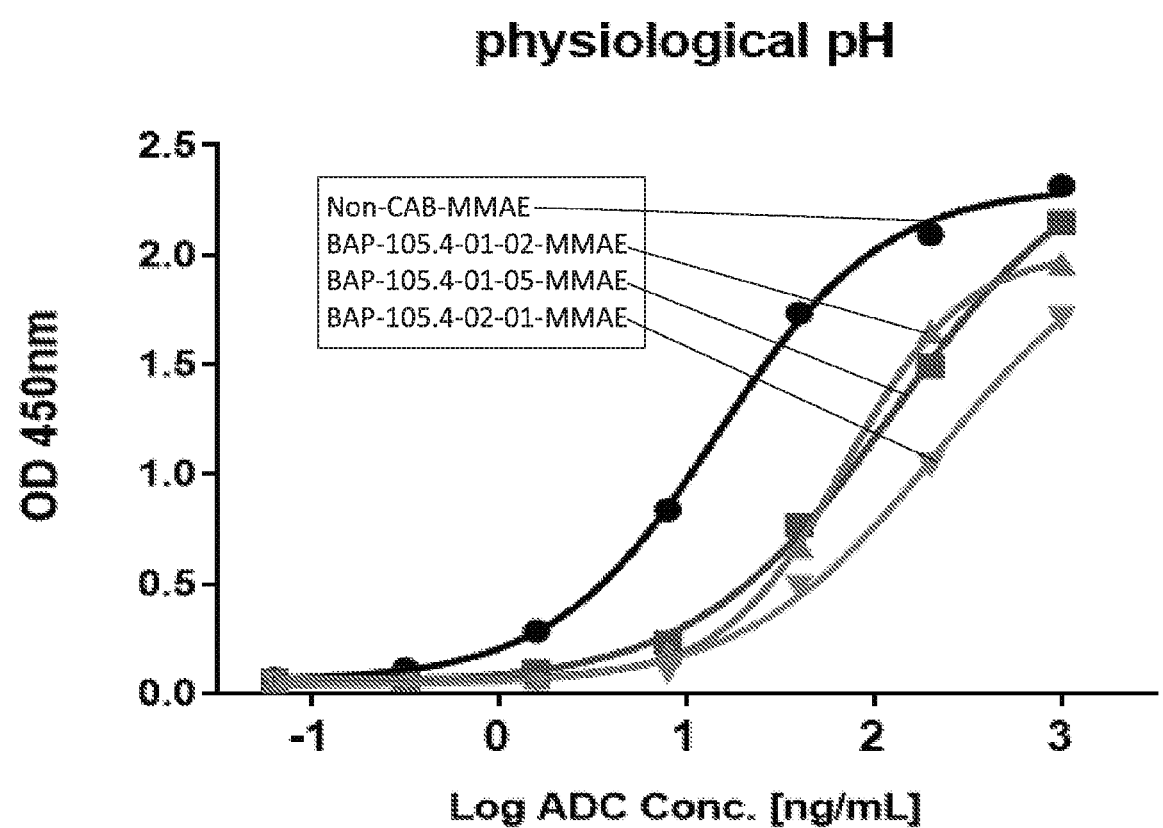

Binding Activity of the Humanized Conditionally Active Anti-EpCAM Antibody ADC in Tumor Microenvironment Selected humanized conditionally active anti-EpCAM antibodies were conjugated to MMAE to produce antibody drug conjugates (ADCs). The humanized conditionally active anti-EpCAM antibodies were BAP-105.4-01-02, BAP-105.4-01-05, and BAP-105.4-02-01. The binding activities of the humanized conditionally active anti-EpCAM antibody conjugates were measured at pH 6.0 to mimic the pH in a tumor microenvironment, and at a normal physiological pH of 7.4. A non-conditionally active antibody antibody was also conjugated to MMAE and used as the negative control. The binding activities of the conjugated humanized conditionally active anti-EpCAM antibodies to the recombinant human EpCAM extracellular domain were measured using ELISA at different ADC concentrations. The ADCs showed higher binding activities at the tumor microenvironment pH in comparison with binding activities at the normal physiological pH. See FIGS. 28A-28B.

Example 17

Figure 29A:
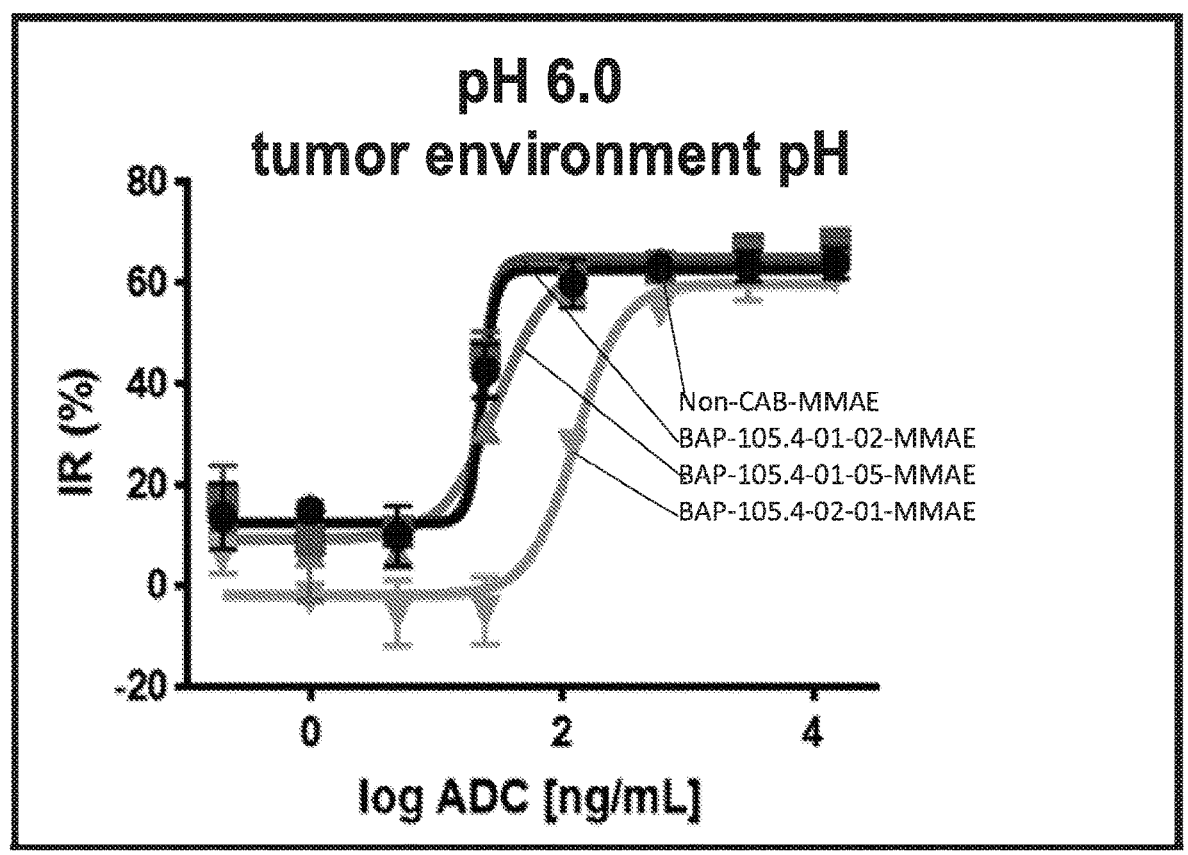
FIGS. 29A-29B show the cytotoxicity of conjugated humanized conditionally active anti-EpCAM antibodies in inhibition of Colo205 cells that express human EpCAM at pH 6.0 (FIG. 29A) and pH 7.4 (FIG. 29B).
Figure 29B:
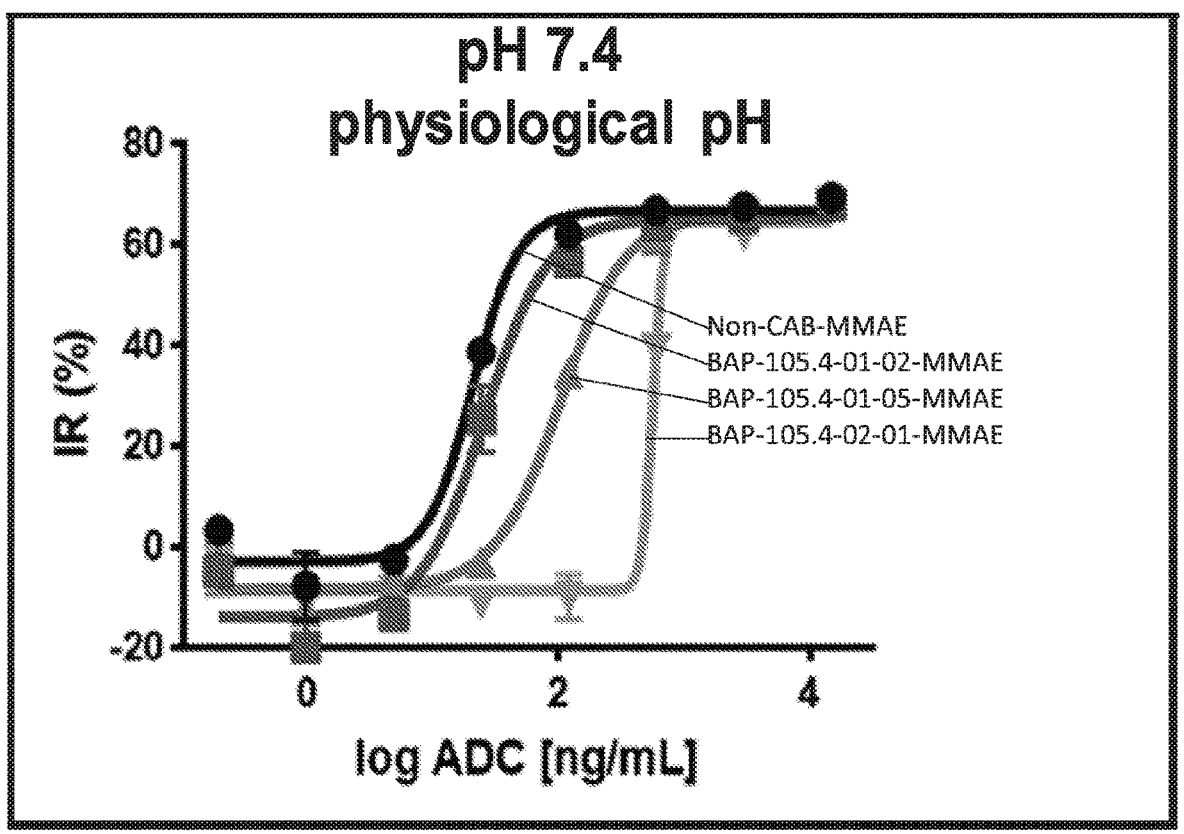

Cytotoxicity of the Humanized Conditionally Active Anti-EpCAM Antibody Conjugates in Inhibition of Colo205 Cells that Express Human EpCAM The ADCs of Example 16 were used to treat human EpCAM expressing Colo205 cells at the tumor microenvironment pH 6.0 and the normal physiological pH 7.4. The ADCs induced greater inhibition rates (IR %) at the tumor microenvironment pH than at the normal physiological pH. FIGS. 29A-29B.

Figure 29C:
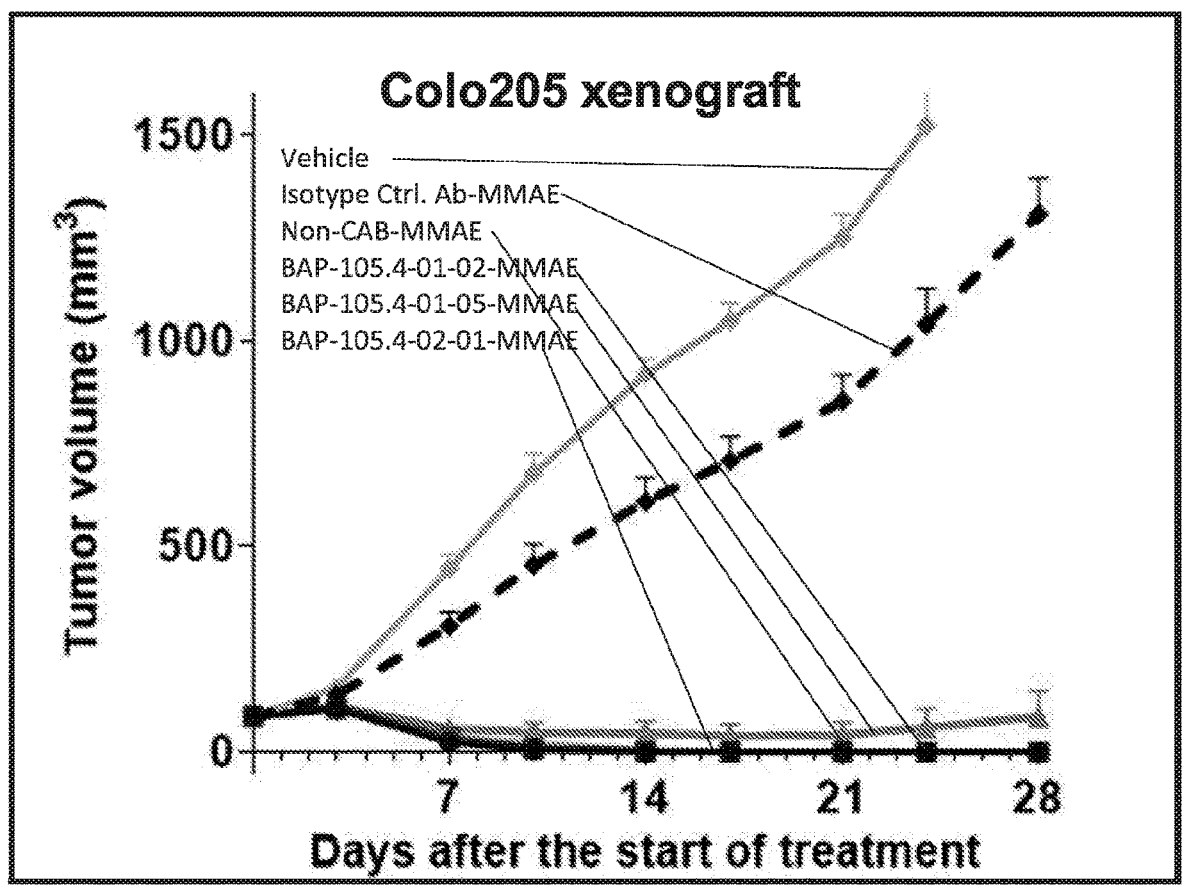
FIG. 29C shows the the effects on tumor volumes of treatment of tumor xenograft mice with conjugated humanized conditionally active anti-EpCAM antibodies.

The ADCs were also used to treat the Colo205 cell induced cancer xenograft models. The Colo205 cells were implanted in immunodeficient mice to induce tumors at a volume of 80-100 mm³. Tumor-bearing animals were randomized to treatment groups with 8 mice per group. Two other negative controls were used for the treatment: vehicle and an isotype matched control ADC (isotype ctrl. ADC). The ADCs were administered at a dose of 3 mg/kg Q4Dx4 (four times every fourth day). The conjugated humanized conditionally active anti-EpCAM antibodies of the present invention achieved complete tumor regression in the xenograft models. See FIG. 29C.

Example 18

Figure 30A:
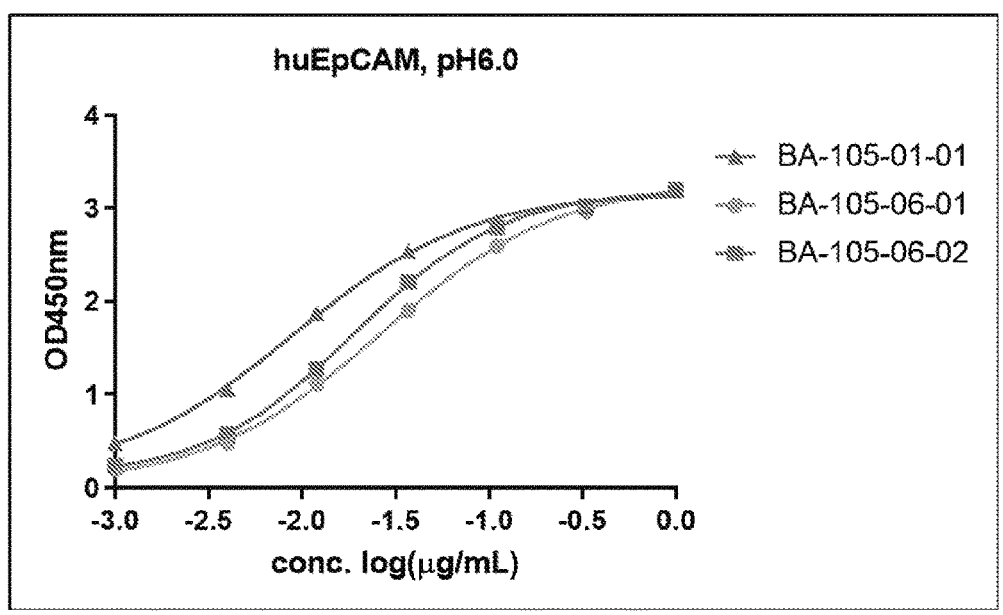
FIGS. 30A-30C show binding activities of additional humanized conditionally active anti-EpCAM antibodies of the present invention to human EpCAM as measured by ELISA.
Figure 30B:
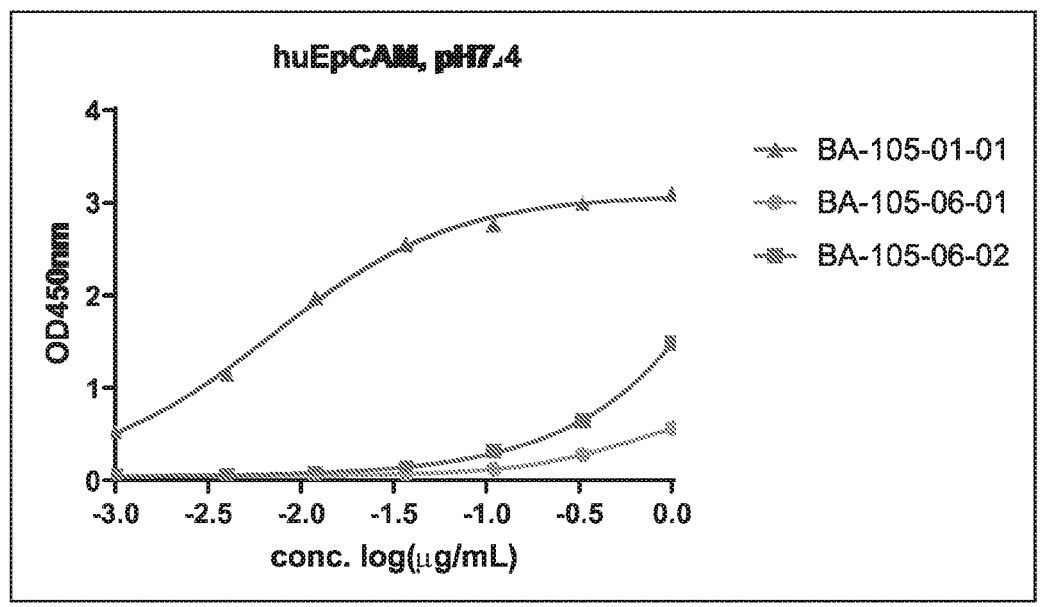
Figure 30C:
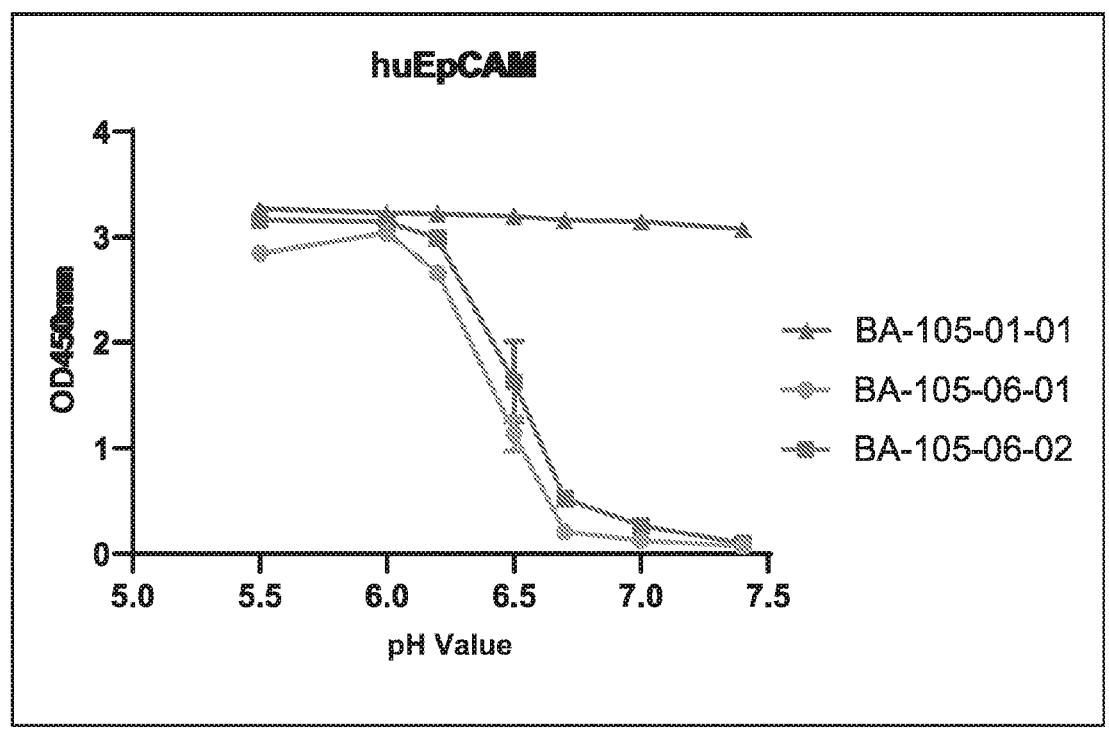
Figure 30D:
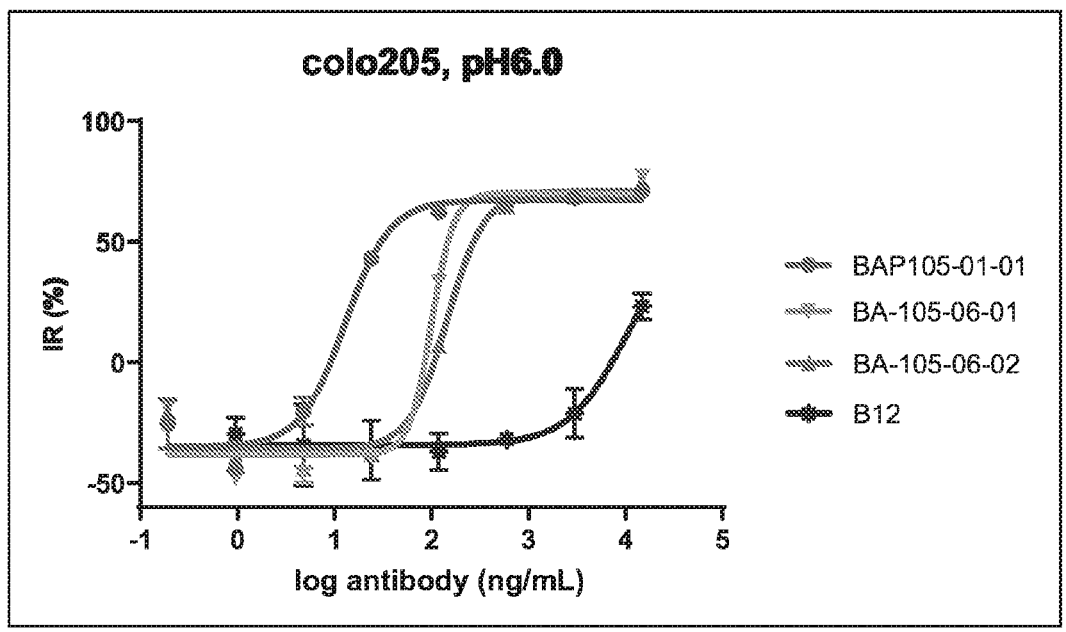
FIGS. 30D-30E show the cell killing activity of MMAE conjugated anti-EpCAM conditionally active antibodies of the present invention for killing human EpCAM expressing Colo205 cells.
Figure 30E:
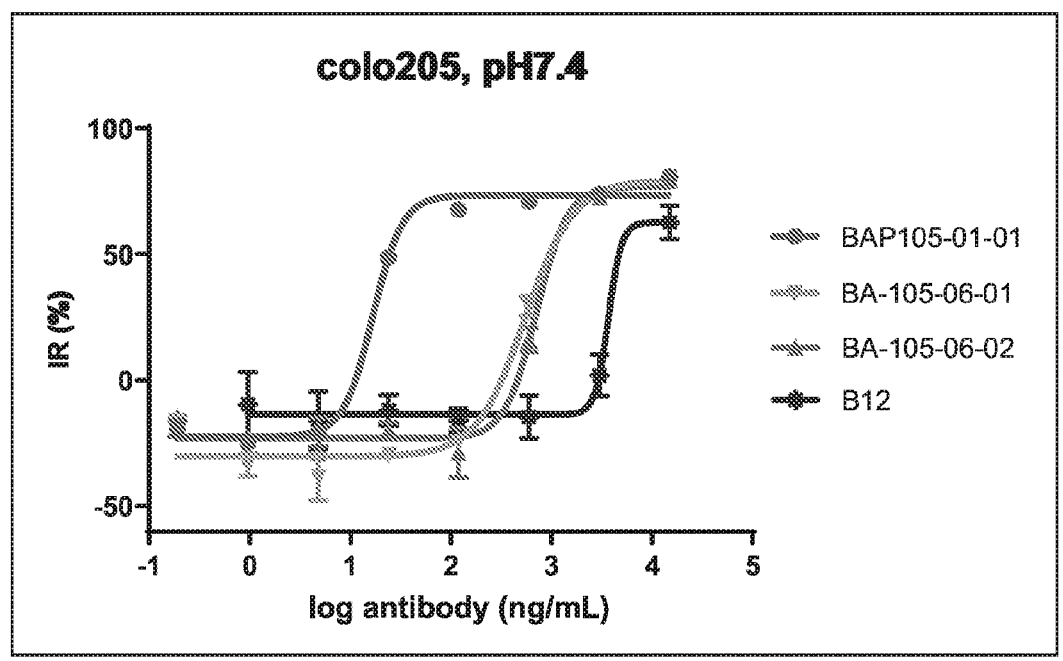

Binding Activity of Humanized Conditionally Active Anti-EpCAM Antibodies to Human EpCAM The binding activities of the humanized conditionally active anti-EpCAM antibodies to human EpCAM were measured by ELISA, using the template antibody BAP 105-01-01 as a control. See FIGS. 30A-30C. The humanized conditionally active anti-EpCAM antibodies used in this example were as follows:

| Humanized Conditionally Active Anti-EpCAM Antibody | Light chain variable region | Heavy Chain Variable Region |
|---|---|---|
| BA-105-06-01 | BAP105-6-VK01 (SEQ ID NO: 29) | BAP105-4-VH05 (SEQ ID NO: 13) |
| BA-105-06-02 | BAP105-6-VK02 (SEQ ID NO: 30) | BAP105-4-VH05 (SEQ ID NO: 13) |

The EC50 values of the humanized conditionally active anti-EpCAM antibodies for binding to human EpCAM at pH 6.0 and pH 7.4 are summarized in Table 22.

TABLE 22

IC50 of humanized conditionally active anti-EpCAM antibodies against human EpCAM

| IC50 (ng/mL) | BA-105-01-01 | BA-105-06-01 | BA-105-06-02 |
|---|---|---|---|
| pH6.0 | 58.63 | 29.92 | 104.7 |
| pH7.4 | 42.26 | 167.5 | 261.9 |
| ratio (pH7.4/pH6.0) | 0.72 | 5.60 | 2.50 |

Example 19

Figure 31A:
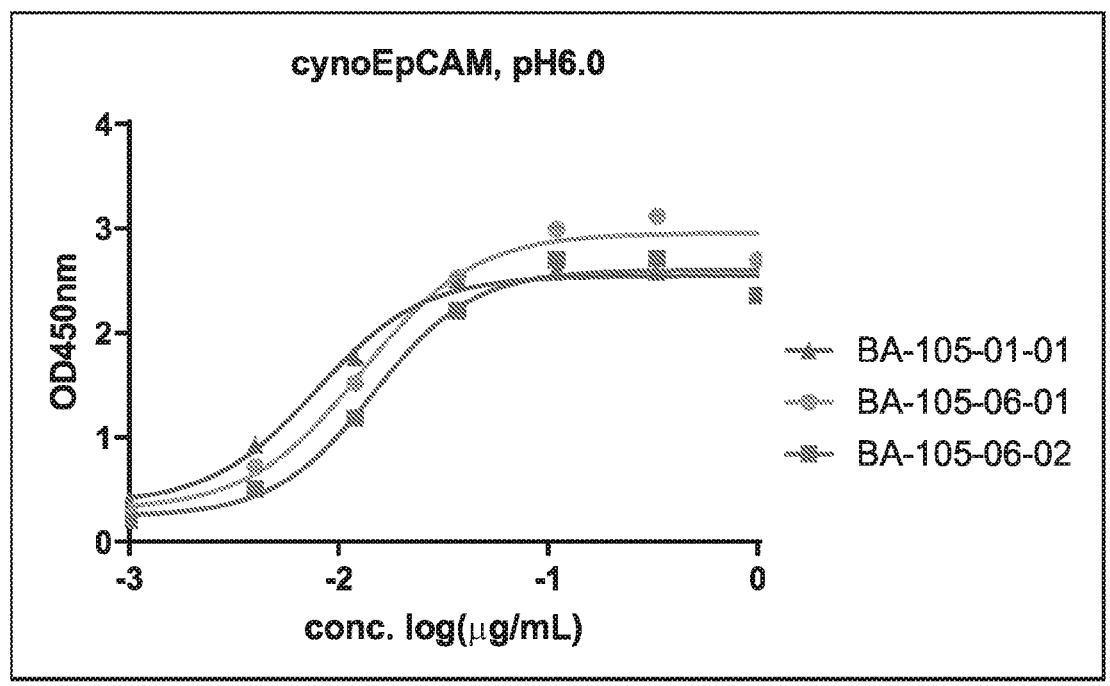
FIGS. 31A-31C show binding activities of additional humanized conditionally active anti-EpCAM antibodies to cyno EpCAM, as measured by ELISA.
Figure 31B:
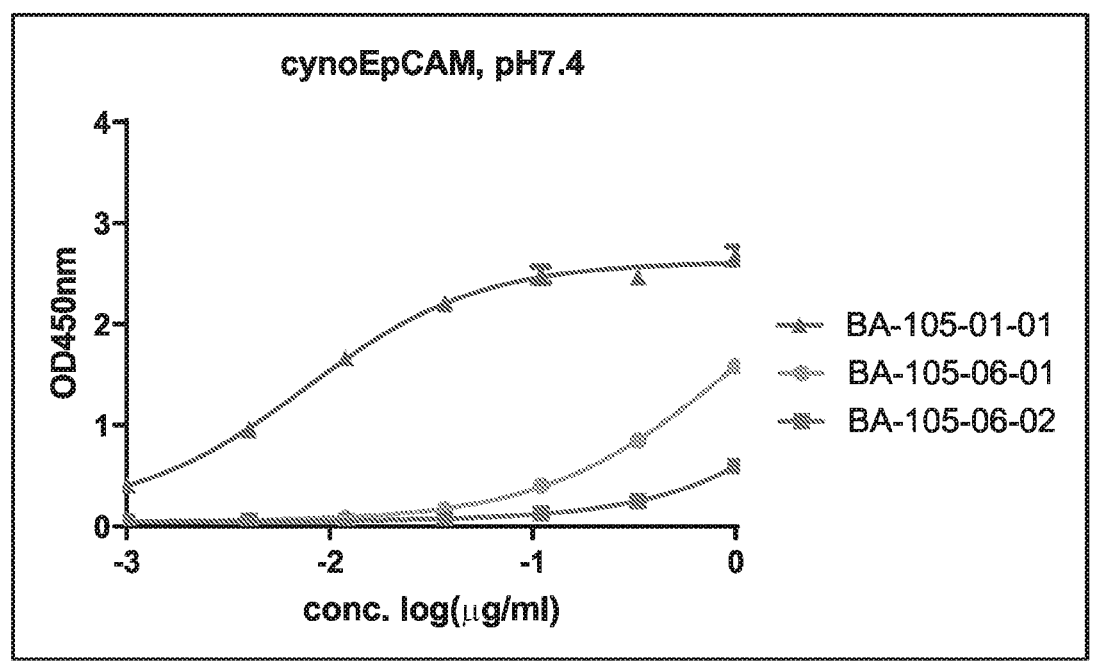
Figure 31C:
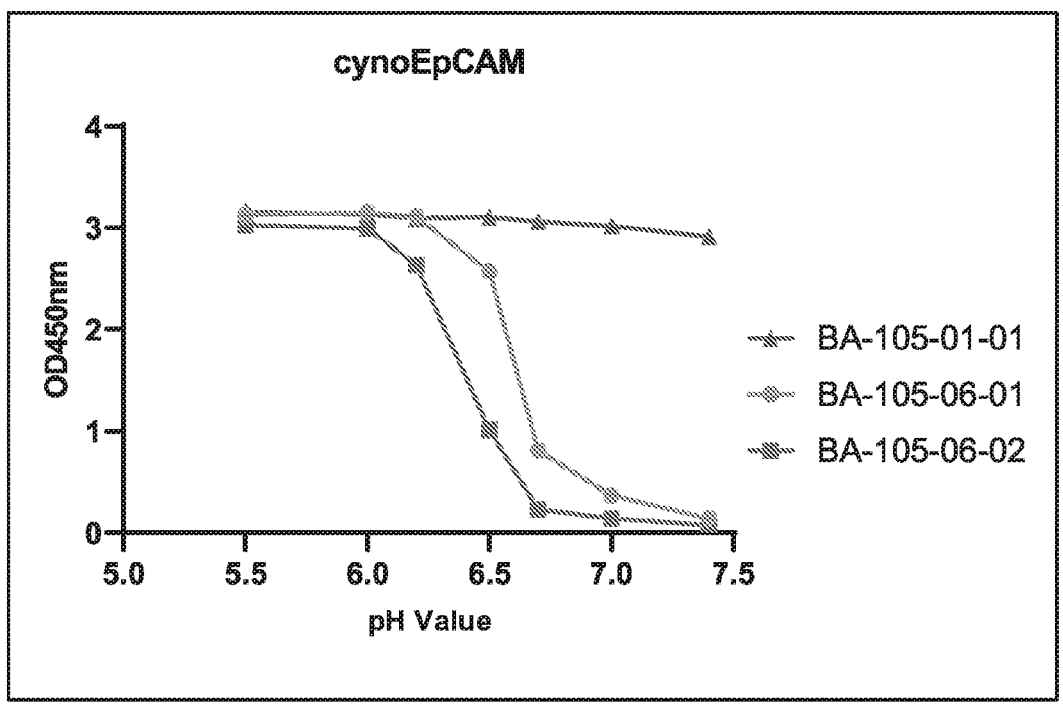
Figure 31D:
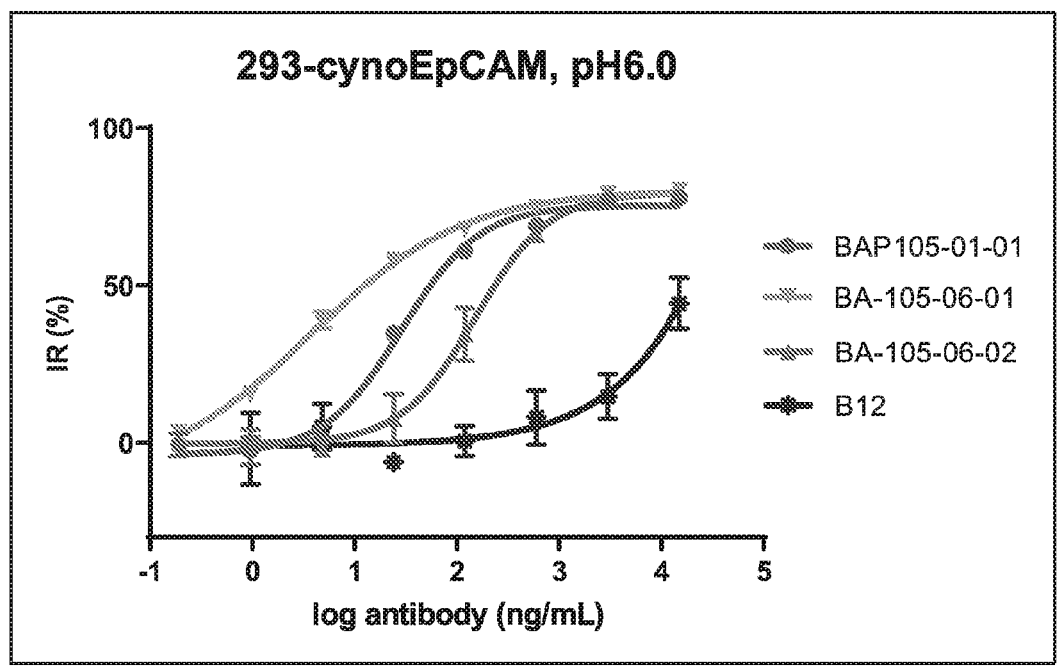
FIGS. 31D-31E show the cell killing activity of MMAE conjugated anti-EpCAM conditionally active antibodies of the present invention for killing HEK293 cells expressing cyno EpCAM.
Figure 31E:
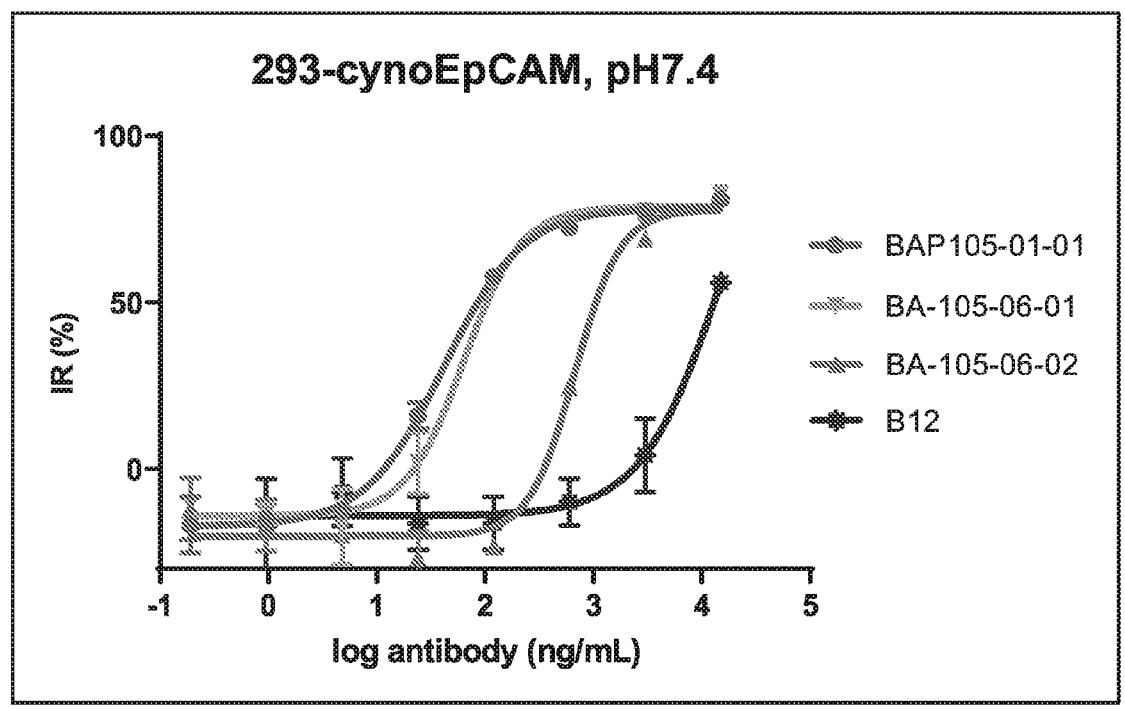

Binding Activity of the Humanized Conditionally Active Anti-EpCAM Antibodies to Cyno EpCAM The binding activities of the humanized conditionally active anti-EpCAM antibodies to cyno EpCAM were similarly measured. See FIGS. 31A-31C. The IC50 for binding to the cyno EpCAM at pH 6.0 and pH 7.4 for the humanized conditionally active anti-EpCAM antibodies of Example 18 are summarized in Table 23.

TABLE 23

IC50 of humanized conditionally active anti-EpCAM antibodies against cyno EpCAM

| IC50 (ng/mL) | BA-105-01-01 | BA-105-06-01 | BA-105-06-02 |
|---|---|---|---|
| pH6.0 | 28.8 | 3.715 | 151.6 |
| pH7.4 | 41.56 | 63.46 | 673.2 |
| ratio (pH7.4/pH6.0 | 1.44 | 17.08 | 4.44 |

Example 20

Cell Killing of the Conditionally Active Anti-EpCAM Antibody Conjugates

Figure 32A:
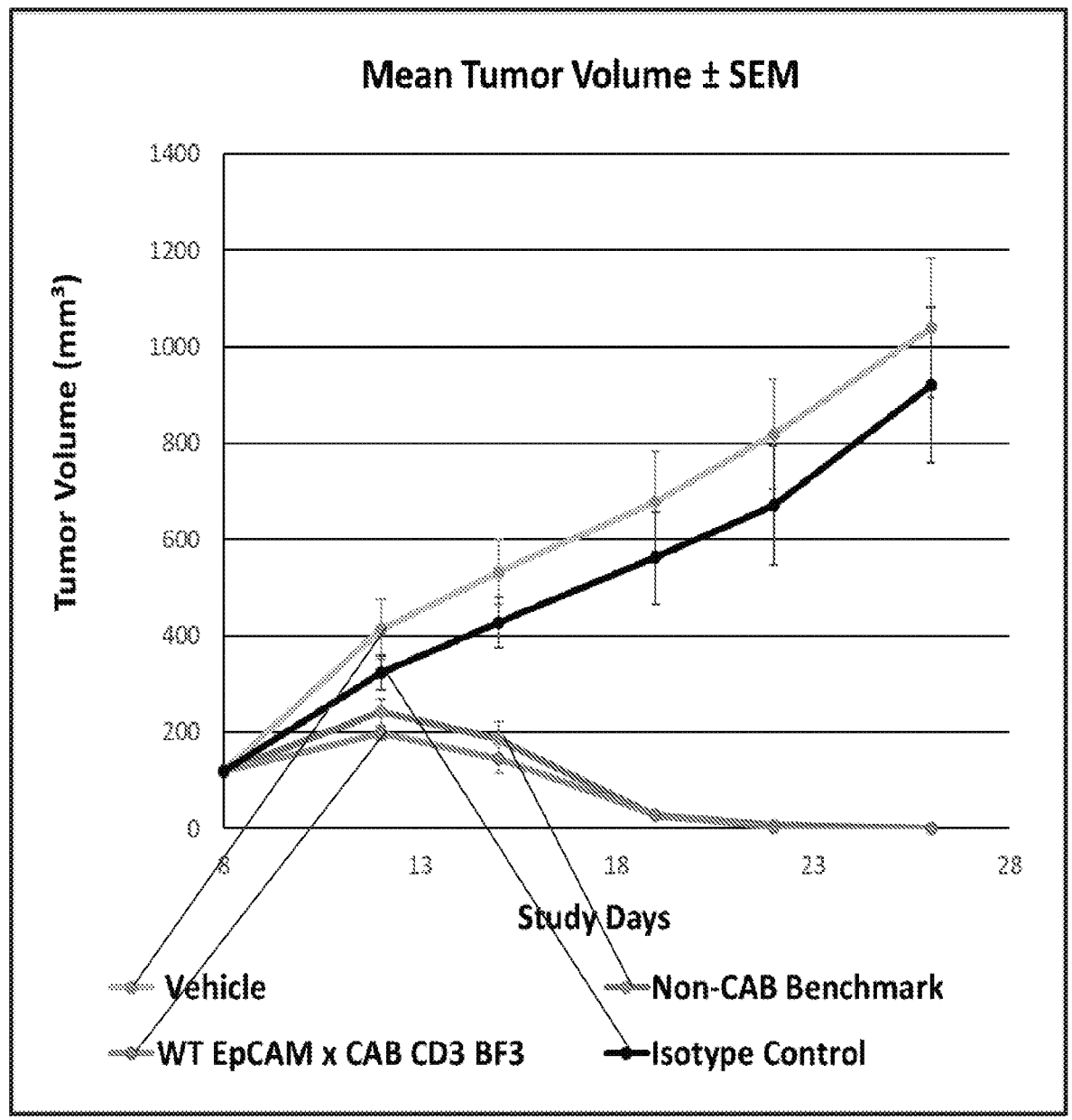
FIG. 32A shows the mean tumor volumes for treatment of tumor xenograft mice by the bispecific antibody (WT EpCAM x CAB-CD3 BA-150-06-BF3) of the present invention in comparison with vehicle, a non-conditionally active antibody benchmark BA-150-06-BF1 and an isotype control.
Figure 32B:
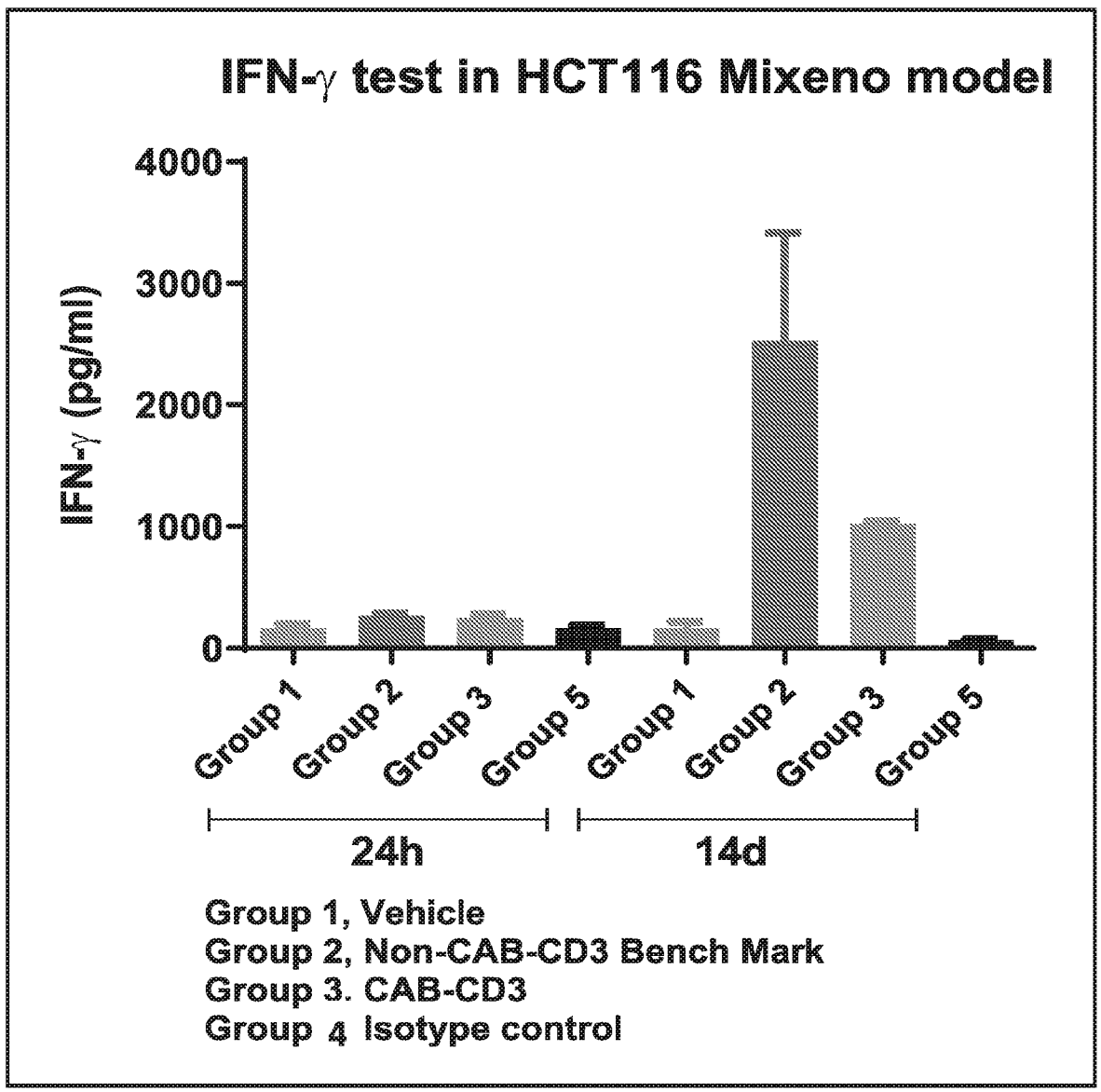
FIG. 32B shows reduced T-cell activation in the peripheral circulation system by the bispecific antibody (WT EpCAM x CAB-CD3 BA-150-06-BF3) of the present invention in comparison with vehicle, a non-conditionally active antibody benchmark BA-150-06-BF1 and an isotype control.

The selected conditionally active anti-EpCAM antibodies BAP-105-06-01 and BAP-105-06-02 were conjugated to monomethyl auristatin E (MMAE), a potent antimitotic agent, to create antibody drug conjugates (ADCs). Antibody BAP-105-01-01 was used as a non-conditionally active antibody control and B12 was used as a negative control. In vitro cell killing of EpCAM expressing Colo205 cells was measured at pH values of 6.0 and 7.4. See FIGS. 32A-32B.

IC50 for the in vitro killing of the Colo205 cells by the humanized conditionally active anti-EpCAM antibodies was also determined and are shown in table 24 below.

TABLE 24

IC50 of humanized conditionally active anti-EpCAM antibodies for the in vitro killing of Colo205 cells

| IC50 (ng/mL) | BA-105-01-01 | BA-105-06-01 | BA-105-06-02 |
|---|---|---|---|
| pH6.0 | 12.94 | 100.6 | 145.7 |
| pH7.4 | 16.81 | 550.5 | 707.9 |
| ratio (pH7.4/pH6.0) | 1.30 | 5.47 | 4.86 |

Example 21

Bispecific Mono Conditionally Active Antibodies

An anti-EpCAM antibody that was not conditionally active was linked to a single chain conditionally active anti-CD3 antibody to form a bispecific antibody (WT EpCAM x CAB-CD3 BA-150-06-BF3 (SEQ ID NOS: 35-38) that had specificity to both EpCAM and CD3. The bispecific antibody was used to treat a tumor xenograft mouse model in a MiXeno mouse model produced by Crown Bioscience (San Diego, Calif.). Specifically, colon cancer cell line HCT116 cells (EpCAM positive) were implanted in triple immunodeficient mice engrafted with human peripheral blood mononucleated cells to induce tumors in the mouse model. When the tumor volume reached approximately 150 mm$^3$, the tumor bearing animals were randomized to 4 treatment groups. The four treatment groups were treated with a vehicle as a negative control (group 1), a non-CAB-CD3 benchmark antibody BA-150-06-BF1 (SEQ ID NOS: 31-34) as a positive control (group 2), the bispecific antibody BA-150-06-BF3 (group 3) or an isotype matched antibody as a negative control (group 4). The antibodies were administered at a dose of 2.5 mg/kg biweekly for 4 weeks.

The bispecific antibody WT EpCAM x CAB-CD3 BA-150-06-BF3 was as effective as the positive control non-CAB-CD3 benchmark antibody BA-150-06-BF1 in causing complete tumor regression in the xenograft mouse model, while the two negative controls failed to cause tumor regression and the size of the tumors continued to increase for the negative control groups. See FIG. 32A.

Anti-CD3 antibodies typically have the side effect in causing T-cell activation in the peripheral circulation system, which may be measured by the serum INF-γ level using a Meso Scale Discovery (MSD) assay. See FIG. 32B. The bispecific antibody WT EpCAM x CAB-CD3 BA-150-06-BF3 caused significantly reduced T-cell activation compared to the positive control non-CAB-CD3 benchmark antibody BA-150-06-BF1. See FIG. 32B. Thus, the bispecific antibody WT EpCAM x CAB-CD3 BA-150-06-BF3, because of having a conditionally active anti-CD3 antibody component, caused significantly reduced side effects but had a comparable therapeutic effect, in comparison with the positive control non-CAB-CD3 benchmark antibody BA-150-06-BF1.

Example 22

Bispecific Dual Conditionally Active Antibodies

A conditionally active anti-EpCAM antibody was linked to a single chain conditionally active anti-CD3 antibody to form a dual conditionally active bispecific antibody (CAB EpCAM x CAB-CD3 BA-150-16-01-02-BF45—SEQ ID NOS: 47-50) that had specificity to both EpCAM and CD3. A mono conditionally active bispecific anti-EpCAM antibody was also made by linking an anti-EpCAM antibody that was not conditionally active to a single chain conditionally active anti-CD3 antibody to form a bispecific antibody (WT EpCAM x CAB-CD3 BA-150-15-01-03-BF46— SEQ ID NOS: 43-46) that had specificity to both EpCAM and CD3. The bispecific antibodies BA-150-16-01-02-BF45 and BA-150-15-01-03-BF46 was used to treat a tumor xenograft mouse model in a MiXeno mouse model produced by Crown Bioscience (San Diego, CA). Specifically, colon cancer cell line HCT116 cells (EpCAM positive) were implanted in triple immunodeficient mice engrafted with human peripheral blood mononucleated cells to induce tumors in the mouse model. When the tumor volume reached approximately 150 mm$^3$, the tumor bearing animals were randomized to five treatment groups. The five treatment groups were treated with a vehicle as a negative control (group 1), a non-CAB-CD3 benchmark antibody BA-150-15-01-03-BF1 (SEQ ID NOS: 39-42) as a positive control (group 2), the dual conditionally active bispecific antibody CAB EpCAM x CAB-CD3 BA- BA-150-16-01-02-BF45 (group 3), an isotype matched antibody as a negative control (group 4) or the mono conditionally active bispecific antibody WT EpCAM x CAB-CD3 BA-150-15-01-03-BF46 (group 5). The antibodies were administered at a dose of 2.5 mg/kg biweekly for 4 weeks.

Figure 33:
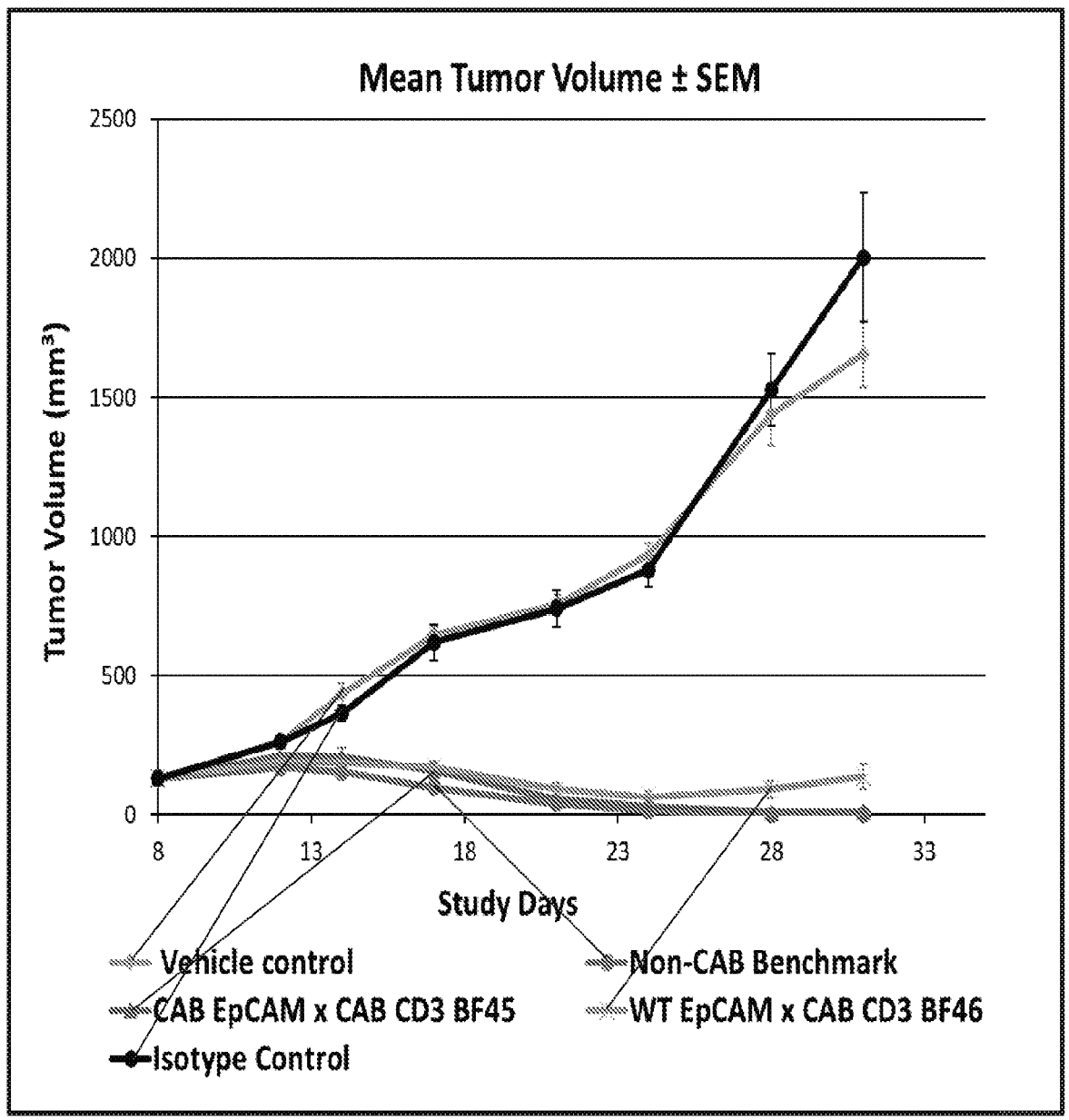
FIG. 33 shows the mean tumor volumes for treatment of tumor xenograft mice by the mono conditionally active bispecific antibody (WT EpCAM x CAB-CD3 BA-150-15-01-03-BF46) of the present invention and the dual conditionally active bispecific antibody (CAB EpCAM x CAB-CD3 BA-150-16-01-02-BF45) of the present invention in comparison with vehicle, a non-conditionally active antibody benchmark BA-150-15-01-03-BF1 and an isotype control.

The dual conditionally active bispecific antibody CAB EpCAM x CAB-CD3 BA-150-16-01-02-BF45 was as effective as the positive control non-CAB-CD3 benchmark antibody BA-150-15-01-03-BF1 in causing complete tumor regression in the xenograft mouse model, while the two negative controls failed to cause tumor regression and the size of the tumors continued to increase for the negative control groups. The dual conditionally active bispecific antibody CAB EpCAM x CAB-CD3 BA-150-16-01-02-BF45 was slightly more effective than the mono conditionally active bispecific antibody WT EpCAM x CAB-CD3 BA-150-15-01-03-BF46. See FIG. 33.

Figure 34:
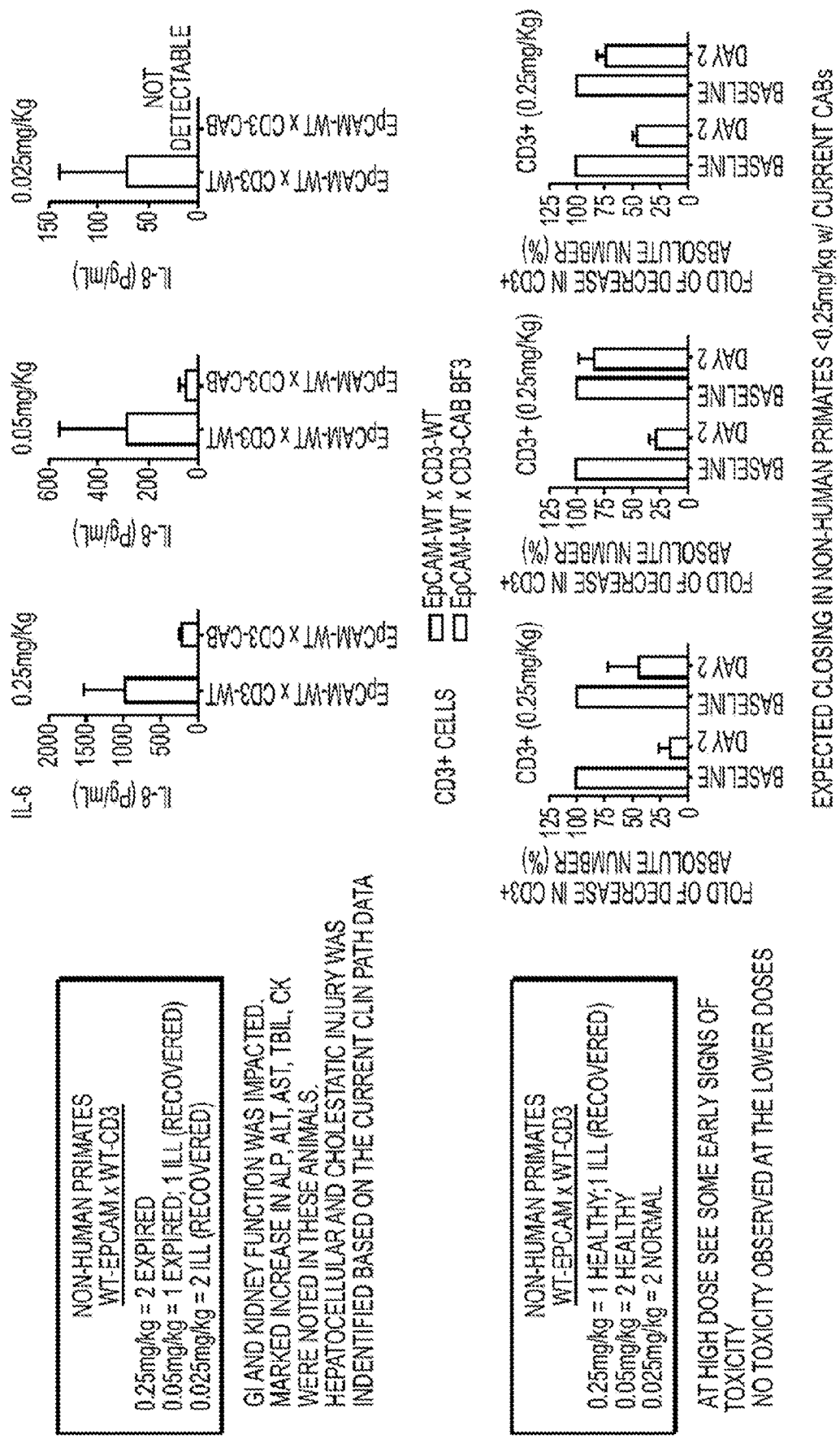
FIG. 34 shows the results of testing the mono conditionally active bispecific antibody WT EpCAM x CAB-CD3 BA-150-06-BF3 was tested against the wild type WT EpCAM x WT CD3 BA-150-06-BF1 antibody for toxicity, effect on Interleukin-6 (IL6) levels and effect on CD3+ levels.

The mono conditionally active bispecific antibody WT EpCAM x CAB-CD3 BA-150-06-BF3 was tested against the wild type WT EpCAM x WT CD3 BA-150-06-BF1 antibody to determine toxicity, effect on Interleukin-6 (IL6) levels and effect on CD3+ levels. The results are shown in FIG. 34. As can be seen from these results the mono conditionally active bispecific antibody WT EpCAM x CAB-CD3 BA-150-06-BF3 was significantly less toxic than the wild type WT EpCAM x WT CD3 BA-150-06-BF1 antibody. Also, the mono conditionally active bispecific antibody WT EpCAM x CAB-CD3 BA-150-06-BF3 resulted in significantly lower levels of the undesirable IL-6 and significantly improved reduction in CD3+ at day 2 of the test, showing effectiveness in tumor treatment.

The sequences of the antibodies, heavy and light chain variable regions and the anti-CD3 scFv's are as follows:
SEQ ID NO: 31=BA-150-06-BF1-VK (anti-EpCAM)
SEQ ID NO: 32=BA-150-06-BF1 light chain
SEQ ID NO: 33=BA-150-06-BF1-anti-CD3-scFv
SEQ ID NO: 34=BA-150-06-BF1-VH (anti-EpCAM)
SEQ ID NO: 35=BA-150-06-BF3-VK (anti-EpCAM)
SEQ ID NO: 36=BA-150-06-BF3 light chain
SEQ ID NO: 37=BA-150-06-BF3-anti-CD3-scFv
SEQ ID NO: 38=BA-150-06-BF3-VH (anti-EpCAM)
SEQ ID NO: 39=BA-150-15-01-03-BF1-VK (anti-EpCAM)

SEQ ID NO: 40=BA-150-15-01-03-BF1 light chain
SEQ ID NO: 41=BA-150-15-01-03-BF1 anti-CD3-scFv
SEQ ID NO: 42=BA-150-15-01-03-BF1-VH (anti-EpCAM)
SEQ ID NO: 43=BA-150-15-01-03-BF46-VK (anti-EpCAM)
SEQ ID NO: 44=BA-150-15-01-03-BF46 light chain
SEQ ID NO: 45=BA-150-15-01-03-BF46-antiCD3-scFV
SEQ ID NO: 46=BA-150-15-01-03-BF46-VH (anti-EpCAM)
SEQ ID NO: 47=BA-150-16-01-02-BF45-VK (anti-EpCAM)
SEQ ID NO: 48=BA-150-16-01-02-BF45 light chain
SEQ ID NO: 49=BA-150-16-01-02-BF45-antiCD3-scFv
SEQ ID NO: 50=BA-150-16-01-02-BF45-VH (anti-EpCAM)

The VK sequence is the light chain variable domain for EpCAM binding.

The light chain sequence is the full length light chain including the VK light chain variable domain for EpCAM binding, the kappa constant region and the anti-CD3-scFv.

The anti-CD3-scFv sequence is the anti-CD3-scFv domain.

The VH sequence is the heavy chain variable domain for EpCAM binding.

Example 23

Epitope Mapping

Construction and Testing of Human/Mouse EpCAM-ECD Chimera

Figure 35:
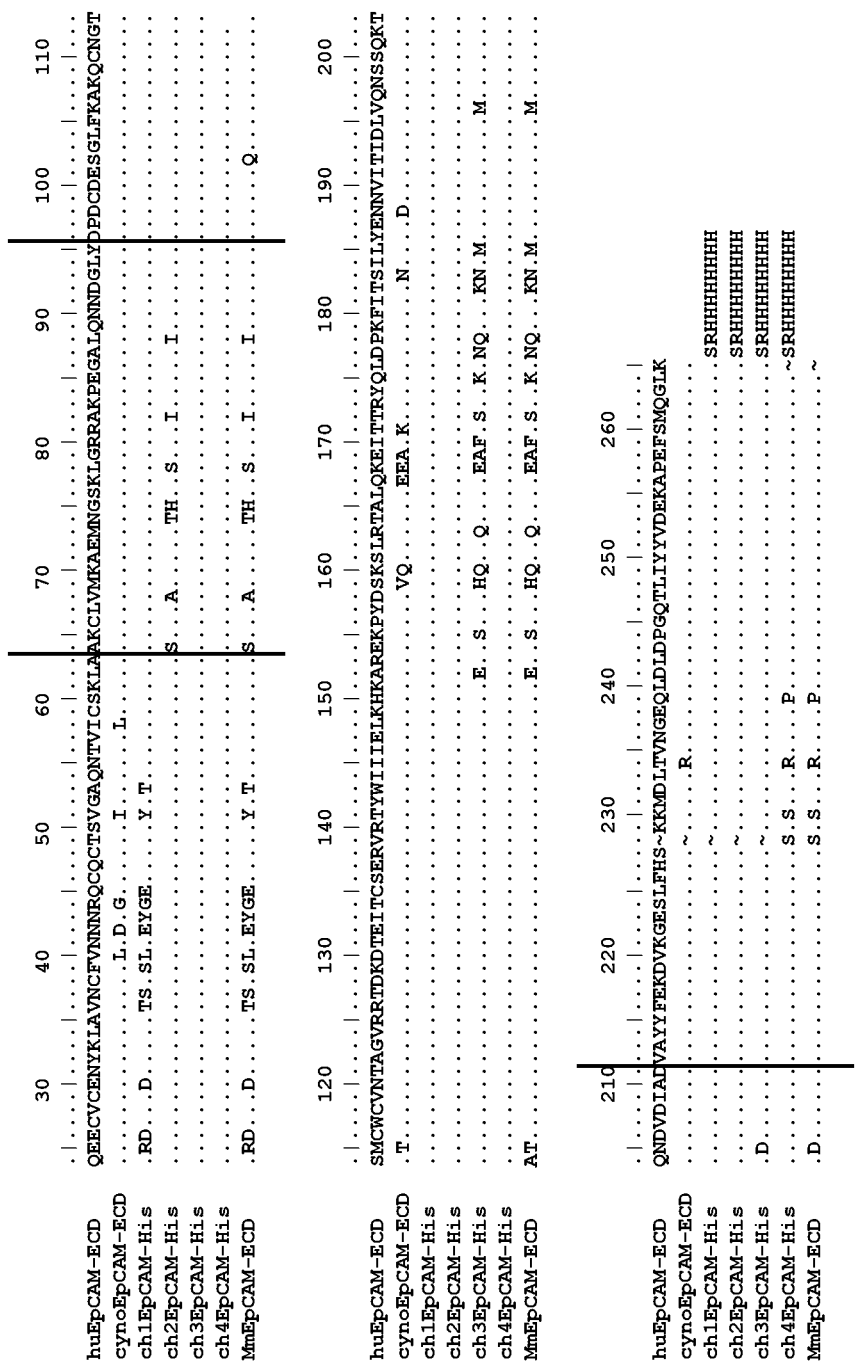
FIG. 35 shows a sequence alignment for four chimeric human/mouse EpCAM-ECD molecules that were constructed, human EpCAM-ECD (top) is used as a reference. Only amino acid differences are shown. The amino acid numbering in the alignment is matched with the numbering in PDB entry 4mvz shown in FIG. 39.
Figure 39:
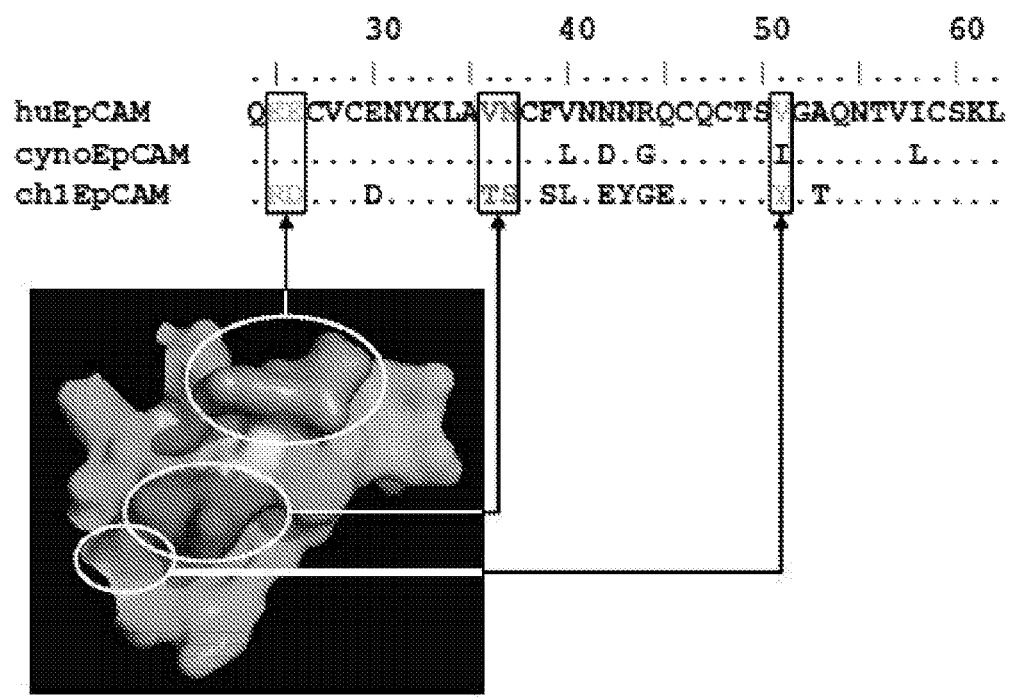
FIG. 39 shows the epitope mapped onto the huEpCAM structure using the amino acid numbering as in in PavgiC et al., Nature Commun. (2014) and the structure from the PDB entry 4mzv, visualized with PyMol.

The clones bind strongly to human and cynomolgus EpCAM extracellular domains, but do not cross react with mouse EpCAM-ECD. In order to identify the binding region on human EpCAM-ECD four chimeric human/mouse EpCAM-ECD molecules were constructed. Fragments of human EPCAM-ECD were replaced with pieces of mouse EpCAM-ECD by PCR. Individual mouse fragments are indicated by black vertical lines as shown in FIG. 35. In the sequence alignment of FIG. 35, human EpCAM-ECD (top) is used as a reference. Identical amino acids in the other molecules are shown as dots, only amino acid differences are shown. The amino acid numbering in the alignment is matched with the numbering in PDB entry 4mvz shown in FIG. 39.

Human, mouse and the four chimeric EpCAM extracellular domains were expressed with a C-terminal His-tag in CHO cells and purified. Binding of clone BA-105-04-01-05 to the different EpCAM ECDs was determined by ELISA.

Figure 36:
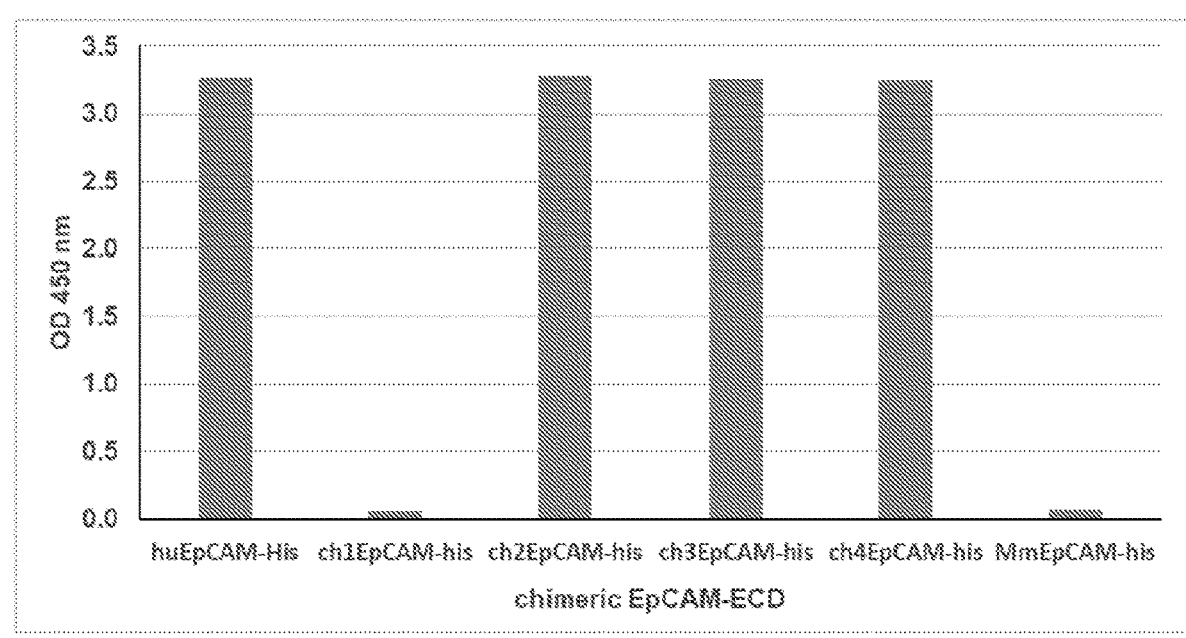
FIG. 36 shows binding data for the anti-EpCAM clone BA-105-04-01-05 (also referred to as: BAP-105.4-01-05) to the different EpCAM ECDs, as determined by ELISA.
Figure 37:
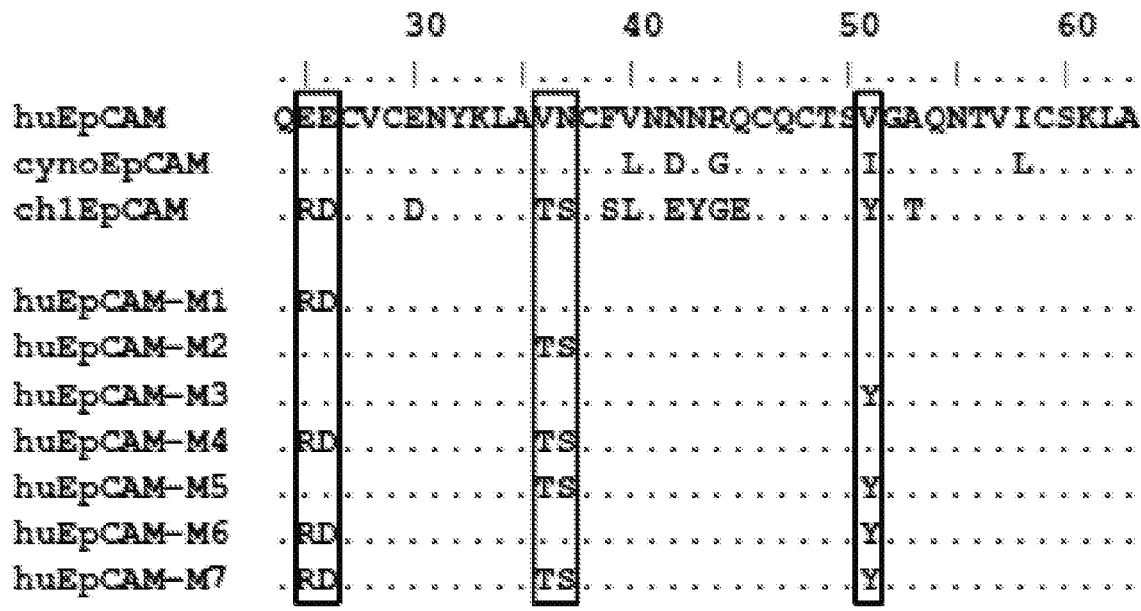
FIG. 37 shows the binding region for BA-105-04-01-05 within the compact, cysteine-rich N-domain of human EpCAM (residues 24-62) and the binding regions of the seven mutants (M1-M7) of the anti-EpCAM clone BA-105-04-01-05. The amino acid numbering in the alignment is matched with the numbering in PDB entry 4mvz shown in FIG. 39.
Figure 38:
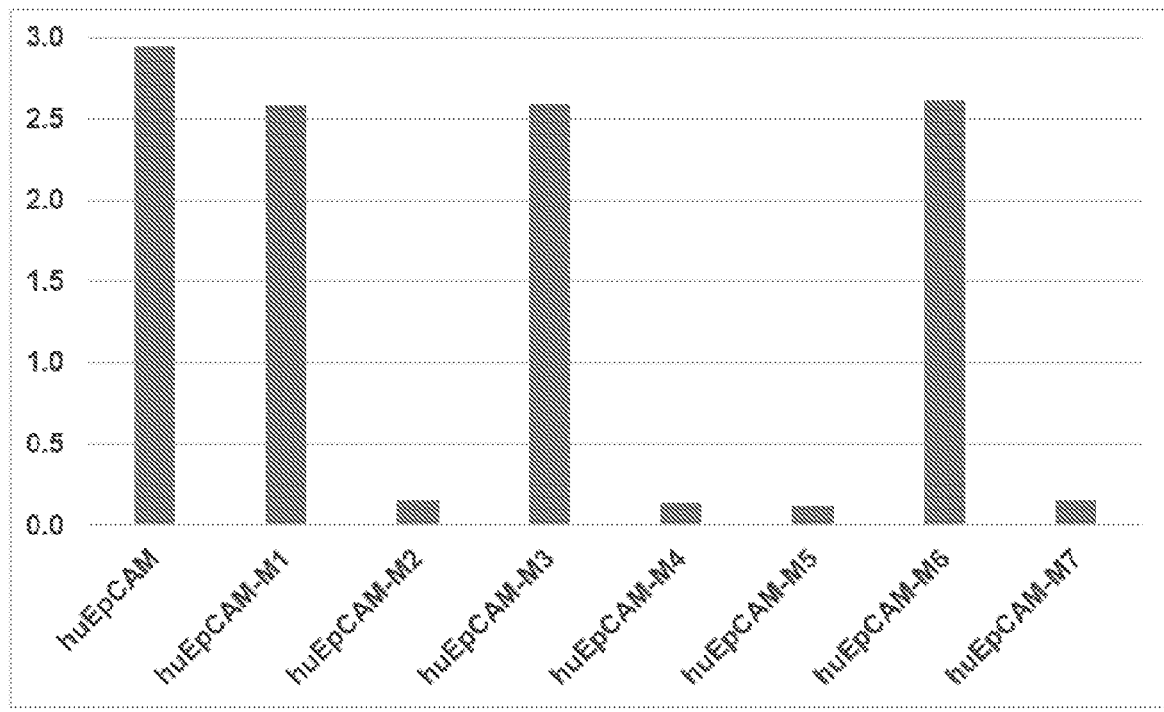
FIG. 38 shows binding data for the seven mutants M1-M7 to huEpCAM, as determined by ELISA.

Good binding was observed to human EpCAM-ECD and chimeric molecules 2, 3, and 4. No binding was observed with chimeric EpCAM-ECD 1 (ch1EpCAM-his) and mouse EpCAM-ECD as shown in FIG. 36. The ELISA data clearly show that the binding region for BA-105-04-01-05 is within the compact, cysteine-rich N-domain of human EpCAM (residues 24-62) as shown in FIG. 37.

Construction and Testing of Human EpCAM-ECD Mutants

To increase the resolution of the epitope analysis mutations were introduced into human EpCAM based on the sequence difference between human, cynomolgus, and mouse EpCAM-ECD.N-domain. A total of seven mutants (M1-M7) were constructed and tested. In the sequence alignment shown in FIG. 37, human EpCAM-ECD (top) is used as reference. Identical amino acids in the other molecules are shown as dots, and thus only amino acid differences are shown. The amino acid numbering in the alignment is matched with the numbering in PDB entry 4mvz shown in FIG. 39.

Changing residues 25/26 and/or 51 to the mouse sequence slightly reduced binding, while changing residues 36/37 completely abolished binding. This indicates that residues 25/26 are major contact points (marked in red in the structure shown in FIG. 39). These two residues are flanked on the surface by residues 25/26 and 51 (marked in orange in FIG. 39) indicating that BA-105-04-01-05 recognizes a non-linear epitope within the N-domain of human EpCAM extracellular domain.

Methods Used in the Examples

The ELISA assay was performed using the following protocol:

1) Coat ELISA plates with 100 μL of 0.5 μg/mL (06_20_17 and 06_28_17 Experiments) or 1 μg/mL (07_06_17 and 07_11_17 Experiments) recombinant EpCAM antigen in carbonate-bicarbonate coating buffer
2) Cover plates with sealing film and incubate overnight at 4° C.
3) Decant plates and tap out residual liquid on a stack of paper towels
4) Wash wells twice by dispensing 200 μL of various pH incubation buffers to the wells according to a sample map and completely aspirate the contents
5) Add 200 μL of various pH incubation buffers to the wells according to the sample map. Cover with sealing film and place the plate onto a plate shaker (set to 200 rpm) for 60 minutes at room temperature
6) Decant plates and tap out residual liquid on a stack of paper towels.
7) Serially dilute test substances in various pH incubation buffers to 250 ng/mL, 100 ng/mL or 25 ng/mL.
8) Add 100 μL/well of diluted test substances to the plates according to the sample map.
9) Cover with sealing film and place the plates onto a plate shaker (set to 200 rpm) for 60 minutes at room temperature.
10) Decant plates and tap out residual liquid on a stack of paper towels.
11) Wash wells three times by dispensing 200 μL of various pH wash buffers to the wells according to the sample map and completely aspirate the contents
12) Dilute the HRP secondary antibody at 1:2500 in various pH incubation buffers
13) Add 100 μL HRP secondary antibody diluted in various pH incubation buffers to each well according to the sample map.
14) Cover with sealing film and place the plates onto a plate shaker (set to 200 rpm) for 60 minutes at room temperature.
15) Decant plates and tap out residual liquid on a stack of paper towels.
16) Wash wells three times by dispensing 200 μL of various pH wash buffer to the wells according to the sample map and completely aspirating the contents
17) Dispense 50 μL per well of the TMB substrate solution into all wells of plates. Incubate at room temperature for 3 minutes.
18) Add 50 μL per well of 1N HCl into all wells of the plates. Read plates at 450 nm using Molecular Device SpectraMax 190 microplate reader.
19) Measure the OD450 nm raw data.

20) Plot the average OD values (from 2 replicates) at the different pH values against the pH of the buffer using Softmax Pro software (Molecular Devices). Curve fitting was done using the 4-parameter model built into the software. The inflection point of the pH curve (50% binding activity) equals parameter C of the fitting equation. Binding activity at pH 6.0 was set to 100%. The pH for 90% binding activity was interpolated from the fitted curve using the "InterpX" function of the Softmax Pro software.

The surface plasma resonance (SPR) assay was performed using the following protocol:

The SPR 2/4 instrument, SPR Affinity Sensors—Amine Flat, and Immobilization buffer kit are manufactured by Sirra Sensors. The SPR sensor contains four flow cells (FC1-FC4), each of which can be addressed individually or in groups. EpCAM extracellular domain was immobilized in FC2 and FC4, while BSA was immobilized in FC1 and FC3 (control surface).

Immobilization was done following the protocol suggested by vendor:
  (1) The activator was prepared by mixing 200 mM EDC and 50 mM NHS (Sierra Sensors) immediately prior to injection. The amine sensor chip was activated for 480s with the mixture at a flow rate of 25 µL/min
  (2) 25 µg/mL of human EpCAM in 10 mM NaAc (pH 5.0) was injected to FC2 and FC4 respectively at a flow rate of 25 µL/min for 480 s. The chip surface was deactivated with 1 M ethanolamine-HCl (Sierra Sensors) running through FC1-4 at a flow rate of 25 µL/min for 480 s.
  (3) The control surface was activated and deactivated using the same conditions, but without injecting protein.
  (4) The running buffer was switched to PBST with the required pH before the analyte injections. The instrument was equilibrated with the running buffer for 1 hour before the first analyte injection.
  (5) All analyte injections were done at 25 µL/min at 25° C.

Flow cell 1 (or 3) without immobilized protein was used as a control surface for reference subtraction. In addition, data with buffer only as the analyte (0 nM analyte) were subtracted from each run. Double subtracted data were fitted with the provided analysis software Analyzer R2 (Sierra Sensors) using a 1:1 binding model. A molecular weight of 146 kDa was used to calculate the molar concentrations of the analytes.

The fluorescence-activated cell sorting (FACS) assay was performed using the following protocol.

Cell staining to determine surface expression of human or cynomolgus EpCAM
  1) Seed $3 \times 10^6$ cells to T-75 flasks and culture according to the instructions of the endor.
  2) On the day of FACS analysis, remove and discard the culture medium.
  3) Briefly rinse the cell layer with PBS solution.
  4) Add 1.5 mL of Detachin solution to each of the T-75 flasks. Wait until the cell layer is dispersed.
  5) Add 4.5 mL of culture media for the corresponding cell lines and resuspend the cells by gentle pipetting.
  6) Pool the cells and transfer the cell suspension to a 50-mL conical tube.
  7) Count the cells with trypan blue staining before centrifugation at 1500 rpm for 5 min at 4° C.
  8) Wash the cells once with PBS and transfer $3 \times 10^5$ cells into an Eppendorf tube.
  9) Add 2 µL of mouse anti-EpCAM (PE conjugated mouse IgG1) or PE-isotype mouse IgG1 in 100 µL of PBS solution with 1% BSA per tube and shake at 100 RPM for one hour on ice.
  10) Wash the cells three times with 150 µL PBS solution.
  11) Fix the cells with 4% PFA for 10 min at ambient temperature, then wash the cells once with PBS.
  12) Resuspend the cells in 100 µL PBS and analyze the cells on NovoCyte flow cytometer.

FACS analysis of CHO cells expressing human EpCAM or cynomolgus EpCAM using the tested antibody.
  1) Harvest the cells (as 3.3, steps 1 through 7), wash the cells once with PBS.
  2) Resuspend the cells at pH 6.0 or pH 7.4 FACS buffer at a concentration of $3 \times 10^6$ cells/mL.
  3) Aliquot $3 \times 10^5$ cells in 100 µL pH 6.0 or pH 7.4 FACS buffer in 96-well U-bottom plates.
  4) Spin down the cells and discard the buffer.
  5) Serially dilute the test articles in 3-fold dilutions starting at 10 µg/mL in pH 6.0 or pH 7.4 FACS buffer.
  6) Add 100 µL/well of the diluted test articles to cells, gently mix well and incubate on ice with shaking (100 rpm) for one hour.
  7) Centrifuge the cells at 1500 rpm for 5 min at 4° C. Wash the cells with 150 µL of pH 6.0 or pH 7.4 wash buffer two times.
  8) Dilute the goat anti-human IgG AF488 antibody 1:300 in pH 6.0 or pH 7.4 FACS buffers.
  9) Add 100 µL of the diluted antibody from step 8) above to the cells and incubate on ice for 45 minutes, protected from light.
  10) Pellet the cells and wash with 150 µL of pH 6.0 or pH 7.4 wash buffer three times.
  11) Fix the ells with 4% PFA diluted in 1×PBS for 10 min at ambient temperature, then wash the cells with 1×PBS.
  12) Resuspend the cells in 100 µL of 1×PBS.
  13) Analyze the cells using a NovoCyte Flow Cytometer using Ex488nm/Em530nm. Collect at least 20,000 cells.

FACS data were analyzed using the nonlinear fit (variable slope, four parameters) model built into GraphPad Prism software version 7.03.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

What is claimed is:

1. Isolated polypeptides comprising a heavy chain variable region and a light chain variable region that specifically bind to human EpCAM, wherein the heavy chain variable region includes three complementarity determining regions having sequences H1, H2, and H3, wherein:
  the H1 sequence is GYTFTSYWMH (SEQ ID NO: 1);
  the H2 sequence is $X_1$IRPSTGYTEYNQKFKD (SEQ ID NO: 2); and
  the H3 sequence is GDNWVGFAN (SEQ ID NO: 3);
    wherein $X_1$ is Y or D; and
the light chain variable region includes three complementarity determining regions having sequences L1, L2, and L3, wherein:
  the L1 sequence is SASSSISYMH (SEQ ID NO: 4);
  the L2 sequence is STSNL$X_2$S (SEQ ID NO: 5); and
  the L3 sequence is $X_3$QWSTY$X_4$T (SEQ ID NO: 6);
    wherein $X_2$ is A or H; $X_3$ is H or E;
    and $X_4$ is H or E; and with the proviso that $X_1$, $X_2$, $X_3$ and $X_4$ cannot be Y, A, H, and H at the same time.

2. The isolated polypeptides of claim 1, wherein the H2 sequence is YIRPSTGYTEYNQKFKD (SEQ ID NO: 22).

3. The isolated polypeptides of claim 1, wherein the H2 sequence is DIRPSTGYTEYNQKFKD (SEQ ID NO: 23).

4. The isolated polypeptides of claim 1, wherein the heavy chain variable region has an amino acid sequence selected from SEQ ID NOS: 7-13.

5. The isolated polypeptides of claim 4, wherein the light chain variable region has an amino acid sequence selected from SEQ ID NOS: 14-21.

6. The isolated polypeptides of claim 1, wherein the L2 sequence is STSNLAS (SEQ ID NO: 24).

7. The isolated polypeptides of claim 1, wherein the L2 sequence is STSNLHS (SEQ ID NO: 25).

8. The isolated polypeptides of claim 1, wherein the L3 sequence is HQWSTYHT (SEQ ID NO: 26).

9. The isolated polypeptides of claim 1, wherein the L3 sequence is HQWSTYET (SEQ ID NO: 27).

10. The isolated polypeptides of claim 1, wherein the L3 sequence is EQWSTYHT (SEQ ID NO: 28).

11. The isolated polypeptides of claim 1, wherein the light chain variable region has an amino acid sequence selected from SEQ ID NOS: 14-21.

12. An antibody or antibody fragment that specifically binds to human EpCAM protein comprising a heavy chain variable region and a light chain variable region, wherein the heavy chain variable region includes three complementarity determining regions, said regions having sequences H1, H2, and H3, wherein:
  the H1 sequence is GYTFTSYWMH (SEQ ID NO: 1);
  the H2 sequence is $X_1$IRPSTGYTEYNQKFKD (SEQ ID NO: 2); and
  the H3 sequence is GDNWVGFAN (SEQ ID NO: 3);
    wherein $X_1$ is Y or D, and
  the light chain variable region includes three complementarity determining regions, said regions having sequences L1, L2, and L3, wherein:
  the L1 sequence is SASSSISYMH (SEQ ID NO: 4);
  the L2 sequence is STSNL$X_2$S (SEQ ID NO: 5); and
  the L3 sequence is $X_3$QWSTY$X_4$T (SEQ ID NO: 6);
    wherein $X_2$ is A or H; $X_3$ is H or E; and $X_4$ is H or E; and with the proviso that $X_1$, $X_2$, $X_3$ and $X_4$, respectively, cannot be Y, A, H, and H at the same time.

13. The antibody or antibody fragment of claim 12, wherein the H2 sequence is YIRPSTGYTEYNQKFKD (SEQ ID NO: 22).

14. The antibody or antibody fragment of claim 12, wherein the H2 sequence is DIRPSTGYTEYNQKFKD (SEQ ID NO: 23).

15. The antibody or antibody fragment of claim 12, wherein the heavy chain variable region has an amino acid sequence selected from SEQ ID NOS: 7-13.

16. The antibody or antibody fragment of claim 12, wherein the L2 sequence is STSNLAS (SEQ ID NO: 24).

17. The antibody or antibody fragment of claim 12, wherein the L2 sequence is STSNLHS (SEQ ID NO: 25).

18. The antibody or antibody fragment of claim 12, wherein the L3 sequence is HQWSTYHT (SEQ ID NO: 26).

19. The antibody or antibody fragment of claim 12, wherein the L3 sequence is HQWSTYET (SEQ ID NO: 27).

20. The antibody or antibody fragment of claim 12, wherein the L3 sequence is EQWSTYHT (SEQ ID NO: 28).

21. The antibody or antibody fragment of claim 12, wherein the light chain variable region has an amino acid sequence selected from SEQ ID NOS: 14-21.

22. The antibody or antibody fragment of claim 12, which comprises a combination of a heavy chain variable region (VH) and a light chain variable region (VL) of a pair of amino acid sequences including six complementarity determining regions, said pair of amino acid sequences being selected from the group consisting of:
- a VH having at least 90% identity to the amino acid sequence of SEQ ID NO: 8 and a VL having at least 90% sequence identity to the amino acid sequence of SEQ ID NO: 14,
- a VH having at least 90% identity to the amino acid sequence of SEQ ID NO: 9 and a VL having at least 90% sequence identity to the amino acid sequence of SEQ ID NO: 14,
- a VH having at least 90% identity to the amino acid sequence of SEQ ID NO: 7 and a VL having at least 90% sequence identity to the amino acid sequence of SEQ ID NO: 15,
- a VH having at least 90% identity to the amino acid sequence of SEQ ID NO: 7 and a VL having at least 90% sequence identity to the amino acid sequence of SEQ ID NO: 16,
- a VH having at least 90% identity to the amino acid sequence of SEQ ID NO: 7 and a VL having at least 90% sequence identity to the amino acid sequence of SEQ ID NO: 17,
- a VH having at least 90% identity to the amino acid sequence of SEQ ID NO: 11 and a VL having at least 90% sequence identity to the amino acid sequence of SEQ ID NO: 20,
- a VH having at least 90% identity to the amino acid sequence of SEQ ID NO: 12 and a VL having at least 90% sequence identity to the amino acid sequence of SEQ ID NO: 21,
- a VH having at least 90% identity to the amino acid sequence of SEQ ID NO: 11 and a VL having at least 90% sequence identity to the amino acid sequence of SEQ ID NO: 18,
- a VH having at least 90% identity to the amino acid sequence of SEQ ID NO: 13 and a VL having at least 90% sequence identity to the amino acid sequence of SEQ ID NO: 18, and
- a VH having at least 90% identity to the amino acid sequence of SEQ ID NO: 10 and a VL having at least 90% sequence identity to the amino acid sequence of SEQ ID NO: 19;
- wherein amino acid sequences of the six complementarity determining regions of said antibody or antibody fragment are identical to the amino acid sequences of SEQ ID NOs: 1 to 6 wherein $X_2$ is A or H; $X_3$ is H or E; and $X_4$ is H or E; and with the proviso that $X_1$, $X_2$, $X_3$ and $X_4$, respectively, cannot be Y, A, H, and H at the same time.

23. The antibody or antibody fragment of claim 22 wherein the pair of amino acid sequences are selected from:
- a VH of SEQ ID NO: 8 and a VL of SEQ ID NO: 14,
- a VH of SEQ ID NO: 9 and a VL of SEQ ID NO: 14,
- a VH of SEQ ID NO: 7 and a VL of SEQ ID NO: 15,
- a VH of SEQ ID NO: 7 and a VL of SEQ ID NO: 16,
- a VH of SEQ ID NO: 7 and a VL of SEQ ID NO: 17,
- a VH of SEQ ID NO: 11 and a VL of SEQ ID NO: 20,
- a VH of SEQ ID NO: 12 and a VL of SEQ ID NO: 21,
- a VH of SEQ ID NO: 11 and a VL of SEQ ID NO: 18,
- a VH of SEQ ID NO: 13 and a VL of SEQ ID NO: 18, and
- a VH of SEQ ID NO: 10 and a VL of SEQ ID NO: 19.

24. The antibody or antibody fragment of claim 12, wherein the antibody or antibody fragment is a multispecific antibody.

25. An immunoconjugate comprising the antibody or antibody fragment of claim 12.

26. The immunoconjugate of claim 25, wherein the immunoconjugate comprises at least one agent selected from a chemotherapeutic agent, a radioactive atom, a cytostatic agent and a cytotoxic agent.

27. An antibody or antibody fragment which comprises a combination of a heavy chain variable region (VH) and a light chain variable region (VL) of a pair of amino acid sequences including six complementarity determining regions, said pair of amino acid sequences being selected from the group consisting of:
- a VH having at least 90% identity to the amino acid sequence of SEQ ID NO: 8 and a VL having at least 90% sequence identity to the amino acid sequence of SEQ ID NO: 14, wherein amino acid sequences of the six complementarity determining regions of said antibody or antibody fragment are identical to the amino acid sequences of the three complementarity determining regions of SEQ ID NO: 8 and the amino acid sequences of the three complementarity determining regions of SEQ ID NO: 14,
- a VH having at least 90% identity to the amino acid sequence of SEQ ID NO: 9 and a VL having at least 90% sequence identity to the amino acid sequence of SEQ ID NO: 14, wherein amino acid sequences of the six complementarity determining regions of said antibody or antibody fragment are identical to the amino acid sequences of the three complementarity determining regions of SEQ ID NO: 9 and the amino acid sequences of the three complementarity determining regions of SEQ ID NO: 14,
- a VH having at least 90% identity to the amino acid sequence of SEQ ID NO: 7 and a VL having at least 90% sequence identity the amino acid sequence of SEQ ID NO: 15, wherein amino acid sequences of the six complementarity determining regions of said antibody or antibody fragment are identical to the amino acid sequences of the three complementarity determining regions of SEQ ID NO: 7 and the amino acid sequences of the three complementarity determining regions of SEQ ID NO: 15,
- a VH having at least 90% identity to the amino acid sequence of SEQ ID NO: 7 and a VL having at least 90% sequence identity to the amino acid sequence of SEQ ID NO: 16, wherein amino acid sequences of the six complementarity determining regions of said antibody or antibody fragment are identical to the amino acid sequences of the three complementarity determining regions of SEQ ID NO: 7 and the amino acid sequences of the three complementarity determining regions of SEQ ID NO: 16,
- a VH having at least 90% identity to the amino acid sequence of SEQ ID NO: 7 and a VL having at least 90% sequence identity to the amino acid sequence of SEQ ID NO: 17, wherein amino acid sequences of the six complementarity determining regions of said antibody or antibody fragment are identical to the amino acid sequences of the three complementarity determining regions of SEQ ID NO: 7 and the amino acid sequences of the three complementarity determining regions of SEQ ID NO: 17,
- a VH having at least 90% identity to the amino acid sequence of SEQ ID NO: 11 and a VL having at least 90% sequence identity to the amino acid sequence of SEQ ID NO: 20, wherein amino acid sequences of the six complementarity determining regions of said antibody or antibody fragment are identical to the amino acid sequences of the three complementarity determining regions of SEQ ID NO: 11 and the amino acid sequences of the three complementarity determining regions of SEQ ID NO: 20, a VH having at least 90% identity to the amino acid sequence of SEQ ID NO: 12 and a VL having at least 90% sequence identity to the amino acid sequence of SEQ ID NO: 21, wherein amino acid sequences of the six complementarity determining regions of said antibody or antibody fragment are identical to the amino acid sequences of the three complementarity determining regions of SEQ ID NO: 12 and the amino acid sequences of the three complementarity determining regions of SEQ ID NO: 21, a VH having at least 90% identity to the amino acid sequence of SEQ ID NO: 11 and a VL having at least 90% sequence identity to the amino acid sequence of SEQ ID NO: 18, wherein amino acid sequences of the six complementarity determining regions of said antibody or antibody fragment are identical to the amino acid sequences of the three complementarity determining regions of SEQ ID NO: 11 and the amino acid sequences of the three complementarity determining regions of SEQ ID NO: 18, a VH having at least 90% identity to the amino acid sequence of SEQ ID NO: 13 and a VL having at least 90% sequence identity to the amino acid sequence of SEQ ID NO: 18, wherein amino acid sequences of the six complementarity determining regions of said antibody or antibody fragment are identical to the amino acid sequences of the three complementarity determining regions of SEQ ID NO: 13 and the amino acid sequences of the three complementarity determining regions of SEQ ID NO: 18, and a VH having at least 90% identity to the amino acid sequence of SEQ ID NO: 10 and a VL having at least 90% sequence identity to the amino acid sequence of SEQ ID NO: 19, wherein amino acid sequences of the six complementarity determining regions of said antibody or antibody fragment are identical to the amino acid sequences of the three complementarity determining regions of SEQ ID NO: 10 and the amino acid sequences of the three complementarity determining regions of SEQ ID NO: 19; and said antibody or antibody fragment specifically binds to human EpCAM protein.

* * * * *